(12) United States Patent
Nesler et al.

(10) Patent No.: US 12,264,828 B2
(45) Date of Patent: Apr. 1, 2025

(54) AIR QUALITY CONTROL AND DISINFECTION SYSTEM

(71) Applicant: Johnson Controls Tyco IP Holdings LLP, Milwaukee, WI (US)

(72) Inventors: Clay G. Nesler, Milwaukee, WI (US); Kirk H. Drees, Cedarburg, WI (US); Matthew J. Deloge, Mequon, WI (US); Jonathan D. Douglas, Mequon, WI (US); Timothy C. Gamroth, Dousman, WI (US); Michael J. Wenzel, Oak Creek, WI (US); Robert D. Turney, Watertown, WI (US); Mohammad N. ElBsat, Milwaukee, WI (US); Joseph F. Mann, Waukesha, WI (US); Matthew J. Ellis, Milwaukee, WI (US); Serdar Suindykov, Shizuoka (JP); James Burke, Milwaukee, WI (US); Thomas M. Seneczko, Milwaukee, WI (US); David S. Eidson, Franklin, WI (US); Ganesh Kalpundi, Milwaukee, WI (US); Renee Clair, Milwaukee, WI (US); Anza D'Antonio, Milwaukee, WI (US); Mark L. Ziolkowski, New Berlin, WI (US)

(73) Assignee: Tyco Fire & Security GmbH, Neuhausen am Rheinfall (CH)

( * ) Notice: Subject to any disclaimer, the term of this patent is extended or adjusted under 35 U.S.C. 154(b) by 0 days.

(21) Appl. No.: 16/927,318

(22) Filed: Jul. 13, 2020

(65) Prior Publication Data
US 2021/0010701 A1    Jan. 14, 2021

Related U.S. Application Data

(60) Provisional application No. 63/047,119, filed on Jul. 1, 2020, provisional application No. 63/046,376, filed
(Continued)

(51) Int. Cl.
*F24F 11/64* (2018.01)
*F24F 3/14* (2006.01)
(Continued)

(52) U.S. Cl.
CPC ............ *F24F 11/0001* (2013.01); *F24F 3/14* (2013.01); *F24F 8/10* (2021.01); *F24F 11/39* (2018.01);
(Continued)

(58) Field of Classification Search
CPC .. F24F 8/10; F24F 8/22; F24F 11/0001; F24F 11/46; F24F 11/64; F24F 11/72;
(Continued)

(56) References Cited

U.S. PATENT DOCUMENTS 5,209,398 A    5/1993   Drees
5,497,452 A    3/1996   Shimizu et al.
(Continued)

FOREIGN PATENT DOCUMENTS

CA    2455689 A1    7/2005
CA    2957726 A1    3/2016
(Continued)

OTHER PUBLICATIONS

G.N. Sze To, C.Y.H. Chao. Review and comparison between the Wells-Riley and dose-response approaches to risk assessment of infectious respiratory diseases. Indoor Air, 20 (2010), pp. 2-16 (Year: 2010).*
(Continued)

*Primary Examiner* — Robert E Fennema
*Assistant Examiner* — Vi N Tran
(74) *Attorney, Agent, or Firm* — Foley & Lardner LLP

(57) ABSTRACT

Systems and methods for reducing health risks with respect to an infectious disease in buildings. Health data for an infectious diseases is used to determine a health risk level for
(Continued)

building spaces and individuals in the building. An air handling action or a disinfection action is performed based on the health risk level.

17 Claims, 69 Drawing Sheets

Related U.S. Application Data on Jun. 30, 2020, provisional application No. 62/873,631, filed on Jul. 12, 2019.

(51) Int. Cl.
| | |
|---|---|
| *F24F 8/10* | (2021.01) |
| *F24F 11/00* | (2018.01) |
| *F24F 11/39* | (2018.01) |
| *F24F 11/46* | (2018.01) |
| *F24F 11/61* | (2018.01) |
| *F24F 11/72* | (2018.01) |
| *G05B 13/04* | (2006.01) |
| *G05B 19/042* | (2006.01) |
| *G16H 40/20* | (2018.01) |
| *G16H 50/30* | (2018.01) |
| *F24F 8/22* | (2021.01) |
| *F24F 110/64* | (2018.01) |
| *F24F 110/65* | (2018.01) |
| *F24F 110/70* | (2018.01) |
| *F24F 110/74* | (2018.01) |
| *F24F 120/10* | (2018.01) |
| *F24F 120/20* | (2018.01) |
| *F24F 140/60* | (2018.01) |

(52) U.S. Cl.
CPC ............. *F24F 11/46* (2018.01); *F24F 11/61* (2018.01); *F24F 11/64* (2018.01); *F24F 11/72* (2018.01); *G05B 13/041* (2013.01); *G05B 19/042* (2013.01); *G16H 40/20* (2018.01); *G16H 50/30* (2018.01); *F24F 8/22* (2021.01); *F24F 2110/64* (2018.01); *F24F 2110/65* (2018.01); *F24F 2110/70* (2018.01); *F24F 2110/74* (2018.01); *F24F 2120/10* (2018.01); *F24F 2120/20* (2018.01); *F24F 2140/60* (2018.01); *G05B 2219/25011* (2013.01); *G05B 2219/2614* (2013.01)

(58) Field of Classification Search
CPC ...... F24F 3/14; F24F 2110/65; F24F 2140/60; F24F 2120/10; F24F 2120/20
See application file for complete search history.

(56) References Cited

U.S. PATENT DOCUMENTS

| | | |
|---|---|---|
| 5,550,752 A | 8/1996 | Federspiel |
| 6,033,302 A | 3/2000 | Ahmed et al. |
| 6,095,426 A | 8/2000 | Ahmed et al. |
| 6,988,671 B2 | 1/2006 | Deluca |
| 7,025,281 B2 | 4/2006 | Deluca |
| 7,099,895 B2 | 8/2006 | Dempsey |
| 7,150,408 B2 | 12/2006 | Deluca |
| 7,222,494 B2 | 5/2007 | Peterson et al. |
| 7,311,752 B2 | 12/2007 | Tepper et al. |
| 7,394,370 B2 | 7/2008 | Chan |
| 7,580,775 B2 | 8/2009 | Kulyk et al. |
| 7,788,189 B2 | 8/2010 | Budike, Jr. |
| 7,817,046 B2 | 10/2010 | Coveley et al. |
| 7,894,946 B2 | 2/2011 | Kulyk et al. |
| 7,941,096 B2 | 5/2011 | Perkins et al. |
| 8,049,614 B2 | 11/2011 | Kahn et al. |
| 8,405,503 B2 | 3/2013 | Wong |
| 8,473,080 B2 | 6/2013 | Seem et al. |
| 8,527,108 B2 | 9/2013 | Kulyk et al. |
| 8,527,109 B2 | 9/2013 | Kulyk et al. |
| 8,862,448 B2 | 10/2014 | Holmes et al. |
| 8,867,993 B1 | 10/2014 | Perkins et al. |
| 8,918,223 B2 | 12/2014 | Kulyk et al. |
| 8,984,464 B1 | 3/2015 | Tabula |
| 9,002,532 B2 | 4/2015 | Asmus |
| 9,075,909 B2 | 7/2015 | Almogy et al. |
| 9,110,647 B2 | 8/2015 | Kulyk et al. |
| 9,235,657 B1 | 1/2016 | Wenzel et al. |
| 9,383,736 B2 | 7/2016 | Honda et al. |
| 9,429,923 B2 | 8/2016 | Ward et al. |
| 9,436,179 B1 | 9/2016 | Turney et al. |
| 9,447,985 B2 | 9/2016 | Johnson |
| 9,465,392 B2 | 10/2016 | Bradley et al. |
| 9,547,353 B1 | 1/2017 | Marr et al. |
| 9,612,601 B2 | 4/2017 | Beyhaghi et al. |
| 9,618,224 B2 | 4/2017 | Emmons et al. |
| 9,696,054 B2 | 7/2017 | Asmus |
| 9,703,339 B2 | 7/2017 | Kulyk et al. |
| 9,741,233 B2 | 8/2017 | Laufer et al. |
| 9,778,639 B2 | 10/2017 | Boettcher et al. |
| 9,810,441 B2 | 11/2017 | Dean-Hendricks et al. |
| 9,832,034 B2 | 11/2017 | Shetty et al. |
| 9,852,481 B1 | 12/2017 | Turney et al. |
| 9,915,438 B2 | 3/2018 | Cheatham et al. |
| 9,982,903 B1 | 5/2018 | Ridder et al. |
| 10,007,259 B2 | 6/2018 | Turney et al. |
| 10,068,116 B2 | 9/2018 | Good et al. |
| 10,071,177 B1 | 9/2018 | Kellogg |
| 10,088,814 B2 | 10/2018 | Wenzel et al. |
| 10,101,730 B2 | 10/2018 | Wenzel et al. |
| 10,101,731 B2 | 10/2018 | Asmus et al. |
| 10,139,877 B2 | 11/2018 | Kulyk et al. |
| 10,175,681 B2 | 1/2019 | Wenzel et al. |
| 10,190,789 B2 | 1/2019 | Mueller et al. |
| 10,198,779 B2 | 2/2019 | Pittman et al. |
| 10,251,610 B2 | 4/2019 | Parthasarathy et al. |
| 10,302,318 B1 | 5/2019 | Chambers |
| 10,359,748 B2 | 7/2019 | Elbsat et al. |
| 10,418,833 B2 | 9/2019 | Wenzel et al. |
| 10,444,210 B2 | 10/2019 | Rawat et al. |
| 10,528,020 B2 | 1/2020 | Drees |
| 10,572,230 B2 | 2/2020 | Lucas et al. |
| 10,628,135 B2 | 4/2020 | Sharma et al. |
| 10,678,227 B2 | 6/2020 | Przybylski et al. |
| 10,706,375 B2 | 7/2020 | Wenzel et al. |
| 10,718,542 B2 | 7/2020 | Alanqar et al. |
| 10,871,756 B2 | 12/2020 | Johnson et al. |
| 10,884,398 B2 | 1/2021 | Elbsat et al. |
| 10,908,578 B2 | 2/2021 | Johnson et al. |
| 10,921,768 B2 | 2/2021 | Johnson et al. |
| 10,928,089 B2 | 2/2021 | Gamroth et al. |
| 10,928,784 B2 | 2/2021 | Craig et al. |
| 10,977,010 B2 | 4/2021 | Sharma et al. |
| 11,068,821 B2 | 7/2021 | Wenzel et al. |
| 11,101,651 B2 | 8/2021 | Pavlak et al. |
| 11,131,473 B2 | 9/2021 | Risbeck et al. |
| 11,137,163 B2 | 10/2021 | Nasis |
| 11,156,978 B2 | 10/2021 | Johnson et al. |
| 11,164,126 B2 | 11/2021 | Elbsat et al. |
| 11,181,289 B2 | 11/2021 | Federspiel et al. |
| 11,182,714 B2 | 11/2021 | Wenzel et al. |
| 11,193,691 B1 | 12/2021 | Guyer et al. |
| 11,269,306 B2 | 3/2022 | Risbeck et al. |
| 11,274,842 B2 | 3/2022 | Gamroth et al. |
| 11,436,386 B2 | 9/2022 | Motahar |
| 11,513,486 B2 | 11/2022 | Kupa et al. |
| 11,668,481 B2 | 6/2023 | Granger et al. |
| 2002/0165671 A1 | 11/2002 | Middya |
| 2003/0055798 A1 | 3/2003 | Hittle et al. |
| 2004/0011066 A1 | 1/2004 | Sugihara et al. |
| 2006/0271210 A1 | 11/2006 | Subbu et al. |
| 2007/0101688 A1 | 5/2007 | Wootton et al. |
| 2007/0131782 A1 | 6/2007 | Ziehr et al. |
| 2007/0150333 A1 | 6/2007 | Hurst et al. |
| 2007/0202798 A1 | 8/2007 | Billiotte et al. |

(56) References Cited

U.S. PATENT DOCUMENTS

| | | |
|---|---|---|
| 2007/0203860 A1 | 8/2007 | Golden et al. |
| 2007/0219645 A1 | 9/2007 | Thomas et al. |
| 2008/0206767 A1 | 8/2008 | Kreiswirth et al. |
| 2008/0243273 A1 | 10/2008 | Robert et al. |
| 2008/0277486 A1 | 11/2008 | Seem et al. |
| 2009/0005912 A1 | 1/2009 | Srivastava et al. |
| 2009/0065596 A1 | 3/2009 | Seem et al. |
| 2009/0078120 A1 | 3/2009 | Kummer et al. |
| 2009/0096416 A1 | 4/2009 | Tonegawa et al. |
| 2009/0117798 A1 | 5/2009 | Takashima et al. |
| 2009/0126382 A1 | 5/2009 | Rubino et al. |
| 2009/0173336 A1 | 7/2009 | Leifer et al. |
| 2009/0265106 A1* | 10/2009 | Bearman .............. G06Q 10/00 701/300 |
| 2009/0292465 A1 | 11/2009 | Kaldewey et al. |
| 2009/0319090 A1 | 12/2009 | Dillon et al. |
| 2010/0017045 A1 | 1/2010 | Nesler et al. |
| 2010/0019050 A1 | 1/2010 | Han et al. |
| 2010/0047115 A1 | 2/2010 | Krichtafovitch et al. |
| 2010/0063832 A1 | 3/2010 | Brown |
| 2010/0070093 A1 | 3/2010 | Harrod et al. |
| 2010/0175556 A1 | 7/2010 | Kummer et al. |
| 2010/0187443 A1 | 7/2010 | Leben |
| 2010/0198611 A1 | 8/2010 | Ruoff et al. |
| 2010/0274612 A1 | 10/2010 | Walker et al. |
| 2011/0011105 A1 | 1/2011 | Valiya Naduvath et al. |
| 2011/0018502 A1 | 1/2011 | Bianciotto et al. |
| 2011/0093249 A1 | 4/2011 | Holmes et al. |
| 2011/0106501 A1 | 5/2011 | Christian et al. |
| 2011/0172981 A1 | 7/2011 | Al-Hashimi et al. |
| 2011/0190946 A1 | 8/2011 | Wong et al. |
| 2011/0204720 A1 | 8/2011 | Ruiz et al. |
| 2011/0231320 A1 | 9/2011 | Irving |
| 2011/0276182 A1 | 11/2011 | Seem et al. |
| 2012/0042356 A1 | 2/2012 | Kubota et al. |
| 2012/0053740 A1 | 3/2012 | Venkatakrishnan et al. |
| 2012/0112883 A1 | 5/2012 | Wallace et al. |
| 2012/0130547 A1 | 5/2012 | Fadell et al. |
| 2012/0130556 A1 | 5/2012 | Marhoefer |
| 2012/0173293 A1 | 7/2012 | Motley et al. |
| 2012/0199003 A1 | 8/2012 | Melikov et al. |
| 2012/0203386 A1 | 8/2012 | Fakos et al. |
| 2012/0240113 A1 | 9/2012 | Hur |
| 2013/0013123 A1 | 1/2013 | Ozaki |
| 2013/0085614 A1 | 4/2013 | Wenzel et al. |
| 2013/0110295 A1 | 5/2013 | Zheng et al. |
| 2013/0116803 A1 | 5/2013 | Gmach et al. |
| 2013/0162037 A1 | 6/2013 | Kim et al. |
| 2013/0166268 A1 | 6/2013 | Leonard et al. |
| 2013/0204443 A1 | 8/2013 | Steven et al. |
| 2013/0238144 A1 | 9/2013 | Shahapurkar et al. |
| 2013/0245847 A1 | 9/2013 | Steven et al. |
| 2013/0247059 A1 | 9/2013 | Amsterdam et al. |
| 2013/0290511 A1 | 10/2013 | Tu et al. |
| 2013/0297084 A1 | 11/2013 | Kubota et al. |
| 2014/0039689 A1 | 2/2014 | Honda et al. |
| 2014/0039709 A1 | 2/2014 | Steven et al. |
| 2014/0114867 A1 | 4/2014 | Volkmann et al. |
| 2014/0156093 A1 | 6/2014 | Brian et al. |
| 2014/0167917 A2 | 6/2014 | Wallace et al. |
| 2014/0236869 A1 | 8/2014 | Fujimaki et al. |
| 2014/0260692 A1 | 9/2014 | Sharp |
| 2014/0277603 A1 | 9/2014 | Ditlow et al. |
| 2014/0277767 A1 | 9/2014 | Othman |
| 2014/0283682 A1 | 9/2014 | Hamann et al. |
| 2014/0324404 A1 | 10/2014 | De La Torre-Bueno |
| 2014/0356229 A1 | 12/2014 | Farren |
| 2015/0028114 A1 | 1/2015 | Rosen |
| 2015/0053366 A1 | 2/2015 | Melsheimer |
| 2015/0097688 A1 | 4/2015 | Bruck et al. |
| 2015/0109442 A1 | 4/2015 | Derenne et al. |
| 2015/0149257 A1 | 5/2015 | Bielat et al. |
| 2015/0190538 A1 | 7/2015 | Olvera et al. |
| 2015/0227848 A1 | 8/2015 | Amid et al. |
| 2015/0278968 A1 | 10/2015 | Steven et al. |
| 2015/0316901 A1 | 11/2015 | Wenzel et al. |
| 2015/0316902 A1 | 11/2015 | Wenzel et al. |
| 2015/0316903 A1 | 11/2015 | Asmus et al. |
| 2015/0316907 A1 | 11/2015 | Elbsat et al. |
| 2015/0331972 A1 | 11/2015 | Mcclure et al. |
| 2015/0354874 A1 | 12/2015 | Cur et al. |
| 2016/0066068 A1 | 3/2016 | Schultz et al. |
| 2016/0079826 A1 | 3/2016 | Paiz et al. |
| 2016/0091904 A1 | 3/2016 | Horesh et al. |
| 2016/0109149 A1 | 4/2016 | Heller |
| 2016/0116181 A1 | 4/2016 | Aultman et al. |
| 2016/0147205 A1 | 5/2016 | Kaufman |
| 2016/0195866 A1 | 7/2016 | Turney et al. |
| 2016/0201933 A1 | 7/2016 | Hester et al. |
| 2016/0210337 A1 | 7/2016 | Constandt |
| 2016/0218543 A1 | 7/2016 | Ishida et al. |
| 2016/0306934 A1 | 10/2016 | Sperry et al. |
| 2016/0313019 A1 | 10/2016 | Mengle et al. |
| 2016/0313751 A1 | 10/2016 | Risbeck et al. |
| 2016/0377306 A1 | 12/2016 | Drees et al. |
| 2017/0003676 A1 | 1/2017 | Yoshida et al. |
| 2017/0011150 A1 | 1/2017 | Sons et al. |
| 2017/0016644 A1 | 1/2017 | Nagarathinam et al. |
| 2017/0031962 A1 | 2/2017 | Turney et al. |
| 2017/0039339 A1* | 2/2017 | Bitran .................. G16H 50/30 |
| 2017/0082305 A1 | 3/2017 | Law |
| 2017/0097163 A1 | 4/2017 | Law et al. |
| 2017/0097616 A1 | 4/2017 | Cozad et al. |
| 2017/0102675 A1 | 4/2017 | Drees |
| 2017/0103483 A1 | 4/2017 | Drees et al. |
| 2017/0104336 A1 | 4/2017 | Elbsat et al. |
| 2017/0104337 A1 | 4/2017 | Drees |
| 2017/0104342 A1 | 4/2017 | Elbsat et al. |
| 2017/0104343 A1 | 4/2017 | ElBsat et al. |
| 2017/0104449 A1 | 4/2017 | Drees |
| 2017/0123440 A1 | 5/2017 | Mangsuli et al. |
| 2017/0147722 A1 | 5/2017 | Greenwood |
| 2017/0176030 A1 | 6/2017 | Emmons et al. |
| 2017/0179716 A1 | 6/2017 | Vitullo et al. |
| 2017/0193792 A1* | 7/2017 | Bermudez Rodriguez ................ G08B 5/224 |
| 2017/0206334 A1 | 7/2017 | Huang |
| 2017/0211837 A1* | 7/2017 | Gupta .................. G05B 13/04 |
| 2017/0212488 A1 | 7/2017 | Kummer et al. |
| 2017/0234559 A1 | 8/2017 | Federspiel et al. |
| 2017/0241658 A1 | 8/2017 | Salsbury et al. |
| 2017/0246331 A1* | 8/2017 | Lloyd .................. A61L 2/084 |
| 2017/0292729 A1 | 10/2017 | Schuler et al. |
| 2017/0300657 A1 | 10/2017 | Barrett et al. |
| 2017/0312379 A1 | 11/2017 | Stibich et al. |
| 2017/0350611 A1 | 12/2017 | Su et al. |
| 2017/0351832 A1* | 12/2017 | Cahan .................. G16H 50/30 |
| 2017/0352119 A1 | 12/2017 | Pittman et al. |
| 2018/0004171 A1 | 1/2018 | Patel et al. |
| 2018/0004172 A1 | 1/2018 | Patel et al. |
| 2018/0004173 A1 | 1/2018 | Patel et al. |
| 2018/0011459 A1 | 1/2018 | Boettcher et al. |
| 2018/0031533 A1 | 2/2018 | Rawat et al. |
| 2018/0052431 A1 | 2/2018 | Shaikh et al. |
| 2018/0052970 A1 | 2/2018 | Boss et al. |
| 2018/0087791 A1 | 3/2018 | Monkkonen et al. |
| 2018/0100663 A1 | 4/2018 | Crimins et al. |
| 2018/0110416 A1 | 4/2018 | Masuda et al. |
| 2018/0117209 A1 | 5/2018 | Clack et al. |
| 2018/0150601 A1* | 5/2018 | Astigarraga .......... G06Q 50/14 |
| 2018/0157535 A1 | 6/2018 | Dushok |
| 2018/0163987 A1 | 6/2018 | Rackes et al. |
| 2018/0185533 A1 | 7/2018 | Lalicki et al. |
| 2018/0196456 A1 | 7/2018 | Elbsat |
| 2018/0197253 A1 | 7/2018 | Elbsat et al. |
| 2018/0204162 A1 | 7/2018 | Endel et al. |
| 2018/0209674 A1 | 7/2018 | Ridder et al. |
| 2018/0209675 A1 | 7/2018 | Ridder |
| 2018/0224814 A1 | 8/2018 | Elbsat et al. |
| 2018/0254632 A1 | 9/2018 | Elbsat et al. |
| 2018/0259918 A1 | 9/2018 | Asmus et al. |
| 2018/0285800 A1 | 10/2018 | Wenzel et al. |
| 2018/0299151 A1 | 10/2018 | Ajax et al. |
| 2018/0306459 A1 | 10/2018 | Turney |

(56) References Cited

U.S. PATENT DOCUMENTS

| | | |
|---|---|---|
| 2018/0313563 A1 | 11/2018 | Turney et al. |
| 2018/0314220 A1 | 11/2018 | Kumar et al. |
| 2018/0318746 A1 | 11/2018 | Thomas |
| 2018/0329374 A1 | 11/2018 | Kelly et al. |
| 2018/0340704 A1 | 11/2018 | Turney et al. |
| 2018/0341255 A1 | 11/2018 | Turney et al. |
| 2018/0356770 A1 | 12/2018 | Elbsat et al. |
| 2018/0356782 A1 | 12/2018 | Elbsat et al. |
| 2018/0357577 A1 | 12/2018 | Elbsat et al. |
| 2018/0372355 A1 | 12/2018 | Mosamkar et al. |
| 2018/0372362 A1 | 12/2018 | Turney et al. |
| 2018/0375444 A1 | 12/2018 | Gamroth |
| 2019/0011145 A1 | 1/2019 | Willmott et al. |
| 2019/0020203 A1 | 1/2019 | Lang et al. |
| 2019/0023099 A1 | 1/2019 | Li et al. |
| 2019/0025774 A1 | 1/2019 | Wenzel et al. |
| 2019/0032942 A1 | 1/2019 | Willmott et al. |
| 2019/0032943 A1 | 1/2019 | Willmott et al. |
| 2019/0032944 A1 | 1/2019 | Wenzel et al. |
| 2019/0032945 A1 | 1/2019 | Willmott et al. |
| 2019/0032947 A1 | 1/2019 | Willmott et al. |
| 2019/0032949 A1 | 1/2019 | Willmott et al. |
| 2019/0052120 A1 | 2/2019 | Huang et al. |
| 2019/0056126 A1 | 2/2019 | Law et al. |
| 2019/0066236 A1 | 2/2019 | Wenzel |
| 2019/0096233 A1 | 3/2019 | Bruck et al. |
| 2019/0107825 A1 | 4/2019 | Wenzel et al. |
| 2019/0108746 A1 | 4/2019 | Chang et al. |
| 2019/0141526 A1 | 5/2019 | Bahrami et al. |
| 2019/0148023 A1* | 5/2019 | Sadilek ............... G06N 3/084 705/2 |
| 2019/0155268 A1 | 5/2019 | Cohen et al. |
| 2019/0163213 A1 | 5/2019 | Ostrye et al. |
| 2019/0163216 A1 | 5/2019 | Ostrye |
| 2019/0182069 A1 | 6/2019 | Gervais |
| 2019/0209806 A1 | 7/2019 | Allen et al. |
| 2019/0213695 A1 | 7/2019 | Elbsat et al. |
| 2019/0216957 A1 | 7/2019 | Hawkins et al. |
| 2019/0219293 A1 | 7/2019 | Wenzel et al. |
| 2019/0235453 A1 | 8/2019 | Turney et al. |
| 2019/0245368 A1 | 8/2019 | Baumgartner et al. |
| 2019/0249897 A1 | 8/2019 | Alcala Perez et al. |
| 2019/0257544 A1 | 8/2019 | Alanqar et al. |
| 2019/0271978 A1 | 9/2019 | Elbsat et al. |
| 2019/0295034 A1 | 9/2019 | Wenzel et al. |
| 2019/0311332 A1 | 10/2019 | Turney et al. |
| 2019/0321504 A1 | 10/2019 | Dayton |
| 2019/0325368 A1 | 10/2019 | Turney et al. |
| 2019/0328920 A1 | 10/2019 | Stibich et al. |
| 2019/0331358 A1 | 10/2019 | Ritmanich et al. |
| 2019/0338974 A1 | 11/2019 | Turney et al. |
| 2019/0339661 A1 | 11/2019 | Pancholi et al. |
| 2019/0340709 A1 | 11/2019 | Elbsat |
| 2019/0347622 A1 | 11/2019 | Elbsat et al. |
| 2020/0009280 A1 | 1/2020 | Kupa et al. |
| 2020/0026249 A1 | 1/2020 | Przybylski et al. |
| 2020/0041158 A1 | 2/2020 | Turney et al. |
| 2020/0090089 A1 | 3/2020 | Aston et al. |
| 2020/0090289 A1 | 3/2020 | Elbsat et al. |
| 2020/0096958 A1 | 3/2020 | Kelly et al. |
| 2020/0096985 A1 | 3/2020 | Wenzel et al. |
| 2020/0103127 A1 | 4/2020 | Chen et al. |
| 2020/0110531 A1 | 4/2020 | Sarang et al. |
| 2020/0124307 A1 | 4/2020 | Ota et al. |
| 2020/0125045 A1 | 4/2020 | Risbeck et al. |
| 2020/0132328 A1 | 4/2020 | Boettcher et al. |
| 2020/0141604 A1 | 5/2020 | Chen et al. |
| 2020/0141734 A1 | 5/2020 | Casarez et al. |
| 2020/0149768 A1 | 5/2020 | Turney et al. |
| 2020/0176124 A1 | 6/2020 | Chatterjea et al. |
| 2020/0176125 A1 | 6/2020 | Chatterjea et al. |
| 2020/0193345 A1 | 6/2020 | Elbsat et al. |
| 2020/0193346 A1 | 6/2020 | Elbsat et al. |
| 2020/0200416 A1* | 6/2020 | Granger ............... G06F 1/163 |
| 2020/0218208 A1 | 7/2020 | Alanqar et al. |
| 2020/0218991 A1 | 7/2020 | Alanqar et al. |
| 2020/0227159 A1 | 7/2020 | Boisvert et al. |
| 2020/0292186 A1 | 9/2020 | Ishibashi et al. |
| 2020/0301408 A1 | 9/2020 | Elbsat et al. |
| 2020/0319610 A1 | 10/2020 | Ray et al. |
| 2020/0327371 A1 | 10/2020 | Sharma et al. |
| 2020/0334967 A1* | 10/2020 | Sharma ............. G08B 21/0453 |
| 2020/0348038 A1 | 11/2020 | Risbeck et al. |
| 2020/0355391 A1 | 11/2020 | Wenzel et al. |
| 2020/0356087 A1 | 11/2020 | Elbsat et al. |
| 2020/0365229 A1 | 11/2020 | Fields et al. |
| 2020/0371482 A1 | 11/2020 | Alanqar et al. |
| 2020/0372588 A1 | 11/2020 | Shi |
| 2020/0406778 A1 | 12/2020 | Langton et al. |
| 2021/0010693 A1 | 1/2021 | Gamroth et al. |
| 2021/0010701 A1 | 1/2021 | Nesler et al. |
| 2021/0011443 A1 | 1/2021 | Mcnamara et al. |
| 2021/0011444 A1 | 1/2021 | Risbeck et al. |
| 2021/0018211 A1 | 1/2021 | Ellis et al. |
| 2021/0025613 A1 | 1/2021 | Knatchbull-Hugessen et al. |
| 2021/0043330 A1 | 2/2021 | Ikeshima |
| 2021/0072742 A1 | 3/2021 | Wu et al. |
| 2021/0108821 A1 | 4/2021 | Turney et al. |
| 2021/0125114 A1 | 4/2021 | Lin et al. |
| 2021/0148592 A1 | 5/2021 | Turney et al. |
| 2021/0173366 A1 | 6/2021 | Turney et al. |
| 2021/0193309 A1 | 6/2021 | Boisvert et al. |
| 2021/0200169 A1 | 7/2021 | Ploegert et al. |
| 2021/0209532 A1 | 7/2021 | Wenzel et al. |
| 2021/0270490 A1 | 9/2021 | Turney et al. |
| 2021/0284040 A1 | 9/2021 | Grunkemeyer et al. |
| 2021/0302052 A1 | 9/2021 | Trinh |
| 2021/0313075 A1 | 10/2021 | Mc Namara et al. |
| 2021/0318010 A1 | 10/2021 | Federspiel et al. |
| 2021/0322613 A1 | 10/2021 | Lacaze et al. |
| 2021/0356916 A1 | 11/2021 | Wenzel et al. |
| 2021/0364181 A1 | 11/2021 | Risbeck et al. |
| 2021/0373973 A1 | 12/2021 | Ekins et al. |
| 2021/0390807 A1 | 12/2021 | Chaurasia et al. |
| 2021/0390812 A1 | 12/2021 | Chaurasia et al. |
| 2021/0391089 A1 | 12/2021 | Eswara et al. |
| 2021/0393834 A1 | 12/2021 | Wellig |
| 2021/0398659 A1 | 12/2021 | Sharma et al. |
| 2021/0398690 A1 | 12/2021 | Dhamija et al. |
| 2021/0398691 A1 | 12/2021 | Dhamija et al. |
| 2022/0011731 A1 | 1/2022 | Risbeck et al. |
| 2022/0035326 A1 | 2/2022 | Peters et al. |
| 2022/0042704 A1 | 2/2022 | Drees et al. |
| 2022/0054687 A1 | 2/2022 | Forzani et al. |
| 2022/0060856 A1 | 2/2022 | Wellig et al. |
| 2022/0062463 A1 | 3/2022 | Ramer et al. |
| 2022/0065479 A1 | 3/2022 | Douglas et al. |
| 2022/0092500 A1 | 3/2022 | Drees et al. |
| 2022/0118875 A1 | 4/2022 | Astorg et al. |
| 2022/0137580 A1 | 5/2022 | Burroughs et al. |
| 2022/0148102 A1 | 5/2022 | Elbsat et al. |
| 2022/0172830 A1 | 6/2022 | Brooks et al. |
| 2022/0203287 A1 | 6/2022 | Wenger et al. |
| 2022/0203288 A1 | 6/2022 | Wenger et al. |
| 2022/0205962 A1 | 6/2022 | Vanderkoy |
| 2022/0207215 A1 | 6/2022 | Liu et al. |
| 2022/0221184 A1 | 7/2022 | Gupta et al. |
| 2022/0228756 A1 | 7/2022 | Gupta et al. |
| 2022/0254483 A1 | 8/2022 | Boisvert et al. |
| 2022/0277851 A1 | 9/2022 | Wellig |
| 2022/0282886 A1 | 9/2022 | Hriljac et al. |
| 2022/0293261 A1 | 9/2022 | Mcbrady et al. |
| 2022/0305438 A1 | 9/2022 | Wenger et al. |
| 2022/0305881 A1 | 9/2022 | Neu et al. |
| 2022/0381471 A1 | 12/2022 | Wenzel et al. |
| 2022/0390137 A1 | 12/2022 | Wenzel et al. |
| 2022/0404049 A1 | 12/2022 | Chang et al. |
| 2022/0404051 A1 | 12/2022 | Chang et al. |
| 2023/0020417 A1 | 1/2023 | Elbsat et al. |
| 2023/0120290 A1 | 4/2023 | Byrne et al. |
| 2023/0248869 A1 | 8/2023 | Bell et al. |
| 2023/0250988 A1 | 8/2023 | Risbeck et al. |
| 2023/0253787 A1 | 8/2023 | Wenzel et al. |

(56) References Cited

U.S. PATENT DOCUMENTS

| | | |
|---|---|---|
| 2023/0324864 A1 | 10/2023 | Bursch et al. |
| 2023/0350365 A1 | 11/2023 | Wenzel et al. |
| 2024/0165286 A1 | 5/2024 | Bonutti et al. |

FOREIGN PATENT DOCUMENTS

| | | |
|---|---|---|
| CA | 3043996 A1 | 2/2018 |
| CN | 2644960 Y | 9/2004 |
| CN | 1916514 A | 2/2007 |
| CN | 101194129 A | 6/2008 |
| CN | 201173923 Y | 12/2008 |
| CN | 101387428 A | 3/2009 |
| CN | 101692025 A | 4/2010 |
| CN | 201517972 U | 6/2010 |
| CN | 201558243 U | 8/2010 |
| CN | 101861552 A | 10/2010 |
| CN | 202568950 U | 12/2012 |
| CN | 203727247 U | 7/2014 |
| CN | 105805888 A | 7/2016 |
| CN | 106415139 A | 2/2017 |
| CN | 106975279 A | 7/2017 |
| CN | 107250928 A | 10/2017 |
| CN | 107252594 A | 10/2017 |
| CN | 107477782 A | 12/2017 |
| CN | 107613895 A | 1/2018 |
| CN | 207035361 U | 2/2018 |
| CN | 107787469 A | 3/2018 |
| CN | 107917484 A | 4/2018 |
| CN | 108507057 A | 9/2018 |
| CN | 108779925 A | 11/2018 |
| CN | 108980988 A | 12/2018 |
| CN | 109196286 A | 1/2019 |
| CN | 109405151 A | 3/2019 |
| CN | 110529988 A | 12/2019 |
| CN | 110671798 A | 1/2020 |
| CN | 110822616 A | 2/2020 |
| CN | 110991764 A | 4/2020 |
| CN | 111370135 A | 7/2020 |
| EP | 1 156 286 A2 | 11/2001 |
| EP | 3 186 687 A4 | 7/2017 |
| EP | 3 497 377 A1 | 6/2019 |
| FR | 3031800 A1 | 7/2016 |
| JP | 2010-128976 A | 6/2010 |
| JP | 2012-533720 A | 12/2012 |
| JP | 2015-152175 A | 8/2015 |
| JP | 2016-138705 A | 8/2016 |
| JP | 06-455326 B2 | 1/2019 |
| KR | 20160137767 A | 12/2016 |
| KR | 20170096092 A | 8/2017 |
| KR | 20170115913 A | 10/2017 |
| KR | 101865143 B1 | 6/2018 |
| KR | 20200047457 A | 5/2020 |
| WO | WO-2005/071815 A1 | 8/2005 |
| WO | WO-2009/157847 A1 | 12/2009 |
| WO | WO-2012/161804 A1 | 11/2012 |
| WO | WO-2013/130956 A1 | 9/2013 |
| WO | WO-2013/186282 A2 | 12/2013 |
| WO | WO-2016/047103 A1 | 3/2016 |
| WO | WO-2016/105347 A1 | 6/2016 |
| WO | WO-2017/109206 A1 | 6/2017 |
| WO | WO-2017/203031 A1 | 11/2017 |
| WO | WO-2018/160412 A1 | 9/2018 |
| WO | WO-2018/226564 A1 | 12/2018 |
| WO | WO-2019/050154 A1 | 3/2019 |
| WO | WO-2019/051893 A1 | 3/2019 |
| WO | WO-2019/157514 A2 | 8/2019 |
| WO | WO-2020/170338 A1 | 8/2020 |
| WO | WO-2021/258116 A1 | 12/2021 |
| WO | WO-2022/098887 A1 | 5/2022 |
| WO | WO-2022/251700 A1 | 12/2022 |

OTHER PUBLICATIONS

Azimi et al., "HVAC filtration for controlling infectious airborne disease transmission in indoor environments: Predicting risk reductions and operational costs," Building and Environment May 13, 2013, 70, pp. 150-160.

International Search Report and Written Opinion on PCT/US2020/041770, dated Nov. 3, 2020, 13 pages.

Joe et al., "Methodology for Modeling the Microbial Contamination of Air Filters," PLoS ONE 9(2) e88514, URL: https://doi.org/10.1371/journal.pone.0088514, Feb. 11, 2014, 9 pages.

Kanaan et al., "New airborne pathogen transport model for upper-room UVGI spaces conditioned by chilled ceiling and mixed displacement ventilation: Enhancing air quality and energy performance," Energy Conversion and Management, Apr. 12, 2014, 85, pp. 50-61.

Liao et al., "A Probabilistic Transmission Dynamic Model to Assess Indoor Airborne Infection Risks," Risk Analysis, 2005, vol. 25, No. 5, pp. 1097-1107.

Noakes et al., "Modelling the transmission of airborne infections in enclosed spaces," Epidemiol. Infect, 2006, vol. 134, pp. 1082-1091.

Stephens, "HVAC filtration and the Wells-Riley approach to assessing risks of infectious airborne diseases," The National Air Filtration Association (NAFA) Foundation, Mar. 1, 2012, 47 pages.

International Search Report and Written Opinion on PCT/US2020/041792, dated Sep. 30, 15 pages.

Aghniaey et al., "The Assumption of Equidistance in the Seven-Point Thermal Sensation Scale and a Comparison between Categorical and Continuous Metrics," University of Georgia College of Engineering, Jan. 18, 2019, 4 pages.

Batterman et al., "Review and Extension of CO2-Based Methods to Determine Ventilation Rates with Application to School Classrooms," International Journal of Environmental Research and Public Health, Feb. 4, 22 pages.

Chen et al., "Occupant Feedback Based Model Predictive Control for Thermal Comfort and Energy Optimization: A Chamber Experimental Evaluation," Applied Energy, 2016, 164, pp. 341-351.

HVAC Filtration and the Wells-Riley Approach to Assessing Risks of Infectious Airborne Diseases (Year: 2012).

Kang et al., "Novel Modeling and Control Strategies for a HVAC System Including Carbon Dioxide Control," Energies, Jun. 2, 2014, 7, pp. 3599-3617.

Lampinen, "Thermodynamics of Humid Air," Sep. 2015, 39 Pages.

Ljung, System Identification: Theory for the User, 1999, 2nd ed., Prentice Hall PTR, Upper Saddle River, 63 pages.

Luo, "Maximizing Thermal Comfort and International Design: Predicting Thermal Comfort in Mixed-mode Office Building in the UK," Loughborough University, Jan. 18, 2019, 4 pages.

Sudhakaran et al., "Temperature, Relative Humidity, and Carbon-Dioxide Modulation in a Near-Zero Energy Efficient Retrofit House," Purdue University, 2016, 11 pages.

Weekly et al., "Modeling and Estimation of the Humans' Effect on the CO2 Dynamics Inside a Conference Room," IEEE Transactions On Control Systems Technology, Sep. 2015, 23.5, 12 pages.

International Search Report and Written Opinion for International Application No. PCT/US2020/041845 dated Jan. 13, 2021, 20 pages.

Noakes et al., "Applying the Wells-Riley equation to the risk of airborne infection in hospital environments: The importance of stochastic and proximity effects," Indoor Air 2008, The 11th Intl Conference on Indoor Air Quality and CI, Aug. 17-22, 2008, Copenhagen, Denmark, 9 pages.

Noakes et al., "Mathematical models for assessing the role of airflow on the risk of airborne infection in hospital wards," Journal of the Royal Society Interface, 2009, 6, S791-S800, 10 pages.

Aliabadi et al., "Preventing Airborne Disease Transmission: Review of Methods for Ventilation Design in Health Care Facilities," SAGE-Hindawi Access to Research Advances in Preventive Medicine, Feb. 2011, vol. 2011, 21 pages.

Azimi et al., "HVAC filtration for controlling infectious airborne disease transmission in indoor environments: Predicting risk reductions and operational costs," Building and Environment, May 2013, 70, pp. 150-160.

(56) References Cited

OTHER PUBLICATIONS

Ching, "An empirical drag coefficient model for simulating the dispersion and deposition of bioaerosol particles in ventilated environments," The Hong Kong Polytechnic University Department of Building Services Engineering, Jun. 2016, 345 pages.
Copeland, "The Impact of Patient Room Design on Airborne Hospital-Acquired Infections (HAI)," Thesis, Kent State University, Degree of Masters of Science in Architecture and Environmental Design, May 2016, 61 pages.
Kumar, "A Simulation Framework to Characterize the Effect of Ventilation Control on Airborne Infectious Disease Transmission in Schools," Thesis, Graduate School of The University of Texas at Austin, May 2019, 53 pages.
Stephens, "HVAC filtration and the Wells-Riley approach to assessing risks of infectious airborne diseases," Wells-Riley & HVAC Filtration for infectious airborne aerosols, NAFA Foundation Report, Mar. 2013, 47 pages.
Buaonanno et al., "Estimation of Airborne Viral Emission: Quanta Emission Rate of SARS-CoV-2 for Infection Risk Assessment," Environment International, 2020, 141, 105794, 9 pages.
CDC—Centers for Disease Control and Prevention, "How Flu Spreads," URL: https://www.cdc.gov/flu/about/disease/spread.htm, Aug. 27, 2018, 1 page.
CDC—Centers for Disease Control and Prevention, "Interim Clinical Guidance for Management of Patients with Confirmed Coronavirus Disease (COVID_19)," URL: https://www.cdc.gov/coronavirus/2019-ncov/hcp/clinical-guidance-management-patients.html, Feb. 2021, 14 pages.
CIRES—Cooperative Institute for Research in Environmental Sciences, "COVID-19 Airborne Transmission Tool Available: New model estimates COVID-19 transmission in classrooms, buses, protests, more," URL: https://cires.colorado.edu/news/covid-19-airborne-transmission-tool-available, Jun. 25, 2020, 7 pages.
EPA—U.S. Environmental Protection Agency, "Exposure Factors Handbook," URL: https://www.epa.gov/expobox/about-exposure-factors-handbook, 2011, 6 pages.
EPA—U.S. Environmental Protection Agency, "Greenhouse Gases Equivalences Calculator-Calculations and References", URL: https://www.epa.gov/energy/greenhouse-gases-equivalencies-calculator-calculations-and-references, retrieved from the internet 9/30/3031, 32 pages.
Fears et al., "Comparative Dynamic Aerosol Efficiencies of Three Emergent Coronaviruses and the Unusual Persistence of Sars-Cov-2 in Aerosol Suspensions," URL: https://www.ncbi.nlm.nih.gov/pmc/articles/PMC7217084/, Apr. 18, 2020, 8 pages.
Johnson et al., "Modality of human expired aerosol size distributions," Journal of Aerosol Science, 2011, 42(12), pp. 839-851.
Kowalski, W., "Ultraviolet germicidal irradiation handbook: UVGI for air and surface disinfection," Springer Science & Business Media, 2010, 504 pages.
Marr et al., "SARS-CoV-2 in Indoor Air: Principles and Scenarios," US Epa Indoor Air Quality Science Webinar, YouTube URL: https://www.youtube.com/watch?v=fSQ0ah_OArU, Jul. 21, 2020, 113 pages.
National Geographic, "Measure the risk of airborne COVID-19 in your office, classroom, or bus ride," URL: https://www.nationalgeographic.com/science/article/how-to-measure-risk-airborne-coronavirus-your-office-classroom-bus-ride-cvd, Aug. 11, 2020, 12 pages.
Van Doremalen et al., "Aerosol and Surface Stability of SARS-CoV-2 as Compared with SARS-CoV-1," URL: https://www.nejm.org/doi/full/10.1056/nejmc2004973, Mar. 17, 2020, 5 pages.
U.S. Appl. No. 17/686,320, filed Mar. 3, 2022.
U.S. Appl. No. 17/733,786, filed Apr. 29, 2022.
U.S. Appl. No. 17/576,615, filed Jan. 14, 2022.
U.S. Appl. No. 17/582,988, filed Jan. 24, 2022.
International Preliminary Report on Patentability on PCT Appl. Ser. No. PCT/US2020/041770 dated Jan. 27, 2022 (8 pages).
International Preliminary Report on Patentability on PCT Appl. Ser. No. PCT/US2020/041792 dated Jan. 27, 2022 (9 pages).
International Preliminary Report on Patentability on PCT Appl. Ser. No. PCT/US2020/041845 dated Jan. 27, 2022 (12 pages).
Hubert et al., Modeling for Residential Electricity Optimization in Dynamic Pricing Environments, IEEE Transactions On Smart Grid, IEEE, USA, Dec. 1, 2012, vol. 3, No. 4 (pp. 2224-2231).
International Preliminary Report Patentability on PCT Appl. Ser. No. PCT/US2018/039119 dated Jan. 2, 2020 (7 pages).
International Search Report and Written Opinion on International Appl. Ser. No. PCT/US2018/039119 dated Oct. 5, 2018 (14 pages).
Coolinglogic, "CoolingLogic: Up early, saving billions." URL: http://coolinglogic.com/documents/MarketingFlyer_FINAL_HiRes8.5x11.pdf, retrieved from internet Oct. 27, 2022 (1 page).
Incomplete File of Communication with Various Companies, etc. in 2016-2021, URL: http://coolinglogic.com/documents/22072101_Letters_and_Signature_Receipts.pdf, published, as one document, on: Jul. 21, 2022 (211 pages).
International Search Report and Written Opinion on PCT Appl. No. PCT/US2022/031438 dated Nov. 8, 2022 (18 pages).
Johnson Heating and Cooling L.L.C., "Divine Grace Building Automation (Images)," URL: http://cooljohnson.com/Building-Automation-Systems-Michigan/Oakland-County-Michigan/Building-Automation-Images.html, retrieved from internet Oct. 27, 2022 (8 pages).
Johnson Heating and Cooling L.L.C., "Divine Grace Building Automation," URL: http://cooljohnson.com/Building-Automation-Systems-Michigan/Oakland-County-Michigan/Building-Automation-Divine-Grace.html, retrieved from internet Oct. 27, 2022 (3 pages).
Johnson Heating and Cooling L.L.C., "Excel Rehabilitation Building Automation," URL: http://cooljohnson.com/Building-Automation-Systems-Michigan/Waterford-Michigan/Building-Automation-System--Excel.html, retrieved from internet Oct. 27, 2022 (2 pages).
Johnson Heating and Cooling L.L.C., "Intertek Testing Services Building Automation," URL: http://cooljohnson.com/Building-Automation-Systems-Michigan/Plymouth-Michigan/Building-Automation-System-Plymouth-Michigan.html, retrieved from internet Oct. 27, 2022 (8 pages).
Johnson Heating and Cooling L.L.C., "Jla Medical Building Building Automation," URL: http://cooljohnson.com/Building-Automation-Systems-Michigan/Waterford-Michigan/Building-Automation-System--JLA.html, retrieved from internet Oct. 27, 2022 (3 pages).
Johnson Heating and Cooling L.L.C., "Mosaic Christian Building Automation (Images)," URL: http://cooljohnson.com/Building-Automation-Systems-Michigan/Detroit/Building-Automation-Images.html, retrieved from internet Oct. 27, 2022 (12 pages).
Johnson Heating and Cooling L.L.C., "Mosaic Christian Building Automation," URL: http://cooljohnson.com/Building-Automation-Systems-Michigan/Detroit/Mosaic-Christian.html, retrieved from internet Oct. 27, 2022 (5 pages).
Johnson Heating and Cooling L.L.C., "Shepherd's Gate Lutheran Church Building Automation," URL: http://cooljohnson.com/Building-Automation-Systems-Michigan/Shelby-Township-Michigan/Building-Automation-Systems-SG.html, retrieved from internet Oct. 27, 2022 (3 pages).
Johnson Heating and Cooling L.L.C., "St. Clair County Residence Building Automation," URL: http://cooljohnson.com/Building-Automation-Systems-Michigan/St-Clair-Michigan/Building-Automation-System-St-Clair-Michigan.html, retrieved from internet Oct. 27, 2022 (4 pages).
Johnson Heating and Cooling L.L.C., "St. Joseph Mercy Oakland U. C. Building Automation," URL: http://cooljohnson.com/Building-Automation-Systems-Michigan/Waterford-Michigan/Building-Automation-Systems-SJMO.html, retrieved from internet Oct. 27, 2022 (2 pages).
Johnson Heating and Cooling L.L.C., "Waterford Internal Medicine Building Automation," URL: http://cooljohnson.com/Building-Automation-Systems-Michigan/Waterford-Michigan/Building-Automation-Systems-WIM.html, retrieved from internet Oct. 27, 2022 (3 pages).
Johnson Heating and Cooling, LLC, "Building Automation Clawson Michigan 2.0," URL: http://cooljohnson.com/Building-Automation-Systems-Michigan/Clawson-Michigan/Building-Automation-Clawson-Manor-2.html, retrieved from the internet Oct. 27, 2022 (6 pages).

(56) References Cited

OTHER PUBLICATIONS

Johnson Heating and Cooling, LLC, "Building Automation Images Clawson Michigan 2.0," URL: http://cooljohnson.com/Building-Automation-Systems-Michigan/Clawson-Michigan/Building-Automation-Clawson-Manor-2-Images.html, retrieved from the internet Oct. 27, 2022 (14 pages).
Johnson Heating and Cooling, LLC, "Building Automation System Clawson Michigan Clawson Manor," URL: http://cooljohnson.com/Building-Automation-Systems-Michigan/Clawson-Michigan/Building-Automation-System-Clawson-Manor.html; retrieved from the internet Oct. 27, 2022 (3 pages).
Johnson Heating and Cooling, LLC, "Building Automation System in Michigan Images," URL: http://cooljohnson.com/Building-Automation-Systems-Michigan/Macomb-County-Michigan/Building-Automation-Images.html; retrieved from the internet Oct. 27, 2022 (13 pages).
Johnson Heating and Cooling, LLC, "Building Automation System in Michigan," URL: http://cooljohnson.com/Building-Automation-Systems-Michigan/Macomb-County-Michigan/Building-Automation-Confidential-Customer.html; retrieved from the internet, Oct. 27, 2022 (4 pages).
Johnson Solid State LLC, "Building Automation Equipment," URL: http://cooljohnson.com/Video/Building_Automation/Confidential_Customer_BLD_2/Building_Automation_Equipment.mp4, retrieved from internet Oct. 27, 2022 (35 pages).
Johnson Solid State LLC, "Building Automation Gui," URL: http://cooljohnson.com/Video/Building_Automation/Confidential_Customer_BLD_2/Building_Automation_GUI.mp4, retrieved from internet Oct. 27, 2022 (24 pages).
Johnson Solid State LLC, "Cooling Logic Overview," URL: http://coolinglogic.com/documents/CoolingLogic_Overview_High_Quality.mp4, retrieved from internet Oct. 27, 2022 (16 pages).
Johnson Solid State LLC, "So what is CoolingLogic™?" URL: http://coolinglogic.com/Coolinglogic-How-it-Works.html, retrieved from the internet Oct. 27, 2022 (3 pages).
Johnson, David, "A Method to Increase HVAC System Efficiency And Decrease Energy Consumption," White Paper: Johnson Solid State, LLC, URL: http://coolinglogic.com/documents/16102106_White_Paper_High_Resolution_Protected.pdf, Sep. 24, 2016 (51 pages).
Johnson, David, "CoolingLogic™: Mosaic Christian Church A Case Study," Report: Johnson Solid State, LLC, URL: http://coolinglogic.com/documents/19020301_Mosaic_Christian_Coolinglogic_Case_Study.pdf, Feb. 2, 2019 (140 pages).
Johnson, David, "Excel Rehabilitation Building Automation: Building Automation System User Manual ," URL: http://cooljohnson.com/Building-Automation-Systems-Michigan/Waterford-Michigan/Building-Automation-System-Excel-Manual.html, 2012 (10 pages).
Johnson, David, "Temperature Control System and Methods for Operating Same," Pre-Publication printout of U.S. Appl. No. 15/231,943, filed Aug. 9, 2016, URL: http://coolinglogic.com/documents/16080901_CIP_As_Filed.pdf (99 pages).
Johnson, David., "CoolingLogic™: Changing the Way You Cool," Report: Johnson Solid State, LLC, URL: http://coolinglogic.com/documents/18111303_Changing_the_way_you_Cool.pdf, Nov. 7, 2018 (12 pages).
Invitation to Pay Additional Fees and, Where Applicable, Protest Fee on PCT Appl. No. PCT/US2022/031438 dated Sep. 2, 2022 (14 pages).
U.S. Appl. No. 63/194,771, filed May 28, 2021.
U.S. Appl. No. 63/220,878, filed Jul. 12, 2021.
Chinese Office Action on CN Appl. No. 202080057416.0 dated Dec. 30, 2022 (12 pages).
Chinese Office Action on CN Appl. No. 202080061895.3 dated Jan. 20, 2023 (6 pages).
EPO Provisional Opinion Accompanying the Partial Search Result for PCT Appl. Ser. No. PCT/US2023/012719 dated Mar. 28, 2023 (15 pages).
European Office Action on EP Appl. No. 20750965.4 dated Mar. 31, 2023 (5 pages).
International Search Report and Written Opinion on PCT Appl. No. PCT/US2022/040332 dated Nov. 22, 2022 (18 pages).
Noakes et al., "Appraising healthcare ventilation design from combined infection control and energy perspective," HVAC & R Research, Aug. 2012, (20 pages).
Afram et al., "Theory and Application of HVAC Control Systems—A review of Model Predictive Control (MPC)," Building and Environment, Feb. 2014, vol. 72 (pp. 343-355).
Ahn et al., "Optimal Control Development for Chilled Water Plants Using a Quadratic Representation," Energy and Buildings, Apr. 2001, vol. 33, No. 4 (pp. 371-378).
Alvarado et al., "A Methodology to Monitor Airborne PM10 Dust Particles Using a Small Unmanned Aerial Vehicle," Sensors, 2017, vol. 17 (25 pages).
Azimi et al., "HVAC filtration for controlling infectious airborne disease transmission in indoor environments: Predicting risk reductions and operational costs," Building and Environment, May 2013, vol. 70 (pp. 150-160).
Beggs et al., "Potential for airborne transmission of infection in the waiting areas of healthcare premises: stochastic analysis using a Monte Carlo model," BMC Infectious Diseases, Aug. 2010, vol. 10 (11 pages).
Ben-David et al., "Interplay of ventilation and filtration: Differential analysis of cost function combining energy use and indoor exposure to PM2.5 and ozone," Building and Environment, Aug. 2017, vol. 128 (pp. 320-335).
Burer et al., "Non-convex Mixed-Integer Nonlinear Programming: A Survey," Surveys in Operations Research and Management Science, Jul. 2012, vol. 17, No. 2 (pp. 97-106).
Cai et al., "Nationwide assessment of energy costs and policies to limit airborne infection risks in U.S. schools," Journal of Building Engineering, Jul. 2021, vol. 45 (pp. 1-12).
Cantoni, A., "Optimal Curve Fitting with Piecewise Linear Functions," IEEE Transactions on Computers, Jan. 1971, vol. 20, No. (pp. 59-67).
Chinese Office Action on CN Appl. No. 202080057416.0 dated Aug. 30, 2023 (37 pages).
Chinese Office Action on CN Appl. No. 202080061895.3 dated Sep. 25, 2023 (12 pages).
Corbin et al., "A Model Predictive Control Optimization Environment for Real-Time Commercial Building Application," Journal of Building Performance Simulation, 2013, (Published online: Jan. 11, 2012) vol. 6, No. 3 (pp. 159-174).
Drgona et al., "All you Need to Know about Model Predictive Control for Buildings," Annual Reviews in Control, 2020, vol. 50 (pp. 190-232).
EPO Notice of Opposition to a European Patent issued in Appl. Ser. No. EP 16165681.4 dated May 2, 2023 (48 pages).
EPO Notice of Opposition to a European Patent issued in Appl. Ser. No. EP 16165681.4 dated May 2, 2023 (51 pages).
EPO Notice of Opposition to a European Patent with Consolidated List issued in EP Appl. Ser. No. 16165681.4 dated May 4, 2023 (4 pages).
EPO Office Action on EP Appl. Ser. No. 16165681.4 dated Apr. 6, 2021 (7 pages).
European Office Action on EP Appl. No. 20751421.7 dated Jul. 16, 2024 (5 pages).
Extended European Search Report on EP Appl. Ser. No. 16165681.4 dated Oct. 20, 2016 (5 pages).
Extended European Search Report on EP Appl. Ser. No. 22177772.5 dated Sep. 26, 2022 (11 pages).
Faulkner et al., "Tradeoffs among indoor air quality, financial costs, and CO2 emissions for HVAC operation strategies to mitigate indoor virus in U.S. office buildings," Building and Environment, Mar. 2022, vol. 221 (pp. 1-15).
Gao et al., "Potential impact of a ventilation intervention for influenza in the context of a dense indoor contact network in Hong Kong," Science of the Total Environment, Apr. 2016, vols. 569-570 (pp. 373-381).
Hackner, J.R., "HVAC system dynamics and energy use in existing buildings," Doctoral Dissertation, University of Madison, Wisconsin, 1984 (174 pages).

(56) References Cited

OTHER PUBLICATIONS

Haves et al., "Model Predictive Control of HVAC Systems: Implementation and Testing at the University of California, Merced," Technical Report, U.S. Department of Energy Office of Scientific and Technical Information, Jun. 29, 2010 (140 pages).
Huang et al., "A New Model Predictive Control Scheme for Energy and Cost Savings in Commercial Buildings: An Airport Terminal Building Case Study," Building and Environment, Jul. 2015, vol. 89 (pp. 203-216).
International Search Report and Written Opinion on PCT Appl. Ser. No. PCT/US2023/020060 dated Sep. 15, 2023 (20 pages).
International Search Report and Written Opinion on PCT Appl. Ser. No. PCT/US2023/012719 dated May 22, 2023 (20 pages).
Kelman et al., "Analysis of Local Optima in Predictive Control for Energy Efficient Buildings," Journal of Building Performance Simulation, Apr. 16, 2012, vol. 6, No. 3 (pp. 236-255).
Koehler et al., "Building Temperature Distributed Control via Explicit MPC and 'Trim and Respond' Methods," European Control Conference (ECC), Jul. 17-19, 2013, Zurich, Switzerland (pp. 4334-4339).
Kwadzogah et al., "Model Predictive Control for HVAC Systems—A Review," 2013 IEEE International Conference on Automation Science and Engineering, Model Predictive Control for HVAC Systems—A Review, 2013 IEEE International Conference on Automation Science and Engineering (CASE), Madison, WI, United States, Aug. 17-20, 2013 (pp. 442-447).
Lee et al., "Life-Cycle Cost Simulation of In-Duct Ultraviolet Germicidal Irradiation Systems," Eleventh International IBPSA Conference, Glasgow, Scotland, Jul. 27-30, 2009 (pp. 1159-1166).
Mckenna et al., "A TRNSYS model of a building HVAC system with GSHP and PCM thermal energy storage-component modelling and validation," Proceedings of BS2013: 13th Conference of International Building Performance Simulation Association, Chambéry, France, Aug. 26-28, 2013 (pp. 3336-3343).
Mossolly et al., "Optimal Control Strategy for a Multizone Air Conditioning System Using a Genetic Algorithm," Energy, Jan. 2009, vol. 34, No. 1 (pp. 58-66).
Nassif et al., "Optimization of HVAC Control System Strategy Using Two-Objective genetic Algorithm," International Journal of HVA C&R Research, Jul. 2005, vol. 11, No. 3 (pp. 459-486).
PCT Invitation to Pay Additional Fees and Where Applicable, Protest Fee for Appl. Ser. No. PCT/US2023/020060 dated Jul. 18, 2023 (14 pages).
Sourbon et al., "Dynamic Thermal Behaviour of Buildings with Concrete Core Activation," Dissertation, Arenberg Doctoral School of Science, Engineering & Technology, Katholieke Universiteit Leuven-Faculty of Engineering Celestijnenlaan: 300A box 2421, B-3001 Heverlee (Belgium) Sep. 2012 (416 pages).
Stluka et al., "Energy Management for Buildings and Microgrids," 2011 50th IEEE Conference on Decision and Control and European Control Conference (CDCECC) Orlando, FL, USA, Dec. 12-15, 2011 (pp. 5150-5157).
Strurznegger, D., "Model Predictive Building Climate Control, Steps Towards Practice," Doctoral Thesis, Automatic Control Laboratory, Zurich, Switzerland, 2014 (176 pages).
Sun et al., Optimal Control of Building HVAC&R Systems Using Complete Simulation-Based Sequential Quadratic Programming (CSB-SQP), Building and Environment, May 2005, vol. 40, No. 5 (pp. 657-669).
Third Party Observation Report on EP Appl. Ser. No. 16165681.4 dated Jan. 15, 2020 (8 pages).
Third Party Observation Report on EP Appl. Ser. No. 16165681.4 dated Oct. 5, 2018 (6 pages).
Verhelst et al., "Study of the Optimal Control Problem Formulation for Modulating Air-to-Water Heat Pumps Connected to a Residential Floor Heating System," Energy and Buildings, Feb. 2012, vol. 45 (pp. 43-53).
Verhelst, C., "Model Predictive Control of Ground Coupled Heat Pump Systems in Office Buildings," Dissertation, Arenberg Doctoral School of Science, Engineering & Technology, Katholieke Universiteit Leuven-Faculty of Engineering Celestijnenlaan : 300A box 2421, B-3001 Heverlee (Belgium) Apr. 20, 2012 (316 pages).
Wang et al., "Model-Based Optimal Control of VAV Air-Conditioning System Using Genetic Algorithm," Building and Environment, Aug. 2000, vol. 35, No. 6 (pp. 471-487).
Wang et al., "Supervisory and Optimal Control of Building HVAC Systems: A Review," HVAC&R Research, Jan. 2008, vol. 14, No. 1 (pp. 3-32).
Xi et al., "Support Vector Regression Model Predictive Control on a HVAC Plant," Control Engineering Practice, Aug. 2007, vol. 15, No. 8 (pp. 897-908).
Yang et al., "Multi-Objective Particle Swarm Optimization for decision-making in building automation," Power and Energy Society General Meeting, Jul. 24, 2011, IEEE (pp. 1-5).
Yao et al., "Global Optimization of a Central Air-Conditioning System Using Decomposition-Coordination Method," Energy and Buildings, May 2010, vol. 42, No. 5 (pp. 570-583).
Chang et al., "A cost-effectiveness assessment of the operational parameters of central HVAC systems during pandemics," Building Simulation, Nov. 2022, vol. 16 (pp. 667-682).
Noakes et al., "Modeling infection risk and energy use of upper-room Ultraviolet Germicidal Irradiation systems in multi-room environments," Jan. 2015, Science and Technology for the Built Environment, vol. 21, No. 1 (pp. 99-111).
Villafruela et al., "Comparison of air change efficiency, contaminant removal effectiveness and infection risk as IAQ indices in isolation rooms," Energy and Buildings, Mar. 2012, vol. 57 (pp. 210-219).
Xu et al., "Simulation-based trade-off modeling for indoor infection risk of airborne diseases, energy consumption, and thermal comfort," Journal of Building Engineering, Jan. 2023, vol. 76, No. 107137 (pp. 1-16).
Yan et al., "Evaluating SARS-CoV-2 airborne quanta transmission and exposure risk in a mechanically ventilated multi zone office building," Building and Environment, Feb. 2022, vol. 219, No. 109184 (pp. 1-15).

* cited by examiner

AIR QUALITY CONTROL AND DISINFECTION SYSTEM

CROSS-REFERENCE TO RELATED PATENT APPLICATION

This application claims the benefit of and priority to U.S. Provisional Patent Application No. 62/873,631 filed Jul. 12, 2019, the entire disclosure of which is incorporated by reference herein.

BACKGROUND

The present disclosure relates generally to building devices of building systems that operate a building. The present disclosure relates more particularly to maintaining a temperature and infection level in the building.

Building devices can operate to affect various conditions in a building. For example, one building device may operate to affect a temperature in the building whereas a second building device may operate to disinfect part of the building. However, if each device is separated, various system may be operating independent from one another and therefore can conflict. In this way, operating conflicting systems can increase costs for maintaining comfortable/preferred conditions in the building and can lead to quicker degradation of the devices.

BRIEF DESCRIPTION OF THE DRAWINGS

Various objects, aspects, features, and advantages of the disclosure will become more apparent and better understood by referring to the detailed description taken in conjunction with the accompanying drawings, in which like reference characters identify corresponding elements throughout. In the drawings, like reference numbers generally indicate identical, functionally similar, and/or structurally similar elements.

DETAILED DESCRIPTION

Building Management System and HVAC System

Figure 1:
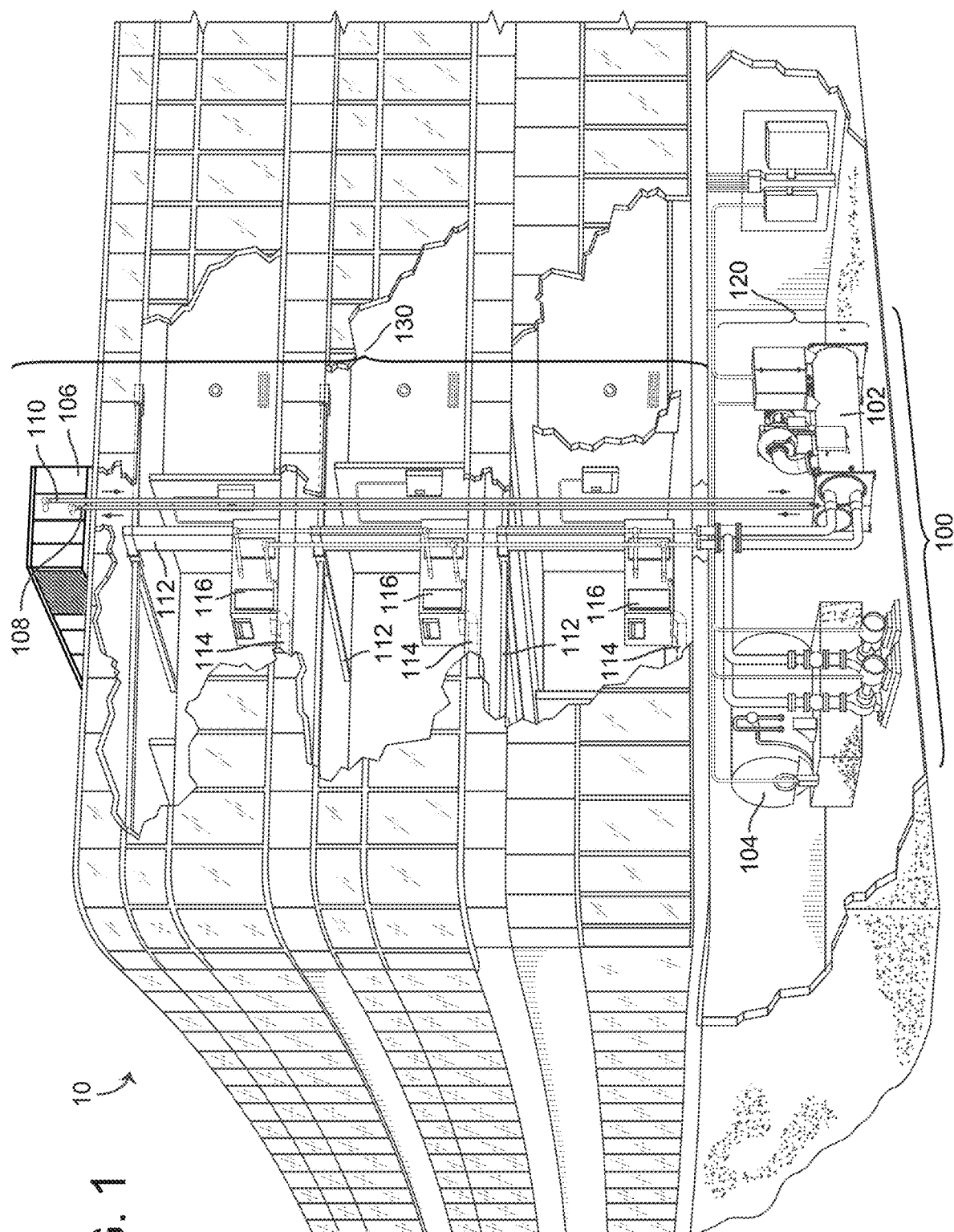
FIG. 1 is an illustration of a building equipped with a HVAC system, according some embodiments.

Referring now to FIGS. 1-4, an exemplary building management system (BMS) and HVAC system in which the systems and methods of some embodiments may be implemented are shown, according to an exemplary embodiment. Referring particularly to FIG. 1, a perspective view of a building 10 is shown. Building 10 is served by a BMS. A BMS can include, for example, an HVAC system, a security system, a lighting system, a fire alerting system, or any other system that is capable of managing building functions or devices, or any combination thereof.

The BMS that serves building 10 includes an HVAC system 100. HVAC system 100 may include a plurality of HVAC devices (e.g., heaters, chillers, air handling units, pumps, fans, thermal energy storage, etc.) configured to provide heating, cooling, ventilation, or other services for building 10. For example, HVAC system 100 is shown to include a waterside system 120 and an airside system 130. Waterside system 120 may provide a heated or chilled fluid to an air handling unit of airside system 130. Airside system 130 may use the heated or chilled fluid to heat or cool an airflow provided to building 10. An exemplary waterside system and airside system which may be used in HVAC system 100 are described in greater detail with reference to FIGS. 2-3.

HVAC system 100 is shown to include a chiller 102, a boiler 104, and a rooftop air handling unit (AHU) 106. Waterside system 120 may use boiler 104 and chiller 102 to heat or cool a working fluid (e.g., water, glycol, etc.) and may circulate the working fluid to AHU 106. In various embodiments, the HVAC devices of waterside system 120 may be located in or around building 10 (as shown in FIG. 1) or at an offsite location such as a central plant (e.g., a chiller plant, a steam plant, a heat plant, etc.). The working fluid may be heated in boiler 104 or cooled in chiller 102, depending on whether heating or cooling is required in building 10. Boiler 104 may add heat to the circulated fluid, for example, by burning a combustible material (e.g., natural gas) or using an electric heating element. Chiller 102 may place the circulated fluid in a heat exchange relationship with another fluid (e.g., a refrigerant) in a heat exchanger (e.g., an evaporator) to absorb heat from the circulated fluid. The working fluid from chiller 102 and/or boiler 104 may be transported to AHU 106 via piping 108.

AHU 106 may place the working fluid in a heat exchange relationship with an airflow passing through AHU 106 (e.g., via one or more stages of cooling coils and/or heating coils). The airflow may be, for example, outside air, return air from within building 10, or a combination of both. AHU 106 may transfer heat between the airflow and the working fluid to provide heating or cooling for the airflow. For example, AHU 106 may include one or more fans or blowers configured to pass the airflow over or through a heat exchanger containing the working fluid. The working fluid may then return to chiller 102 or boiler 104 via piping 110.

Airside system 130 may deliver the airflow supplied by AHU 106 (i.e., the supply airflow) to building 10 via air supply ducts 112 and may provide return air from building 10 to AHU 106 via air return ducts 114. In some embodiments, airside system 130 includes multiple variable air volume (VAV) units 116. For example, airside system 130 is shown to include a separate VAV unit 116 on each floor or zone of building 10. VAV units 116 may include dampers or other flow control elements that can be operated to control an amount of the supply airflow provided to individual zones of building 10. In other embodiments, airside system 130 delivers the supply airflow into one or more zones of building 10 (e.g., via supply ducts 112) without using intermediate VAV units 116 or other flow control elements. AHU 106 may include various sensors (e.g., temperature sensors, pressure sensors, etc.) configured to measure attributes of the supply airflow. AHU 106 may receive input from sensors located within AHU 106 and/or within the building zone and may adjust the flow rate, temperature, or other attributes of the supply airflow through AHU 106 to achieve setpoint conditions for the building zone.

Figure 2:
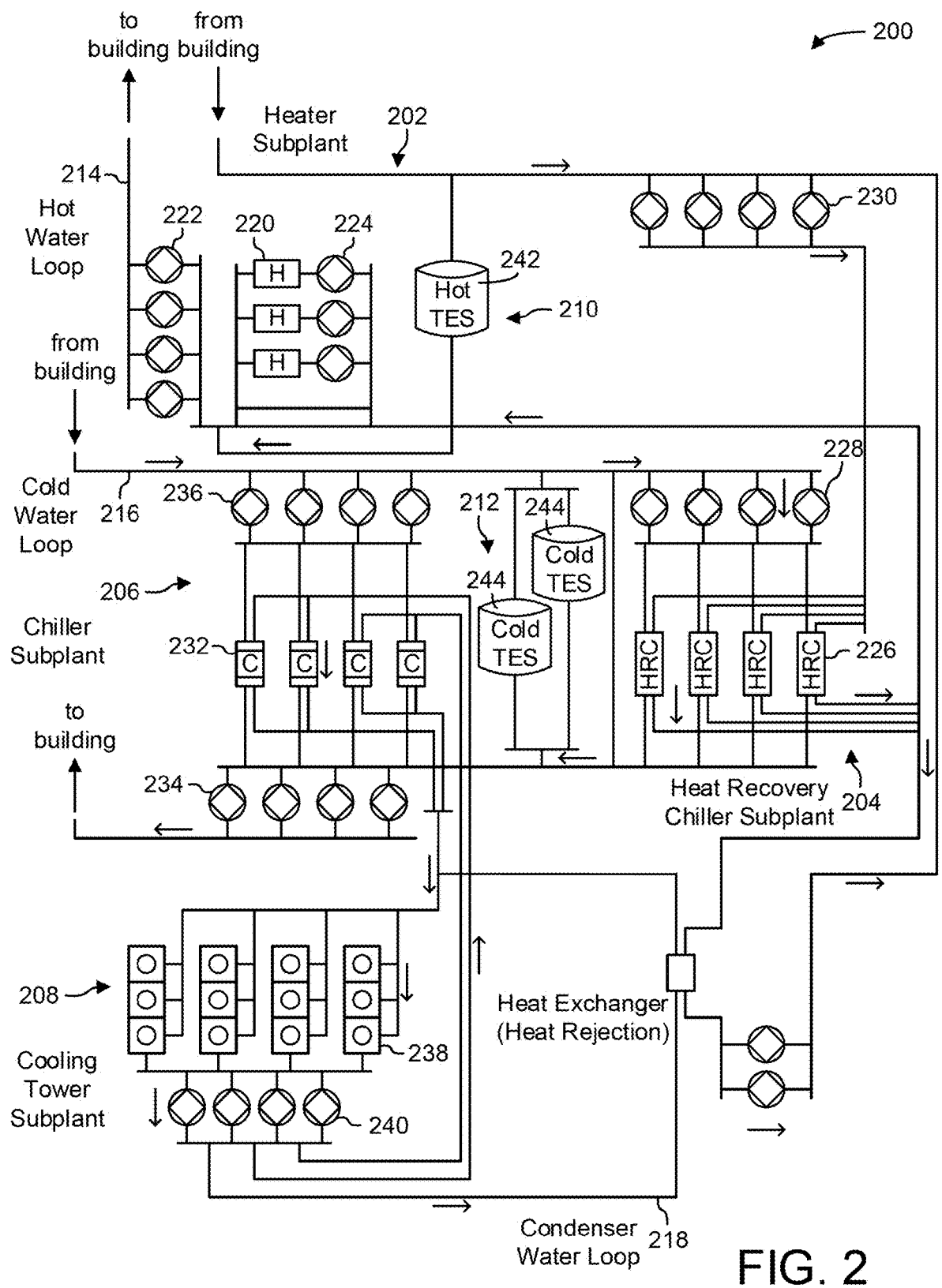
FIG. 2 is a block diagram of a waterside system that may be used in conjunction with the building of FIG. 1, according to some embodiments.

Referring now to FIG. 2, a block diagram of a waterside system 200 is shown, according to one embodiment. In various embodiments, waterside system 200 may supplement or replace waterside system 120 in HVAC system 100 or may be implemented separate from HVAC system 100. When implemented in HVAC system 100, waterside system 200 may include a subset of the HVAC devices in HVAC system 100 (e.g., boiler 104, chiller 102, pumps, valves, etc.) and may operate to supply a heated or chilled fluid to AHU 106. The HVAC devices of waterside system 200 may be located within building 10 (e.g., as components of waterside system 120) or at an offsite location such as a central plant.

In FIG. 2, waterside system 200 is shown as a central plant having a plurality of subplants 202-212. Subplants 202-212 are shown to include a heater subplant 202, a heat recovery chiller subplant 204, a chiller subplant 206, a cooling tower subplant 208, a hot thermal energy storage (TES) subplant 210, and a cold thermal energy storage (TES) subplant 212. Subplants 202-212 consume resources (e.g., water, natural gas, electricity, etc.) from utilities to serve the thermal energy loads (e.g., hot water, cold water, heating, cooling, etc.) of a building or campus. For example, heater subplant 202 may be configured to heat water in a hot water loop 214 that circulates the hot water between heater subplant 202 and building 10. Chiller subplant 206 may be configured to chill water in a cold water loop 216 that circulates the cold water between the chiller subplant 206 and the building 10. Heat recovery chiller subplant 204 may be configured to transfer heat from cold water loop 216 to hot water loop 214 to provide additional heating for the hot water and additional cooling for the cold water. Condenser water loop 218 may absorb heat from the cold water in chiller subplant 206 and reject the absorbed heat in cooling tower subplant 208 or transfer the absorbed heat to hot water loop 214. Hot TES subplant 210 and cold TES subplant 212 may store hot and cold thermal energy, respectively, for subsequent use.

Hot water loop 214 and cold water loop 216 may deliver the heated and/or chilled water to air handlers located on the rooftop of building 10 (e.g., AHU 106) or to individual floors or zones of building 10 (e.g., VAV units 116). The air handlers push air past heat exchangers (e.g., heating coils or cooling coils) through which the water flows to provide heating or cooling for the air. The heated or cooled air may be delivered to individual zones of building 10 to serve the thermal energy loads of building 10. The water then returns to subplants 202-212 to receive further heating or cooling.

Although subplants 202-212 are shown and described as heating and cooling water for circulation to a building, it is understood that any other type of working fluid (e.g., glycol, $CO_2$, etc.) may be used in place of or in addition to water to serve the thermal energy loads. In other embodiments, subplants 202-212 may provide heating and/or cooling directly to the building or campus without requiring an intermediate heat transfer fluid. These and other variations to waterside system 200 are within the teachings of the present invention.

Each of subplants 202-212 may include a variety of equipment configured to facilitate the functions of the subplant. For example, heater subplant 202 is shown to include a plurality of heating elements 220 (e.g., boilers, electric heaters, etc.) configured to add heat to the hot water in hot water loop 214. Heater subplant 202 is also shown to include several pumps 222 and 224 configured to circulate the hot water in hot water loop 214 and to control the flow rate of the hot water through individual heating elements 220. Chiller subplant 206 is shown to include a plurality of chillers 232 configured to remove heat from the cold water in cold water loop 216. Chiller subplant 206 is also shown to include several pumps 234 and 236 configured to circulate the cold water in cold water loop 216 and to control the flow rate of the cold water through individual chillers 232.

Heat recovery chiller subplant 204 is shown to include a plurality of heat recovery heat exchangers 226 (e.g., refrigeration circuits) configured to transfer heat from cold water loop 216 to hot water loop 214. Heat recovery chiller subplant 204 is also shown to include several pumps 228 and 230 configured to circulate the hot water and/or cold water through heat recovery heat exchangers 226 and to control the flow rate of the water through individual heat recovery heat exchangers 226. Cooling tower subplant 208 is shown to include a plurality of cooling towers 238 configured to remove heat from the condenser water in condenser water loop 218. Cooling tower subplant 208 is also shown to include several pumps 240 configured to circulate the condenser water in condenser water loop 218 and to control the flow rate of the condenser water through individual cooling towers 238.

Hot TES subplant 210 is shown to include a hot TES tank 242 configured to store the hot water for later use. Hot TES subplant 210 may also include one or more pumps or valves configured to control the flow rate of the hot water into or out of hot TES tank 242. Cold TES subplant 212 is shown to include cold TES tanks 244 configured to store the cold water for later use. Cold TES subplant 212 may also include one or more pumps or valves configured to control the flow rate of the cold water into or out of cold TES tanks 244.

In some embodiments, one or more of the pumps in waterside system 200 (e.g., pumps 222, 224, 228, 230, 234, 236, and/or 240) or pipelines in waterside system 200 include an isolation valve associated therewith. Isolation valves may be integrated with the pumps or positioned upstream or downstream of the pumps to control the fluid flows in waterside system 200. In various embodiments, waterside system 200 may include more, fewer, or different types of devices and/or subplants based on the particular configuration of waterside system 200 and the types of loads served by waterside system 200.

Figure 3:
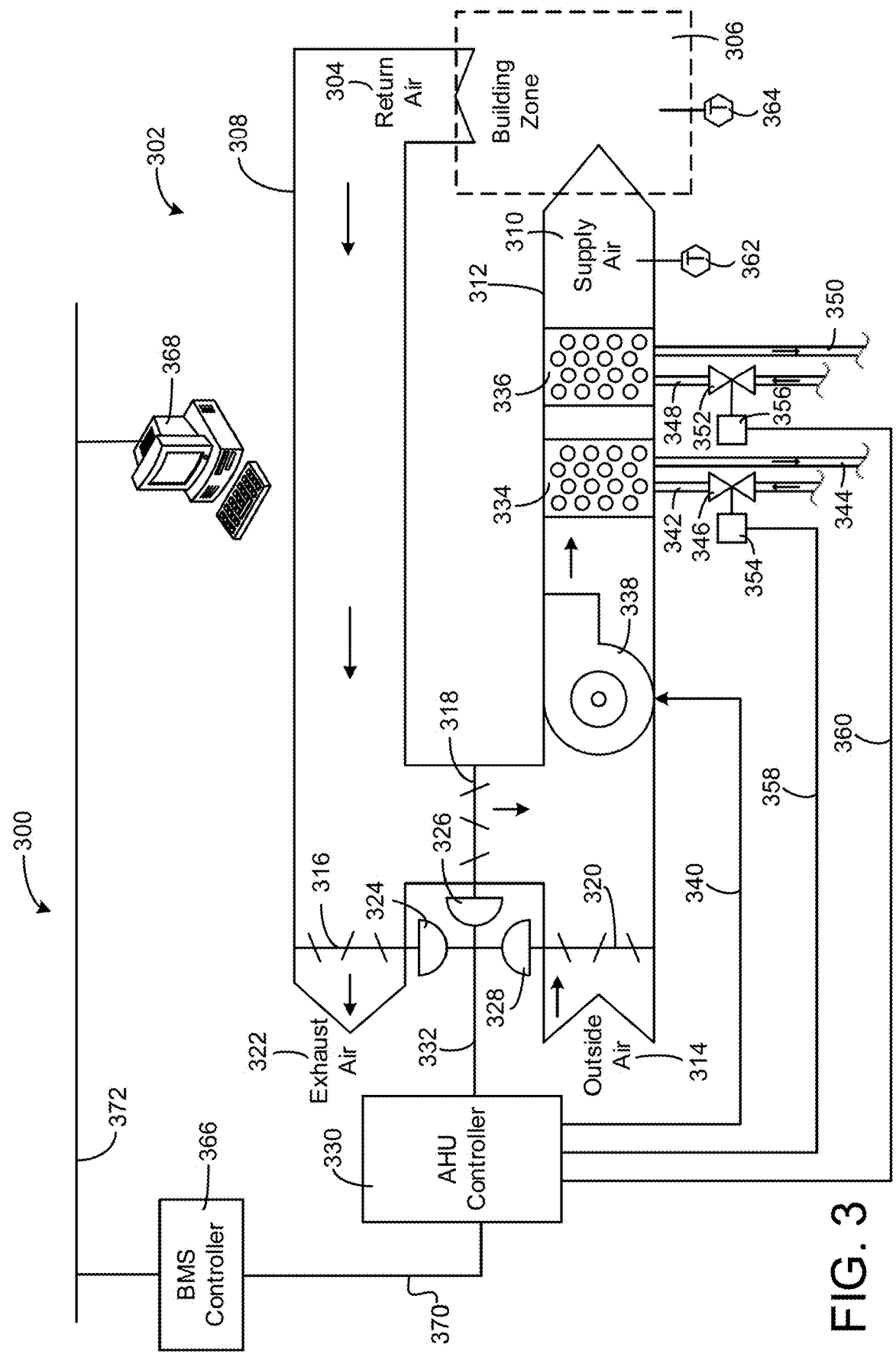
FIG. 3 is a block diagram of an airside system that may be used in conjunction with the building of FIG. 1, according to some embodiments.

Referring now to FIG. 3, a block diagram of an airside system 300 is shown, according to an exemplary embodiment. In various embodiments, airside system 300 may supplement or replace airside system 130 in HVAC system 100 or may be implemented separate from HVAC system 100. When implemented in HVAC system 100, airside system 300 may include a subset of the HVAC devices in HVAC system 100 (e.g., AHU 106, VAV units 116, ducts 112-114, fans, dampers, etc.) and may be located in or around building 10. Airside system 300 may operate to heat or cool an airflow provided to building 10 using a heated or chilled fluid provided by waterside system 200.

In FIG. 3, airside system 300 is shown to include an economizer-type air handling unit (AHU) 302. Economizer-type AHUs vary the amount of outside air and return air used by the air handling unit for heating or cooling. For example, AHU 302 may receive return air 304 from building zone 306 via return air duct 308 and may deliver supply air 310 to building zone 306 via supply air duct 312. In some embodiments, AHU 302 is a rooftop unit located on the roof of building 10 (e.g., AHU 106 as shown in FIG. 1) or otherwise positioned to receive both return air 304 and outside air 314. AHU 302 may be configured to operate exhaust air damper 316, mixing damper 318, and outside air damper 320 to control an amount of outside air 314 and return air 304 that combine to form supply air 310. Any return air 304 that does not pass through mixing damper 318 may be exhausted from AHU 302 through exhaust damper 316 as exhaust air 322.

Each of dampers 316-320 may be operated by an actuator. For example, exhaust air damper 316 may be operated by actuator 324, mixing damper 318 may be operated by actuator 326, and outside air damper 320 may be operated by actuator 328. Actuators 324-328 may communicate with an AHU controller 330 via a communications link 332. Actuators 324-328 may receive control signals from AHU controller 330 and may provide feedback signals to AHU controller 330. Feedback signals may include, for example, an indication of a current actuator or damper position, an amount of torque or force exerted by the actuator, diagnostic information (e.g., results of diagnostic tests performed by actuators 324-328), status information, commissioning information, configuration settings, calibration data, and/or other types of information or data that may be collected, stored, or used by actuators 324-328. AHU controller 330 may be an economizer controller configured to use one or more control algorithms (e.g., state-based algorithms, extremum seeking control (ESC) algorithms, proportional-integral (PI) control algorithms, proportional-integral-derivative (PID) control algorithms, model predictive control (MPC) algorithms, feedback control algorithms, etc.) to control actuators 324-328.

Still referring to FIG. 3, AHU 302 is shown to include a cooling coil 334, a heating coil 336, and a fan 338 positioned within supply air duct 312. Fan 338 may be configured to force supply air 310 through cooling coil 334 and/or heating coil 336 and provide supply air 310 to building zone 306. AHU controller 330 may communicate with fan 338 via communications link 340 to control a flow rate of supply air 310. In some embodiments, AHU controller 330 controls an amount of heating or cooling applied to supply air 310 by modulating a speed of fan 338.

Cooling coil 334 may receive a chilled fluid from waterside system 200 (e.g., from cold water loop 216) via piping 342 and may return the chilled fluid to waterside system 200 via piping 344. Valve 346 may be positioned along piping 342 or piping 344 to control a flow rate of the chilled fluid through cooling coil 334. In some embodiments, cooling coil 334 includes multiple stages of cooling coils that can be independently activated and deactivated (e.g., by AHU controller 330, by BMS controller 366, etc.) to modulate an amount of cooling applied to supply air 310.

Heating coil 336 may receive a heated fluid from waterside system 200 (e.g., from hot water loop 214) via piping 348 and may return the heated fluid to waterside system 200 via piping 350. Valve 352 may be positioned along piping 348 or piping 350 to control a flow rate of the heated fluid through heating coil 336. In some embodiments, heating coil 336 includes multiple stages of heating coils that can be independently activated and deactivated (e.g., by AHU controller 330, by BMS controller 366, etc.) to modulate an amount of heating applied to supply air 310.

Each of valves 346 and 352 may be controlled by an actuator. For example, valve 346 may be controlled by actuator 354 and valve 352 may be controlled by actuator 356. Actuators 354-356 may communicate with AHU controller 330 via communications links 358-360. Actuators 354-356 may receive control signals from AHU controller 330 and may provide feedback signals to controller 330. In some embodiments, AHU controller 330 receives a measurement of the supply air temperature from a temperature sensor 362 positioned in supply air duct 312 (e.g., downstream of cooling coil 334 and/or heating coil 336). AHU controller 330 may also receive a measurement of the temperature of building zone 306 from a temperature sensor 364 located in building zone 306.

In some embodiments, AHU controller 330 operates valves 346 and 352 via actuators 354-356 to modulate an amount of heating or cooling provided to supply air 310 (e.g., to achieve a setpoint temperature for supply air 310 or to maintain the temperature of supply air 310 within a setpoint temperature range). The positions of valves 346 and 352 affect the amount of heating or cooling provided to supply air 310 by cooling coil 334 or heating coil 336 and may correlate with the amount of energy consumed to achieve a desired supply air temperature. AHU 330 may control the temperature of supply air 310 and/or building zone 306 by activating or deactivating coils 334-336, adjusting a speed of fan 338, or a combination of both.

Still referring to FIG. 3, airside system 300 is shown to include a building management system (BMS) controller 366 and a client device 368. BMS controller 366 may include one or more computer systems (e.g., servers, supervisory controllers, subsystem controllers, etc.) that serve as system level controllers, application or data servers, head nodes, or master controllers for airside system 300, waterside system 200, HVAC system 100, and/or other controllable systems that serve building 10. BMS controller 366 may communicate with multiple downstream building systems or subsystems (e.g., HVAC system 100, a security system, a lighting system, waterside system 200, etc.) via a communications link 370 according to like or disparate protocols (e.g., LON, BACnet, etc.). In various embodiments, AHU controller 330 and BMS controller 366 may be separate (as shown in FIG. 3) or integrated. In an integrated implementation, AHU controller 330 may be a software module configured for execution by a processor of BMS controller 366.

In some embodiments, AHU controller 330 receives information from BMS controller 366 (e.g., commands, setpoints, operating boundaries, etc.) and provides information to BMS controller 366 (e.g., temperature measurements, valve or actuator positions, operating statuses, diagnostics, etc.). For example, AHU controller 330 may provide BMS controller 366 with temperature measurements from temperature sensors 362-364, equipment on/off states, equipment operating capacities, and/or any other information that can be used by BMS controller 366 to monitor or control a variable state or condition within building zone 306.

Client device 368 may include one or more human-machine interfaces or client interfaces (e.g., graphical user interfaces, reporting interfaces, text-based computer interfaces, client-facing web services, web servers that provide pages to web clients, etc.) for controlling, viewing, or otherwise interacting with HVAC system 100, its subsystems, and/or devices. Client device 368 may be a computer workstation, a client terminal, a remote or local interface, or any other type of user interface device. Client device 368 may be a stationary terminal or a mobile device. For example, client device 368 may be a desktop computer, a computer server with a user interface, a laptop computer, a tablet, a smartphone, a PDA, or any other type of mobile or non-mobile device. Client device 368 may communicate with BMS controller 366 and/or AHU controller 330 via communications link 372.

Figure 4:
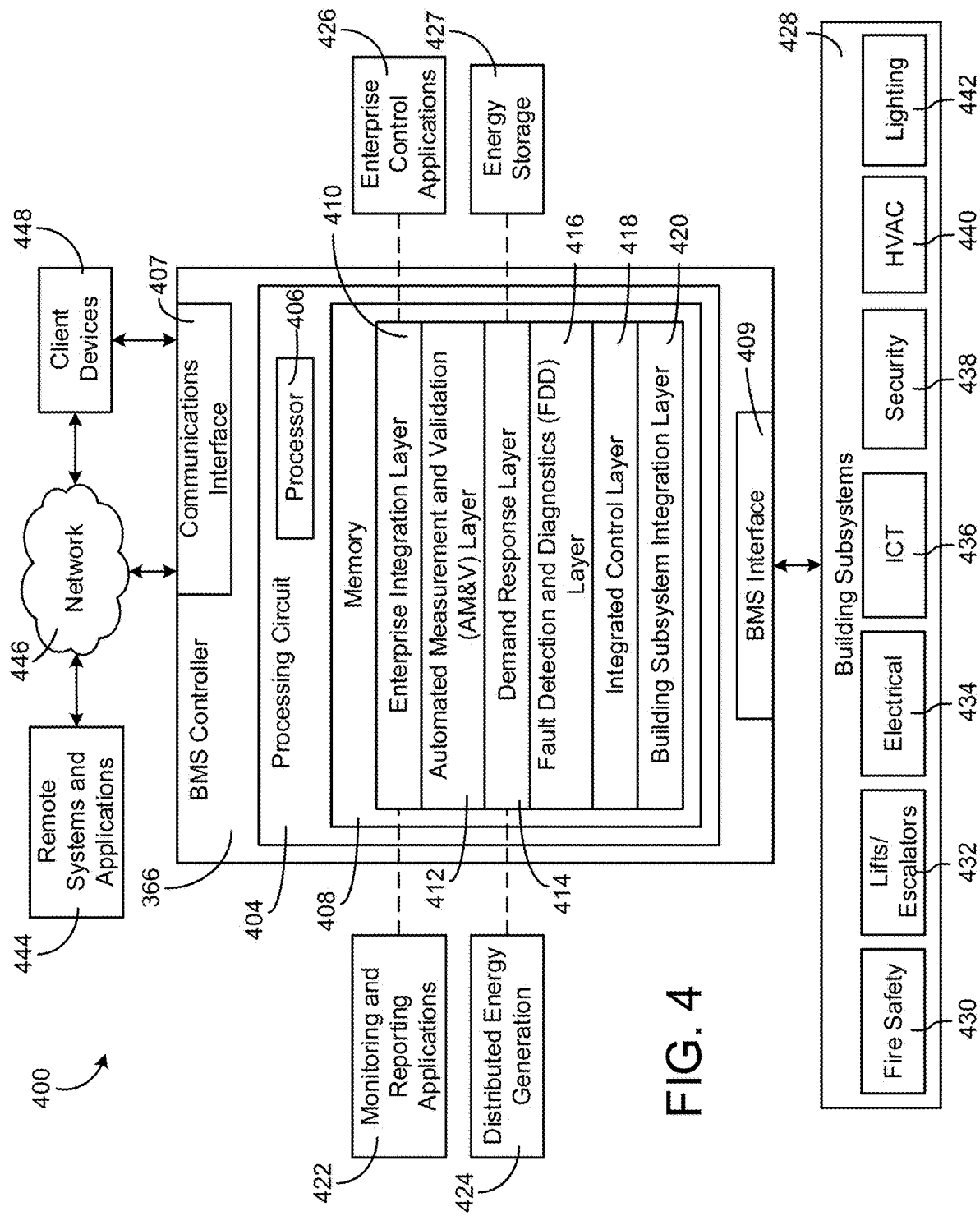
FIG. 4 is a block diagram of a building management system (BMS) that may be used to monitor and/or control the building of FIG. 1, according to some embodiments.

Referring now to FIG. 4, a block diagram of a building management system (BMS) 400 is shown, according to an exemplary embodiment. BMS 400 may be implemented in building 10 to automatically monitor and control various building functions. BMS 400 is shown to include BMS controller 366 and a plurality of building subsystems 428. Building subsystems 428 are shown to include a building electrical subsystem 434, an information communication technology (ICT) subsystem 436, a security subsystem 438, a HVAC subsystem 440, a lighting subsystem 442, a lift/escalators subsystem 432, and a fire safety subsystem 430. In various embodiments, building subsystems 428 can include fewer, additional, or alternative subsystems. For example, building subsystems 428 may also or alternatively include a refrigeration subsystem, an advertising or signage subsystem, a cooking subsystem, a vending subsystem, a printer or copy service subsystem, or any other type of building subsystem that uses controllable equipment and/or sensors to monitor or control building 10. In some embodiments, building subsystems 428 include waterside system 200 and/or airside system 300, as described with reference to FIGS. 2-3.

Each of building subsystems 428 may include any number of devices, controllers, and connections for completing its individual functions and control activities. HVAC subsystem 440 may include many of the same components as HVAC system 100, as described with reference to FIGS. 1-3. For example, HVAC subsystem 440 may include a chiller, a boiler, any number of air handling units, economizers, field controllers, supervisory controllers, actuators, temperature sensors, and other devices for controlling the temperature, humidity, airflow, or other variable conditions within building 10. Lighting subsystem 442 may include any number of light fixtures, ballasts, lighting sensors, dimmers, or other devices configured to controllably adjust the amount of light provided to a building space. Security subsystem 438 may include occupancy sensors, video surveillance cameras, digital video recorders, video processing servers, intrusion detection devices, access control devices and servers, or other security-related devices.

Still referring to FIG. 4, BMS controller 366 is shown to include a communications interface 407 and a BMS interface 409. Interface 407 may facilitate communications between BMS controller 366 and external applications (e.g., monitoring and reporting applications 422, enterprise control applications 426, remote systems and applications 444, applications residing on client devices 448, etc.) for allowing user control, monitoring, and adjustment to BMS controller 366 and/or subsystems 428. Interface 407 may also facilitate communications between BMS controller 366 and client devices 448. BMS interface 409 may facilitate communications between BMS controller 366 and building subsystems 428 (e.g., HVAC, lighting security, lifts, power distribution, business, etc.).

Interfaces 407, 409 can be or include wired or wireless communications interfaces (e.g., jacks, antennas, transmitters, receivers, transceivers, wire terminals, etc.) for conducting data communications with building subsystems 428 or other external systems or devices. In various embodiments, communications via interfaces 407, 409 may be direct (e.g., local wired or wireless communications) or via a communications network 446 (e.g., a WAN, the Internet, a cellular network, etc.). For example, interfaces 407, 409 can include an Ethernet card and port for sending and receiving data via an Ethernet-based communications link or network. In another example, interfaces 407, 409 can include a WiFi transceiver for communicating via a wireless communications network. In another example, one or both of interfaces 407, 409 may include cellular or mobile phone communications transceivers. In one embodiment, communications interface 407 is a power line communications interface and BMS interface 409 is an Ethernet interface. In other embodiments, both communications interface 407 and BMS interface 409 are Ethernet interfaces or are the same Ethernet interface.

Still referring to FIG. 4, BMS controller 366 is shown to include a processing circuit 404 including a processor 406 and memory 408. Processing circuit 404 may be communicably connected to BMS interface 409 and/or communications interface 407 such that processing circuit 404 and the various components thereof can send and receive data via interfaces 407, 409. Processor 406 can be implemented as a general purpose processor, an application specific integrated circuit (ASIC), one or more field programmable gate arrays (FPGAs), a group of processing components, or other suitable electronic processing components.

Memory 408 (e.g., memory, memory unit, storage device, etc.) may include one or more devices (e.g., RAM, ROM, flash memory, hard disk storage, etc.) for storing data and/or computer code for completing or facilitating the various processes, layers and modules described in the present application. Memory 408 may be or include volatile memory or non-volatile memory. Memory 408 may include database components, object code components, script components, or any other type of information structure for supporting the various activities and information structures described in the present application. According to an exemplary embodiment, memory 408 is communicably connected to processor 406 via processing circuit 404 and includes computer code for executing (e.g., by processing circuit 404 and/or processor 406) one or more processes described herein.

In some embodiments, BMS controller 366 is implemented within a single computer (e.g., one server, one housing, etc.). In various other embodiments BMS controller 366 may be distributed across multiple servers or computers (e.g., that can exist in distributed locations). Further, while FIG. 4 shows applications 422 and 426 as existing outside of BMS controller 366, in some embodiments, applications 422 and 426 may be hosted within BMS controller 366 (e.g., within memory 408).

Still referring to FIG. 4, memory 408 is shown to include an enterprise integration layer 410, an automated measurement and validation (AM&V) layer 412, a demand response (DR) layer 414, a fault detection and diagnostics (FDD) layer 416, an integrated control layer 418, and a building subsystem integration layer 420. Layers 410-420 may be configured to receive inputs from building subsystems 428 and other data sources, determine optimal control actions for building subsystems 428 based on the inputs, generate control signals based on the optimal control actions, and provide the generated control signals to building subsystems 428. The following paragraphs describe some of the general functions performed by each of layers 410-420 in BMS 400.

Enterprise integration layer 410 may be configured to serve clients or local applications with information and services to support a variety of enterprise-level applications. For example, enterprise control applications 426 may be configured to provide subsystem-spanning control to a graphical user interface (GUI) or to any number of enterprise-level business applications (e.g., accounting systems, user identification systems, etc.). Enterprise control applications 426 may also or alternatively be configured to provide configuration GUIs for configuring BMS controller 366. In yet other embodiments, enterprise control applications 426 can work with layers 410-420 to optimize building performance (e.g., efficiency, energy use, comfort, or safety) based on inputs received at interface 407 and/or BMS interface 409.

Building subsystem integration layer 420 may be configured to manage communications between BMS controller 366 and building subsystems 428. For example, building subsystem integration layer 420 may receive sensor data and input signals from building subsystems 428 and provide output data and control signals to building subsystems 428. Building subsystem integration layer 420 may also be configured to manage communications between building subsystems 428. Building subsystem integration layer 420 translate communications (e.g., sensor data, input signals, output signals, etc.) across a plurality of multi-vendor/multi-protocol systems.

Demand response layer 414 may be configured to optimize resource usage (e.g., electricity use, natural gas use, water use, etc.) and/or the monetary cost of such resource usage in response to satisfy the demand of building 10. The optimization may be based on time-of-use prices, curtailment signals, energy availability, or other data received from utility providers, distributed energy generation systems 424, from energy storage 427 (e.g., hot TES 242, cold TES 244, etc.), or from other sources. Demand response layer 414 may receive inputs from other layers of BMS controller 366 (e.g., building subsystem integration layer 420, integrated control layer 418, etc.). The inputs received from other layers may include environmental or sensor inputs such as temperature, carbon dioxide levels, relative humidity levels, air quality sensor outputs, occupancy sensor outputs, room schedules, and the like. The inputs may also include inputs such as electrical use (e.g., expressed in kWh), thermal load measurements, pricing information, projected pricing, smoothed pricing, curtailment signals from utilities, and the like.

According to an exemplary embodiment, demand response layer 414 includes control logic for responding to the data and signals it receives. These responses can include communicating with the control algorithms in integrated control layer 418, changing control strategies, changing setpoints, or activating/deactivating building equipment or subsystems in a controlled manner. Demand response layer 414 may also include control logic configured to determine when to utilize stored energy. For example, demand response layer 414 may determine to begin using energy from energy storage 427 just prior to the beginning of a peak use hour.

In some embodiments, demand response layer 414 includes a control module configured to actively initiate control actions (e.g., automatically changing setpoints) which minimize energy costs based on one or more inputs representative of or based on demand (e.g., price, a curtailment signal, a demand level, etc.). In some embodiments, demand response layer 414 uses equipment models to determine an optimal set of control actions. The equipment models may include, for example, thermodynamic models describing the inputs, outputs, and/or functions performed by various sets of building equipment. Equipment models may represent collections of building equipment (e.g., subplants, chiller arrays, etc.) or individual devices (e.g., individual chillers, heaters, pumps, etc.).

Demand response layer 414 may further include or draw upon one or more demand response policy definitions (e.g., databases, XML files, etc.). The policy definitions may be edited or adjusted by a user (e.g., via a graphical user interface) so that the control actions initiated in response to demand inputs may be tailored for the user's application, desired comfort level, particular building equipment, or based on other concerns. For example, the demand response policy definitions can specify which equipment may be turned on or off in response to particular demand inputs, how long a system or piece of equipment should be turned off, what setpoints can be changed, what the allowable set point adjustment range is, how long to hold a high demand setpoint before returning to a normally scheduled setpoint, how close to approach capacity limits, which equipment modes to utilize, the energy transfer rates (e.g., the maximum rate, an alarm rate, other rate boundary information, etc.) into and out of energy storage devices (e.g., thermal storage tanks, battery banks, etc.), and when to dispatch on-site generation of energy (e.g., via fuel cells, a motor generator set, etc.).

Integrated control layer 418 may be configured to use the data input or output of building subsystem integration layer 420 and/or demand response layer 414 to make control decisions. Due to the subsystem integration provided by building subsystem integration layer 420, integrated control layer 418 can integrate control activities of the subsystems 428 such that the subsystems 428 behave as a single integrated supersystem. In an exemplary embodiment, integrated control layer 418 includes control logic that uses inputs and outputs from a plurality of building subsystems to provide greater comfort and energy savings relative to the comfort and energy savings that separate subsystems could provide alone. For example, integrated control layer 418 may be configured to use an input from a first subsystem to make an energy-saving control decision for a second subsystem. Results of these decisions can be communicated back to building subsystem integration layer 420.

Integrated control layer 418 is shown to be logically below demand response layer 414. Integrated control layer 418 may be configured to enhance the effectiveness of demand response layer 414 by enabling building subsystems 428 and their respective control loops to be controlled in coordination with demand response layer 414. This configuration may advantageously reduce disruptive demand response behavior relative to conventional systems. For example, integrated control layer 418 may be configured to assure that a demand response-driven upward adjustment to the setpoint for chilled water temperature (or another component that directly or indirectly affects temperature) does not result in an increase in fan energy (or other energy used to cool a space) that would result in greater total building energy use than was saved at the chiller.

Integrated control layer 418 may be configured to provide feedback to demand response layer 414 so that demand response layer 414 checks that constraints (e.g., temperature, lighting levels, etc.) are properly maintained even while demanded load shedding is in progress. The constraints may also include setpoint or sensed boundaries relating to safety, equipment operating limits and performance, comfort, fire codes, electrical codes, energy codes, and the like. Integrated control layer 418 is also logically below fault detection and diagnostics layer 416 and automated measurement and validation layer 412. Integrated control layer 418 may be configured to provide calculated inputs (e.g., aggregations) to these higher levels based on outputs from more than one building subsystem.

Automated measurement and validation (AM&V) layer 412 may be configured to verify that control strategies commanded by integrated control layer 418 or demand response layer 414 are working properly (e.g., using data aggregated by AM&V layer 412, integrated control layer 418, building subsystem integration layer 420, FDD layer 416, or otherwise). The calculations made by AM&V layer 412 may be based on building system energy models and/or equipment models for individual BMS devices or subsystems. For example, AM&V layer 412 may compare a model-predicted output with an actual output from building subsystems 428 to determine an accuracy of the model.

Fault detection and diagnostics (FDD) layer 416 may be configured to provide on-going fault detection for building subsystems 428, building subsystem devices (i.e., building equipment), and control algorithms used by demand response layer 414 and integrated control layer 418. FDD layer 416 may receive data inputs from integrated control layer 418, directly from one or more building subsystems or devices, or from another data source. FDD layer 416 may automatically diagnose and respond to detected faults. The responses to detected or diagnosed faults may include providing an alert message to a user, a maintenance scheduling system, or a control algorithm configured to attempt to repair the fault or to work-around the fault.

FDD layer 416 may be configured to output a specific identification of the faulty component or cause of the fault (e.g., loose damper linkage) using detailed subsystem inputs available at building subsystem integration layer 420. In other exemplary embodiments, FDD layer 416 is configured to provide "fault" events to integrated control layer 418 which executes control strategies and policies in response to the received fault events. According to an exemplary embodiment, FDD layer 416 (or a policy executed by an integrated control engine or business rules engine) may shut-down systems or direct control activities around faulty devices or systems to reduce energy waste, extend equipment life, or assure proper control response.

FDD layer 416 may be configured to store or access a variety of different system data stores (or data points for live data). FDD layer 416 may use some content of the data stores to identify faults at the equipment level (e.g., specific chiller, specific AHU, specific terminal unit, etc.) and other content to identify faults at component or subsystem levels. For example, building subsystems 428 may generate temporal (i.e., time-series) data indicating the performance of BMS 400 and the various components thereof. The data generated by building subsystems 428 may include measured or calculated values that exhibit statistical characteristics and provide information about how the corresponding system or process (e.g., a temperature control process, a flow control process, etc.) is performing in terms of error from its setpoint. These processes can be examined by FDD layer 416 to expose when the system begins to degrade in performance and alert a user to repair the fault before it becomes more severe.

Heat Maps

Figure 5:
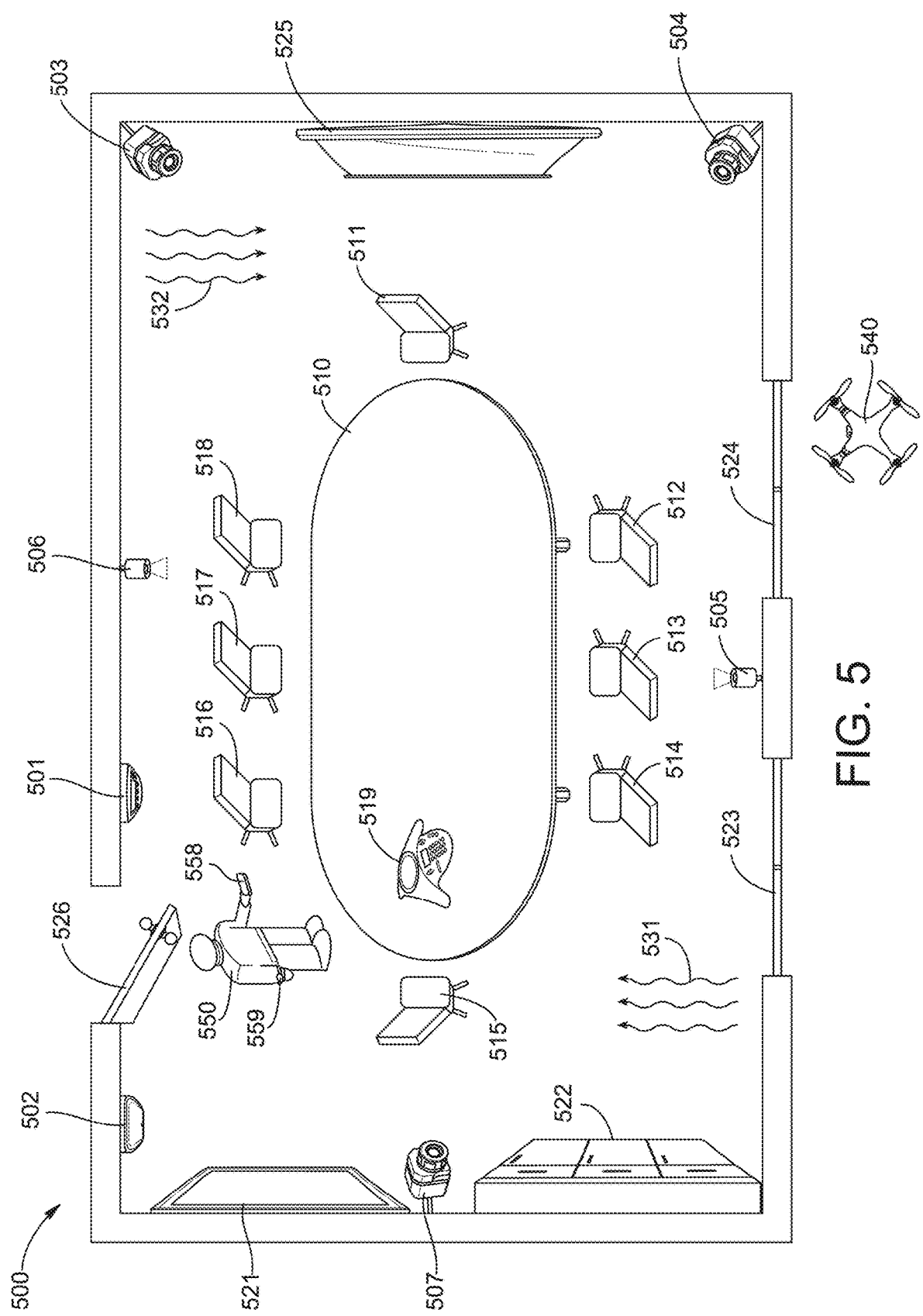
FIG. 5 is an illustration of a conference room within the building of FIG. 1, according to some embodiments.

Turning now to FIG. 5, an example room such as a conference room 500 within building 10 is shown, according to some embodiments. Room 500 includes a sensor package 502 and a thermostat 501 both mounted on a wall near a door 526 in some embodiments. Room 500 can be any type of room including a theater, an auditorium, an office, sleeping quarters, cafeteria, a class room, a hospital room, a hotel room, etc. Sensor package 502 represents a typical device for providing input (e.g., temperature, humidity, air quality) about room 500 to BMS 400 and/or to thermostat 501. Thermostat 501 may have temperature sensing capabilities built-in, however, if thermostat 501 is determined to be in a poor location for temperature sensing, then sensor package 502 may be installed in room 500 to provide additional temperature input to thermostat 501. Sensor package 502 may also provide inputs related to humidity, air quality (e.g., volatile organic compounds), air flow, etc. to thermostat 501 and/or BMS 400. However, these inputs provided by sensor package 502 are still relatively limited to the specific area of the room in which sensor package 502 is located. Moreover, sensor package 502 is typically mounted high on a wall and designed to blend in with the surroundings such that it is hard to notice. Accordingly, systems that rely on inputs from thermostat 501 and/or sensor package 502 may not be able to detect how the environment varies within a building space such as conference room 500.

As shown in FIG. 5, conference room 500 includes various devices in addition to thermostat 501 and sensor package 502 that can provide more granular and comprehensive input data to a building control system such as BMS 400 according to some embodiments. Conference room 500 includes a plurality of thermographic cameras 503, 504, and 507 as well as infrared sensors 505 and 506 in some embodiments. FIG. 5 also shows a drone 540 outside of conference room 500 that can obtain thermal video and/or images as well as other data associated with room 500 through windows 523 and 524. These devices can measure an amount of thermal energy present throughout room 500. For example, a thermal image produced by camera 503 can indicate an amount of British thermal units (BTUs) present at over 1,000 locations within room 500. In some embodiments, the drone 540 is provided within the room 500 and travels throughout the interior of the building.

It should be noted that a variety of thermal imaging devices can be used to generate a heat map of a building space. In general, a thermal imaging device can detect infrared energy emitted, reflected, or transmitted by all materials. Thermal imaging devices can factor in emissivity of various materials and can have an emissivity table stored in memory and accessible by users. Thermal imaging devices can detect temperatures of various objects as well as atmospheric temperature. Thermal imaging devices can also detect other information such as distance to various objects and relative humidity levels. In some embodiments, multiple thermal imaging devices (e.g., cameras 503, 506, 507) are used in a building and data from the devices is stitched together to generate a thermal image of a larger building space. Moreover, these devices can be integrated with other types of cameras such as security cameras throughout a building. Thermal imaging devices can be deployed in various configurations throughout a building to perform one or more of the functions described herein.

Conference room 500 is also shown to include a table 510 with chairs 511, 512, 513, 514, 515, 516, 517, and 518. Additionally, conference room 500 is shown to include a phone 519 as well as a whiteboard 521, cabinets 522, and a projector screen 525. FIG. 5 also shows the location of two air vents with conference room 500: vent 531 and vent 532. Vent 531 and vent 532 may be connected to supply ducts 112 as described above. In some embodiments, the heat maps produced by one or more of thermographic cameras 503, 504, 507, infrared sensors 505 and 506, and drone 540 can be used to alert a user 550 of where to sit with conference room 500. For example, based on preferences of user 550, BMS 400 may send an alert to user 550 indicating that user 550 should sit in chair 512 for a meeting occurring in conference room 500. More detail regarding this functionality is described below. The preferences of user 550 can be related to the preferred temperature for user 550, whether user 550 typically feels hot or cold in room 500 or other parts of building 10, and whether user 550 has just come from outside where the temperature was hotter or colder than room temperature. Depending on those preferences, user 550 can be directed to hotter or warmer parts of the room (e.g., user 550 who generally feels cold in room 500 is directed to warmer positions in the room or vice versa, user 550 who has just arrived from outside where outside temperatures are colder than room temperatures is directed to a warmer position or vice versa, or user 550 is directed to a position most matching his or her preferred temperature). The preferred temperature can be calculated in light of factors including drafts, humidity, etc. For example, the preferred temperature may be lower when the humidity is above a user preference or is otherwise high.

Figure 6:
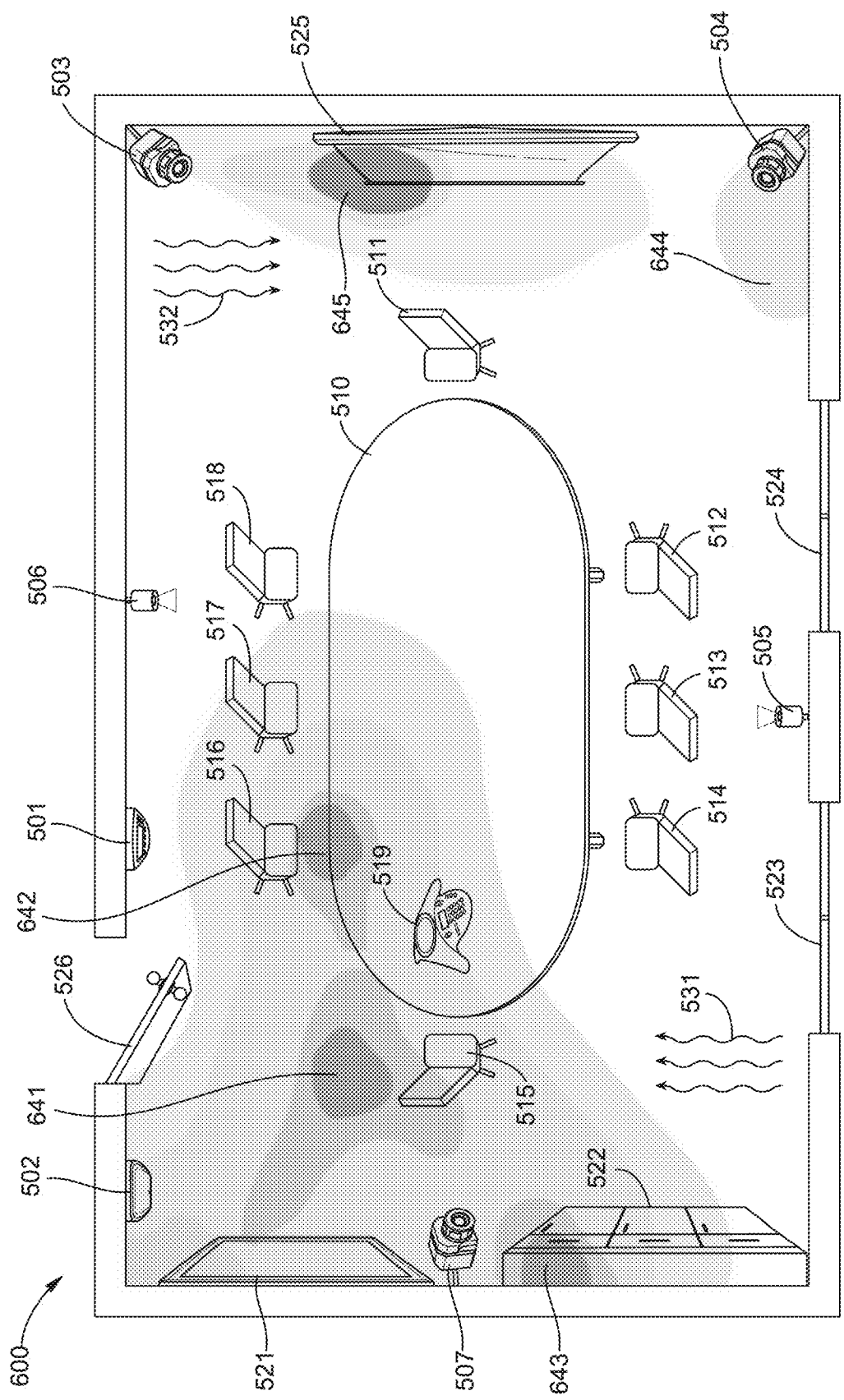
FIG. 6 is an illustration of a heat map that can be generated for the conference room of FIG. 5, according to some embodiments.

Turning to FIG. 6, an example heat map 600 of conference room 500 is shown, according to some embodiments. Heat map 600 can both provide more granular inputs to a building control system such as BMS 400 as well as provide useful information to building occupants. While heat map 600 is shown in greyscale, it will be appreciated that heat map 600 can include coloring to indicate which areas of conference room 500 are hotter than others. For example, when heat map 600 is viewed by user 550, area 641 may be shown in red to indicate that area 641 is hotter than other areas of room 500 such as area 644 (e.g., may be shown in yellow or orange). Heat map 600 can provide a holistic view of how temperature within room 500 varies. As shown in FIG. 6, heat map 600 indicates that room 500 has four "hot spots" as indicated by areas 641, 642, 643, and 645. For example, these hot spots may indicate temperature readings of 75 degrees Fahrenheit or higher. Heat map 600 also indicates some warmer areas of room 500 such as area 644 (e.g., 70-75 degrees Fahrenheit) and some cooler areas of room 500 (e.g., 65-70 degrees Fahrenheit). Heat map 600 indicates that the temperature in room 500 near windows 523 and 524 is colder than the temperature in room 500 near projector screen 525, for example.

As shown in FIG. 6, sensor package 502 is located in an area of conference room 500 that is relatively warm compared to other parts of conference room 500. As mentioned above, this may lead to undesirable climate control of conference room 500. For example, a controller (e.g., BMS controller 366) may determine that the temperature of room 500 is 72 degrees Fahrenheit using a temperature reading from sensor package 502. The controller may then determine that 72 degrees Fahrenheit is higher than a temperature setpoint for room 500 and may coordinate the release of cool air into room 500 through vents 531 and 532. However, the average temperature of room 500 may not be 72 degrees as indicated by sensor package 502 and thus room 500 may be unnecessarily cooled. This and similar phenomenon can lead to both inaccurate (e.g., wrong temperature) and inefficient (e.g., wasted energy) climate control.

Figure 7:
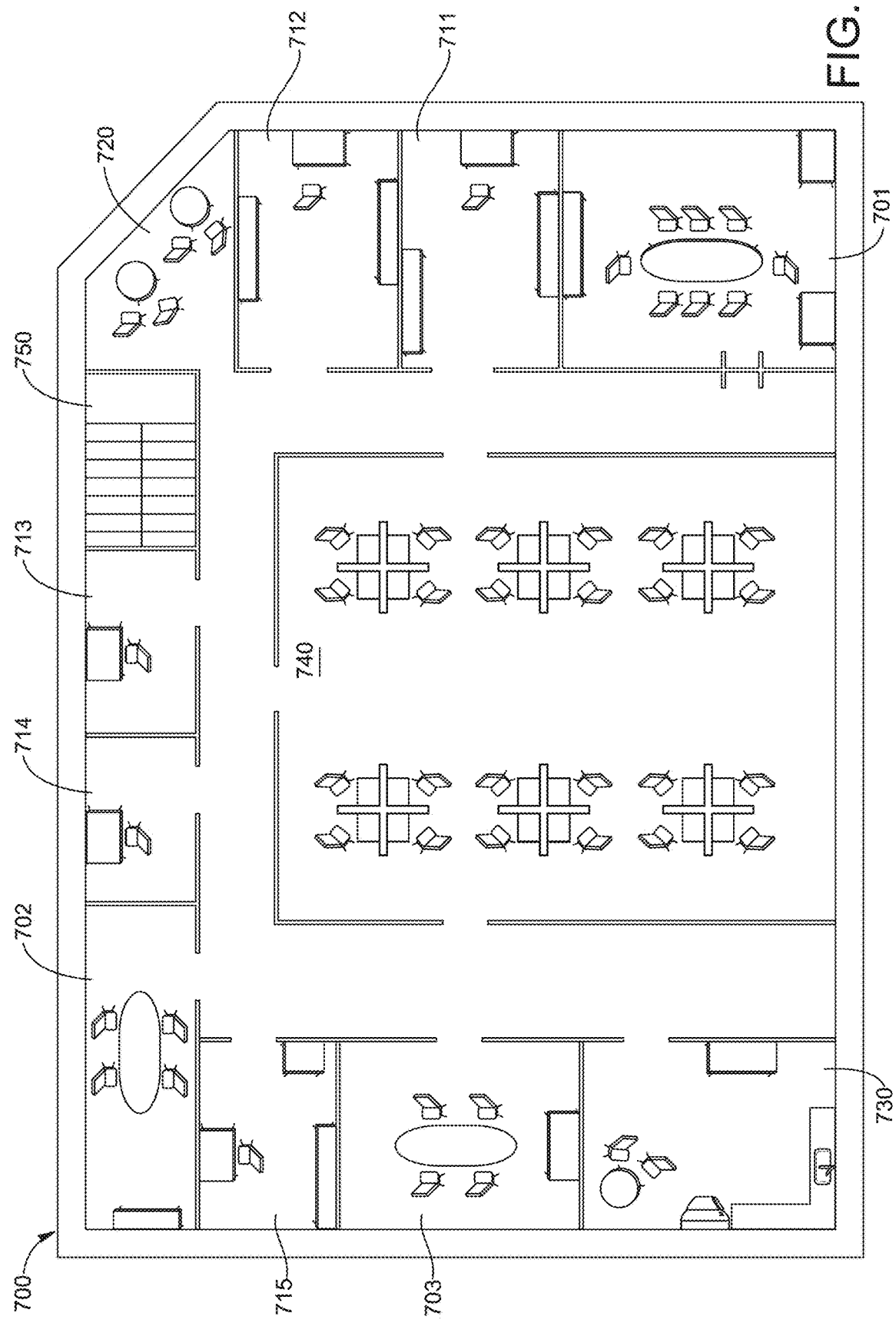
FIG. 7 is an illustration of a floor within the building of FIG. 1, according to some embodiments.

Turning to FIG. 7, an example floor 700 within building 10 is shown, according to some embodiments. Heat maps such as heat map 600 can be generated for any type of building space including floors, rooms, HVAC zones, etc. Floor 700 is shown to include a plurality of conference rooms 701, 702, and 703 and a plurality of individual offices 711, 712, 713, 714, and 715. Floor 700 is also shown to include a lounge area 720, a kitchen area 730, a shared workspace 740 (e.g., cubicles), and stairs 750. Thermal imaging devices and other types of sensors can be strategically placed throughout floor 700 such that a heat map can be generated for the entire floor. For example, thermographic cameras similar to cameras 503, 504, and 507 described above can be placed in hallways and rooms of floor 700.

Figure 8:
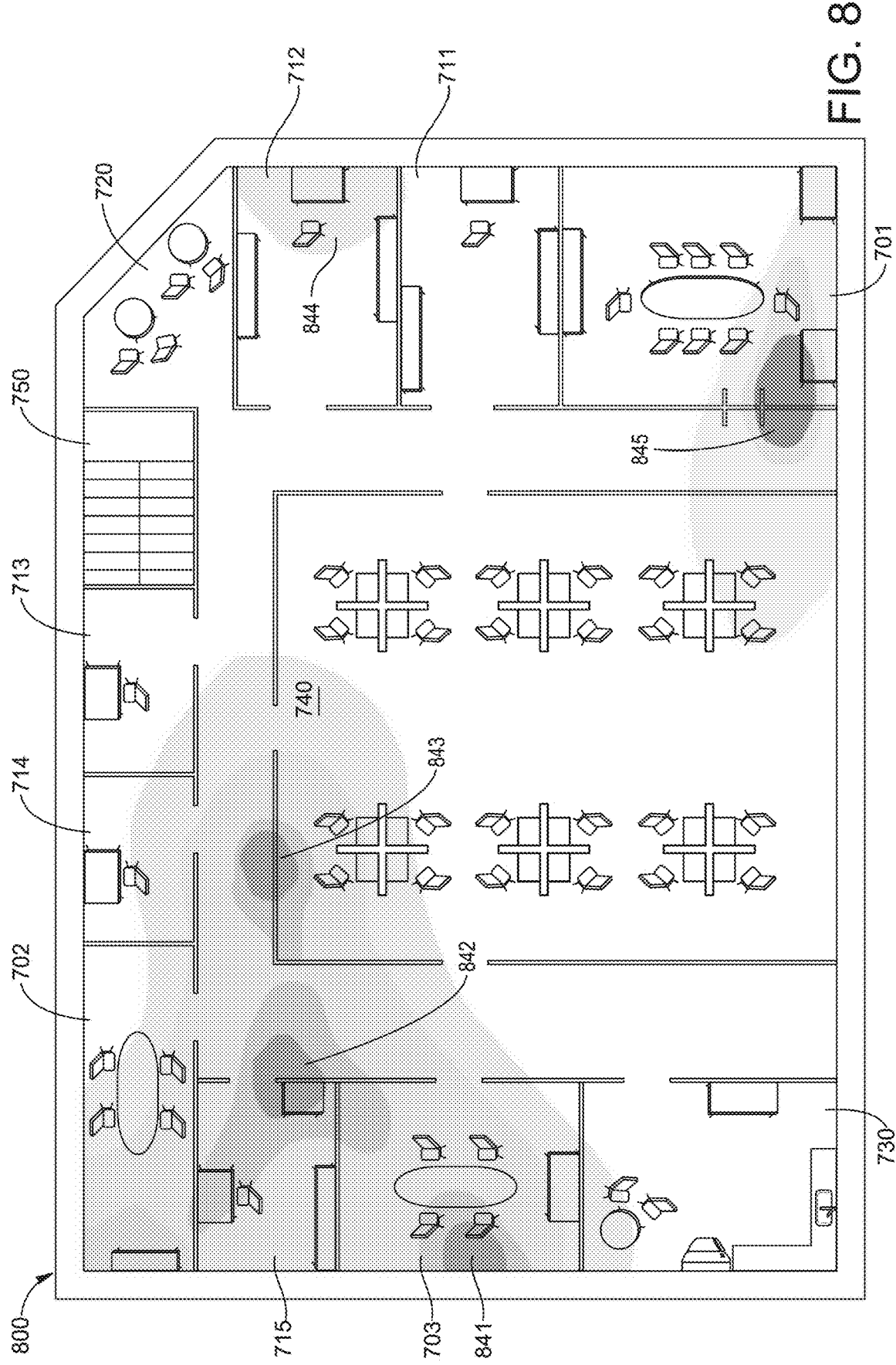
FIG. 8 is an illustration of a heat map that can be generated for the floor of FIG. 7, according to some embodiments.

Turning to FIG. 8, an example heat map 800 of floor 700 is shown, according to some embodiments. Similar to heat map 600, heat map 800 can both provide more granular inputs to a building control system such as BMS 400 as well as provide useful information to building occupants. As shown, heat map 800 indicates four "hot spots" 841, 842, 843, and 845. Heat map 800 also indicates a warmer area 844 present in office 712. When used as an input to a building control system, heat map 800 can indicate that areas of floor 700 such as office 715 and conference room 703 should be cooled while areas of floor 700 such as kitchen 730 and office 711 should not be cooled.

Figure 9:
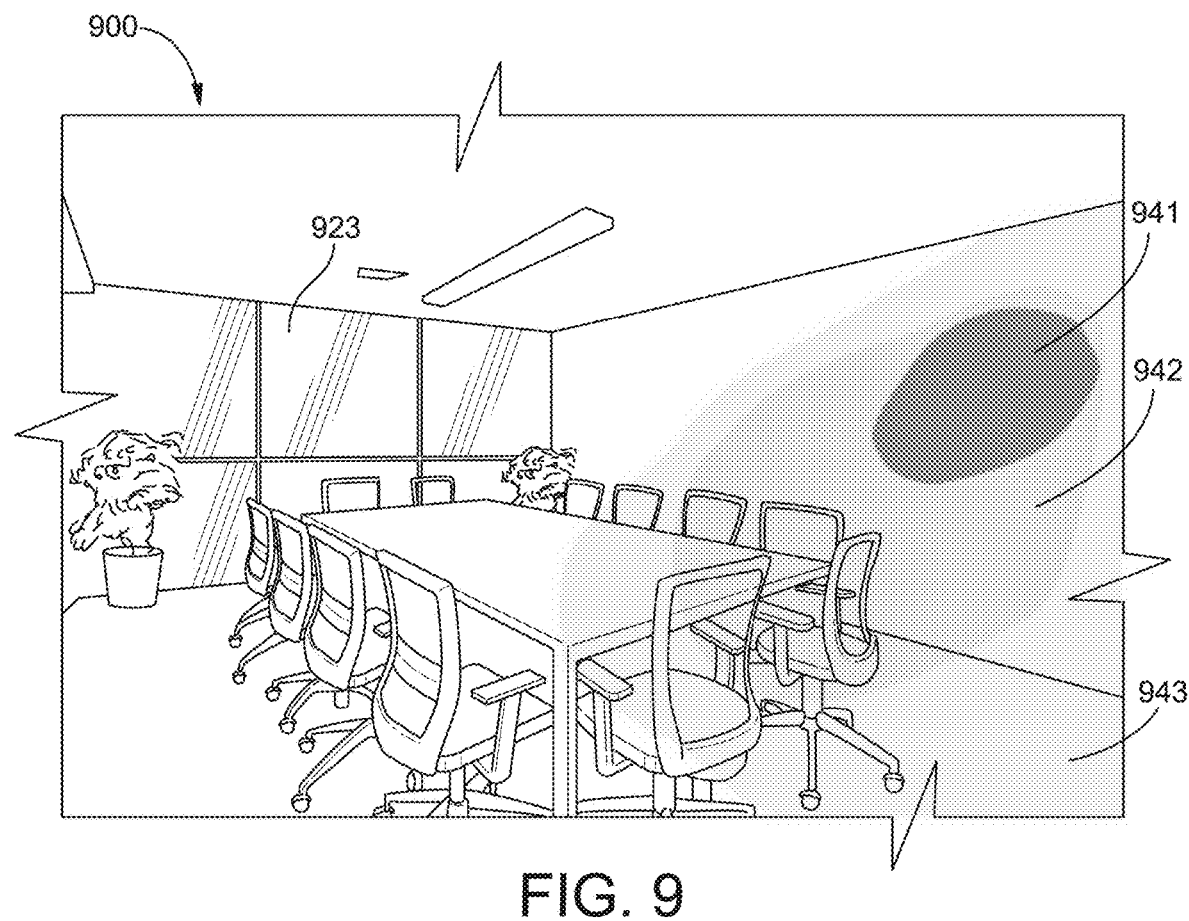
FIG. 9 is an illustration of a three-dimensional heat map that can be generated for a room within the building of FIG. 1, according to some embodiments.

Turning to FIG. 9, an example three-dimensional heat map 900 is shown, according to some embodiments. As shown, heat map 900 provides a three-dimensional indication of heat distribution in a room. Heat map 900 indicates that a hot area 941 exists toward the ceiling and away from windows 923. Heat map 900 also indicates a warm area 942 and a slightly warm area 943 surrounding hot area 941. Three-dimensional heat maps such as heat map 900 can provide even more granular input to a building control system than two-dimensional heat maps. For example, heat map 900 can give a better true measure for heat in a room from head to foot while discrete sensors (e.g., sensor package 502) only provide input at one level. Further, three-dimensional heat maps such as heat map 900 can provide input necessary to control temperature at different levels of a room or other building space such as sitting level, standing level, or yoga level.

While many examples described herein refer to temperature-based heat maps, it should be noted that maps can be generated to indicate a variety of variables in a building space. For example, similar approaches can be used to generate a map showing air quality, air flow, lighting, coverage of security cameras, etc. It will be appreciated that the present disclosure is not limited to temperature-based maps. Heat maps and other similar visualizations can be generated for infectious disease prevention and disinfection system control. These visualizations can be generated based on occupancy data, health risk data (e.g. from a health authority source), and other types of data, and can provide a user with an efficient and straightforward view of health risks within a building. In some implementations, data from a building information model (BIM) can be used with respect to maps and other visualizations.

For example, health risk visualizations can be presented on a user interface and can recommend locations within a building to host a desired event, paths to get to desired locations, and other types of suggestions and recommendations to minimize health risk while occupying and using a building. The recommended paths, for example, can be overlaid on a floorplan to assist users in understanding how to navigate through the building in a safe manner. Maps for assessing health risk within a building can also be used for control purposes, such as identifying locations where an air handling action (e.g. using more outdoor air) or a disinfection action (e.g. using disinfectant light) should be performed to reduce health risks for building occupants. Further, temperature and/or occupancy based heat maps can be used for contact tracing and evaluation of social distancing performance using location-based services within a building. For example, scenario analysis can be performed to identify building occupants that have had close contact and/or prolonged contact with an individual determined to be infected with an infectious disease, as well as evaluate occupants with the greatest potential to infect others based on historical patterns regarding use of different spaces within the building. The system can further use identifiers (e.g. persistent identifiers) to track certain individuals based on sensitivity levels to infectious disease (e.g. high risk, low risk, etc.) and building controls can be adjusted in different spaces based on whether individuals with high sensitivity to infectious diseases are occupying the space or are planned to occupy the space. The heat maps can be used to determine intensity of use in a given space (currently and historically), identify spaces in the building that need to be cleaned, and other uses. Individual heat maps can also be generated to allow an individual to better understand time spent in certain building spaces and how the individual could modify behavior to reduce health risks. Health risk visualizations can also be used to identify areas within a building that need cleaning supplies and/or need cleaning service performed after a period of high intensity use.

Figure 10:
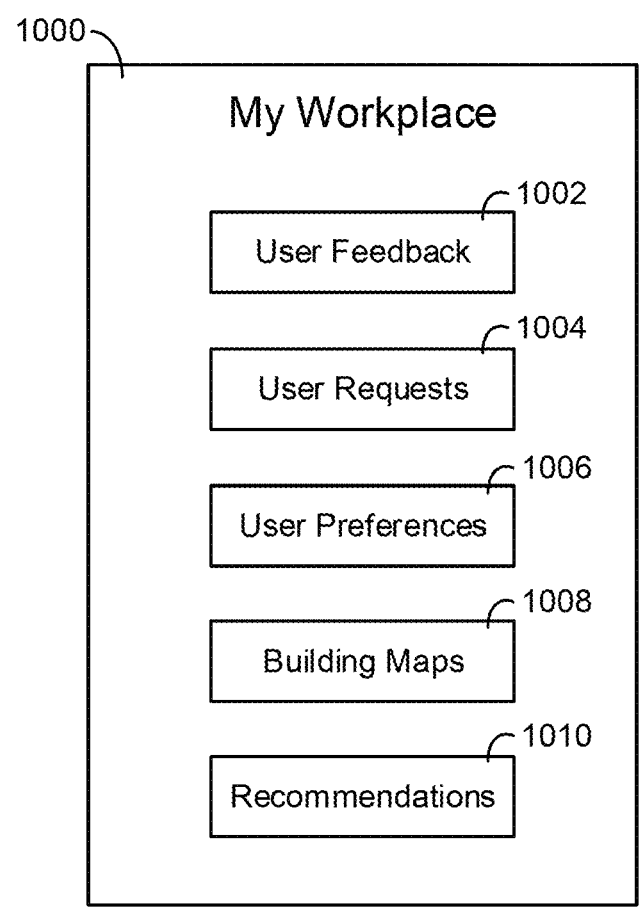
FIG. 10 is block diagram showing components of a user interface associated with the BMS of FIG. 4, according to some embodiments.

Turning to FIG. 10, a block diagram showing components of an example user interface 1000 is shown, according to some embodiments. Interface 1000 can be generated by a building control system such as BMS 400 for presentation to a user such as user 550. Interface 1000 can be presented to a user via a variety of devices such as smartphone 558 and wearable device 559. Interface 1000 can also be presented to a user via user devices such as tablets, personal computers, laptops, vehicles, thermostats, etc. Interface 1000 allows building occupants to become more connected to a building such as building 10. In some embodiments, interface 1000 is associated with a mobile application.

Interface 1000 is shown to include a user feedback element 1002. Via interface 1000, user 550 can provide feedback regarding the building environment such that BMS 400 can react accordingly. User 550 can provide this feedback in various ways including voice inputs, text inputs, selection of an icon, selection of an item from a list (e.g., drop-down list), etc. For example, user 550 may arrive at building 10 to begin a day of work. User 550 may enter an office space and feel overly warm. Accordingly, user 550 may provide input to BMS 400 via interface 1000 to indicate that it is too hot in the office space. BMS 400 may then cool the office space to accommodate the user. Other types of feedback related to building 10 may be related to cleanliness, supplies (e.g., paper towel), food, beverages, humidity, air quality, lighting, security, and other types of feedback. Further, user devices such as smartphone 558 and wearable device 559 can be configured to provide feedback about building 10 and/or user 550 to BMS 400 automatically. For example, wearable device 559 can be configured to sense various biometric information related to user 550 (e.g., heart rate, body temperature) and provide such information to BMS 400. Additionally, smartphone 558 can be configured to sense temperature and provide such information to BMS 400.

Interface 1000 is also shown to include a user requests element 1004. Via interface 1000, user 550 may also make requests associated with building 10. For example, user 550 may make a request to schedule a meeting and reserve a conference room in building 10. User 550 may also make requests related to food (e.g., cafeteria menu), beverages (e.g., order coffee), parking, traffic, supplies (e.g., office supplies), heating and cooling, and other types of requests associated with building 10. As another example, user 550 may make requests to set up a presentation in a specific room such that the presentation plays when a meeting begins. The ability to make these types of requests through interface 1000 allows user 550 to interact with building 10 in a variety of customizable ways.

Interface 1000 is also shown to include a user preferences element 1006. Via interface 1000, user 550 can provide BMS 400 with a variety of different preferences related to building 10. For example, user 550 can configure preferred temperatures (e.g., 70 degrees Fahrenheit), preferred meeting rooms, preferred lighting, preferred parking spots, favorite food and beverages, and preferred presentation styles among other preferences. As another example, user 550 may configure a preferred route home to be used for traffic information. This functionality allows BMS 400 to create a profile for user 550 that can be used for a variety of purposes. The profile may also contain information related to employment of user 550 (e.g., job title, role, permissions) as well as other information related to the user (e.g., office, devices, name, ID, birthday, email address, phone number).

Interface 1000 is also shown to include a building maps element 1008. Via interface 1000, BMS 400 can present a variety of maps to user 550 that provide various information about building 10. For example, interface 1000 may present any of heat maps 600, 800, and 900 described above as well as other similar maps. In some embodiments, user 550 can use a map such as heat map 800 to select a specific conference room for a meeting. Referring to heat map 800, if user 550 prefers warmer environments, then user 550 may choose to schedule a meeting in conference room 703. User 550 can also view different types of maps such as simple floor plans or air quality maps similar to heat map 800. User 550 may also view maps related to parking, for example. In some embodiments, the maps viewed via interface 1000 are interactive. For example, user 550 may select a specific conference room (e.g., conference room 703) to view a schedule associated with the room. User 550 may also view historical information related to the room (e.g., average temperature over last 30 days) and other information associated with a room (e.g., lighting, number of seats, projector, whiteboard). User 550 may also select various areas of the map to view the specific temperature (or air quality, etc.) reading at a "hot spot" such as area 841. This functionality allows user 550 to easily view a variety of information about building 10.

Interface 1000 is also shown to include a recommendations element 1010. Via interface 1000, BMS 400 can provide a variety of feedback to user 550 to improve the user experience and connection to building 10. In some embodiments, BMS 400 uses preferences associated with user 550 in addition to maps such as heat map 800 to provide such feedback to user 550. The recommendations can be made in response to a user request or can be made organically (e.g., in response to a change in a building parameter). For example, if user 550 makes a request to schedule a conference room, BMS 400 may evaluate the request in accordance with a list of available conference rooms as well as the preferences of user 550. BMS 400 may determine that conference room 701 should be scheduled since it has enough seats, is close to the meeting attendees' offices, matches the temperature preferences of user 550, etc.

Figure 11:
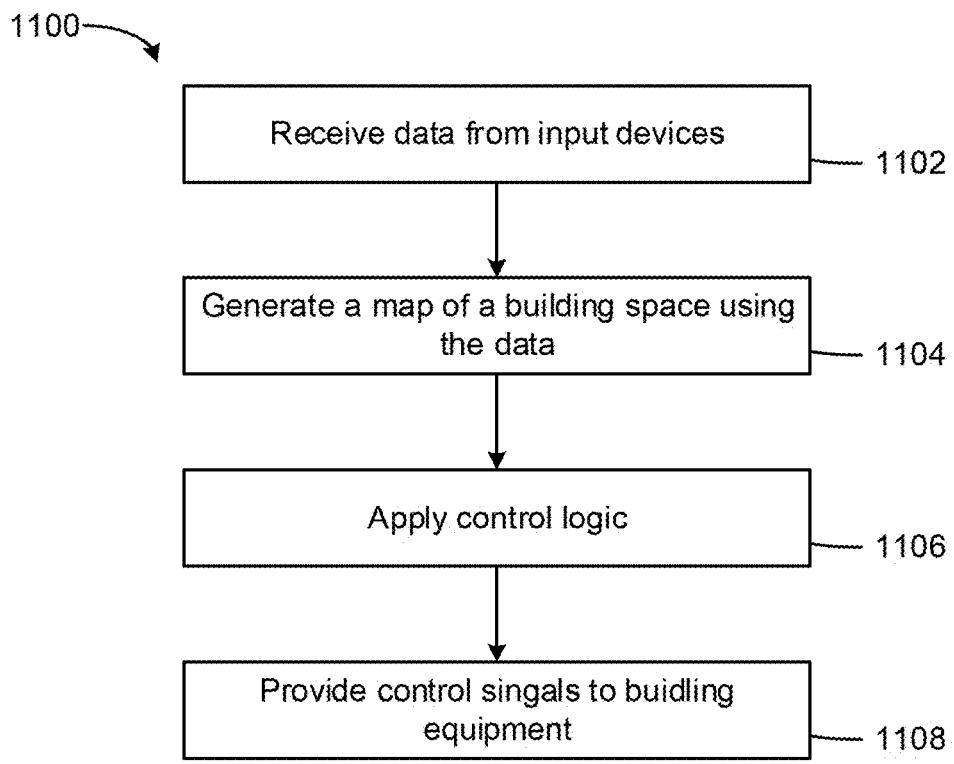
FIG. 11 is a flow diagram of a process for controlling building equipment, according to some embodiments.

Turning to FIG. 11, an example process 1100 for controlling building equipment is shown, according to some embodiments. Process 1100 can be used to achieve more effective and efficient control of building equipment related to HVAC, lighting, security, etc. Process 1100 generally involves generating a map of a building space such that a building control system is aware of variable conditions throughout the entire building space instead of only being aware of variable conditions at select locations within the building space. For example, as described above, heat map 800 can be generated using one or more input devices (e.g., thermal imaging devices) to provide BMS 400 with comprehensive input data related to floor 700. This data can facilitate more effective and efficient control of building systems such as HVAC and security.

Process 1100 is shown to include receiving data from one or more input devices (step 1102). The input devices may be any of the devices described above. For example, BMS 400 and components thereof (e.g., controllers and gateways) may receive thermal image data from cameras 503, 504, and 507 as described above. BMS 400 may also receive data from infrared sensors 505 and 506, drone 540, and other sensors and input devices associated with building 10. These input devices can provide BMS 400 with orders of magnitude more data related to building 10 when compared to other systems that rely solely on data from devices such as thermostat 501 and sensor package 502. Input devices may also include sensors such as air quality sensors, lighting sensors, humidity sensors, air flow sensors, and other types of sensors that can obtain data about building 10. Input devices may also include user devices such as smartphone 558 and wearable device 559. This data can be leveraged to facilitate more effective and efficient control of building 10.

Process 1100 is also shown to include generating a map of a building space using the data from the one or more input devices (step 1104). For example, the data received in step 1102 can be used to generate maps such as heat maps 600, 800, and 900 discussed above. Similar maps can also be generated for air quality, humidity, lighting, security (e.g., camera coverage), fire (e.g., sprinkler coverage, location of fire alarms), and other variables associated with building 10. As discussed, these maps can provide BMS 400 with more comprehensive input data when compared to systems that rely on only a few inputs from a few sensors located in a few spots in a building space. The map may be a two-dimensional map (e.g., map 800) or a three-dimensional map (e.g., map 900). The map may also be stitched together using data from multiple different input devices (e.g., thermal imaging devices) as discussed above.

Process 1100 is also shown to include applying control logic (step 1106). A variety of different approaches are contemplated to evaluate the map and/or associated data generated in step 1104. For example, a rules-based approach can be implemented to trigger certain actions in response to parameters exceeding predetermined thresholds. Machine learning and artificial intelligence models (e.g., neural networks, random forests, logistic regression, support vector machines) can also be trained and implemented to analyze various types of maps and data from the input devices. Further, any of the control algorithms and strategies described above (e.g., ESC, PI, PID, MPC) can be implemented. The control logic applied in step 1106 may be applied in a variety of places within BMS 400 such as BMS controller 366, a more local controller such as AHU controller 330, VAV boxes, and other cloud-based or on on-premises servers or controllers.

Process 1100 is also shown to include providing one or more control signals to building equipment (step 1108). The control signals affect the operation of various types of building equipment such as described above (e.g., chiller 102, AHU 106, VAV units 116). Consider an example where BMS 400 generates heat map 800 at step 1104. In this example, the control logic applied in step 1106 may allow BMS 400 determine that conference rooms 702 and 703 along with office 715 should be cooled. However, based on heat map 800, BMS 400 may determine that areas of floor 700 such as office 711 and lounge area 720 do not need to be cooled. Accordingly, BMS 400 can provide control signals only where necessary (e.g., closest VAV box) to cool rooms 702, 703, and 715. As another example, referring back to the example conference room 500, BMS 400 may provide a control signal that causes cool air to be released from vent 532 such that only a certain zone of conference room 500 is cooled. Control signals may also be provided to smart devices within building 10 such as adjustment of smart blinds on windows 523 and 524 in response to a lighting map and/or user preferences.

Figure 12:
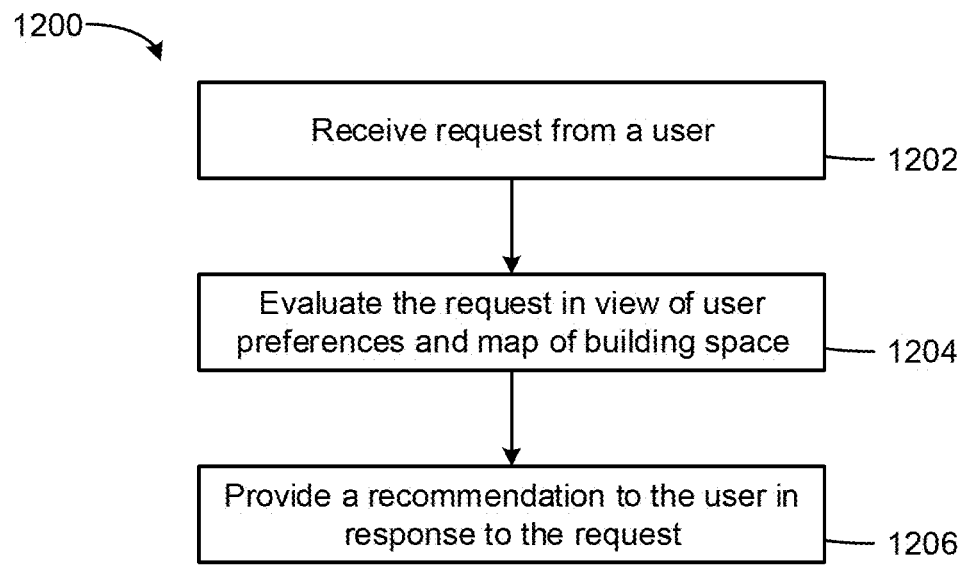
FIG. 12 is a flow diagram of a process for user interaction with the BMS of FIG. 4, according to some embodiments.

Turning to FIG. 12, an example process 1200 for user interaction with a building management system is shown, according to some embodiments. Process 1200 can be performed by BMS 400 through interaction with user 550 via interface 1000, for example. Process 1200 allows building occupants to become more connected to a building. As a result, the user experience may be improved for building occupants.

Process 1200 is shown to include receiving a request from a user (step 1202). The request may be any of the requests described above such as scheduling a meeting room, ordering food or beverages, changing temperature or lighting of a building space, requesting access to a restricted area, setting up a presentation in a conference room, and checking if a parking spot is available, among other types of requests. The request can be made by interacting with interface 1000 as presented via a user device such as a smartphone, a tablet, a wearable device (e.g., watch), a vehicle (e.g., electric vehicle), a laptop, etc. For example, user 550 can interact with interface 1000 through voice commands, text inputs, actions performed on a touch screen, and submitting files such as pictures or videos.

Process 1200 is also shown to include evaluating the request from the user in view of preferences associated with the user and a map of a building space (step 1204). As discussed above, user 550 can configure a variety of preferences within BMS 400 such as preferred temperatures and lighting via interface 1000. BMS 400 can accordingly build a profile associated with the user that can be used to optimize the experience of the user. BMS 400 can also generate maps associated with a building space such as heat maps 600, 800, and 900 described above. Consider an example where the request received in step 1202 is a request to schedule a conference room for a meeting. In step 1204, BMS 400 may then evaluate the request in view of the user preferences (e.g., user prefers warmer temperature) and heat map 800. In some embodiments, the request received in step 1202 is less urgent (e.g., request for meeting next week) and the evaluation in step 1204 is based on historical data (e.g., average heat map over past month).

Process 1200 is also shown to include providing a recommendation to the user in response to the request (step 1206). The recommendation may be any of a variety of recommendations such as a conference room, a location within a room (e.g., chair 512), a recommended parking spot, a food or beverage item, a building parameter (e.g., temperature setpoint, lighting type), a method of security access (e.g., access badge, iris scan), a time (e.g., when cafeteria is less crowded), and a variety of other types of recommendations related to user experience in a building. The more comprehensive input data available to BMS 400 via the input devices described above (e.g., thermal imaging devices) facilitates the ability of BMS 400 to provide more tailored recommendations to users. The recommendations can be provided to the user via interface 1000 such as through visual indications or audio indications.

Figure 13:
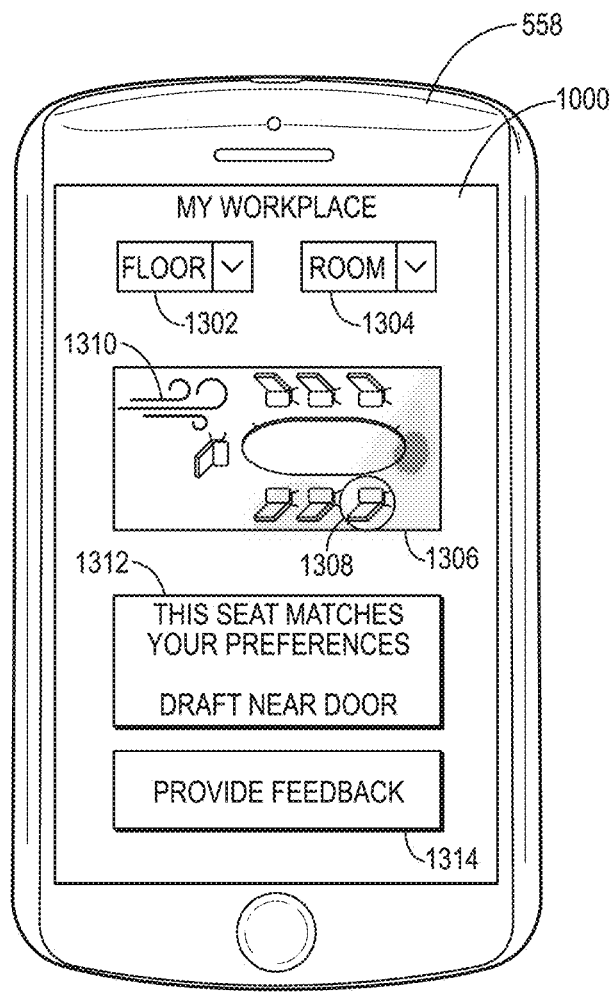
FIG. 13 is an illustration of an example of the user interface of FIG. 10 presented on a smartphone, according to some embodiments.

Turning to FIG. 13, an example of interface 1000 presented to user 550 via smartphone 558 is shown, according to some embodiments. As shown in FIG. 13, interface 1000 includes a drop-down list 1302 that allows user 550 to select a specific floor in building 10 and a drop-down list 1304 that allows user 550 to select a room within building 10. In some embodiments, the rooms that appear in drop-down list 1304 are associated with a floor selected via drop-down list 1302. Further, FIG. 13 shows a heat map 1306 of the room selected via drop-down lists 1302 and 1304. In some embodiments, an application running on smartphone 558 (or a server or controller associated with BMS 400) is configured to send an alert (e.g., push notification, text message, virtual assistant) to user 550 at a specified time interval (e.g., 5 minutes) before an event (e.g., meeting) occurring in a room or other building space (e.g., auditorium). User 550 may then respond to the alert (e.g., by selecting the push notification, selecting a link provided in a text message, providing a voice input) such that the building space associated with the event is auto-populated in interface 1000. The application running on smartphone 558 can also be configured to send the alert based on a location of user 550 (e.g., when nearing a room).

As shown in FIG. 13, the heat map 1306 presented via interface 1000 includes a seat recommendation 1308 and an indication of a draft 1310 present in the room. FIG. 13 also shows that interface 1000 may include textual feedback about a building space (reference 1312) as well as allow the user to provide feedback about the building space (reference 1314). As shown in FIG. 13, seat recommendation 1308 suggests that user 550 should sit in a warmer area of the room as indicated by the heat map 1306. As discussed above, seat recommendation 1308 may be generated based on both known preferences of user 550 (e.g., prefers warmer temperatures) as well as heat map 1306. Additionally, interface 1000 alerts user 550 of draft 1310 so that user 550 knows to stay away from the door.

Figure 14:
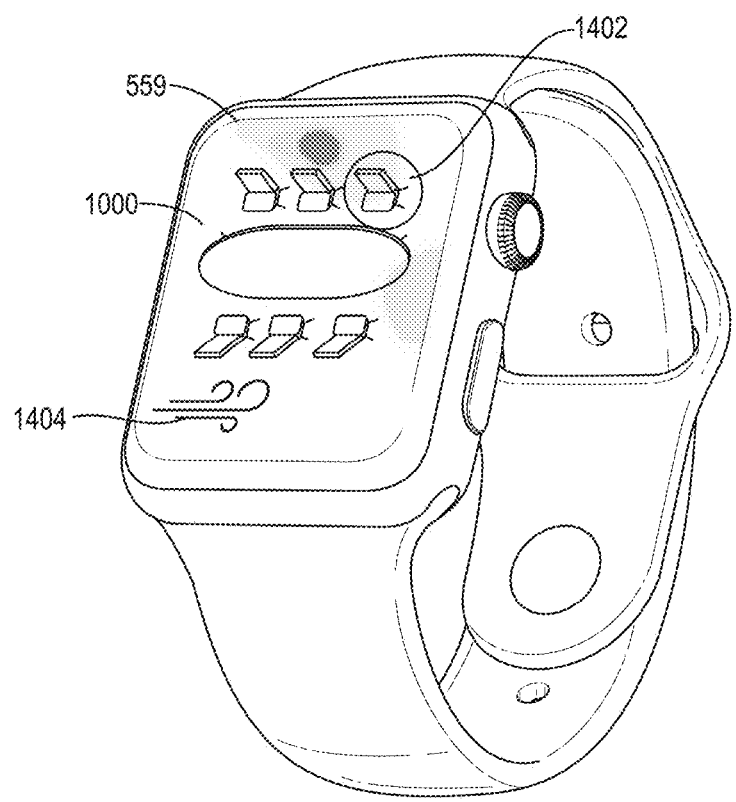
FIG. 14 is an illustration of an example of the user interface of FIG. 10 presented on a wearable device, according to some embodiments.

Turning to FIG. 14, an example of interface 1000 presented to user 550 via wearable device 559 is shown, according to some embodiments. Wearable device 559 may be connected to smartphone 558 (e.g., via Bluetooth). As shown in FIG. 14, the entirety of interface 1000 presented on wearable device 559 is a heat map. Similar to heat map 1306, the heat map shown in FIG. 14 includes a seat recommendation 1402 and an indication of a draft 1404. An application installed on wearable device 559 and/or smartphone 558 may be configured to display the heat map shown in FIG. 14 according to a time or location as discussed above. Interface 1000 as presented via wearable device 559 can provide a quick and easy way for user 550 to view maps and recommendations associated with building 10 as described above.

Model Predictive Control for a Non-Uniform Environmental Condition

Overview

Referring generally to FIGS. 15-24, systems and methods for managing occupant comfort in a zone (e.g., a room, a space, a collection of rooms, a collection of spaces, etc.) of a building are shown, according to some embodiments. In some embodiments, the zone may have a non-uniform distribution of an environmental condition in a zone that can result in an environmental condition gradient throughout the zone. The environmental condition gradient may indicate that a value of an environmental condition at one location in the zone is not the same as a value of the environmental condition at a different location in the zone. For example, a current temperature value at one location in the zone may be 70° F. while a current temperature value at a different location in the zone may be 72° F. Varying temperatures in the zone may lead to occupant discomfort if a location of the occupant is not at a comfortable temperature. For this reason, even if an environmental sensor (e.g., a temperature sensor) indicates a temperature is comfortable at a location of the environmental sensor, it may be necessary to account for indications of occupant comfort to determine if occupant comfort is maintained at other locations in the zone. As such, occupant comfort data may be required to be gathered and correlated to measurements gathered by the environmental sensor(s) to ensure occupant comfort in the zone is maintained.

In FIGS. 15-24 below, a non-uniform temperature distribution is frequently referred to. It should be understood that temperature is used for ease of explanation as a non-uniform distribution of air may result in other environmental conditions (e.g., humidity, air quality, light intensity, etc.) varying in a zone. Regardless of what environmental condition(s) vary across a zone due to the non-uniform distribution of environmental conditions, similar approaches to the systems and methods described below with reference to FIGS. 15-24 can be used to maintain occupant comfort in the zone.

Occupant Comfort Management System

Figure 15:
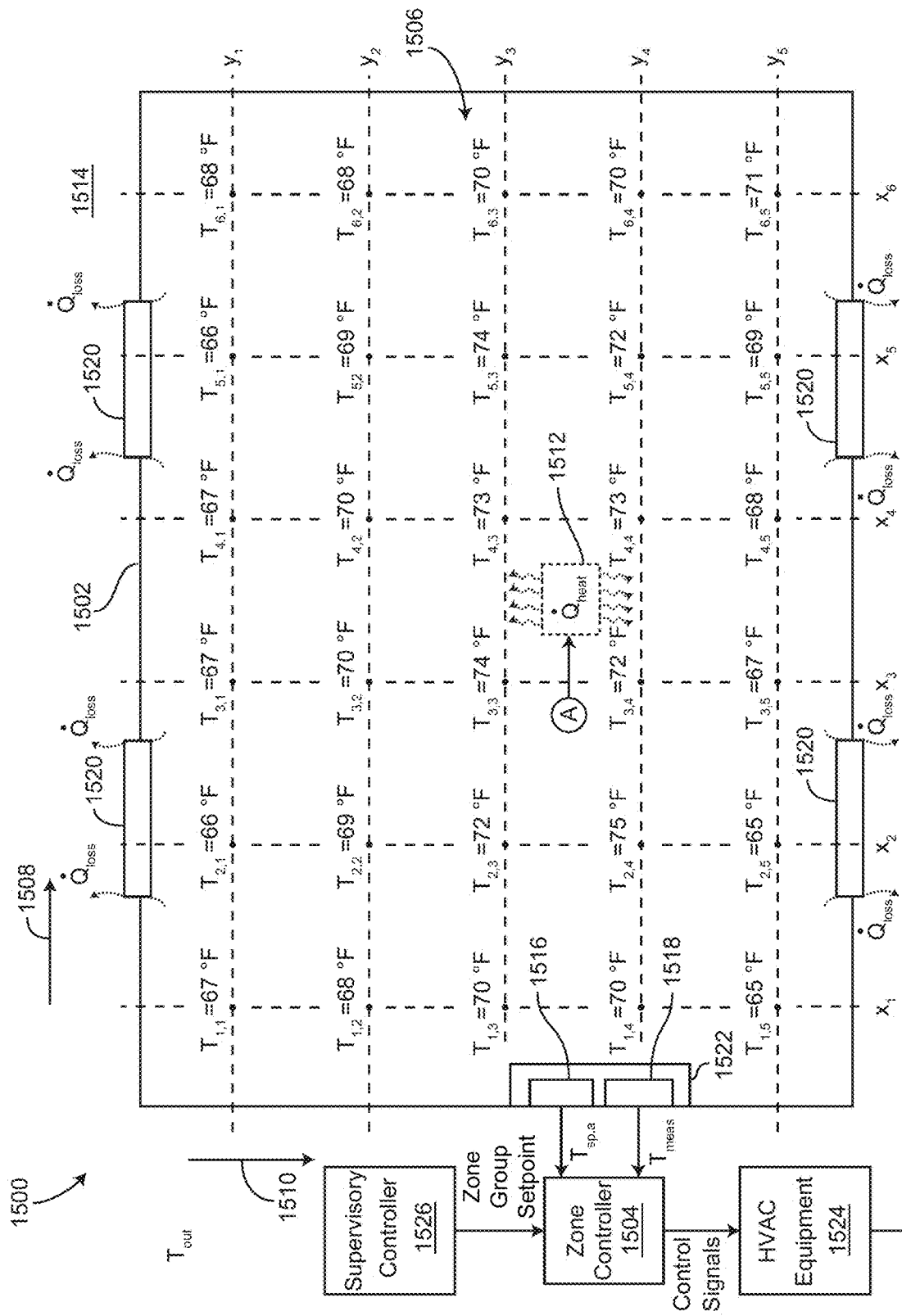
FIG. 15 is a block diagram of an occupant comfort management system including a zone controller, according to some embodiments.

Referring now to FIG. 15, an occupant comfort management system 1500 is shown, according to some embodiments. Occupant comfort management system 1500 is shown to include a zone 1506. In some embodiments, zone 1506 is a zone of building 10. As shown in FIG. 15, a non-uniform temperature distribution exists throughout zone 1506. The non-uniform temperature distribution can be detrimental to occupant comfort as an occupant's perceived level of comfort may not be reflected by devices in zone 1506 that determine current environmental conditions (e.g., a current temperature) based on environmental condition data for zone 1506.

Occupant comfort management system 1500 illustrates a temperature gradient throughout zone 1506. A temperature at each location in zone 1506 can be represented as:

$$T_{x,y} = Z° F.$$

where $T_{x,y}$ is a temperature at location x, y, and Z is a temperature in degrees Fahrenheit. Each temperature $T_{x,y}$, is shown to fall at an intersection between a point on an X-axis 1508 and a Y-axis 1510. For example, $T_{4,3}$ is shown to fall at an intersection of $x_4$ and $y_3$ on X-axis 1508 and Y-axis 1510 respectively. In some embodiments, differing temperature values at various locations of zone 1506 indicate the non-uniform temperature distribution. If the temperature distribution of zone 1506 was uniform, all of the temperatures at the various locations of zone 1506 would be equal (e.g., $T_{1,1}=T_{2,1}=T_{3,1}$, etc.). Although temperature values are shown at each intersection of coordinates in FIG. 15, there may only be a limited number of temperature sensors in zone 1506. As the limited number of temperatures sensors may be located only at specific locations (e.g., on walls) in zone 1506, a temperature at many locations in zone 1506 may be unknown due to a lack of available temperature sensors to measure the temperature at each location in zone 1506.

Still referring to FIG. 15, occupant comfort management system 1500 is shown to include a supervisory controller 1526, a zone controller 1504, and HVAC equipment 1524. In occupant comfort management system 1500, supervisory controller 1526 can provide a zone group setpoint (e.g., a zone group temperature setpoint) to zone controller 1504. In some embodiments, supervisory controller 1526 provides a zone group temperature setpoint $T_{sp,g}$ where $T_{sp,g}$ is a particular temperature setpoint provided to all zones in a zone group (i.e., a grouping of individual zones). In some embodiments, if zone 1506 does not belong to a zone group, $T_{sp,g}$ is a zone temperature setpoint specific to zone 1506 as determined by supervisory controller 1526. In some embodiments, supervisory controller 1526 provides a maximum zone group setpoint and a minimum zone group setpoint for an environmental condition indicating a maximum and a minimum allowable value of the environmental condition. For example, supervisory controller 1526 can provide a maximum zone group temperature setpoint $T_{max,j}$ and a minimum zone group temperature $T_{min,j}$ for a zone group j. $T_{max,j}$ and $T_{min,j}$ can set a maximum and a minimum allowable temperature for the group to which zone 1506 belongs.

In some embodiments, supervisory controller 1526 determines $T_{sp,g}$, $T_{max,j}$, and/or $T_{min,j}$ based on performing model predictive control (MPC) for the zone group j. MPC can determine setpoint values that are expected to maintain occupant comfort across some and/or all zones in the zone group j while optimizing (e.g., reducing) costs related to operating building equipment (e.g., HVAC equipment 1524) to maintain occupant comfort. As MPC performed by supervisory controller 1526 is applied to all zones in the zone group j collectively, $T_{sp,g}$, $T_{max,j}$, and/or $T_{min,j}$ may or may not maintain occupant comfort at an optimized cost in each zone of the zone group j. As such, it may be necessary to determine adjusted zone setpoints for some and/or all zones in the zone group j to ensure occupant comfort is maintained and costs are optimized (e.g., reduced).

Occupant comfort management system 1500 is also shown to include a thermostat 1522. Thermostat 1522 may be any thermostat that can service zone 1506. In some embodiments, thermostat 1522 communicates with zone controller 1504 via a wired and/or wireless connection. Thermostat 1522 may include wired or wireless interfaces (e.g., jacks, antennas, transmitters, receivers, transceivers, wire terminals, etc.) for conducting data communications with various systems, devices, or networks (e.g., zone controller 1504). For example, thermostat 1522 may include an Ethernet card and port for sending and receiving data via an Ethernet-based communications network and/or a WiFi transceiver for communicating via a wireless communications network. Thermostat 1522 may be configured to communicate via local area networks or wide area networks (e.g., the Internet, a building WAN, etc.) and may use a variety of communications protocols (e.g., BACnet, IP, LON, etc.).

Thermostat 1522 is shown to include a user interface 1516 and temperature sensor 1518. Temperature sensor 1518 can be configured to measure a current temperature in zone 1506. If temperature sensor 1518 measures the current temperature, temperature sensor 1518 can provide the measured current temperature $T_{meas}$ to zone controller 1504. In some embodiments, temperature sensor 1518 communicates $T_{meas}$ to zone controller 1504 via thermostat 1522. However, if a non-uniform temperature distribution is present in zone 1506, the measured current temperature may not reflect the current temperature at all locations in zone 1506. For example, temperature sensor 1518 may measure the current temperature at a closest location $T_{1,4}$, and determine that the current temperature in zone 1506 is 70° F. even though the temperature at other locations of zone 1506 is not 70° F. (e.g., $T_{2,5}$=65° F.). As such, $T_{meas}$ as measured by temperature sensor 1518 may not be accurate for determining occupant comfort for an occupant in zone 1506.

User interface 1516 of thermostat 1522 may be able to communicate an occupant adjusted setpoint $T_{sp,a}$, to zone controller 1504 via thermostat 1522. User interface 1516 may be any interface (e.g., graphical user interfaces, reporting interfaces, text-based computer interfaces, etc.) capable of facilitating an occupant to interact with thermostat 1522. In some embodiments, user interface 1516 allows an occupant to modify a setpoint in zone 1506. For example, an occupant may determine that a current temperature setpoint in zone 1506 is too cold and can increase the current temperature setpoint via user interface 1516. In some embodiments, an occupant setpoint adjustment indicates that an occupant is uncomfortable in current environmental conditions of zone 1506. These indications that an occupant is uncomfortable can be used by zone controller 1504 when determining an adjusted zone setpoint for zone 1506 as described in greater detail below with reference to FIG. 17.

In some embodiments, zone controller 1504 generates control signals to provide to HVAC equipment 1524. Zone controller 1504 may be a component of supervisory controller 1526, an independent controller connected to and/or a part of zone 1506, a component hosted on a cloud-based service, etc., according to various embodiments. In some embodiments, some and/or all of the functionality of zone controller 1504 may be incorporated in thermostat 1522. Zone controller 1504 can communicate control signals to HVAC equipment 1524. The control signals generated by zone controller 1504 can operate HVAC equipment 1524 to affect a variable state or condition of zone 1506. For example, a control signal may operate a heater of HVAC equipment 1524 in order to increase a temperature of zone 1506. In some embodiments, HVAC equipment 1524 includes other building devices operable to affect other variable states or conditions of zone 1506. For example, HVAC equipment 1524 may include an indoor unit (IDU) of a variable refrigerant flow (VRF) system.

The control signals generated by zone controller 1504 can be based on adjusted zone setpoints for zone 1506. To determine the adjusted zone setpoints, zone controller 1504 can adjust zone group setpoints provided by supervisory controller 1526 based on a model for managing occupant comfort in zone 1506. Zone controller 1504 can determine various adjusted zone setpoints for zone 1506 such as, for example, adjusted zone temperature setpoints, adjusted zone humidity setpoints, adjusted zone air quality setpoints, or any other environmental condition setpoints for managing occupant comfort in zone 1506. The control signals provided to HVAC equipment 1524 can be generated based on the adjusted zone setpoints as to operate HVAC equipment 1524 to achieve the adjusted zone setpoints. Generating the control signals by zone controller 1504 is described in greater detail below with reference to FIG. 17.

When determining the control signals, zone controller 1504 can account for learned occupant preferences for occupants of zone 1506. In some embodiments, the learned occupant preferences allow zone controller 1504 to maintain occupant comfort in zone 1506 even if a non-uniform distribution of air is present. In some embodiments, a non-uniform temperature distribution results from relative distances between various locations in zone 1506 and from locations where heat is emitted such as a location of an air duct 1512. In some embodiments, HVAC equipment 1524 is not located within zone 1506. If HVAC equipment 1524 is not located within zone 1506, HVAC equipment 1524 can provide heated/cooled air into zone 1506 via air duct 1512. In some embodiments, HVAC equipment 1524 is within zone 1506. If HVAC equipment 1524 is within zone 1506, HVAC equipment 1524 can affect environmental conditions (e.g., temperature) in zone 1506 directly and may not utilize air duct 1512. In some embodiments, a distance between a location in zone 1506 and air duct 1512 and/or HVAC equipment 1524 results in a varying heat disturbance $\dot{Q}_{heat}$ experienced by the location as compared to a different location in zone 1506. For example, a temperature close to air duct 1512 may have a temperature of $T_{3,3}=74°$ F., while temperature far from air duct 1512 is shown as $T_{6,1}=68°$ F. As such, when generating the control signals, zone controller 1504 may be required to account for occupant preferences to ensure occupant comfort is maintained as various locations in zone 1506 may experience different heat disturbances.

Occupant comfort management system 1500 is also shown to include a space boundary 1502. Space boundary 1502 can be any boundary between zone 1506 and an external space (e.g., outdoors, another zone in building 10, etc.). For example, space boundary 1502 may be a wall between zone 1506 and an outdoor environment 1514. Similarly, occupant comfort management system 1500 is also shown to include multiple windows 1520. In some embodiments, windows 1520 and space boundary 1502 result in heat loss, represented as $Q_{loss}$, for zone 1506 due to an outside air temperature $T_{out}$. Depending on a value of $T_{out}$, a heat transfer may occur between zone 1506 (e.g., via windows 1520) and outdoor environment 1514. In some embodiments, $Q_{loss}$ contributes to the non-uniform temperature distribution of zone 1506. For example, location 2,5 in zone 1506 is shown close to window 1520 and has a current temperature of $T_{2,5}=65°$ F. However, a location that is further from window 1520 and is shown to have a higher current temperature of $T_{2,3}=72°$ F. Depending on occupant preferences, an occupant may be comfortable at one of location 2,5 and location 2,3, but not the other due to the variation in temperature between the locations. As such, zone controller 1504 may need to account for occupant comfort preferences as temperature sensors in zone 1506 may not properly detect the heat loss/gain via windows 1520, space boundary 1502, etc. when determining adjusted zone setpoints and generating the control signals to ensure occupant comfort.

Based on the control signals generated by zone controller 1504, zone controller 1504 can communicate the control signals to HVAC equipment 1524. Communication between zone controller 1504 and HVAC equipment 1524 may be via a wired and/or wireless communication. For example, zone controller 1504 and HVAC equipment 1524 may communicate via local area networks or wide area networks (e.g., the Internet, a building WAN, etc.) and may use a variety of communications protocols (e.g., BACnet, IP, LON, etc.) to facilitate the communication. If the control signals are received by HVAC equipment 1524, HVAC equipment 1524 can be operated based on the control signals. HVAC equipment 1524 can be operated to affect a variable state or condition of zone 1506. For example, the control signals may indicate a heater of HVAC equipment 1524 should increase a temperature of zone 1506. The control signals provided by zone controller 1504 can allow HVAC equipment 1524 to achieve an adjusted zone setpoint determined by zone controller 1504. As such, the one or more control signals based on the adjusted zone setpoint may operate HVAC equipment 1524 to maintain an adequate level of occupant comfort at as many locations in zone 1506 as possible and/or as many locations in zone 1506 where occupants are present.

Figure 16:
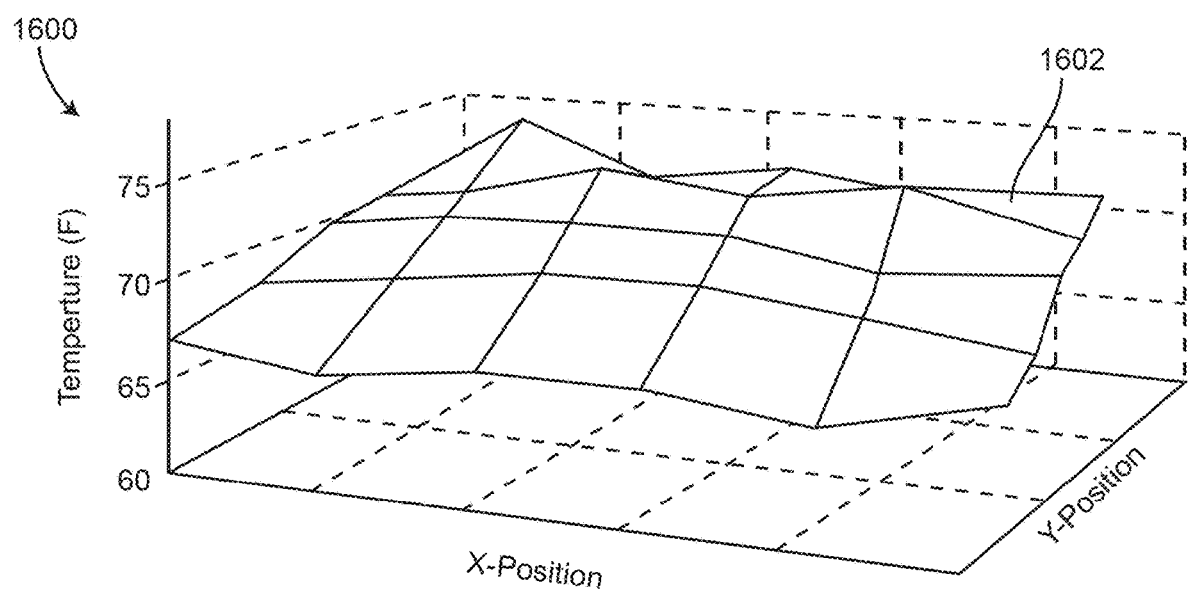
FIG. 16 is a graph illustrating a temperature distribution across a zone, according to some embodiments.

Referring now to FIG. 16, a three-dimensional graph 1600 of temperature distribution in zone 1506 is shown, according to some embodiments. Three-dimensional graph 1600 is shown to include a spatial mapping 1602. In some embodiments, spatial mapping 1602 illustrates the non-uniform temperature distribution of zone 1506. Particularly, spatial mapping 1602 is shown to include some X and Y coordinate positions (i.e., locations of zone 1506) that have a higher/lower temperature than other X and Y coordinate positions (i.e., other locations of zone 1506). If zone 1506 were to have a uniform distribution of air, spatial mapping 1602 may be planar as the uniform distribution of air may indicate that a current temperature at all locations in zone 1506 is the same.

Figure 17:
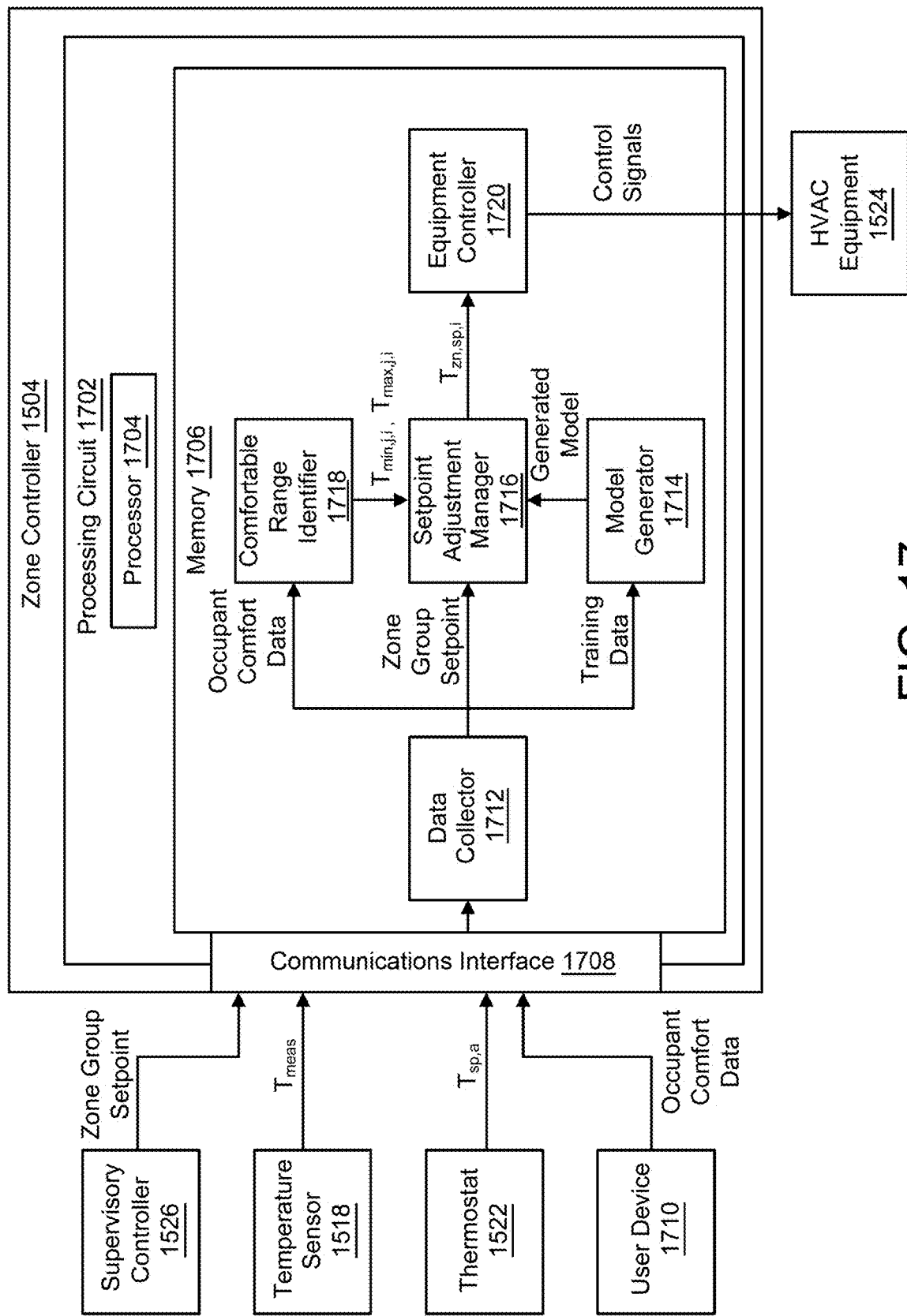
FIG. 17 is a block diagram illustrating the zone controller of FIG. 15 in greater detail, according to some embodiments.

Referring now to FIG. 17, zone controller 1504 as described with reference to FIG. 15 is shown in greater detail, according to some embodiments. As described above, zone controller 1504 can determine an adjusted zone setpoint for an environmental condition (e.g., temperature) and provide control signals to HVAC equipment 1524 based on the adjusted zone setpoint. HVAC equipment 1524 can operate based on the control signals as to maintain an adequate level of occupant comfort throughout zone 1506 and/or at an acceptable amount of locations in zone 1506 (e.g., locations where occupants are present). As described herein, an acceptable/adequate level of occupant comfort can indicate a value of an environmental condition that is comfortable to occupants in zone 1506.

Zone controller 1504 is shown to include a processing circuit 1702. Processing circuit 1702 is shown to include a processor 1704 and memory 1706. Processor 1704 may be a general purpose or specific purpose processor, an application specific integrated circuit (ASIC), one or more field programmable gate arrays (FPGAs), a group of processing components, or other suitable processing components. Processor 1704 may be configured to execute computer code or instructions stored in memory 1706 or received from other computer readable media (e.g., CDROM, network storage, a remote server, etc.).

Memory 1706 may include one or more devices (e.g., memory units, memory devices, storage devices, etc.) for storing data and/or computer code for completing and/or facilitating the various processes described in the present disclosure. Memory 1706 may include random access memory (RAM), read-only memory (ROM), hard drive storage, temporary storage, non-volatile memory, flash memory, optical memory, or any other suitable memory for storing software objects and/or computer instructions. Memory 1706 may include database components, object code components, script components, or any other type of information structure for supporting the various activities and information structures described in the present disclosure. Memory 1706 may be communicably connected to processor 1704 via processing circuit 1702 and may include computer code for executing (e.g., by processor 1704) one or more processes described herein. In some embodiments, one or more components of memory 1706 are a single component. However, each component of memory 1706 is shown independently for ease of explanation.

Zone controller 1504 is also shown to include a communications interface 1708. Communications interface 1708 may include wired or wireless interfaces (e.g., jacks, antennas, transmitters, receivers, transceivers, wire terminals, etc.) for conducting data communications with various systems, devices, or networks. For example, communications interface 1708 may include an Ethernet card and port for sending and receiving data via an Ethernet-based communications network and/or a WiFi transceiver for communicating via a wireless communications network. Communications interface 1708 may be configured to communicate via local area networks or wide area networks (e.g., the Internet, a building WAN, etc.) and may use a variety of communications protocols (e.g., BACnet, IP, LON, etc.).

Communications interface 1708 may be a network interface configured to facilitate electronic data communications between zone controller 1504 and various external systems or devices (e.g., HVAC equipment 1524, temperature sensor 1518, thermostat 1522, supervisory controller 1526, etc.). For example, zone controller 1504 can receive an occupant setpoint adjustment $T_{sp,a}$, from thermostat 1522, a measured current temperature $T_{meas}$ from temperature sensor 1518, and a zone group temperature setpoint $T_{sp,g}$ from supervisory controller 1526 via communications interface 1708. In some embodiments, communications interface 1708 facilitates communication of control signals between an equipment controller 1720 and HVAC equipment 1524.

Still referring to FIG. 17, memory 1706 is shown to include a data collector 1712. In some embodiments, data collector 1712 is configured to receive data from various sources (e.g., temperature sensor 1518, thermostat 1522, supervisory controller 1526, a user device 1710 etc.) and communicate said data between components of memory 1706. For example, data collector 1712 is shown to communicate occupant comfort data to a comfortable range identifier 1718, a zone group setpoint to setpoint adjustment manager 1716, and training data to a model generator 1714. In some embodiments, data collector 1712 receives sensor and/or input signals and coverts said signals to time series data. Time series data may allow zone controller 1504 to determine how occupant comfort preferences change over time (e.g., over a course of a day) as to maintain adequate levels of occupant comfort in zone 1506 even if a non-uniform distribution of air exists.

Memory 1706 is also shown to include comfortable range identifier 1718. Comfortable range identifier 1718 is shown to receive occupant comfort data from data collector 1712. The occupant comfort data provided by data collector 1712 may originate from user device 1710. As described in greater detail below, an occupant may be requested to indicate a current level of comfort, how comfortable they were over a course of a day, etc. Said indications can be provided by user device 1710 as comfort data to zone controller 1504. In some embodiments, thermostat 1522 includes some and/or all of the functionality of user device 1710. As such, thermostat 1522 may be able to provide occupant comfort data to zone controller 1504. In some embodiments, user device 1710 includes some and/or all of the functionality of thermostat 1522. As such, an occupant may be able to adjust a zone setpoint via user device 1710.

In some embodiments, comfortable range identifier 1718 is configured to identify a minimum zone temperature $T_{min,j,i}$ and a maximum zone temperature $T_{max,j,i}$ for a zone i (e.g., zone 1506) based on the occupant comfort data. The occupant comfort data provided to comfortable range identifier 1718 can indicate information regarding occupant comfort preferences. For example, an occupant can perform an occupant setpoint adjustment to adjust a temperature setpoint of zone 1506 from 67° F. to 71° F. The occupant setpoint adjustment can indicate that the occupant is uncomfortable given the current temperature of 67° F. in zone 1506. As such, the occupant setpoint adjustment can be included in the occupant comfort data and utilized by comfortable range identifier 1718 to determine a comfort range (i.e., as defined by $T_{min,j,i}$ and $T_{max,j,i}$ that maintains occupant comfort in zone 1506. Further, the adjusted temperature setpoint can be used along with other adjusted temperature setpoints to determine comfort ranges throughout a day.

As comfortable range identifier 1718 gathers additional occupant comfort data, $T_{min,j,i}$ and $T_{max,j,i}$ can be determined more accurately by comfortable range identifier 1718 to better reflect occupant preferences. However, the comfort range defined by $T_{min,j,i}$ and $T_{max,j,i}$ may be required to have a minimum size (e.g., 2 degrees Fahrenheit, 3 degrees Fahrenheit, etc.) as to allow a cost optimization to optimize (e.g., reduce) costs related to maintaining the comfort range. If the comfort range is too small, HVAC equipment 1524 or other building equipment may be required to be operated very frequently and may consume more power, thereby increasing costs. In this way, if setpoint adjustment manager 1716 performs MPC to determine an optimal value of $T_{zn,sp,i}$, MPC has some flexibility to determine a more cost-effective zone temperature setpoint.

Memory 1706 is also shown to include model generator 1714. Model generator 1714 can generate a setpoint adjustment model that can be used by setpoint adjustment manager 1716 in conjunction with $T_{min,j,i}$ and $T_{max,j,i}$ to determine a value of $T_{zn,sp,i}$ to provide to equipment controller 1720. The setpoint adjustment model generated by model generator 1714 can be any type of model including, for example, a neural network model. In some embodiments, model generator 1714 generates the setpoint adjustment model in response to a determination that a setpoint adjustment model does not exist, a current setpoint adjustment model should be replaced, etc. In some embodiments, an occupant of zone 1506 provides an indication to model generator 1714 to generate the setpoint adjustment model (e.g., by starting a model training process). In some embodiments, comfortable range identifier 1718 and model generator 1714 are included in a single component of memory 1706. If comfortable range identifier 1718 and model generator 1714 are included in the single component, the setpoint adjustment model generated by model generator 1714 may be trained based on $T_{min,j,i}$ and $T_{max,j,i}$ such that the setpoint adjustment model is trained to only output possible zone temperature setpoint values within the comfort range set by $T_{min,j,i}$ and $T_{max,j,i}$.

Model generator 1714 is shown to receive training data from data collector 1712. The training data can include any information applicable to generating the setpoint adjustment model. For example, the training data may include the occupant comfort data, environmental condition data indicating environmental conditions in zone 1506, temperature measurements provided by temperature sensor 1518, adjusted temperature setpoints provided by thermostat 1522, etc. To collect the training data, model generator 1714 can perform various actions to determine how occupants react to various conditions in zone 1506. Based on the collected training data, the setpoint adjustment model can correlate temperature sensor measurements with expected levels of occupant comfort.

In some embodiments, the training data is collected by monitoring occupant adjustments to setpoints. Each time an occupant manually adjusts a setpoint, model generator 1714 may determine that a current setpoint in zone 1506 is not optimal and generate/update the setpoint adjustment model to reflect the occupant setpoint adjustment. For example, if an occupant increases a temperature setpoint in zone 1506 via thermostat 1522, the increase may indicate that a current temperature setpoint indicated by temperature sensor 1518 is too cold. In general, an occupant setpoint adjustment is an indication that an occupant is uncomfortable. Based on occupant setpoint adjustments and attributes of when the occupant setpoint adjustments are made (e.g., time of day, day of the week, outside air temperature, humidity, measured zone temperature, solar effects, etc.), additional training data can be determined by zone controller 1504 for generating/updating the setpoint adjustment model. As additional training data is gathered, the setpoint adjustment model can be refined as to more accurately model occupant comfort for various conditions.

In some embodiments, the training data is collected by performing experiments on zone 1506. During an experiment, occupant comfort data can be gathered to determine how occupants respond to the experiment. For example, an experiment may include determining an experimental setpoint, operating HVAC equipment 1524 to maintain the experimental setpoint over the course of a day, and polling occupants for an occupant comfort rating for the day. On a next day (or a next time period), the experimental setpoint can be set to a different constant value and polling of occupants is repeated. The polling may be conducted by user device 1710, thermostat 1522, etc. Based on results of the polling, occupant comfort data related to the various experimental setpoints can be gathered. For example, if a first experimental setpoint for a first day resulted in high occupant comfort ratings, the first experimental setpoint may be close to an optimal comfort value provided conditions (e.g., measured temperature) during the first day. However, if a second experimental setpoint for a second day resulted in low occupant comfort ratings, the low occupant comfort ratings may indicate that the second experimental setpoint is not close to the optimal comfort value provided conditions of the second day. To perform the experiment, model generator 1714 can generate an experimental model to provide to setpoint adjustment manager 1716. Based on the experimental model, setpoint adjustment manager 1716 can determine $T_{zn,sp,i}$ based on the experimental model. Finally, equipment controller 1720 can generate control signals to operate HVAC equipment 1524 based on $T_{zn,sp,i}$. As HVAC equipment 1524 is operated based on the control signals, occupant comfort data based on effects of said operation can be gathered as training data.

In some embodiments, model generator 1714 generates experimental models to test how occupants respond to various setpoints. Specifically, model generator 1714 may generate experimental models to test how occupants respond to operation of HVAC equipment 1524 that is estimated to reduce costs (e.g., reduce power consumption costs, reduce maintenance costs, etc.). As more experimental models are tested, the training data set may grow, thereby giving model generator 1714 more information with which to generate/update the setpoint adjustment model based on.

In some embodiments, the training data is collected via an occupant voting system. In some embodiments, the voting system includes a voting method (e.g., a mobile application, a website, a paper survey, etc.) that occupants can rate their occupant comfort level through. For example, the occupant voting system may include a mobile application that requests an occupant to rate their occupant comfort level three time per day (e.g., once in the morning, once in the afternoon, and once in the evening). In some embodiments, the occupant voting system can aggregate all occupant comfort level ratings for each voting session to determine if setpoints maintained a high level of occupant comfort. Based on voting results and attributes of time periods when the voting results are collected (e.g., time of day, day of the week, outside air temperature, humidity, solar effects, etc.), a setpoint adjustment model can be generated/updated by model generator 1714 to be able to more precisely model occupant comfort.

In some embodiments, occupant comfort data is collected through monitoring occupants for visible indications of occupant comfort. Visible indications of occupant comfort can be captured by a visual detection device in zone 1506. For example, thermostat 1522 may include the visual detection device in order to monitor occupant comfort in zone 1506. A visible indication of occupant discomfort may be, for example, an occupant shivering, an occupant sweating, body heat captured by an IR video camera, skin color (e.g., red skin may indicate the occupant is cold), etc. Based on the visible indications of occupants and attributes of time periods when the visible indications are measured (e.g., time of day, day of the week, weather conditions, outside air temperature, humidity, solar effects, etc.), model generator 1714 can generate/update a setpoint adjustment model to be able to more precisely model occupant comfort given various conditions of zone 1506.

In some embodiments, the setpoint adjustment model generated by model generator 1714 is a convolutional neural network (CNN). A CNN is a type of feed-forward artificial neural network in which the connectivity pattern between its neurons is inspired by the organization of the animal visual cortex. Individual cortical neurons respond to stimuli in a restricted region of space known as the receptive field. The receptive fields of different neurons partially overlap such that they tile the visual field. The response of an individual neuron to stimuli within its receptive field can be approximated mathematically by a convolution operation. The CNN is also known as shift invariant or space invariant artificial neural network (SIANN), which is named based on its shared weights architecture and translation invariance characteristics. An example of a CNN is described in greater detail below with reference to FIG. 24.

In some embodiments, model generator 1714 updates an existing setpoint adjustment model based on new training data. A new setpoint adjustment model may not need to be generated every time new training data is received. Instead, updating the existing setpoint adjustment model can ensure the new training data is accounted for without undergoing a computationally intensive model generation process. Model generator 1714 can use the existing setpoint adjustment model and the training data provided by data collector 1712 to update the setpoint adjustment model based on new information provided to zone controller 1504. In some embodiments, the setpoint adjustment model generated by model generator 1714 becomes antiquated as time progresses if the setpoint adjustment model is not updated.

Updating the setpoint adjustment model can reflect changes in building 10, zone 1506, occupant preferences, etc., to better maintain occupant comfort. For example, if new HVAC devices are added to zone 1506 and the setpoint adjustment model is not updated, setpoint adjustment manager 1716 may not be determine adequate values of $T_{zn,sp,i}$. As such, model generator 1714 can update the setpoint adjustment model as needed to ensure setpoint adjustment manager 1716 can determine adequate values of $T_{zn,sp,i}$ based on the setpoint adjustment model as time progresses. In some embodiments, model generator 1714 automatically updated the setpoint adjustment model as needed. In some embodiments, an occupant of zone 1506 can indicate that model generator 1714 should update the setpoint adjustment model.

In some embodiments, model generator 1714 is configured to determine when the setpoint adjustment model has deviated too far from an accurate model of a comfort range for zone 1506, such that the setpoint adjustment model may not benefit significantly from updates. If model generator 1714 determines the setpoint adjustment model has deviated too far from an accurate representation of occupant comfort in zone 1506, model generator 1714 may generate a new setpoint adjustment model. In some embodiments, if a new setpoint adjustment model is generated by model generator 1714, a current setpoint adjustment model may be discarded and replaced by the new setpoint adjustment model.

In some embodiments, the setpoint adjustment model generated by model generator 1714 utilizes the zone group setpoint $T_{sp,g}$ provided by supervisory controller 1526 to determine $T_{zn,sp,i}$. The setpoint adjustment model may implicitly indicate a setpoint weighting $w_i$ and a temperature offset $T_{offset,i}$ for a zone i. In some embodiments, $w_i$ and $T_{offset,i}$ are included in the setpoint adjustment model in order to adjust the zone group temperature setpoint $T_{sp,g}$ to reflect occupant preferences in zone 1506. For example, the setpoint adjustment model may utilize $w_i$ and $T_{offset,i}$ to determine $T_{zn,sp,i}$ in the following equation:

$$T_{zn,sp,i} = w_i T_{sp,g} + T_{offset,i}$$

where $w_i$ is the setpoint weighting determined by model generator 1714 for a zone i, $T_{sp,g}$ is the zone group temperature setpoint for a zone group that zone i belongs to as determined by supervisory controller 1526, and $T_{offset,i}$ is the temperature offset determined by model generator 1714 for zone i. Setpoint adjustment manager 1716 can utilize the setpoint adjustment model to determine $T_{zn,sp,i}$ as described in greater detail below.

In some embodiments, $w_i$ and $T_{offset,i}$ are determined by model generator 1714 based on a regression analysis performed by model generator 1714. In some embodiments, the regression analysis determines an association between group temperature setpoints provided by supervisory controller 1526 and temperature setpoints based on occupant setpoint adjustments. The regression analysis performed by model generator 1714 may generate a regression line that can be described by various functions (e.g., a linear function, a quadratic function, a piecewise function, etc.) For example, if the regression analysis generates a linear regression line (i.e., in the form of y=mx+b), $w_i$ can represent a slope of the linear regression line and $T_{offset,i}$ can represent a y-intercept of the linear regression line. As such, $w_i$ and $T_{offset,i}$ can be determined based on how occupant preferences differ from setpoints generated for the zone group to which zone 1506 belongs. Values of $w_i$ and $T_{offset,i}$ may indicate how accurate/inaccurate $T_{sp,g}$ is for maintaining occupant comfort in zone 1506. For example, $w_i$=1.5 and $T_{offset,i}$=2° F. may indicate that $T_{sp,g}$ is fairly inaccurate for maintaining occupant comfort in zone 1506.

In some embodiments, a default state of $w_i$ and $T_{offset,i}$ is $w_i$=1 and $T_{offset,i}$=0. $w_i$=1 and $T_{offset,i}$=0 may indicate that model generator 1714 has determined that the zone group temperature setpoint $T_{sp,g}$ provided by supervisory controller 1526 is the same as what model generator 1714 determines to maintain occupant comfort based on the training data (i.e., $T_{sp,g}$ is an optimal temperature for zone 1506 given current conditions in zone 1506). In some embodiments, $w_i$ and/or $T_{offset,i}$ may differ from the default state if $T_{sp,g}$ does not reflect occupant preferences in zone 1506 as determined by model generator 1714 based on the training data. For example, $w_i$=1.05 and $T_{offset,i}$=1.5 may be determined by model generator 1714 if the training data indicates occupants in zone 1506 prefer zone 1506 to be warmer than the zone group temperature setpoints provided by supervisory controller 1526. As such, if setpoint adjustment manager 1716 utilizes the generated model including $w_i$=1.05 and $T_{offset,i}$=1.5, the zone temperature setpoint $T_{zn,sp,i}$ can be adjusted accordingly as described in greater detail below.

In some embodiments, model generator 1714 generates the setpoint adjustment model indicating $w_i$ and $T_{offset,i}$ if a zone comfort range for occupants of zone 1506 (i.e., as defined by $T_{max,j,i}$ and $T_{min,j,i}$) is the same as a range defined by a minimum and maximum zone group temperature defined by $T_{max,j}$ and $T_{min,j}$ provided by supervisory controller 1526. However, if the zone comfort range is not the same as the zone group comfort range, model generator 1714 may generate the setpoint adjustment model to scale the adjusted zone temperature based on an amount in which the zone comfort range and the zone group comfort range differ. For example, the setpoint adjustment model may allow setpoint adjustment manager 1716 to scale $T_{zn,sp,i}$ by the following equation:

$$T_{zn,sp,i} = \frac{T_{max,j,i} - T_{min,j,i}}{T_{max,j} - T_{min,j}} (T_{sp,g} - T_{min,j}) + T_{min,j,i}$$

where $T_{max,j,i}$ is a maximum zone temperature for a zone i (e.g., zone 1506) in a zone group j, $T_{min,j,i}$ is a minimum zone temperature for zone i in zone group j, $T_{max,j}$ is a maximum zone group temperature for zone group j, $T_{min,j}$ is a minimum zone group temperature for zone group j, and $T_{sp,g}$ is the zone group temperature setpoint provided to all zones in zone group j by supervisory controller 1526. In some embodiments, the above equation models how setpoint adjustment manager 1716 determines a value of $T_{zn,sp,i}$ that results in an acceptable level of occupant comfort in zone i by utilizing the setpoint adjustment model generated by model generator 1714.

Model generator 1714 is shown to provide the generated model (i.e., the setpoint adjustment model) to setpoint adjustment manager 1716. Setpoint adjustment manager 1716 is also shown to receive a zone group setpoint (e.g., $T_{sp,g}$, $T_{max,j}$, and/or $T_{min,j}$) from data collector 1712 and $T_{min,j,i}$ and $T_{max,j,i}$ from comfortable range identifier 1718. In some embodiments, setpoint adjustment manager 1716 determines the adjusted zone setpoint $T_{zn,sp,i}$ to provide to equipment controller 1720 by performing MPC to determine a zone temperature setpoint that maintains occupant comfort and optimizes (e.g., reduces) costs. To perform MPC, setpoint adjustment manager 1716 can utilize the generated model provided by model generator 1714 to generate zone temperature setpoints and can determine, via MPC, which zone temperature setpoint best optimizes costs and maintains occupant comfort. Setpoint adjustment manager 1716 can also ensure any generated zone temperature setpoints meet constraints set by the comfortable range (i.e., the generated zone temperature setpoints are greater than or equal to $T_{min,j,i}$ and are less than or equal to $T_{max,j,i}$).

In some embodiments, setpoint adjustment manager 1716 performs MPC utilizing the setpoint adjustment model provided by model generator 1714 to determine an optimal zone temperature setpoint $T_{zn,sp,i}$. If setpoint adjustment manager 1716 performs MPC, setpoint adjustment manager 1716 can determine what zone temperature setpoint in the comfort range set by $T_{min,j,i}$ and $T_{max,j,i}$ maintains occupant comfort at a most optimized (e.g., reduced) cost. To perform MPC, setpoint adjustment manager 1716 may use the measured temperature $T_{meas}$ provided by temperature sensor 1518. As the setpoint adjustment model generated by model generator 1714 can be trained to correlate temperature readings with occupant comfort, setpoint adjustment manager 1716 can utilize said correlation to determine what zone temperature setpoints are expected to maintain occupant comfort. Based on zone temperature setpoints that do maintain occupant comfort, setpoint adjustment manager 1716 can determine what specific zone temperature setpoint results in optimized costs. In some embodiments, setpoint adjustment manager 1716 includes any of the functionality of the economic model predictive control system described with reference to U.S. patent application Ser. No. 15/473,496, filed Mar. 29, 2017, to generate the zone temperature setpoint, the entire disclosure of which is incorporated by reference herein.

In some embodiments, setpoint adjustment manager 1716 determines the zone temperature setpoint by determining how the zone group temperature setpoint provided by supervisory controller 1526 can be adjusted based on preferences of occupants in zone 1506. Setpoint adjustment manager 1716 can use $T_{sp,g}$ as input to the generated model to determine $T_{zn,sp,i}$. For example, if the regression analysis performed by model generator 1714 indicates a relationship between the zone group setpoint and occupant preferred setpoints follows a linear relationship, $T_{zn,sp,i}$ may be determined by the following equation as described above:

$$T_{zn,sp,i} = w_i T_{sp,g} T_{offset,i}$$

where $w_i$ is the setpoint weighting determined by model generator 1714, $T_{sp,g}$ is the group temperature setpoint for a zone group that zone i belongs to as determined by supervisory controller 1526, and $T_{offset,i}$ is the temperature offset determined by model generator 1714. As mentioned previously, the default state of $w_i$ and $T_{offset,i}$ may be $w_i=1$ and $T_{offset,i}=0$. If the generated model indicates default state is appropriate to maintain occupant comfort, $T_{zn,sp,i}$ may be effectively determined based on the generated model via the following equation:

$$T_{zn,sp,i} = T_{sp,g}$$

where the adjusted zone setpoint $T_{zn,sp,i}$ for zone i is equal to the group temperature setpoint for the zone group to which zone i belongs.

However, $T_{zn,sp,i}$ may nonetheless be constrained by $T_{min,j,i}$ and $T_{max,j,i}$ provided by comfortable range identifier 1718. $T_{min,j,i}$ and $T_{max,j,i}$ ensure that if the setpoint adjustment model is inaccurate and/or the zone group setpoint is far from what is considered comfortable in zone 1506, $T_{zn,sp,i}$ can still be an adequate zone temperature setpoint. For example, if the zone group temperature is generated by MPC expecting that few occupants will be present (e.g., on a weekend), the zone group temperature may be low as to optimize (e.g., reduce) costs such that building equipment does not need to be operated frequently. However, if zone 1506 of the zone group is expected to have many occupants at that time (e.g., for a meeting), the zone group temperature setpoint applied to the setpoint adjustment model may not result in an adequate zone temperature setpoint even if the setpoint adjustment model is otherwise accurate. For example, if the zone group temperature is 60° F., and the weight and offset terms determined by model generator 1714 are $w_i=1.05$ and $T_{offset,i}=0.5$ respectively, $T_{zn,sp,i}$ can be calculated by:

$$T_{zn,sp,i} = 1.05 \times 60 + 0.5 = 63.5° F.$$

If 63.5° F. is uncomfortable for occupants of zone 1506, setpoint adjustment manager 1716 can constrain $T_{zn,sp,i}$ to be within the comfort range set by $T_{min,j,i}$ and $T_{max,j,i}$. For example, if $T_{min,j,i}=68°$ F. and $T_{max,j,i}=72°$ F., setpoint adjustment manager 1716 can increase $T_{zn,sp,i}$ 63.5° F. to at least 68° F. to ensure occupant comfort is maintained in zone 1506. As illustrated by the above example, even if the generated model is accurate, uncomfortable temperature setpoints can still be generated. In this way, setpoint adjustment manager 1716 may require values of $T_{min,j,i}$ and $T_{max,j,i}$ to ensure values of $T_{zn,sp,i}$ maintain occupant comfort regardless if $T_{sp,g}$ does not maintain occupant comfort and/or the generated model is inaccurate.

Setpoint adjustment manager 1716 can determine that a difference between a minimum and maximum zone group temperature provided by supervisory controller 1526 differs from a difference between a minimum and maximum zone temperature identified by comfortable range identifier 1718. Based on said determination, setpoint adjustment manager 1716 may be required to provide additional inputs to the generated model when performing MPC to determine a zone temperature setpoint. For example, if the minimum and the maximum zone group temperature are 68° F. and 72° F. respectively, the minimum and maximum zone temperatures are 73° F. and 76° F. respectively, and a zone group temperature setpoint is a 70° F., setpoint adjustment manager 1716 can calculate a value of $T_{zn,sp,i}$ using the generated model as:

$$T_{zn,sp,i} = \frac{76° F. - 73° F.}{72° F. - 68° F.}(70° F. - 68° F.) + 73° F. = 1.5° F. + 73° F. = 74.5° F.$$

where $T_{zn,sp,i}=74.5°$ F. is a scaled value based how a difference between the minimum and maximum zone group temperatures differs from a difference between the minimum and maximum zone temperatures. Particularly, $T_{zn,sp,i}$ of the above example is shown to be scaled by ¾ as the difference between the minimum and maximum zone temperatures is smaller than the difference between the minimum and maximum zone group temperatures.

In some embodiments, $T_{zn,sp,i}$ is determined based on a cost optimization performed by setpoint adjustment manager 1716. In some embodiments, $T_{sp,g}$ provided to zone controller 1504 is determined based on a cost optimization performed by supervisory controller 1526 for a zone group to which zone 1506 belongs. Supervisory controller 1526 can be configured to determine a value of $T_{sp,g}$ for a zone group to optimize (e.g., reduce) costs for maintaining occupant comfort across zones of the zone group. Based on an optimized value of $T_{sp,g}$, setpoint adjustment manager 1716 can perform a cost optimization when determining a value of $T_{zn,sp,i}$ utilizing the setpoint adjustment model provided by model generator 1714. Setpoint adjustment manager 1716 can determine an optimal value of $T_{zn,sp,i}$ that optimizes (e.g., reduces) a cost of operating HVAC equipment 1524 and maintains occupant comfort in zone 1506. The optimal value can be constrained by the zone comfort range identified by comfortable range identifier 1718. In other words, the optimal value of $T_{zn,sp,i}$ may be determined as to be within the comfort range defined by $T_{min,j,i}$ and $T_{max,j,i}$ to adhere to preferences of occupants. However, the optimal value of $T_{zn,sp,i}$ may or may not be an ideal comfort value (i.e., a comfort value that maximizes occupant comfort) for occupant comfort if the ideal comfort value does not minimize costs. The optimal value of $T_{zn,sp,i}$ can be any value within the comfort range that results in a highest optimization (e.g., reduction) of costs of operating HVAC equipment 1524. It should be noted the optimal value of $T_{zn,sp,i}$ may or may not indicate an ideal (i.e., a perfect) solution. In some embodiments, the optimal value of $T_{zn,sp,i}$ refers to a zone temperature setpoint determined by setpoint adjustment manager 1716 to optimize (e.g., reduce) costs and maintain occupant comfort.

In some embodiments, in order to perform MPC to determine the optimal value of $T_{zn,sp,i}$, setpoint adjustment manager 1716 may account for a thermal model that predicts a temperature of zone 1506 as a function of an output of HVAC equipment 1524. The thermal model can allow setpoint adjustment manager 1716 to estimate a change in the temperature of zone 1506 based on operation of HVAC equipment 1524. Setpoint adjustment manager 1716 can utilize the thermal model to determine what value of $T_{zn,sp,i}$ at a current time optimizes costs by reducing costs related to operating HVAC equipment 1524.

If setpoint adjustment manager 1716 determines a value of $T_{zn,sp,i}$, setpoint adjustment manager 1716 can communicate $T_{zn,sp,i}$ to equipment controller 1720. Based on $T_{zn,sp,i}$, equipment controller 1720 can generate control signals for HVAC equipment 1524. The control signals generated by equipment controller 1720 can operate particular devices of HVAC equipment 1524 in order to achieve the zone temperature setpoint. For example, if $T_{zn,sp,i}=71°$ F. and a current temperature in zone 1506 is 75° F., an air conditioner of HVAC equipment 1524 may be operated to provide cooled air to zone 1506 (e.g., via air duct 1512). Equipment controller 1720 can communicate the control signals to HVAC equipment 1524 via communications interface 1708. If the control signals are received, devices of HVAC equipment 1524 can operate based on the control signals to achieve the zone temperature setpoint.

Figure 18:
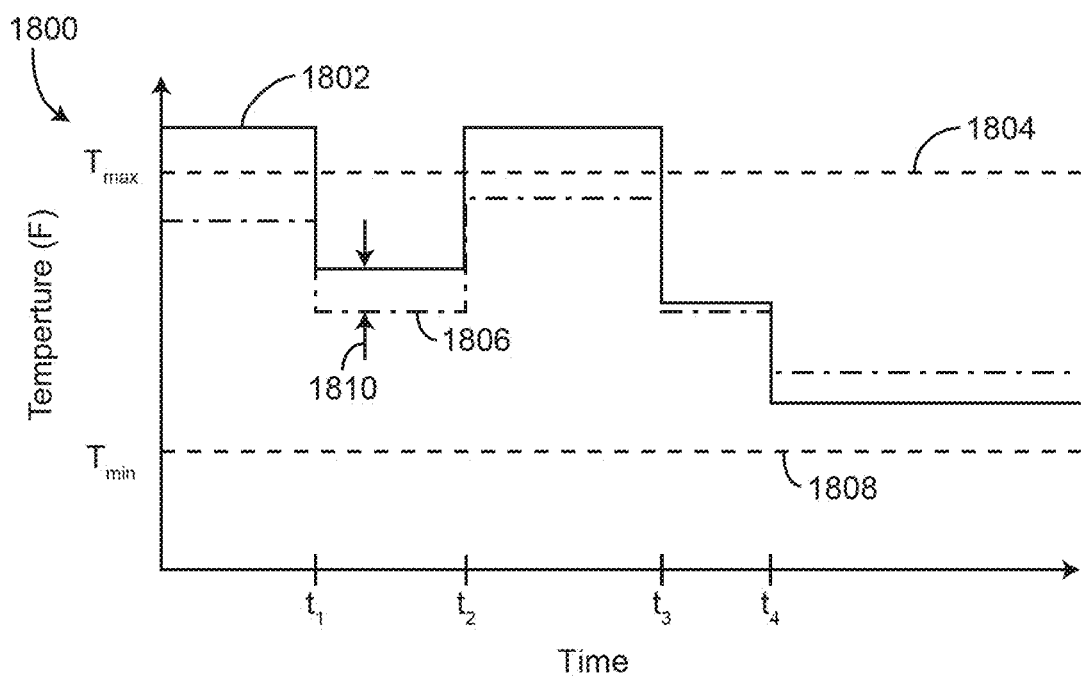
FIG. 18 is a graph illustrating temperature of a zone over time based on occupant setpoint adjustments as compared to zone group temperature setpoints, according to some embodiments.

Referring now to FIG. 18, a graph 1800 illustrating temperature of a zone over time based on occupant setpoint adjustments as compared to zone group temperature setpoints is shown, according to some embodiments. In some embodiments, occupant setpoint adjustments indicate that an occupant is uncomfortable in the zone due to a non-uniform distribution of an environmental condition (e.g., temperature, humidity, air quality, etc.). As such, graph 1800 can illustrate a difference between setpoints determined by model predictive control (MPC) decisions of supervisory controller 1526 and by occupant setpoint adjustments.

Graph 1800 is shown to include a series 1802 and a series 1806. In some embodiments, series 1802 illustrates changes to a setpoint value made by an occupant (i.e., occupant setpoint adjustments). In some embodiments, series 1806 illustrates setpoint values determined by MPC decisions of supervisory controller 1526. Series 1806 may be generated by supervisory controller 1526 to reduce costs related to maintaining occupant comfort in zone 1506. Graph 1800 is also shown to include a maximum temperature 1804 as $T_{max}$ and a minimum temperature 1808 as $T_{min}$. In some embodiments, $T_{max}$ and $T_{min}$ are a maximum and a minimum allowable temperature of series 1806 that maintain occupant comfort as expected by supervisory controller 1526. $T_{max}$ and $T_{min}$ can be determined by supervisory controller 1526 as a maximum and minimum temperature setpoint that are expected maintains occupant comfort in zone 1506. As such, series 1806 is shown to only include temperature setpoints within maximum temperature 1804 and minimum temperature 1808. However, as maximum temperature 1804 and minimum temperature 1808 are applied for a zone group, they may not reflect preferences of occupants in a particular zone. Due to this, series 1802 is shown to include temperature setpoints from occupant setpoint adjustments that are outside the range set by maximum temperature 1804 and minimum temperature 1808.

Series 1802 is shown to include four setpoint adjustment times $t_1$, $t_2$, $t_3$, and $t_4$. At each setpoint adjustment time, series 1802 and series 1806 are shown to have a setpoint value change. In series 1802, each setpoint value change may be the result of an occupant setpoint adjustment. In series 1806, each setpoint value change may be the result of one or more MPC decisions indicating that a current setpoint value should be adjusted. For example, at time $t_3$, series 1802 and series 1806 experience a setpoint value reduction. Series 1802 may experience the setpoint value reduction due to an occupant performing an occupant setpoint adjustment that decreases a temperature setpoint. Series 1806 may experience the setpoint value reduction due to an MPC decision determining a current temperature setpoint value is too high and does not optimize costs and/or is not expected to maintain occupant comfort in the zone group. In graph 1800, series 1802 and series 1806 are shown to experience setpoint value changes at the same time. However, series 1802 and series 1806 may experience setpoint value changes at different times. For example, an occupant may perform an occupant setpoint adjustment at a particular time as reflected in series 1802, but series 1806 may not reflect a setpoint change until after the occupant setpoint adjustment occurs.

Graph 1800 is shown to include a difference 1810 between series 1802 and series 1806. In some embodiments, difference 1810 illustrates that occupant preferences for temperature over time are not the same as a setpoint value determined by MPC performed by supervisory controller 1526 for the zone group. For example, between times $t_1$ and $t_2$, series 1802 is shown to be greater than series 1806, which may indicate that an occupant prefers a temperature setpoint higher than determined by MPC decisions of supervisory controller 1526. Similarly, beginning at time $t_4$, series 1802 is shown to be less than series 1806, which may indicate that a temperature setpoint determined by MPC is too warm for occupant preferences. As such, graph 1800 illustrates how temperature setpoint values determined by supervisory controller 1526 may not always maintain occupant comfort in a specific zone of the zone group.

Figure 19:
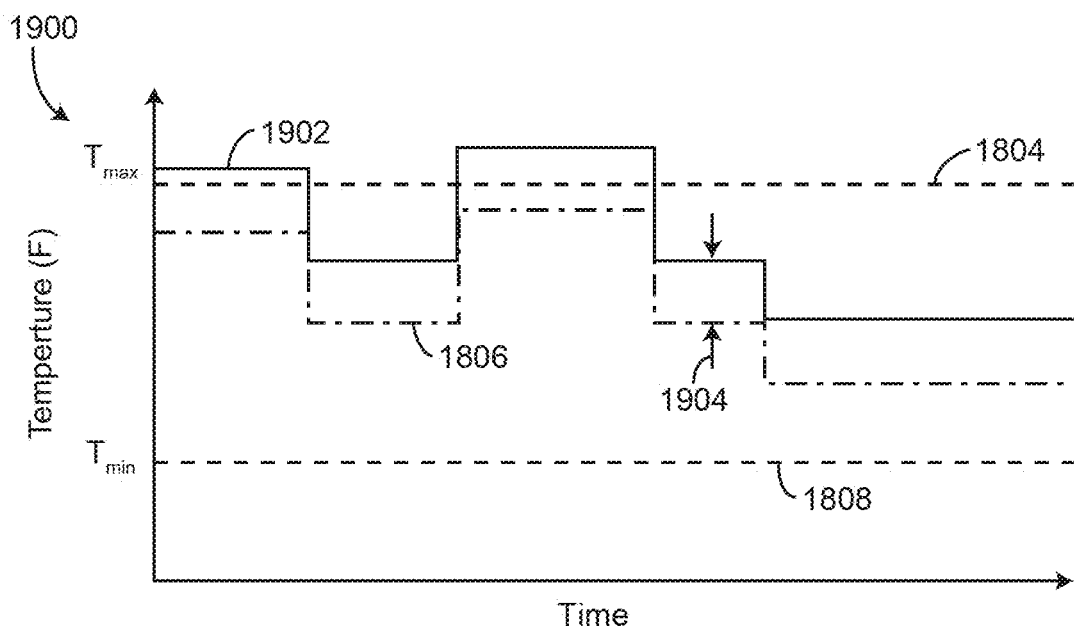
FIG. 19 is a graph illustrating an adjusted temperature setpoint for a zone over time as compared to zone group temperature setpoints, according to some embodiments.

Referring now to FIG. 19, a graph 1900 illustrating an adjusted temperature setpoint for a zone over time as compared to zone group temperature setpoints is shown, according to some embodiments. In some embodiments, graph 1900 is similar to and/or the same as graph 1800 described with reference to FIG. 19. Graph 1900 is shown to include a series 1902. Series 1902 may illustrate adjusted temperature setpoint values that account for occupant comfort based on zone group temperature setpoints originally provided by supervisory controller 1526. Based on the zone group temperature setpoints, values of series 1902 can be scaled and adjusted as to adhere to preferences of occupants in zone 1506. In some embodiments, series 1902 illustrates outputs of applying zone group temperature setpoints to the setpoint adjustment model generated by model generator 1714, effectively captured by the following equation:

$$T_{zn,sp,i} = \frac{T_{max,j,i} - T_{min,j,i}}{T_{max,j} - T_{min,j}}(T_{sp,g} - T_{min,j}) + T_{min,j,i}$$

where all variables are the same as described above with reference to FIG. 17.

In some embodiments, occupant setpoint adjustments indicate an occupant is uncomfortable with current environmental conditions (e.g., temperature, humidity, air quality, etc.). In some embodiments, the more frequent occupant setpoint adjustments occur and/or a magnitude of each occupant setpoint adjustment may indicate how uncomfortable an occupant is. For example, the magnitude and frequency of occupant setpoint adjustments can be related to a degree of occupant discomfort. In this way, frequent and large setpoint changes may indicate a higher degree of occupant discomfort, while less frequent and smaller setpoint changes may indicate a lower degree of occupant discomfort. These indications of occupant comfort can be utilized by model generator 1714 when generating a setpoint adjustment model used to maintain occupant comfort. Model generator 1714 can also utilize information provided by supervisory controller 1526 regarding the zone group to which zone 1506 belongs when generating the setpoint adjustment model. Using the setpoint adjustment model, zone temperature setpoints can be determined by scaling and adjusting the zone group temperature setpoints based on occupant preferences as illustrated by series 1902.

Graph 1900 is also shown to include a difference 1904 between series 1902 and series 1806. In some embodiments, difference 1904 illustrates the scaling and adjustment applied to series 1902 based on series 1806. If occupant preferences in zone 1506 are not reflected in zone group temperature setpoints provided by supervisory controller 1526 (i.e., values of series 1806), the zone group temperature setpoints should be modified for zone 1506 to meet the occupant preferences. As such, difference 1904 can illustrate an amount by which the zone group temperature setpoints need to be modified to meet the occupant preferences.

Figure 20:
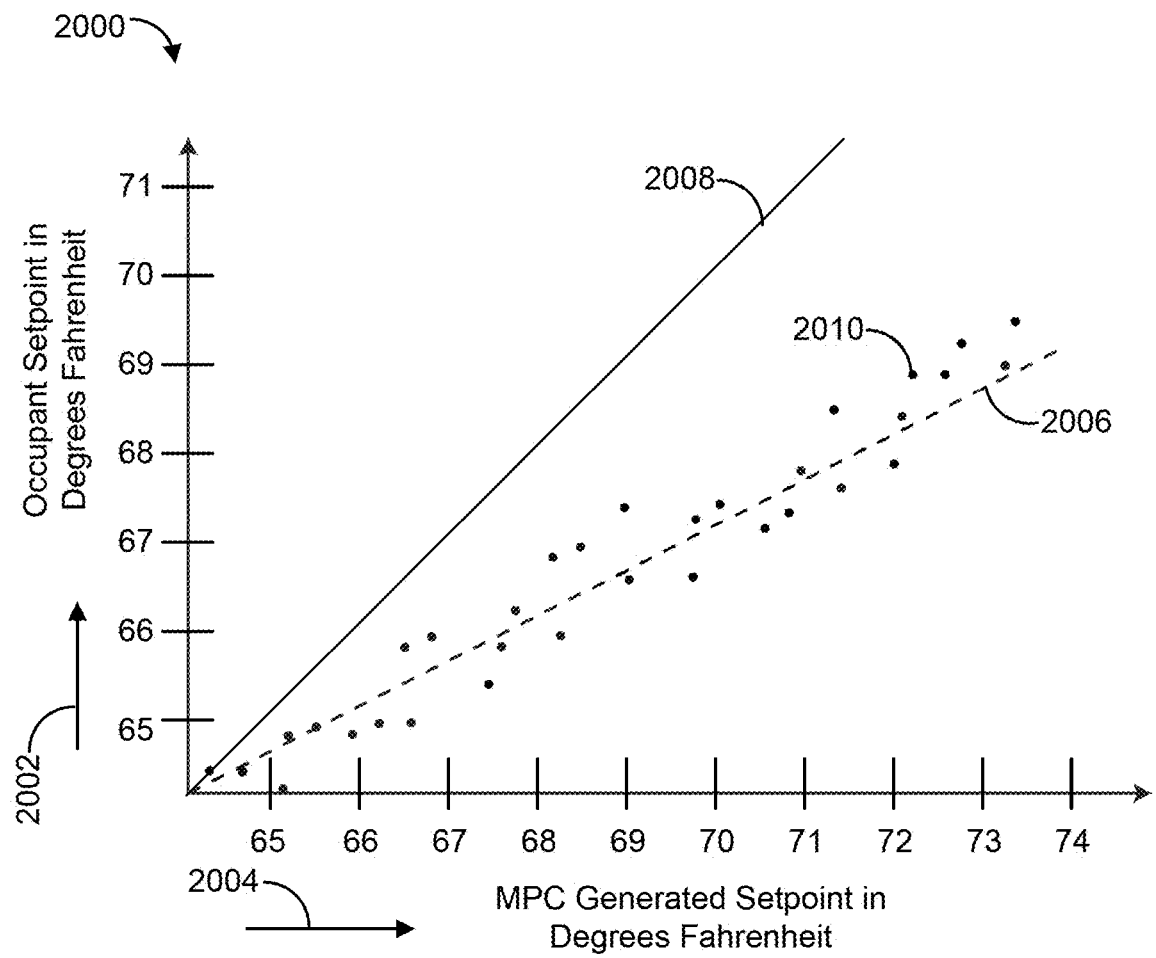
FIG. 20 is a graph illustrating a regression analysis between model predictive control generated setpoints and occupant setpoints, according to some embodiments.

Referring now to FIG. 20, a graph 2000 illustrating a regression analysis between MPC generated setpoints and occupant setpoints is shown, according to some embodiments. The occupant setpoints shown along a Y-axis 2002 can be determined based on occupant setpoint adjustments made over time for a specific zone (e.g., zone 1506). The MPC generated setpoints along an X-axis 2004 can be determined based on temperature setpoints for a zone group generated by MPC over time (e.g., by supervisory controller 1526). Graph 2000 can illustrate how occupant preferences may not align with setpoints generated for the zone group to which the specific zone belongs. Specifically, graph 2000 illustrates an embodiment where occupants may prefer a cooler temperature than determined by MPC.

Graph 2000 is shown to include points 2010. Each point 2010 represents how an occupant setpoint for the specific zone compares to a setpoint generated for the zone group by MPC. For example, a point 2010 may indicate an occupant setpoint for a particular time is 67° F. whereas an MPC generated setpoint is 70° F. for the zone group for the particular time. If enough points 2010 are determined, a regression analysis can be performed on determine a relationship between the occupant setpoints and the MPC generated zone group setpoints. As shown in graph 2000, a regression line 2006 is shown as a result of the regression analysis. Particularly, regression line 2006 is shown to have a slope of 0<slope<1. Purely for sake of example, we can assume the slope of regression line 2006 to be 0.6. Likewise, regression line 2006 can have a y-intercept, however the y-intercept is not shown due to graph 2000 illustrating temperatures starting at 65° F. Purely for sake of example, we can assume the y-intercept of regression line 2006 to be 21° F. As such, regression line 2006 can have the form of:

$$\text{Occupant}_{sp} = 0.6 \times T_{sp,g} + 21° \text{ F.}$$

where $\text{Occupant}_{sp}$ is a temperature setpoint comfortable for occupants and $T_{sp,g}$ is a setpoint generated by MPC for the zone group.

Regression line 2006 is shown to differ from a non-adjusted line 2008. Non-adjusted line 2008 may illustrate a model resulting from values of the weighting and offset being $w_i=1$ and $T_{offset,i}=0$. In other words, non-adjusted line 2008 can illustrate a model where the MPC generated setpoints are always the same as occupant setpoints. As such, non-adjusted line 2008 can illustrate a situation where temperature setpoints that optimize (e.g., reduce) costs also maximize occupant comfort.

Model generator 1714 can utilize regression line 2006 when generating a setpoint adjustment model. The setpoint adjustment model generated by model generator 1714 can utilize the slope and the y-intercept of regression line 2006 to model a temperature setpoint that is comfortable for occupants based on a zone group temperature setpoint. As described in greater detail above with reference to FIG. 17, model generator 1714 can generate a model reflecting $T_{zn,sp,i}=w_iT_{sp,g}+T_{offset,i}$ where the slope of regression line 2006 is $w_i$ and the y-intercept of regression line 2006 is $T_{offset,i}$.

Figure 21:
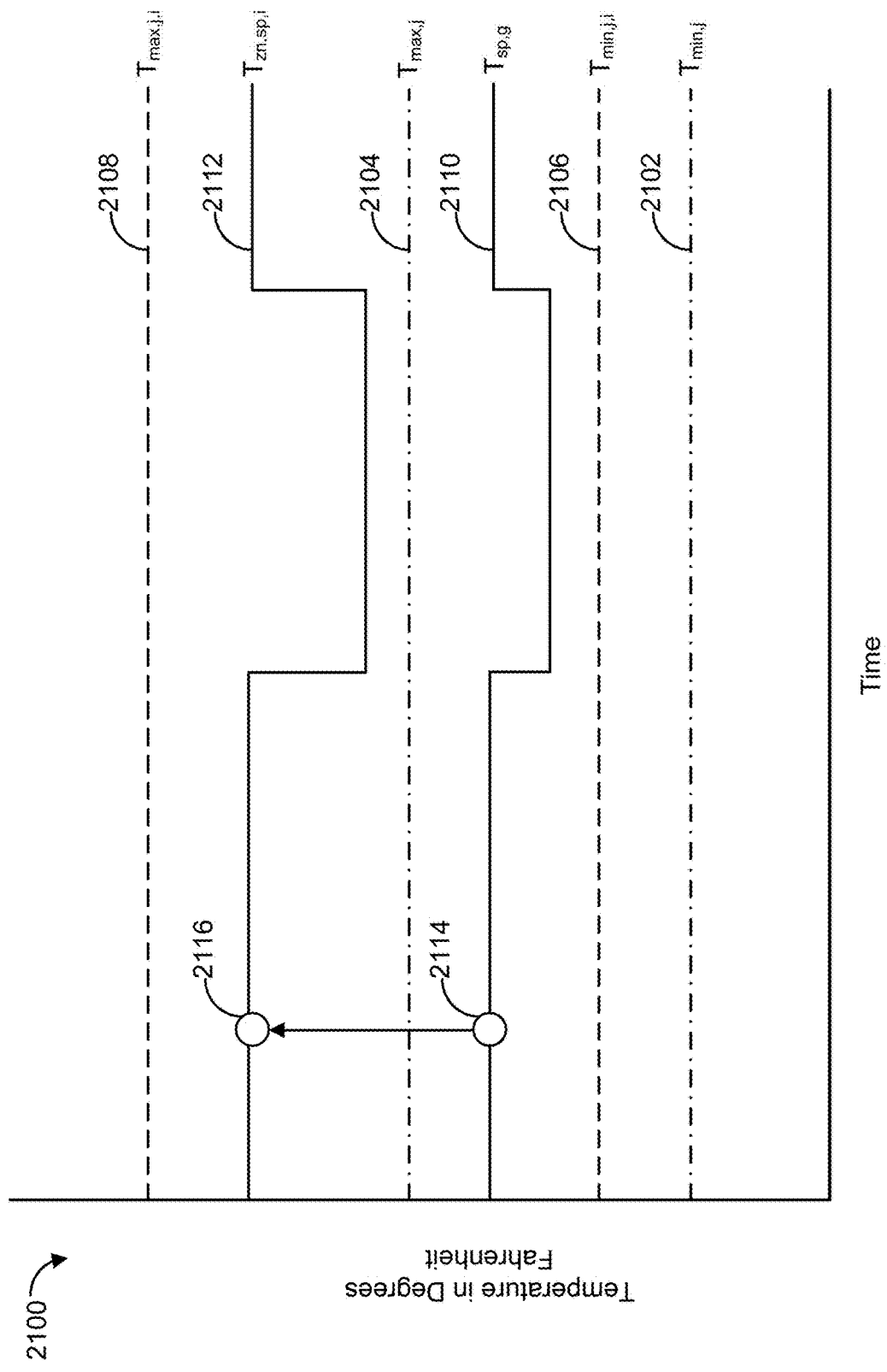
FIG. 21 is a graph illustrating how zone temperature setpoints can be scaled based on zone group temperature setpoints, according to some embodiments.

Referring now to FIG. 21, a graph 2100 illustrating how zone temperature setpoints can be scaled based on zone group temperature setpoints is shown, according to some embodiments. Graph 2100 is shown to include a minimum zone group temperature setpoint 2102 and a maximum zone group temperature setpoint 2104. Minimum zone group temperature setpoint 2102 and maximum zone group temperature setpoint 2104 can be received from supervisory controller 1526 based on MPC performed by supervisory controller 1526 for a zone group j. Graph 2100 is also shown to include a minimum zone temperature setpoint 2106 and a maximum zone temperature setpoint 2108. Minimum zone temperature setpoint 2106 and maximum zone temperature setpoint 2108 can be determined by comfortable range identifier 1718 based on occupant comfort data. Minimum zone temperature setpoint 2106 and maximum zone temperature setpoint 2108 can be determined based on a maximum and a minimum temperature setpoint that maintain occupant comfort as defined in greater detail above with reference to FIG. 17.

Graph 2100 is also shown to include a series 2110 and a series 2112. Series 2110 can illustrate zone group temperature setpoints over a time period. Series 2110 is shown to include a zone group temperature setpoint 2114 which is a particular value of series 2110 in the time period. Likewise, series 2112 can illustrate zone temperature setpoints over the time period. Series 2112 is shown to include a zone temperature setpoint 2116 which is a particular value of series 2112.

In some embodiments, a setpoint adjustment model generated by model generator 1714 accounts for a need to scale values if converting zone group temperature setpoints to zone temperature setpoints. In graph 2100, a difference between $T_{max,j,i}$ and $T_{min,j,i}$ is shown to be larger than a difference between $T_{max,j}$ and $T_{min,j}$. As such, the setpoint adjustment model may not be able to determine values of series 2112 as the setpoint adjustment model generated based on regression line 2006 as described with reference to FIG. 20. The setpoint adjustment model trained to determine values of series 2112 based on values of series 2110 may indicate the following relationship:

$$T_{zn,sp,i} = \frac{T_{max,j,i} - T_{min,j,i}}{T_{max,j} - T_{min,j}}(T_{sp,g} - T_{min,j}) + T_{min,j,i}$$

as described in greater detail above with reference to FIG. 17. In this way, the setpoint adjustment model can scale values of series 2110 to appropriately reflect the comfort range set by minimum zone temperature setpoint 2106 and maximum zone temperature setpoint 2108. More specifically, zone temperature setpoint 2116 can be determined by the above relationship by utilizing zone group temperature setpoint 2114 and some and/or all of setpoints 2102-2110. It should be appreciated that graph 2100 is not drawn to scale.

Figure 22:
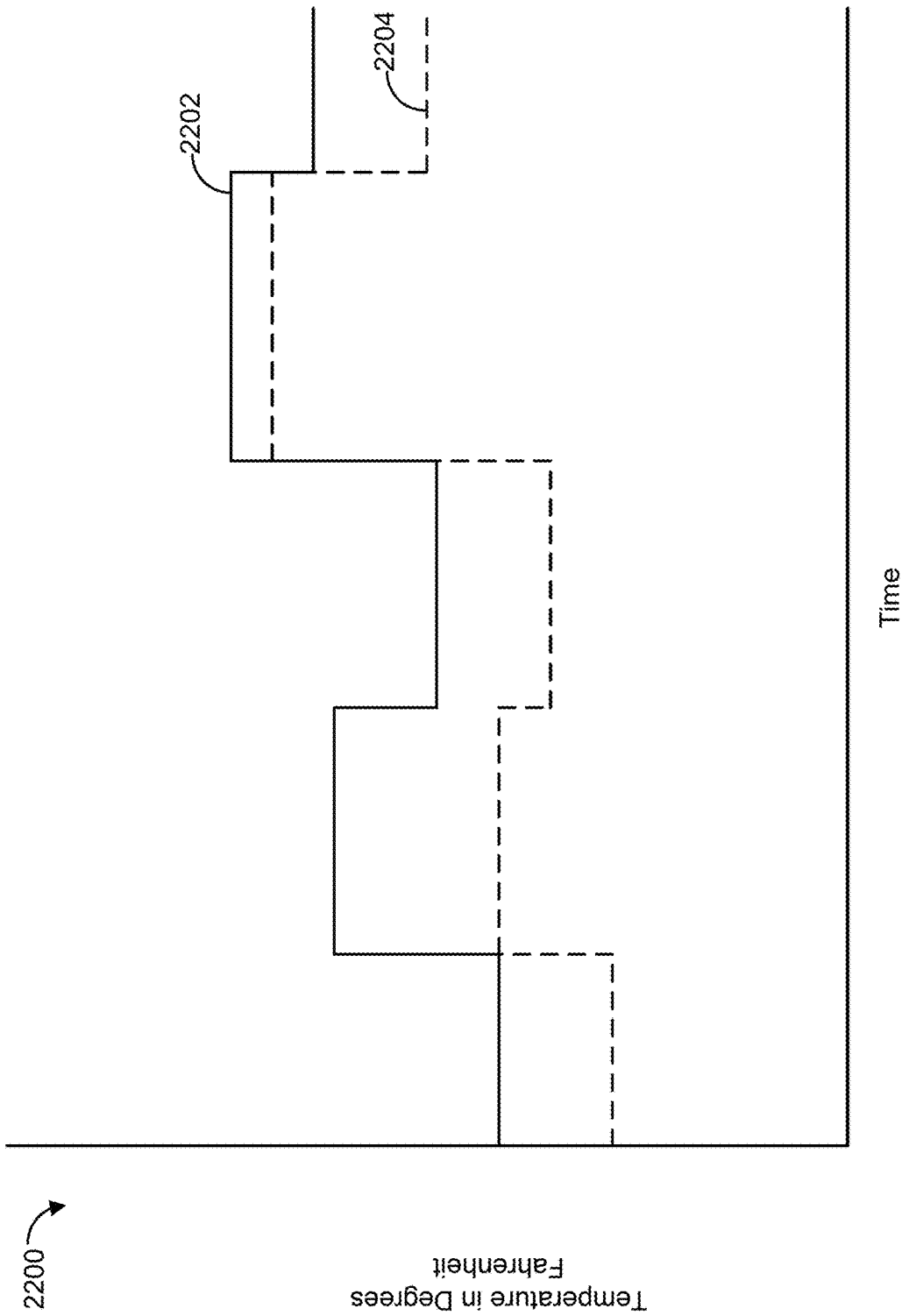
FIG. 22 is a graph illustrating how zone group temperature setpoints and zone temperature setpoints may differ, according to some embodiments.

Referring now to FIG. 22, a graph 2200 illustrating how zone group temperature setpoints and zone temperature setpoints may differ is shown, according to some embodiments. Graph 2200 is shown to include a series 2202 and a series 2204. Series 2202 illustrates zone group temperature setpoints over time as generated by supervisory controller 1526. Series 2204, however, illustrates zone temperature setpoints generated by setpoint adjustment manager 1716 based on a setpoint adjustment model provided by model generator 1714.

Graph 2200 illustrates how zone group temperature setpoints may not maintain adequate levels of occupant comfort. If the zone group temperature setpoints were to maintain adequate levels of occupant comfort, series 2202 and series 2204 may be the same. However, as series 2202 and series 2204 are not the same, graph 2200 illustrates a need to adjust temperature setpoints for a zone group to temperature setpoints for a zone of the zone group. In some embodiments, series 2202 and series 2204 are similar to and/or the same as series 2110 and series 2112 as described with reference to FIG. 21 respectively.

Figure 23:
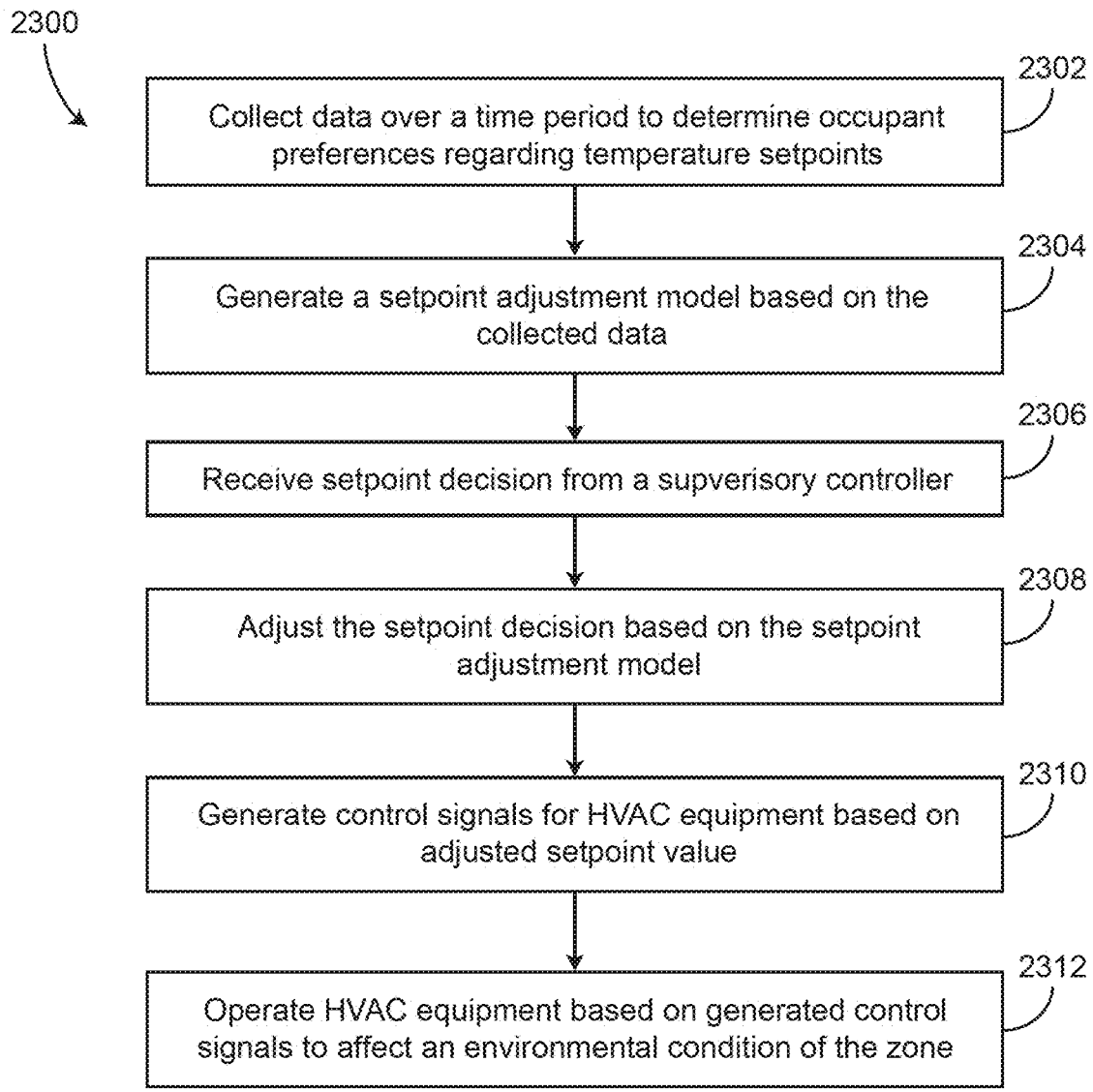
FIG. 23 is a flow diagram of a process for operating HVAC equipment to affect an environmental condition in a zone, according to some embodiments.

Referring now to FIG. 23, a process 2300 for operating HVAC equipment to affect an environmental condition in a zone is shown, according to some embodiments. Process 2300 can facilitate a supervisory controller (e.g., supervisory controller 1526) to maintain a comfortable air distribution throughout some and/or all of the zone in order to maintain occupant comfort. In some embodiments, a non-uniform temperature distribution can result in an occupant being uncomfortable in the zone. However, an environmental sensor in the zone may indicate an environmental condition meets a preference of the occupant if a location of the sensor is comfortable. As such, process 2300 can allow occupant comfort to be maintained by determining occupant preferences and how they correlate with conditions in the zone.

Process 2300 is shown to include collecting data over a time period to determine occupant preferences regarding temperature setpoints (step 2302), according to some embodiments. In some embodiments, the collected data indicates an occupant desired minimum zone temperature and an occupant desired maximum zone temperature that still maintain occupant comfort. Based on the minimum and maximum occupant desired zone temperatures, a temperature setpoint in the zone can be restricted from falling below the occupant desired minimum zone temperature or exceeding the occupant desired maximum zone temperature. The occupant desired minimum zone temperature and the occupant desired maximum zone temperature can be gathered, for example, by polling occupants, by monitoring setpoint adjustments made by occupants, by monitoring and recording occupant reactions to setpoints, etc. In some embodiments, the collected information is utilized to generate a setpoint adjustment model modeling occupant comfort in the zone. In some embodiments, step 2302 is performed by data collector 1712 and/or comfortable range identifier 1718.

Process 2300 is shown to include generating a setpoint adjustment model based on the collected data (step 2304), according to some embodiments. The setpoint adjustment model generated in step 2304 can be any model useful for determining if setpoint adjustments should be made. For example, the setpoint adjustment model may be a neural network model. To generate the setpoint adjustment model, the data collected in step 2302 can be used as training data. For example, if an occupant is frequently adjusting a temperature setpoint of the zone, the occupant may be uncomfortable provided current temperature setpoints. The setpoint adjustment model can be generated based on knowledge that the occupant frequently adjusts the temperature setpoint. Based on the setpoint adjustment model, adjusted zone setpoints can be generated to better maintain occupant comfort going forward in comparison to the current temperature setpoints. In some embodiments, step 2304 is performed by model generator 1714.

Process 2300 is shown to include receiving a setpoint decision from a supervisory controller (step 2306), according to some embodiments. In some embodiments, the setpoint decision is a setpoint value for a zone group that is provided to all zones in the zone group. In some embodiments, the setpoint decision is based on a cost optimization, such that the setpoint decision reduces costs for maintaining occupant comfort in the zone group. In some embodiments, step 2306 is performed by supervisory controller 1526 and/or data collector 1712.

Process 2300 is shown to include adjusting the setpoint decision based on the setpoint adjustment model (step 2308), according to some embodiments. In some embodiments, the setpoint decision is adjusted to result in an adequate level of occupant comfort in the zone. As the setpoint decision received in step 2306 is not guaranteed to maintain occupant comfort in the zone, the setpoint adjustment model can adjust the setpoint decision based on occupant preferences trained into the setpoint adjustment model. In some embodiments, the adjusted setpoint value is constrained by the minimum and maximum occupant desired zone temperatures determined in step 2302. As such, the adjusted setpoint value may be required to be within a range set by the minimum and maximum occupant desired zone temperatures. In some embodiments, the adjusted setpoint value is determined based on an output of the setpoint adjustment model. In some embodiments, the adjusted setpoint value is determined based on an MPC process utilizing various outputs of the setpoint adjustment model expected to maintain occupant comfort in the zone. If the adjusted setpoint value is determined based on the MPC process, the adjusted setpoint value may maintain occupant comfort and optimize costs related to operating building equipment affecting environmental conditions of the zone. In some embodiments, step 2308 is performed by setpoint adjustment manager 1716.

Process 2300 is shown to include generating control signals for HVAC equipment based on the adjusted setpoint value (step 2310), according to some embodiments. The control signals may include information such as, for example, the adjusted setpoint value to operate the HVAC equipment to achieve, what HVAC devices should be operated, how to operate said HVAC devices, when to operate said HVAC devices, etc. Advantageously, the control signals can operate the HVAC equipment such that an adequate level of occupant comfort is maintained such that occupants are not uncomfortable. Further, the control signals can reduce costs related to operating the HVAC equipment such that the HVAC equipment is operated enough to maintain occupant comfort without consuming excessive resources to do so. In some embodiments, step 2310 is performed by equipment controller 1720.

Process 2300 is shown to include operating HVAC equipment based on the generated control signals to affect an environmental condition of the zone (step 2312), according to some embodiments. By operating the HVAC equipment based on the generated control signals, an adequate level of occupant comfort can be achieved. For example, the control signals may operate a heater of the HVAC equipment in order to increase a temperature in the zone. In some embodiments, the HVAC equipment is operated to achieve the adjusted setpoint value determined in step 2308. By operating the HVAC equipment to achieve the adjusted setpoint value, occupant comfort can be maintained and costs may be optimized (e.g., reduced). In some embodiments, step 2312 is performed by HVAC equipment 1524.

Figure 24:
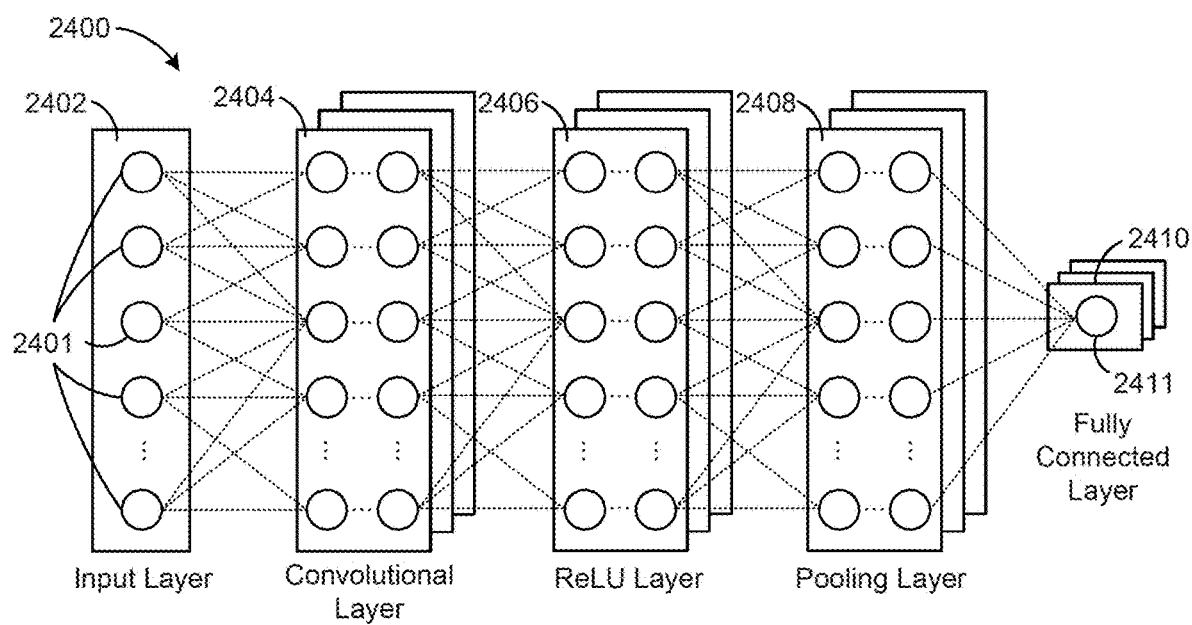
FIG. 24 is a block diagram of a convolutional neural network, according to some embodiments.

Referring now to FIG. 24, an example of a CNN 2400 is shown, according to an exemplary embodiment. CNN 2400 is shown to include a sequence of layers including an input layer 2402, a convolutional layer 2404, a rectified linear unit (ReLU) layer 2406, a pooling layer 2408, and a fully connected layer 2410 (i.e., an output layer). Each of layers 2402-2410 may transform one volume of activations to another through a differentiable function. Layers 2402-2410 can be stacked to form CNN 2400. Unlike a regular (i.e., non-convolutional) neural network, layers 2402-2410 may have neurons arranged in 3 dimensions: width, height, depth. The depth of the neurons refers to the third dimension of an activation volume, not to the depth of CNN 2400, which may refer to the total number of layers in CNN 2400. Some neurons in one or more of layers of CNN 2400 may only be connected to a small region of the layer before or after it, instead of all of the neurons in a fully-connected manner. In some embodiments, the final output layer of CNN 2400 (i.e., fully connected layer 2410) is a single vector of class scores, arranged along the depth dimension.

In some embodiments, CNN 2400 is used to generate an optimal zone temperature setpoint for zone 1506 via MPC performed by setpoint adjustment manager 1716. The zone temperature setpoint can be used by equipment controller to generate one or more control signals to control HVAC equipment 1524. When setpoint adjustment manager 1716 determines an optimal zone temperature setpoint for zone 1506, the optimal zone temperature setpoint can be generated within constraints determined by comfortable range identifier 1718. Although these specific examples are discussed in detail, it should be understood that CNN 2400 can be used to generate models and any other constraints necessary to maintain occupant comfort in zone 1506.

Input layer 2402 is shown to include a set of input neurons 2401. Each of input neurons 2401 may correspond to a variable that can be collected by data collector 1712 and used as an input to CNN 2400. For example, input neurons 2401 may correspond to variables such as outdoor air temperature (OAT) (e.g., a temperature value in degrees F. or degrees C.), the day of the week (e.g., 1=Sunday, 2=Monday, . . . , 7=Saturday), the day of the year (e.g., 0=January 1st, 1=January 2nd, . . . , 365=December 31st), a binary occupancy value for a building zone (e.g., 0=unoccupied, 1=occupied), a percentage of occupancy for the building zone (e.g., 0% if the building zone is unoccupied, 30% of the building zone is at 30% of maximum occupancy, 100% of the building zone is fully occupied, etc.), a measured temperature of zone 1506 (e.g., a temperature value in degrees F. or degrees C.), occupant comfort levels (e.g., ratings on a 0 to 5 scale collected via user device 1710), or any other variable that may be relevant to generating an appropriate comfort range.

Convolutional layer 2404 may receive input from input layer 2402 and provide output to ReLU layer 2406. In some embodiments, convolutional layer 2404 is the core building block of CNN 2400. The parameters of convolutional layer 2404 may include a set of learnable filters (or kernels), which have a small receptive field, but extend through the full depth of the input volume. During the forward pass, each filter may be convolved across the width and height of the input volume, computing the dot product between the entries of the filter and entries within input layer 2402 and producing a 2-dimensional activation map of that filter. As a result, CNN 2400 learns filters that activate when it detects some specific type of feature indicated by input layer 2402. Stacking the activation maps for all filters along the depth dimension forms the full output volume of convolutional layer 2404. Every entry in the output volume can thus also be interpreted as an output of a neuron that looks at a small region in input layer 2402 and shares parameters with neurons in the same activation map. In some embodiments, CNN 2400 includes more than one convolutional layer 2404.

ReLU layer 2406 may receive input from convolutional layer 2404 and may provide output to fully connected layer 2410. ReLU is the abbreviation of Rectified Linear Units. ReLu layer 2406 may apply a non-saturating activation function such as $f(x)=\max(0,x)$ to the input from convolutional layer 2404. ReLU layer 2406 may function to increase the nonlinear properties of the decision function and of the overall network without affecting the receptive fields of convolutional layer 2404. Other functions can also be used in ReLU layer 2406 to increase nonlinearity including, for example, the saturating hyperbolic tangent $f(x)=\tan h(x)$ or $f(x)=|\tan h(x)|$ and the sigmoid function $f(x)=(1+e^{-x})^{-1}$. The inclusion of ReLU layer 2406 may cause CNN 2400 to train several times faster without a significant penalty to generalization accuracy.

Pooling layer 2408 may receive input from ReLU layer 2406 and provide output to fully connected layer 2410. Pooling layer 2408 can be configured to perform a pooling operation on the input received from ReLU layer 2406. Pooling is a form of non-linear down-sampling. Pooling layer 2408 can use any of a variety of non-linear functions to implement pooling, including for example max pooling. Pooling layer 2408 can be configured to partition the input from ReLU layer 2406 into a set of non-overlapping sub-regions and, for each such sub-region, output the maximum. The intuition is that the exact location of a feature is less important than its rough location relative to other features.

Pooling layer 2408 serves to progressively reduce the spatial size of the representation, to reduce the number of parameters and amount of computation in the network, and hence to also control overfitting. Accordingly, pooling layer 2408 provides a form of translation invariance.

In some embodiments, pooling layer 2408 operates independently on every depth slice of the input and resizes it spatially. For example, pooling layer 2408 may include filters of size 2×2 applied with a stride of 2 down-samples at every depth slice in the input by 2 along both width and height, discarding 75% of the activations. In this case, every max operation is over 4 numbers. The depth dimension remains unchanged. In addition to max pooling, pooling layer 2408 can also perform other functions, such as average pooling or L2-norm pooling.

In some embodiments, CNN 2400 includes multiple instances of convolutional layer 2404, ReLU layer 2406, and pooling layer 2408. For example, pooling layer 2408 may be followed by another instance of convolutional layer 2404, which may be followed by another instance of ReLU layer 2406, which may be followed by another instance of pooling layer 2408. Although only one set of layers 2404-2408 is shown in FIG. 24, it is understood that CNN 2400 may include one or more sets of layers 2404-2408 between input layer 2402 and fully connected layer 2410. Accordingly, CNN 2400 may be an "M-layer" CNN, where M is the total number of layers between input layer 2402 and fully connected layer 2410.

Fully connected layer 2410 is the final layer in CNN 2400 and may be referred to as an output layer. Fully connected layer 2410 may follow one or more sets of layers 2404-2408 and may be perform the high-level reasoning in CNN 2400. In some embodiments, output neurons 2411 in fully connected layer 2410 may have full connections to all activations in the previous layer (i.e., an instance of pooling layer 2408). The activations of output neurons 2411 can hence be computed with a matrix multiplication followed by a bias offset. In some embodiments, output neurons 2411 within fully connected layer 2410 are arranged as a single vector of class scores along the depth dimension of CNN 2400.

In some embodiments, each of output neurons 2411 represents a threshold value (e.g., a boundary value, a boundary range around a setpoint, etc.) which can be used to formulate the zone temperature setpoint by setpoint adjustment manager 1716. For example, one or more of output neurons 2411 may represent possible zone temperature setpoints for zone 1506. The possible zone temperature setpoints can be used by setpoint adjustment manager 1716 to generate an optimal zone temperature setpoint for zone 1506.

In some embodiments, model generator 1714 utilizes training data from sources such as manual adjustments to setpoints made by occupants, experiments on setpoints, and/or occupant voting regarding comfort levels to determine accuracy of a setpoint adjustment model generated by CNN 2400. If the training data indicates the setpoint adjustment model generated by CNN 2400 maintains adequate levels of occupant comfort, CNN 2400 may be reinforced, such that the reinforcement indicates a current setpoint adjustment model accurately models occupant comfort in zone 1506. However, if the comfort data indicates the setpoint adjustment model generated by CNN 2400 does not maintain adequate levels of occupant comfort, CNN 2400 may be updated and/or regenerated to provide a more accurate setpoint adjustment model.

Disinfection Control Subsystem

Figure 25A:
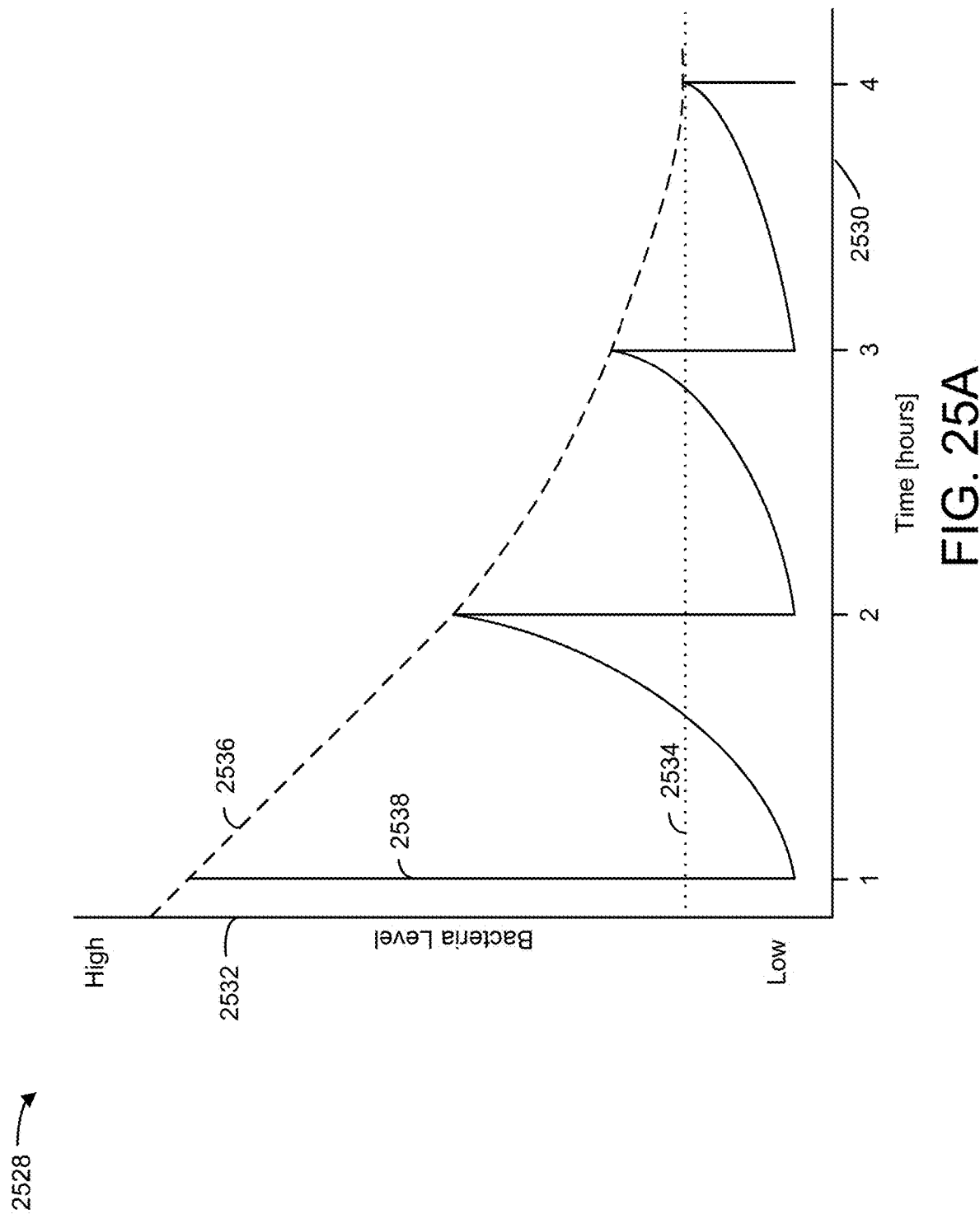
FIG. 25A is a graph illustrating the bacteria levels over time based on different disinfection operations, according to some embodiments.

Referring now to FIG. 25A, a bacteria level graph 2528 is shown illustrating bacteria growth over time based on different disinfection operations, according to some embodiments. Bacteria level graph 2528 includes time on the horizontal axis 2530, according to some embodiment. The use of a time scale in hours is intended for exemplary purposes only and is not intended to be limiting. It should be understood that the time scale (e.g., seconds, minutes, hours, days) illustrated on the horizontal axis 2530 may depend on individual disinfection system parameters, user preferences, and/or other data which is collected for use in disinfection operations.

Bacteria level graph 2528 is also shown to include bacteria level corresponding to a percentage of bacteria eliminated on the vertical axis 2532, according to some embodiments. In some embodiments, the bacteria levels on the vertical axis 2532 range from a low level of bacteria to a high level. In such embodiments, the low level of bacteria corresponds to a higher percentage of bacteria eliminated relative the percentage of bacteria eliminated at the low level. The threshold line 2534 represents a predetermined percentage of bacteria eliminated which a controller (e.g., a controller included in disinfection subsystem 450, BMS controller 366, etc.) determines control commands for various disinfection mechanisms to achieve such a percentage of bacteria removed. As such the percentage defined by the threshold line 2534 is configurable based on user preference, disinfection parameters, information retrieved from a health authority information source, etc.

Continuous disinfection operation 2536 represents the percentage of bacteria removed over time based on a disinfection operation configured to continuously perform a disinfection operation, according to some embodiments. In some embodiments, and as will be described in greater detail below, the results of continuous disinfection operation 2536 are achieved by a visible light disinfection operation. As such, due to visible light disinfection operations being substantially harmless relative ultraviolet disinfection operations, it is advantageous to continuously operate visible light disinfection operations to provide a continuous disinfection to a space, surface, etc.

Episodic disinfection operation 2538 represented the percentage of bacteria removed over time based on a disinfection operation configured to intermittently perform a disinfection operation, according to some embodiments. In some embodiments, and as will be described in greater detail below, the results of episodic disinfection operation 2538 are achieved by an ultraviolet disinfection operation. As such, due to ultraviolet disinfection operations being potentially harmful to occupants present during an ultraviolet disinfection operation, it is advantageous to perform such disinfection operations while occupants are absent an area to which the disinfection operation is applied. In some embodiments, and as will be described in greater detail below, the intervals at which the episodic disinfection operation 2538 is applied depends on HVAC schedules. For example, an ultraviolet disinfection cycle may be applied at the same time an AHU is operating.

Both continuous disinfection operation 2536 and episodic disinfection operation 2538 are shown to level at approximately the percentage defined by the threshold line 2534, according to some embodiments. As such, the control commands determined by a controller operating to control the corresponding mechanisms respectively associated with continuous disinfection operation 2536 and episodic disinfection operation 2538 are determined in part based on the percentage defined by the threshold line 2534, according to some embodiments.

Figure 25B:
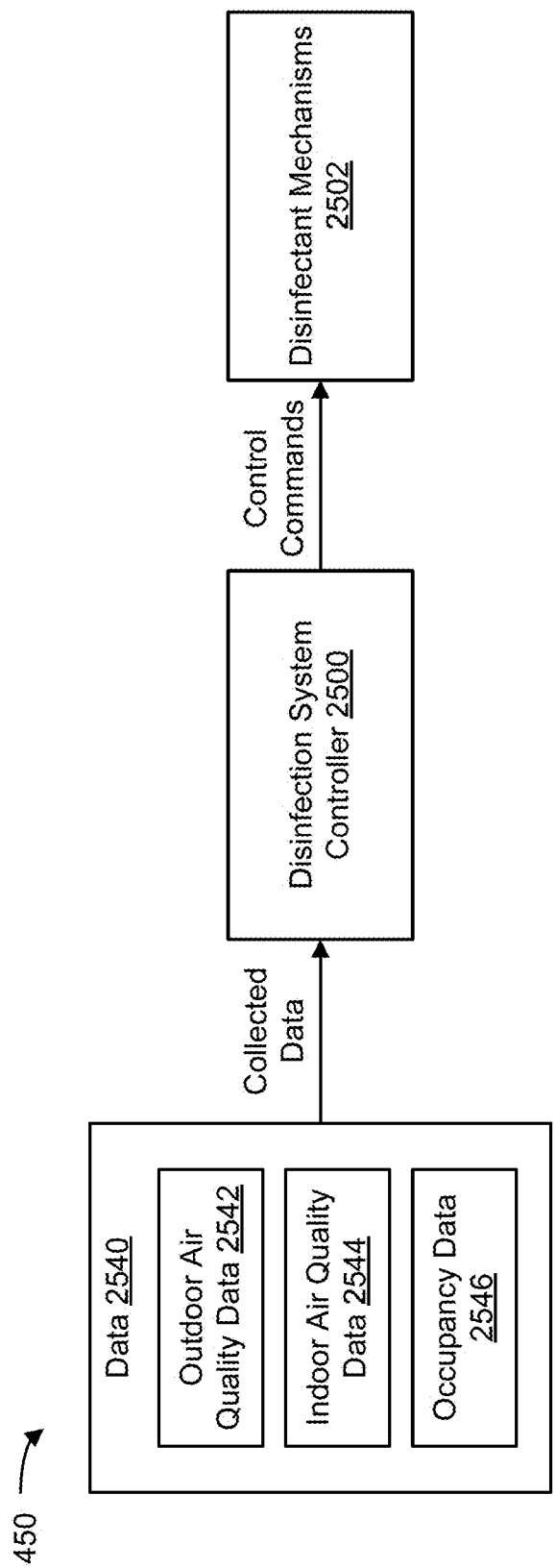
FIG. 25B is a block diagram illustrating a disinfection subsystem, according to some embodiments.

Referring now to FIG. 25B, a block diagram illustrating a high-level overview of disinfection subsystem 450 is shown, according to some embodiments. Disinfection subsystem 450 is shown to include a disinfection system controller 2500 configured to receive collected data from data 2540 and generate control commands for disinfectant mechanisms 2502, according to some embodiments. In some embodiments, disinfection system controller 2500 continuously processes the collected data from data 2540 to optimize the disinfection operations performed by disinfectant mechanisms 2502.

The collected data provided to disinfection system controller 2500 by data 2540 is shown to include outdoor air quality data 2542, indoor air quality data 2544, and occupancy data 2546, according to some embodiments. Outdoor air quality data 2542 corresponds to the air quality of the environment outside a building. As such, the outdoor air quality data 2542 may correspond to a neighborhood in which a particular building is located, a town, a county, etc. Indoor air quality data 2544 corresponds to the air quality of the air within a building in which disinfection subsystem 450 is implemented, according to some embodiments. In some embodiments occupancy data 2546 corresponds to the number of people present in one or more spaces at a given point in time. In some embodiments, data 2542 includes additional data such as, but not limited to, user inputs, security subsystem data (e.g., door lock schedule), fire safety subsystem, etc. Each of the data may be collected by sensors included in the disinfectant mechanisms 2502, BMS 400, and/or external, standalone devices, according to some embodiments. In some embodiments, the data is collected from an external source. For example, outdoor air quality data 2542 may be provided by a weather agency.

As will be described in greater detail below, disinfection system controller 2500 uses the collected data to determine the control commands which operation disinfectant mechanisms 2502. In some embodiments, disinfection system controller 2500 generates control commands based on HVAC cycles. For example, as previously described, disinfection system controller 2500 generates control commands to operate an HVAC disinfection system based on when the associated HVAC system is operating.

Disinfection subsystem 450, as well as BMS 400 more generally, can be configured to model the probability of infectious disease spread within building 10. For example, probability of infection spread within a building can be determined based on a number of factors, including occupancy data, the quanta generation rate of the infectious disease, a clean air ventilation rate, and other factors. The Wells-Riley equation can be used to model probability of infection spread, for example, and is denoted as follows:

$$P_{infection} = \frac{cases}{susceptibles} = 1 - e^{-Iqpt/V_{clean}}$$

In the Wells-Riley equation, the variable "cases" represents the number of infected individuals in the building, the variable "susceptibles" represents the number of susceptible individuals in the building, the variable "I" represents the number of infector individuals, the variable "p" represents the pulmonary ventilation rate of an individual (typically about 0.38 m³/hour), the variable "q" represents the quanta generation rate of the infectious disease (1/hour-person), the variable "t" represents exposure time (hours), and the variable "$V_{clean}$" represents a clean air ventilation rate associated with a building space (m³/hour).

The ability to model probability spread using approaches such as Wells-Riley and other approaches can facilitate improvements in terms of preventing infectious disease spread within buildings. As discussed above, visualizations of health risks such as heat maps and other visualizations can be generated to both assist individuals in safely navigating through the building as well as directing targeted actions to minimize health risks. It should be noted that use of infection controls such as disinfection subsystem 450 can reduce health risks, but can also lead to increased energy costs. BMS 400 can be configured to allow users to provide inputs regarding the balance between reducing health risks and reducing energy costs. For example, users can assign a first weighting to denote the importance of reducing health risks and a second weight to denote the importance of reducing energy consumption. To assist in this process, various scores can be developed based on predetermined rules, learning models trained with historical data, etc. to provide grades for buildings with respect to health risks and energy consumption. Heat maps and air quality maps as discussed above can also be used to minimize health risks and probability of infection spread.

Figure 25C:
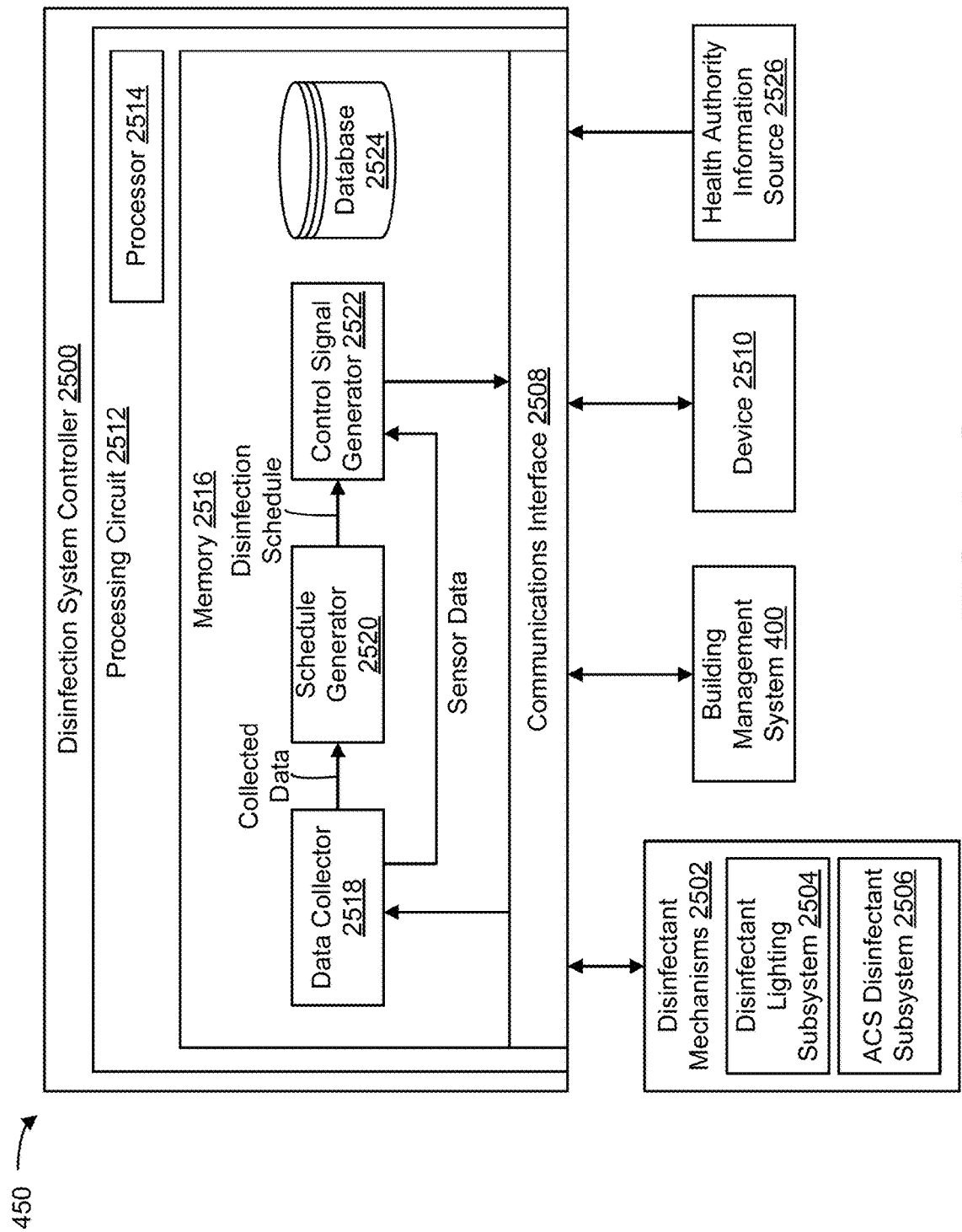
FIG. 25C is a block diagram of a disinfection subsystem controller which can be used to control various disinfectant mechanisms, according to some embodiments.

Referring now to FIG. 25C, a block diagram illustrating the disinfection subsystem 450 in greater detail is shown, according to some embodiments. Disinfection subsystem 450 may be implemented in a building (e.g., building 100) to automatically monitor and/or control various disinfectant mechanisms. Disinfection subsystem 450 is shown to include a disinfection system controller 2500 and a plurality of disinfectant mechanisms 2502 configured to perform one or more disinfection techniques, according to some embodiments. Disinfectant mechanisms 2502 are shown to include a disinfectant lighting subsystem 2504 and an access control system (ACS) disinfectant subsystem 2506. In some embodiments, disinfectant mechanisms 2502 can include fewer, additional, or alternative mechanisms configured to perform one or more disinfection techniques. For example, disinfectant mechanisms 2502 may also, or alternatively, include an aerosol mechanism configured to apply (e.g., spray) a disinfectant aerosol to one or more spaces included in a building. Although disinfection system controller 2500 is shown as a discrete controller, it should be understood that the control activities performed by disinfection system controller 2500 may alternatively be performed by BMS controller 366 such that BMS controller 366 controls the disinfectant mechanisms 2502. Additionally, although reference made herein is associated with a system, the methods and components disclosed herein may be associated with a subsystem. Thus, any reference made to a system may also be made to a subsystem.

Each of disinfectant mechanisms 2502 may include any number of devices, controllers, sensors, and connections for completing respective functions and control activities. For example, disinfectant lighting subsystem 2504 may include any number of lighting fixtures (e.g., LED, etc.), occupancy sensors, individual lighting fixture controllers, and other devices for controlling a disinfection technique within one or more spaces. Each of disinfectant mechanisms 2502 will be described in greater detail below. Disinfectant lighting subsystem 2504 can be configured to use a variety of different types of disinfectant lighting, including ultraviolet light (UV), far-UVC light, blue light (e.g. 405 nm), and other suitable disinfectant lighting can be used.

Disinfection system controller 2500 is shown to communicate with disinfectant mechanisms 2502 via a communications interface 2508. In some embodiments, communications interface 2508 facilitates communications between disinfection system controller 2500, disinfectant mechanisms 2502, BMS 400, and/or a device 2510. Communications interface 2508 can be or include any number of, or combination of, wired or wireless communications interfaces (e.g., jacks, antennas, transmitters, receivers, transceivers, wire terminals, etc.) for conducting data communications between disinfection system controller 2500, disinfectant mechanisms 2502, BMS 400, device 2510, and/or any other external systems or devices. In various embodiments, communication via communications interface 2508 may be direct (e.g., local wired or wireless communications) or via a communications network (e.g., a Wan, the Internet, a cellular network, etc.). For example, communications interface 2508 can include an Ethernet card and port for sending and receiving data via an Ethernet-based communications link or network. In another example, communications interface 2508 can include a WiFi transceiver for communicating via a wireless communications network. In yet another example, communications interface 2508 may include cellular or mobile phone communications transceivers.

In some embodiments, BMS 400 is implemented in the same building in which the disinfection subsystem 450 is implemented and may be configured to automatically monitor and control various building functions. As previously described, BMS 400 may include any number of, or combination of, building subsystems (e.g., HVAC subsystem, lighting subsystem, security subsystem, etc.). Within each building subsystem included in the BMS 400, any number of, or combination of devices, controllers, connections, and/or sensors may be provided to facilitate the functions and control activities of each individual building subsystem. In some embodiments, disinfection system controller 2500 communicates with any number of sensors included in the BMS 400 to facilitate the control of disinfectant mechanisms 2502. For example, disinfection system controller 2500 may receive data from an occupancy sensor provided by a security subsystem in BMS 400 in order to determine whether a control signal may be transmitted to disinfectant lighting subsystem 2504 to perform a disinfection process. In some embodiments, disinfection system controller 2500 communicates with one or more of the building subsystems 428. For example, disinfection system controller 2500 may transmit a lock request to security subsystem 438 in order to lock the doors to a particular one or more zones in which a disinfection technique will be performed.

In the embodiment illustrated in FIG. 25C, disinfection subsystem 450 includes a discrete control system separate from BMS 400 such that the devices, subsystems, and otherwise any other component included in disinfection subsystem 450 is not controlled by BMS 400. In some embodiments, various components included in disinfection subsystem 450 communicate with BMS 400 to provide pertinent data (e.g., occupancy, security, etc.) between each system. For example, BMS 400 may provide a security schedule (e.g., a schedule of locked spaces that are inaccessible to occupants) to disinfection system controller 2500 for use in determining a schedule of administering disinfectant processes by disinfectant mechanisms 2502. In another example, disinfection system controller 2500 may provide disinfectant data (e.g., a schedule of times at which one or more disinfectant processes are performed) to BMS 400 for use in determining a security schedule (e.g., a schedule to lock doors to one or more spaces in which the one or more disinfectant processes are occurring). In some embodiments, disinfection subsystem 450 is included as a building subsystem included in BMS 400 such that BMS 400 monitors and controls the functions, devices, and systems of disinfection subsystem 450.

Disinfection system controller 2500 is shown to communicate with a device 2510. In some embodiments, device 2510 includes a wireless sensor. For example, device 2510 may include wireless communications abilities and may be able to transmit measured data values to controller 2500. Device 2510 may be a wireless standalone sensor that is not part of another device. For example, device 2510 may be a wireless sensor hidden in a wall, attached to a light fixture, etc. and may be battery operated. In some embodiments, device 2510 is integrated with a subsystem of disinfectant mechanisms 2502. For example, device 2510 may be a sensor installed in a duct of disinfectant lighting subsystem 2504. Device 2510 may contain one or more of a variety of sensors (e.g., occupancy, air quality, air flow, temperature sensors, pressure sensors, etc.) used to monitor a building environment.

In some embodiments, device 2510 may be a smartphone or tablet allowing a user to customize, edit, or otherwise adjust various disinfection parameters (e.g., number of cycles, length of dosage, etc.) and/or view data. In other embodiments, device 2510 may be a laptop or desktop computer, and may not be wireless. Device 2510 may be any device which is capable of communication with disinfection system controller 2500 and is not limited to the explicitly enumerated devices. It is contemplated that device 2510 may communicate with disinfectant mechanisms 2502 directly. Disinfection system controller 2500 may transmit disinfection data to device 2510 for processing or analysis. Disinfection data may include any relevant data obtained from a component within the building or pertaining to a portion or subsystem of the disinfection subsystem 450. For example, disinfection data may be data from sensors, status control signals, feedback signals from a device, calculated metrics, setpoints, configuration parameters, etc.

Device 2510 may transmit control data to disinfection system controller 2500 in some embodiments. Control data may be any data which affects operation of the disinfection subsystem 450. In some embodiments, the control data specifies a duty cycle, a dose, a dosage schedule, and/or other parameters for disinfection operations. In some embodiments, control data may activate a disinfection technique performed by disinfectant mechanisms 2502 through disinfection system controller 2500. For example, device 2510 may send a signal with a command to enable disinfectant lighting fixtures of disinfectant lighting subsystem 2504. Device 2510 may receive disinfection data from disinfection system controller 2500 through communications interface 2508 for viewing/analysis by a user. In some embodiments, the device 2510 can provide control commands to an aerosol disinfectant system.

Still referring to FIG. 25C, disinfection system controller 2500 is shown to include a processing circuit 2512. Processing circuit 2512 includes a processor 2514 and memory 2516. Processor 2514 can be implemented as a general-purpose processor, an application specific integrated circuit (ASIC), one or more field programmable gate arrays (FPGAs), a group of processing components, or other suitable electronic processing components.

Memory 2516 (e.g., memory, memory unit, storage device, etc.) may include one or more devices (e.g., RAM, ROM, Flash memory, hard disk storage, etc.) for storing data and/or computer code for completing or facilitating the various processes, layers and modules described in the present application. Memory 2516 may be or include volatile memory or non-volatile memory. Memory 2516 may include database components, object code components, script components, or any other type of information structure for supporting the various activities and information structures described in the present application. According to an exemplary embodiment, memory 2516 is communicably connected to processor 2514 via processing circuit 2512 and includes computer code for executing (e.g., by processing circuit 2512 and/or processor 2514) one or more processes described herein.

In some embodiments, disinfection system controller 2500 is implemented within a single computer (e.g., one server, one housing, etc.). In various other embodiments, disinfection system controller 2500 may be distributed across multiple servers or computers (e.g., that can exist in distributed locations). For example, disinfection system controller 2500 may be implemented as part of a METASYS® brand building automation system, as sold by Johnson Controls Inc. In other embodiments, disinfection system controller 2500 may be a component of a remote computing system or cloud-based computing system configured to receive and process data from one or more disinfection management systems. For example, disinfection system controller 2500 may be implemented as part of a PANOPTIX® brand building efficiency platform, as sold by Johnson Controls Inc. In other embodiments, disinfection system controller 2500 may be a component of a subsystem level controller, a device controller, a field controller, a computer workstation, a client device, or any other system or device that receives and processes data.

Still referring to FIG. 25C, memory 2516 is shown to include a data collector 2518. In some embodiments, data collector 2518 is configured to receive data from various sources (e.g., sensors included in each of the plurality of disinfectant mechanisms 2502, sensors included in BMS 400, device 2510, and a health authority information source (HATS) 2526, etc.) and transmit received data between components of memory 2516. For example, data collector 2518 is shown to communicate collected data to a schedule generator 2520 for use by schedule generator 2520 to generate a disinfection schedule defining when and where disinfection cycles, parameters, and/or characteristics. In some embodiments, the disinfection system controller 2500 does not include schedule generator 2520. In such embodiments, data collector 2518 provides sensor data directly to the control signal generator 2522. Each of the components included in the disinfection system controller 2500 will be described in greater detail below.

Data collector 2518 may be configured to parse data received by disinfection system controller 2500. For example, a message containing multiple data values (e.g., measured values) may be received by disinfection system controller 2500. Data collector 2518 may be configured to parse the message and extract the multiple data values. Data collector 2518 may provide one value at a time to control signal generator 2522 and/or schedule generator 2520. In yet other embodiments, data collector 2518 may provide only values of a certain type to control signal generator 2522. For example, data collector 2518 may only provide measured values to control signal generator 2522. In some embodiments, data collector 2518 can work with control signal generator 2522 to optimize disinfection techniques (e.g., duration, energy use, cycles, or safety) based on inputs received at communications interface 2508.

Memory 2516 is also shown to include a schedule generator 2520, according to some embodiments. In some embodiments, schedule generator 2520 is configured to generate a disinfection schedule that can be used by control signal generator 2522 to determine times at which control actions for the disinfectant mechanisms 2502. The disinfection model generated by schedule generator 2520 can be any type of model including, for example, a neural network model. In some embodiments, schedule generator 2520 generates the disinfection model in response to a determination that a disinfection model does not exist, a current disinfection model should be replaced, etc. In some embodiments, a user provides an indication to schedule generator 2520 to generate the disinfection model (e.g., by starting a model training process).

Schedule generator 2520 is shown to receive training data from data collector 2518. The training data can include any information applicable to generating the disinfection model. For example, the training data may include occupancy data provided by sensors in disinfectant mechanisms 2502 and/or building management system 400, air quality data provided by sensors in disinfectant mechanisms 2502 and/or building management system 400, pathogen data provided by HAIS 2526, disinfection parameters provided by HAIS 2526, etc. Based on the collected training data, the schedule generator 2520 can generate a disinfection model correlating various data (e.g., occupancy, air quality, etc.) with disinfection parameters (e.g., light intensity, number of cycles, duration, etc.).

In some embodiments, schedule generator 2520 updates an existing disinfection model based on new training data. A new disinfection model may not need to be generated every time new training data is received. Instead, updating the disinfection model can ensure the new training data is account for without undergoing a computationally intensive model generation process. Schedule generator 2520 can use an existing disinfection model and new training data provided by data collector 2518 to update the existing disinfection model based on new information provided to data collector 2518. In some embodiments, the disinfection model generated by schedule generator 2520 becomes antiquated as time progresses if the disinfection model is not update. Updating the disinfection model can reflect changes in building 100, disinfection parameters provided by HAIS 2526, pathogen information provided by HAIS 2526, etc. to better disinfect one or more zones. For example, if there is an outbreak of a new strain of influenza and the disinfection model is not updated, control signal generator 2522 may not generate control signals with adequate disinfection parameters. As such, schedule generator 2520 can update the disinfection model as needed to ensure that control signal generator 2522 generates control signals with adequate disinfection parameters. In some embodiments, model generator 2520 automatically updates the disinfection model as needed. In some embodiments, a user can indicate that model generator 2520 should update the disinfection model.

Still referring to FIG. 25C, the control signal generator 2522 is shown to receive a disinfection model from model generator 2520, according to some embodiments. Based on the disinfection model, control signal generator 2522 can generate control signals for disinfectant mechanisms 2502. The control signals generated by control signal generator 2522 can operate particular devices of disinfectant mechanisms 2502 in order to provide adequate disinfection to one or more zones in a building. In some embodiments, control signal generator 2522 receives sensor data from data collector 2518. In such embodiments, control signal generator 2522 performs a feedback control process to generate control signals for disinfectant mechanisms 2502. Control signal generator 2522 can communicate the control signals to disinfectant mechanisms 2502 via communications interface 2508. If the control signals are received, devices of disinfectant mechanisms 2502 can operate based on the control signals to perform various disinfection techniques.

In some embodiments, control signal generator 2522 uses any of a variety of model-based control methodologies (e.g., state-based algorithms, extremum seeking control (ESC) algorithms, proportional-integral (PI) control algorithms, proportional-integral-derivative (PID) control algorithms, model predictive control (MPC) algorithms, feedback control algorithms, etc.) to generate control signals for disinfectant mechanisms 2502. In some embodiments, the control signals generated by control signal generator 2522 include commands to operate disinfectant mechanisms 2505. In some embodiments, control signal generator 2522 generates control signals for other systems not associated with disinfection subsystem 450 (e.g., BMS 400 and/or BMS subsystems). For example, control signal generator 2522 may generate a control signal for disinfectant lighting subsystem 2504 to perform a disinfection technique in a particular space and may also generate a control signal for a security subsystem included in BMS 400 such that the security subsystem included in BMS 400 locks one or more doors that access the particular space while disinfectant lighting subsystem 2504 performs the disinfection process.

Memory 2516 is also shown to include a database 2524 configured to store data (e.g., data received from disinfectant mechanisms 2502, device 2510, BMS 400, HAIS 2526, etc.), according to some embodiments. In some embodiments, database 2524 is a memory bank of memory 2516 configured to store healthcare data collected from HAIS 2526, disinfection technique data collected from the disinfectant mechanisms 2502 (e.g., process duration, number of disinfection techniques conducted over a given period, etc.), and any other type of data useful for the operation and/or monitoring of the disinfection subsystem 450. In some embodiments, a user can access the data stored in database 2524 via device 2510. In some embodiments, the data stored in database 2524 is accessible by HAIS 2526.

Disinfection controller 2500 is also shown to communicate with a health authority information source (HATS) 2526, according to some embodiments. In general, HAIS 2526 provides healthcare data used to adjust disinfection parameters of the disinfection techniques performed by the disinfectant mechanisms 2502. Examples of disinfection parameters may include specified wavelengths of germicidal light waves, duration of disinfection techniques, frequency of technique performances, light intensity of the germicidal light waves, etc. HAIS 2526 can also provide data regarding spread of infectious disease, such as quanta generation rates of various infectious diseases, data regarding individuals who have been infected and/or tested for infectious diseases, recommended treatments and procedures regarding the infectious disease, and other types of data related to infectious diseases. In some embodiments, the data collector 2518 collects healthcare data received from HAIS 2526 as part of training data transmitted to model generator 2520. In some embodiments, the HAIS 2526 is the Centers for Disease Control. In some embodiments, HAIS 2526 is the World Health Organization. In some embodiments, the HAIS 2526 is any healthcare data source from which healthcare data is collected. Exemplary healthcare data collected from HAIS 2526 and implementation of the healthcare data will be explained in greater detail with reference to each of disinfectant mechanisms 2502. Advantageously, by communicating with and collecting healthcare data from HAIS 2526, the components included in disinfection subsystem 44 can perform disinfection techniques with an optimal number of cycles, duration, and wavelength of light.

Disinfectant Lighting Subsystem

Figure 26:
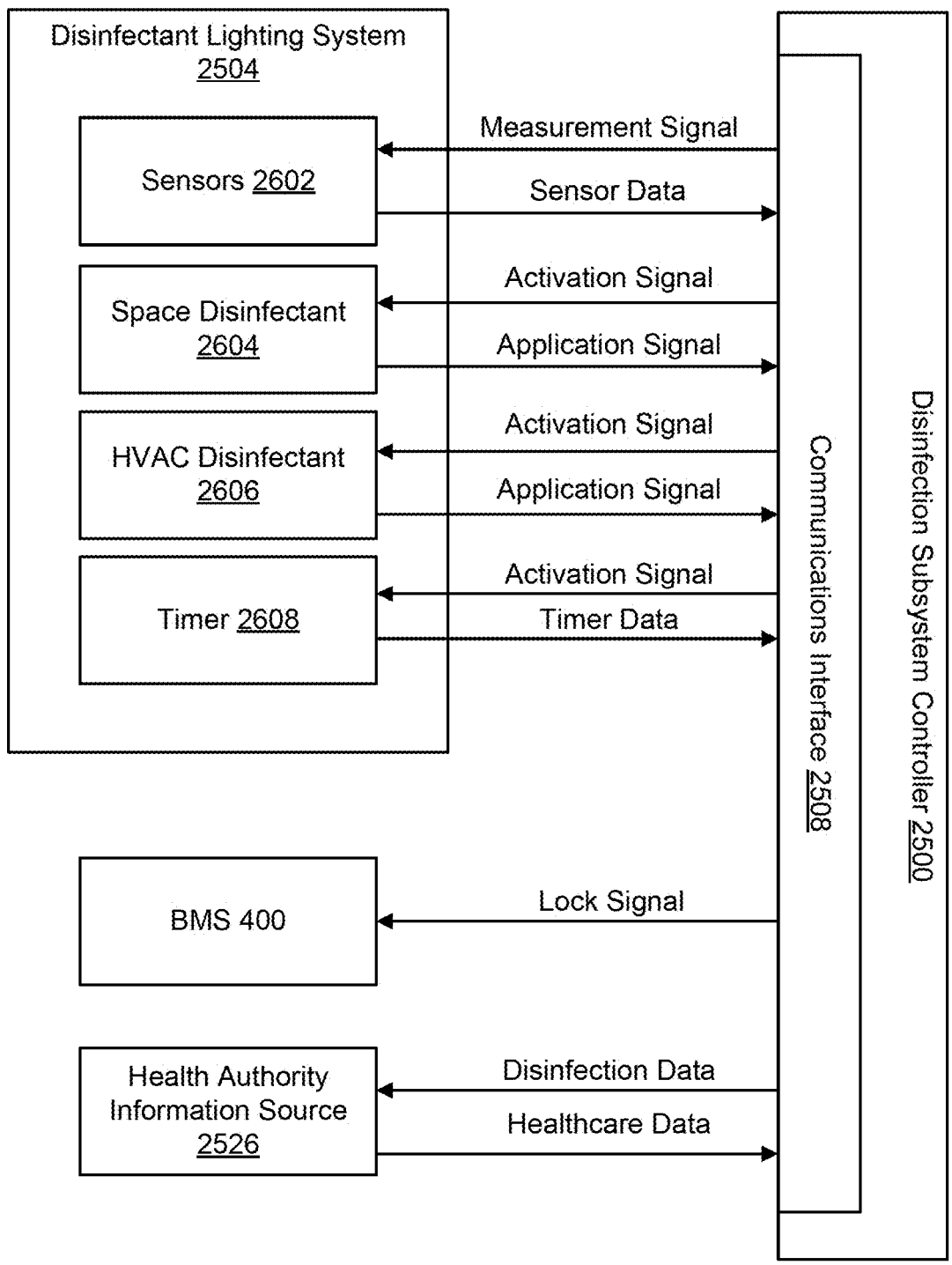
FIG. 26 is a block diagram illustrating a disinfectant lighting subsystem which can be controlled by the disinfection subsystem controller of FIG. 25C, according to some embodiments.

Referring now to FIG. 26, a block diagram illustrating the disinfectant lighting subsystem 2504 in greater detail is shown, according to some embodiments. In general, disinfectant lighting subsystem 2504 is configured to apply germicidal dosages of light waves (e.g., visible light, ultraviolet radiation (UVC), etc.) to various locations, spaces, and zones in or around a building and/or campus. The disinfectant lighting subsystem 2504 is configured to adapt various disinfection parameters such as disinfection periods (e.g., the duration of time for applying a disinfection process), frequency of performing disinfection techniques, wavelengths of emitted germicidal wavelengths, etc. based on at least one of sensor data, healthcare data, and/or predictive modeling. Disinfectant lighting subsystem 2504 is shown to include sensors 2602, a space disinfectant 2604, and a HVAC disinfectant 2606, according to some embodiments. In some embodiments, disinfectant lighting subsystem 2504 includes additional modules, components, and/or devices (e.g., one or more light switches, timers, etc.) to facilitate the operation of disinfectant lighting subsystem 2504.

Sensors 2602 are shown to communicate with disinfection system controller 2500 via communications interface 2508. More specifically, sensors 2602 are shown to receive a measurement signal from disinfection controller 2500 indicating a measurement request to be performed by sensors 2602. Accordingly, the sensors 2602 transmit the requested sensor data to disinfection controller 2500. In some embodiments, the sensors 2602 continuously collect sensor data and transmit said sensor data to disinfection controller 2500. In various embodiments, the sensors 2602 provide measured sensor data of the space, zone, or area in which each instance of sensors 2602 is implemented. In some embodiments, the measured data can include air quality, humidity, temperature, occupancy, lighting, etc. In some embodiments, sensors 2602 are one or more occupancy sensors (e.g., passive IR sensors, ultrasonic sensors, etc.) configured to detect the presence of one or more occupants within a predetermined region. For example, sensors 2602 may be a passive IR sensor configured to detect an occupant present in a vestibule of a building. In some embodiments, sensors 2602 are included as components provided by a separate subsystem (e.g., a security subsystem provided by BMS 400) such that sensors 2602 provide data to disinfection system controller 2500. The types of sensors that sensors 2602 may operate as are not intended to be limiting. Any type of sensor may be used to collect data of a space. For example, sensors 2602 may be operable as an air quality sensor structured to collect data related to air quality (e.g., particulate matter). In another example, the sensor 2602 are operable as humidity sensors structure to collect data related to the humidity levels of a space.

In some embodiments, sensors 2602 are provided as discrete components that are located disparate the space disinfectant 2604. For example, sensors 2602 may be a wall-mounted sensor that is not physically coupled to space disinfectant 2604. In some embodiments, sensors 2602 are provided as a component of space disinfectant 2604 such that sensors 2602 is physically, electrically, and/or communicatively coupled to the space disinfectant 2604.

The sensors 2602 may provide the occupancy data to disinfection system controller 2500 to determine an opportunity at which a disinfection technique performed by space disinfectant 2604 and/or HVAC disinfectant 2606 may be performed. In some embodiments, the opportunity at which a disinfection technique performed by disinfectant lighting 2504 involves the disinfection system controller 2500 receiving data from sensors 2602 that an occupant is not present in the predetermined region which the sensors 2602 observe. For example, disinfection system controller 2500 may provide an activation to signal to space disinfectant lighting 2504 to perform a disinfection technique upon disinfection system controller 2500 receiving data from the sensors 2602 indicating no occupants are present in the predetermined region associated with the sensors 2602. In some embodiments, sensors 2602 continuously measure data (e.g., occupancy data) and continuously provide data to controller 2500.

In some embodiments, sensors 2602 periodically measure data based on a disinfection schedule provided by HAIS 2526 and/or database 2524. In some such embodiments, sensors 2602 begin measuring occupancy for a predetermined time period before a scheduled disinfection technique is performed. For example, for a disinfection technique scheduled to begin at 2:00 am, sensors 2602 may begin collecting data (e.g., occupancy) for 5 minutes prior the beginning of the disinfection technique (i.e., sensors 2602 begin collecting data and providing collected data to disinfection system controller 2500 at 1:55 am). In some embodiments, sensors 2602 are configured to continuously collect data throughout the duration of a disinfection process. In some such embodiments, sensors 2602 are configured to transmit a warning signal to disinfection controller 2500 and/or space disinfectant 2604 upon an occupant entering a space that is experiencing a disinfection technique such that the warning signal stops the disinfection process.

Space disinfectant 2604 is shown to communicate with disinfection system controller 2500 via communications interface 2508 and is configured to administer a disinfection technique based upon receiving an activation signal from the disinfection system controller 2500, according to some embodiments. Accordingly, the space disinfectant 2604 transmits an application signal to the disinfection controller 2500 indicating the space disinfectant 2604 is performing a disinfection technique. The space disinfectant 2604 may be any lighting fixture capable of emitting light waves in the germicidal, visible light spectrum (approximately 400 nm-450 nm). In some embodiments, space disinfectant 2604 is also, or otherwise alternatively, capable of emitting UVC within the germicidal spectrum. The space disinfectant 2604 may be provided as a ceiling mounted light (e.g., chandeliers, track lighting, recessed lighting, etc.) configured to be attached to, on, or within a ceiling. In some embodiments, space disinfectant 2604 is configured to emit variable wavelengths that are adjusted before, during, or after a performance of disinfection technique. In some embodiments, space disinfectant 2604 is provided as a wall-mounted or a floor lamp.

HVAC disinfectant 2606 is shown to communication with disinfection system controller 2500 via communications interface 2508 and is configured to administer a disinfection technique upon receiving an activation signal from the disinfection system controller 2500, according to some embodiments. Accordingly, the HVAC disinfectant 2606 transmits an application signal to the disinfection controller 2500 indicating the HVAC disinfectant 2606 is performing a disinfection technique. According to an exemplary embodiment, the HVAC disinfectant 2606 includes one or more lighting fixtures attached to various HVAC components, devices, systems, and any other mechanism and configured to emit germicidal light waves. For example, HVAC disinfectant 2606 includes a lighting fixture installed, mounted, or otherwise attached to the inside wall of an air plenum. The HVAC disinfectant 2606 emits germicidal light waves as air passes the light source and substantially disinfects the air prior to the air entering a zone. HVAC disinfectant will be described in greater detail with reference to FIGS. 28 & 29.

Disinfectant lighting subsystem 2504 is also shown to include a timer 2608, according to some embodiments. In some embodiments, timer 2608 is configured to count down from a predetermined period of time (e.g., 15 seconds, 30 seconds, 1 minute, etc.). In some embodiments, the period of time from which the timer 2608 counts down is configurable based on user preference or healthcare data and/or disinfection parameters received from HAIS 2526. The timer 2608 receives an activation signal from the disinfection system controller 2500 configured to activate the timer 2608 and begin a countdown, according to some embodiments. In some embodiments, the timer 2608 is configured to begin a countdown from the predetermined period of time upon an occupancy sensor (e.g., sensors 2602) transmitting a signal that an occupant has vacated a predetermined region or space. The timer 2608 is also shown to provide timer data to disinfection system controller 2500, according to some embodiments. The timer data may include information such as countdown period, activation time, etc.

HAIS 2526 is also shown to provide healthcare data to disinfection system controller 2500. In some embodiments, the healthcare data provided to disinfection system controller 2500 is used by disinfection system controller 2500 to generate control decisions that operate the space disinfectant 2604 and/or HVAC disinfectant 2606. For example, healthcare data provided by HAIS 2526 may consists of an amount of time for which the space disinfectant 2604 should perform a disinfection technique. Disinfection system controller 2500 may receive the amount of time and generate a control signal operating the space disinfectant 2604 for the amount of time defined in the healthcare data provided by HAIS 2526. As previously described, the healthcare data received from HAIS is used to adjust various disinfection parameters of the disinfection techniques performed by disinfectant lighting subsystem 2504. In some embodiments, the disinfection controller 2500 provides disinfection data to HAIS 2526. Disinfection data provided to HAIS 2526 may include wavelength of germicidal light emitted, duration, sensor data, etc.

The disinfection system controller 2500 is shown to communicate with BMS 400, according to an exemplary embodiment. In some embodiments, disinfection system controller 2500 transmits lock signals to a security subsystem (e.g., security subsystem 438) to lock one or more doors that access a disinfection zones. As used herein, the term "disinfection zone" is referred to as one or more spaces that is or will be experiencing a disinfection process.

Figure 27:
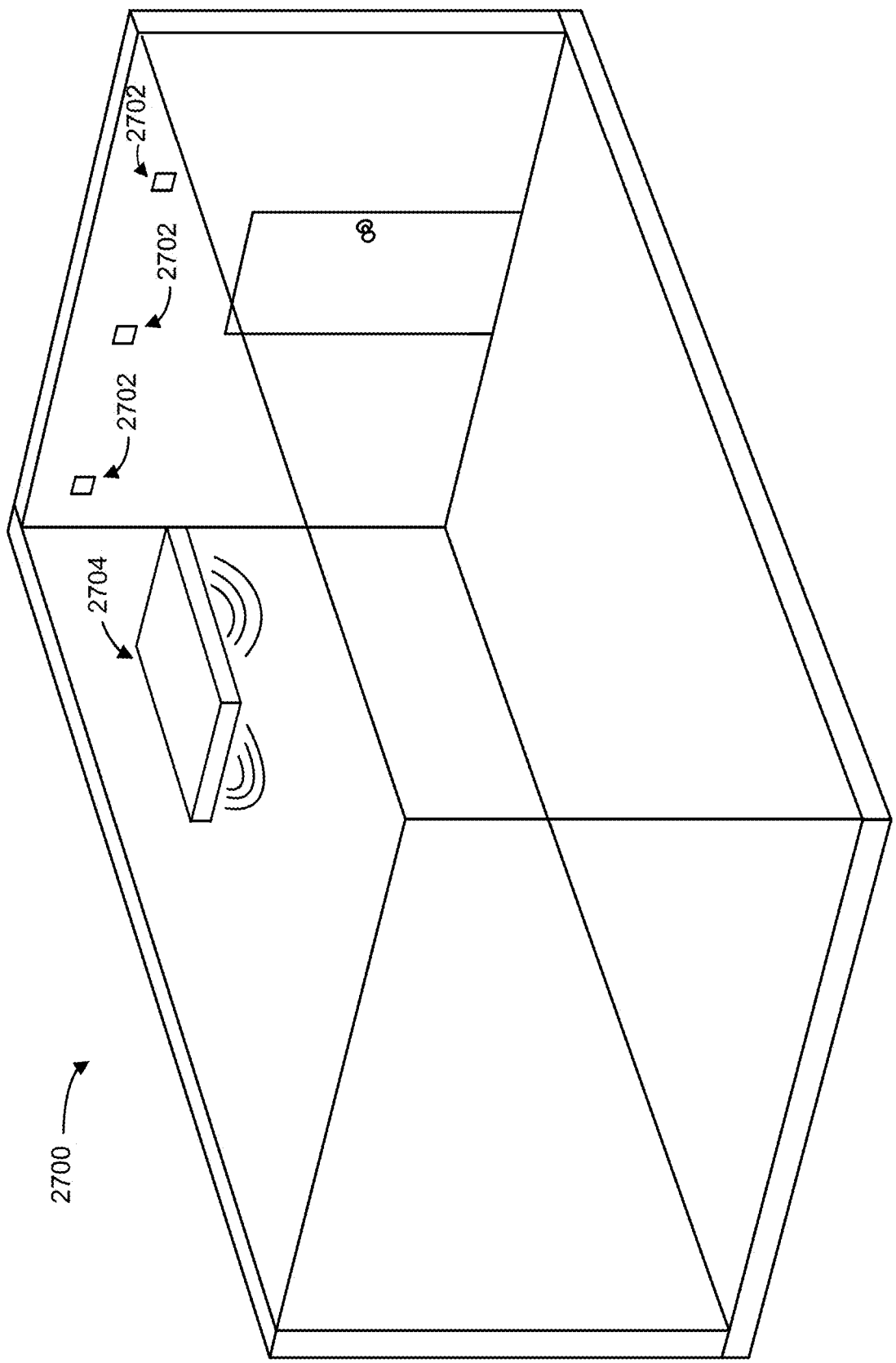
FIG. 27 is a drawing of a space equipped with the disinfectant lighting subsystem of FIG. 26, according to some embodiments.

Referring now to FIG. 27, an example environment 2700 in which the space disinfectant 2604 can be implemented is shown, according to some embodiments. Example environment 2700 may be a singular space (e.g., a vestibule, a bathroom, a room, a zone, etc.) included in a building (e.g., building 100). In some embodiments, environment 2700 may include multiple zones (e.g., a common area with hallways extending from the common area, a group of classrooms, a group of offices). The structure, features, and/or otherwise layout of environment 2700 is not intended to be limiting.

The sensors 2702 are shown to be mounted, attached, and/or installed on the walls in the environment 2700. In some embodiments, each of the sensors 2702 measures the same environmental variable (e.g., occupancy, temperature, light, etc.). For example, the sensors 2702 may each be an occupancy sensor configured to detect the presence of at least one occupant within the environment 2700. In some embodiments, one or more of the sensors 2702 may measure a different environmental variables. For example, a first sensor include in sensors 2702 may measure occupancy, a second sensor included in sensors 2702 may measure temperature, and a third sensor included in sensors 2702 may measure light.

The sensors 2702 illustrated in the environment 2700 are shown to include three instances of sensors 2702. In some embodiments, additional or fewer instances of sensors 2702 are provided in environment 2700. Additionally, as previously described, although the sensors 2702 are shown to be discrete, wall-mounted devices, it should be understood that the sensors 2702 may additionally and/or alternatively be provided as a component coupled with the disinfectant source 2704. In some embodiments, the sensors 2702 include at least one sensor configured to measure air quality of environment 2700. In some such embodiments, air quality data is transmitted to disinfection controller 2500 to determine performing a disinfection technique based on the air quality (measured by sensors 2702) decreasing below a predetermined threshold value. In some embodiments, the predetermined threshold value is defined by data received from HAIS 2526.

Disinfectant source 2704 is shown to be a ceiling-mounted lighting fixture configured to emit light to a space defined by environment 2700. In some embodiments, disinfectant source 2704 is configured to provide variable wavelengths within the visible spectrum. For example, disinfectant source 2704 may emit a non-germicidal wavelength within the visible light spectrum during normal operation (e.g., not performing a disinfection process) and may adjust the emission to a germicidal wavelength within the visible light spectrum while performing a disinfection process. The disinfectant source 2704 may separately, or in addition to, emit germicidal UVC.

Although the exemplary embodiment of environment 2700 illustrated in FIG. 27 includes one instant of the disinfectant source 2704, it should be understood that environment 2700 may include additional or any number of instances of disinfectant source 2704. Additionally, the disinfectant source 2704 may include any number of bulbs within the lighting fixture defining the disinfectant source 2704 and may provide any number of, or combination of, bulb structures (e.g., globe, candelabra, capsule, etc.).

HVAC Disinfectant

Figure 28:
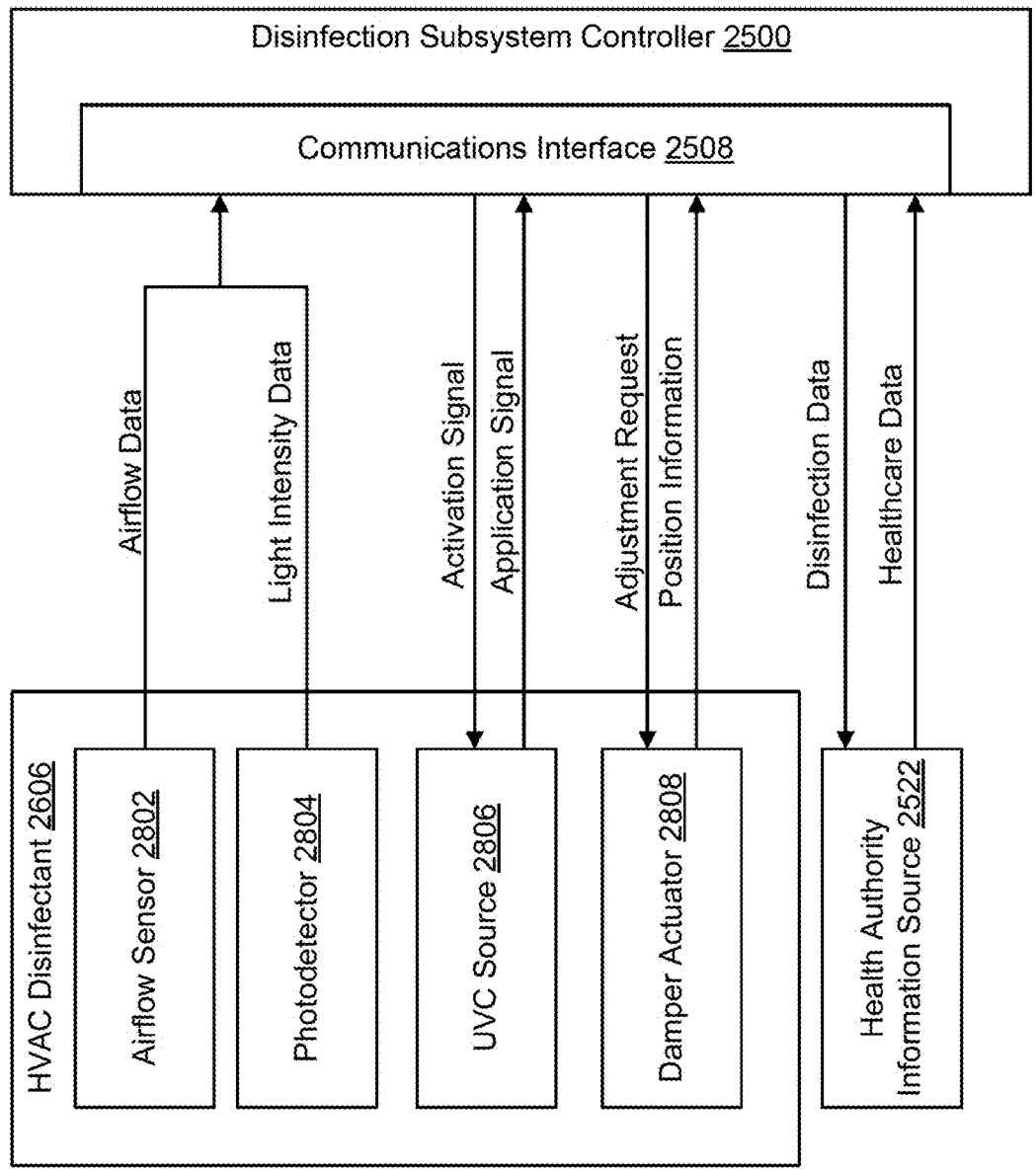
FIG. 28 is a block diagram illustrating an HVAC disinfectant subsystem which can be controlled by the disinfection subsystem controller of FIG. 25C, according to some embodiments.

Referring now to FIG. 28, a block diagram illustrating the HVAC disinfectant 2606 in greater detail is shown, according to some embodiments. The HVAC disinfectant 2606 is configured to perform disinfection techniques to various HVAC components, devices, and/or systems. For example, and as will be described in greater detail with reference to FIG. 29, HVAC disinfectant 2606 includes various components configured to disinfect air passing through a plenum and/or other HVAC components. Other HVAC devices, systems, and components that may include disinfection features controlled by HVAC disinfectant 2606 may include variable air volume boxes, air handling units, heaters, etc.

HVAC disinfectant 2606 is shown to include an airflow sensor 2802 configured to collect volumetric flow rate of air data, according to some embodiments. Various examples of airflow sensors include, but are not limited to, vane sensors, vortex sensors, etc. Airflow sensor 2802 is shown to provide flow data to disinfection system controller 2500. As will be described in greater detail below, the airflow sensor 2802 provides flow data to disinfection system controller 2500 for use by controller 2500 in determining damper positions (e.g., fully open, fully closed, partially open, partially closed, etc.) for optimizing the disinfection of air. In various embodiments, more than one airflow sensors 2802 are included to provide airflow data used for determining a difference in airflow as air passes through an object (e.g., a filter, a damper, etc.).

Still referring to FIG. 28, HVAC disinfectant 2606 is also shown to include a photodetector 2804 configured to collect light intensity data, according to some embodiments. Various examples of photodetectors include, but are not limited to, photodiodes, photoresistors, thermal detectors, etc. Photodetector 2804 is shown to provide light intensity data to disinfection controller 2500. In various embodiments, the photodetector 2804 is located proximate a UVC source 2806 and collects light intensity data of the UVC source 2806. As will be described in greater detail below, the photodetector 2804 provides light intensity data to disinfection subsystem controller for use by controller 2500 in (e.g., fully open, fully closed, partially open, partially closed, etc.) optimizing the disinfection of air. In some embodiments, the light intensity data collected by photodetector 2804 is used to generate a replacement warning indicating that the UVC source 2806 needs to be replaced (e.g., the UVC source 2806 is burning out). In some embodiments, controller 2500 uses the light intensity data collected by photodetector 2804 in conjunction with the airflow data collected by airflow sensors 2802 to determine optimal disinfection control actions.

HVAC disinfectant 2606 is also shown to include a UVC source 2806 configured to emit germicidal ultraviolet rays of variable wavelengths, according to an exemplary embodiment. In some embodiments, UVC source 2806 communicates with disinfection system controller 2500 via communications interface 2508 and is configured to administer a disinfection technique based upon receiving an activation signal from the disinfection system controller 2500. In some embodiments, the UVC source 2806 is configured to emit germicidal rays approximately in the visible light spectrum. For example, UVC source 2806 may emit a non-germicidal wavelength within the visible light spectrum during normal operation (e.g., not performing a disinfection process) and may adjust the emission to a germicidal wavelength within the visible light spectrum while performing a disinfection process. In some embodiments, UVC source 2806 is an LED array.

HVAC disinfectant 2606 is also shown to include a damper actuator 2808 configured to adjust a damper position to optimize disinfection of air passing a UVC source (e.g., UVC source 2806), according to some embodiments. More specifically, by adjusting the position of a damper, the damper actuator 2808 impacts the flow rate of air past UVC source 2806 by adjusting the cross-sectional area of an exit aperture of the plenum. Damper actuator 2808 may be any type of damper actuator such as electric or pneumatic. The damper actuator 2808 is shown to receive an adjustment request from disinfection system controller 2500 indicating the damper actuator 2808 to adjust the position of a damper. As will be described in greater detail below, the disinfection system controller 2500 uses flow data and/or light intensity data to determine adjustment requests for damper actuator 2808 to change the position of a damper and optimize disinfection of the air. For example, upon receiving light intensity data indicating that the UVC source 2806 is dimming (e.g., light intensity is reducing, UVC source 2806 is burning out, UVC source 2806 is working at lower-than-normal power), the damper actuator 2808 may at least partially close the associated damper to reduce the airflow past the UVC source 2806 in order to substantially maintain the same or similar disinfection effectiveness of UVC source 2806 working at normal power.

Figure 29:
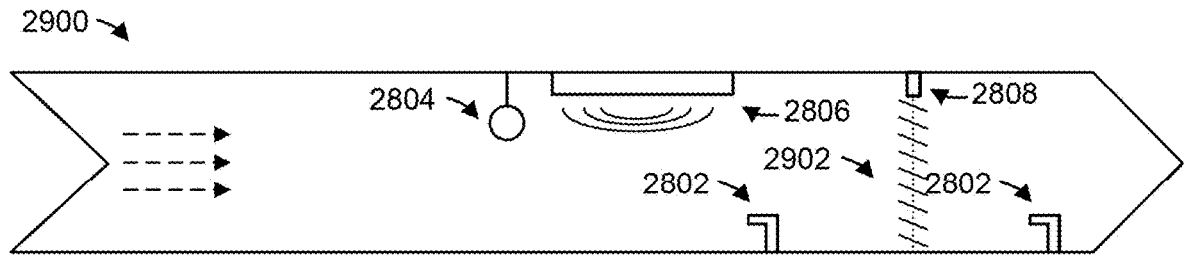
FIG. 29 is a drawing of a plenum equipped with the HVAC disinfectant subsystem of FIG. 28, according to some embodiments.

Referring now to FIG. 29, a plenum 2900 in which the HVAC disinfectant 2606 can be implemented is shown, according to some embodiments. Plenum 2900 may be a single plenum included in a building (e.g., building 100). In some embodiments, plenum 2900 may include multiple plenums. For example, plenum 2900 may be a hub that includes more than one plenum 2900 extending outwardly from the hub. The structure, features, and/or otherwise layout of plenum 2900 are not intended to be limiting. It should also be understood that the use of plenum 2900 is intended for exemplary purposes. HVAC disinfectant may be implemented in any other HVAC device, system, or component such as an air handling unit or a VAV box.

Plenum 2900 is shown to include two instances of airflow sensor 2802 configured to measure a differential airflow through a damper 2902, according to some embodiments. The differential airflow measured by the airflow sensor 2802 is used in part to determine a position of the damper 2902. Accordingly, the damper actuator 2808 is controlled by disinfection system controller 2500 based on the airflow data collected by airflow sensors 2802 and light intensity measured by photodetector 2804. As shown, the photodetector 2804 is located proximate the UVC source 2806 and is configured to measure the intensity of the light emitted by the UVC source 2806. In general, as the light intensity reduces, the damper will be adjusted to a more closed position reducing the plenum exit cross-sectional area and airflow past the UVC source 2806.

Dashed lines represent the direction of air flow through the plenum. As air flows through the plenum 2900, the air passes by the UVC source 2806 prior to passing through the damper 2902, according to an exemplary embodiment. As previously described, the light intensity data collected by photodetector 2804 is used with the airflow data collected by airflow sensor 2802 to determine positions of the damper 2902. If the photodetector 2804 detects the intensity of the light emitted by the UVC source 2806 is reducing (e.g., the light emitted is dimming), then disinfection system controller 2500 commands damper actuator 2808 to at least partially close the damper 2902 to reduce the airflow rate of the air past the UVC source 2806.

Space Disinfection Method

Figure 30:
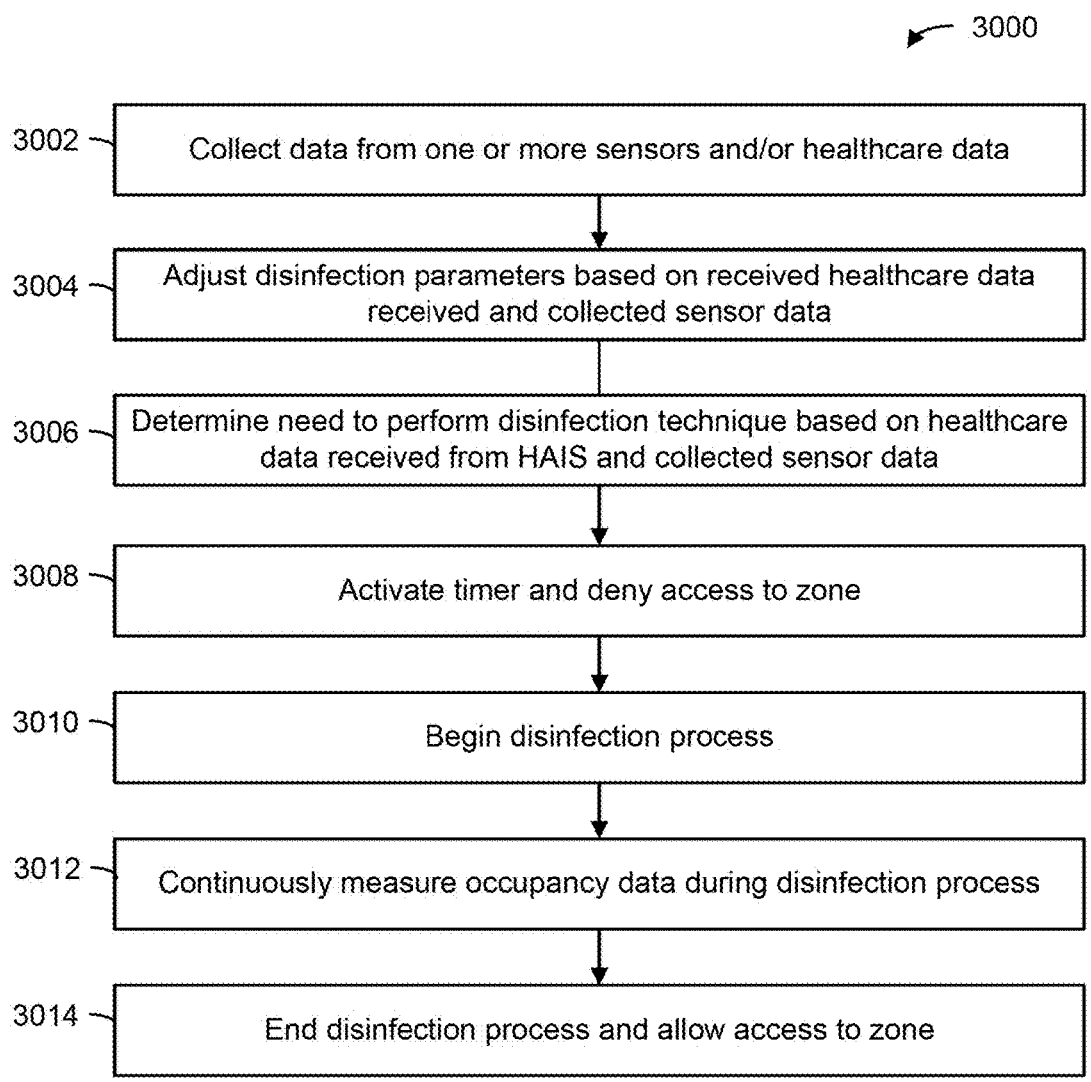
FIG. 30 is a flowchart illustrating a process of disinfecting a space which can be performed by the disinfectant lighting subsystem of FIG. 26, according to some embodiments.

Referring now to FIG. 30, a process 3000 for disinfecting a space is shown, according to some embodiments. Process 3000 can facilitate a disinfection subsystem controller (e.g., disinfection system controller 2500) to transmit activation signals to a disinfection source (e.g., disinfectant source 2704) configured to perform a disinfection technique based on the received activation signal. In some embodiments, general disinfection techniques such as expelling disinfectant aerosols and manual cleaning of various surfaces in a zone results in time-consuming tasks and inadequate disinfection of the surfaces. As such, process 3000 can allow for the disinfection techniques to be adjusted based on various sensor data and healthcare information.

Process 3000 is shown to include collecting data from one or more sensors (step 3002), according to some embodiments. In some embodiments, the data collected from one or more sensors (e.g., sensors 2602) includes occupancy data and/or air quality of a zone in which the one or more sensors are located. The collected sensor data can be used to determine the need to perform a disinfection technique. For example, performing a disinfection technique may be necessary upon detecting that a particular number of occupants have passed through a zone. In another example, performing a disinfection technique may be necessary upon detecting that the air quality of a zone has reduced to less than a predetermined threshold value. In some embodiments, the sensor data is continuously collected. In other embodiments, the sensor data is collected at predetermined intervals (e.g., every minute, every 5 minutes, etc.). In various embodiments, the sensor data is collected when a change in sensor data is detected. For example, an occupancy sensor detects that an occupant has entered a previously-unoccupied zone and records the presence of an occupant based on the change in occupancy data. In some embodiments, the data is collected upon an indication of a disinfection model update. For example, based upon a user determining that a disinfection model (as can be generated by model generator 2520) requires an update, current data (e.g., air quality, occupancy, humidity, etc.) is collected by sensors 2602. In some embodiments, data is collected by sensors 2602 based upon a schedule for one or more zones. For example, a schedule may indicate that a meeting will occur in a particular zone at a particular time. Data may be collected by sensors 2602 during and/or after the scheduled meeting.

Step 3002 is also shown to include collecting healthcare data from a health authority (e.g., health authority information source 2032), according to some embodiments. In some embodiments, the healthcare data collected from a health authority includes disinfection parameters (e.g., disinfection cycle duration, period of time between cycles, wavelength emission, current pathogen alerts, etc.). In some embodiments, the healthcare data is collected upon an indication of a disinfection model update. In some embodiments, the healthcare data is continuously collected. In other embodiments, the healthcare data is collected at predetermined intervals. The collected healthcare data may indicate the need to perform a disinfection process. For example, the collected healthcare data may indicate an outbreak of a particular illness and includes updated disinfection parameters associated with the particular illness and a request to perform a disinfection technique according to the updated disinfection parameters.

Process 3000 is shown to include adjusting disinfection parameters based on received healthcare data and collected sensor data (step 3004), according to some embodiments. In some embodiments, adjusting disinfection parameters includes changing one or more of disinfection cycle duration, disinfection period, intensity of germicidal light, and wavelength emitted by the disinfection source. In some embodiments, adjusting disinfection parameters includes using the collected data to update a disinfection model.

Process 3000 is shown to include determining the need to perform a disinfection technique based on healthcare data and/or collected sensors data (step 3006), according to some embodiments. In some embodiments, healthcare data received from a health authority (e.g., HAIS 2526) indicates a request to perform a disinfection technique. In some embodiments, collected sensor data indicates a need to perform a disinfection technique. For example, collected air quality data that is below a predetermined threshold value may indicate that a disinfection technique is to be performed. Other examples of sensor data indicating a need to perform a disinfection technique include humidity of a space above a predetermined threshold value, occupancy data indicating a predetermined number of occupants have passed and now vacated a zone, etc. In some embodiments, a disinfection model indicates the need to perform a disinfection technique.

Process 3000 is shown to involve activating a timer (e.g., timer 2608) and denying access to one or more zones (step 3008), according to some embodiments. In some embodiments, activating a timer involves preventing a disinfection technique performance during the duration of the timer. The timer duration may be configurable. In some embodiments, denying access to a zone involves locking exterior doors or other access points such that occupants may not enter a predetermined one or more zones. In such embodiments, the interior doorknobs (e.g., the doorknobs facing the interior of the predetermined one or more zones) remain unlocked such that occupants in the zone may vacate. In further embodiments, audible and/or visual warnings are activated upon the activation of the timer. For example, an announcement indicating 30 seconds remain until a disinfection technique begins. As such, the announcement may motivate occupants to vacate the particular zone.

Process 3000 is shown to involve beginning a disinfection technique (step 3010), according to some embodiments. In some embodiments, beginning a disinfection technique involves activating one or more disinfection sources (e.g., a UVC source, a visible light disinfector, etc.). In such embodiments, the one or more disinfection sources are activated upon the completion of a countdown.

Process 3000 is shown to involve continuously measure occupancy data during a disinfection technique (step 3012), according to some embodiments. In some embodiments, measuring occupancy data involves determining if an occupant has entered a particular zone in which a disinfection technique is occurring. In such embodiments, a deactivation signal is transmitted to stop the disinfection process. For example, upon an occupant entering a zone in which a disinfection technique is occurring, one or more occupancy sensors detect the presence of the occupant in the zone. As such, a signal is transmitted to deactivate (e.g., turn off, adjust wavelength to a substantially safe value, etc.) the germicidal disinfection process.

Process 3000 is shown to involve ending the disinfection technique and allowing access to a particular zone (step 3014), according to some embodiments. In some embodiments, occupants are allowed access to the particular zone upon completion of a countdown that begins following the end of the disinfection cycle. Such a countdown may help ensure that the disinfectant sources have been turn off or otherwise adjusted to a safe operation mode. In some embodiments, allowing access may involve unlocking one or more doors to the particular zone. In further embodiments, ending a disinfection technique includes transmitting various data to designated receivers (e.g., disinfection system controller 2500, HAIS 2526, etc.).

HVAC Disinfection Method

Figure 31:
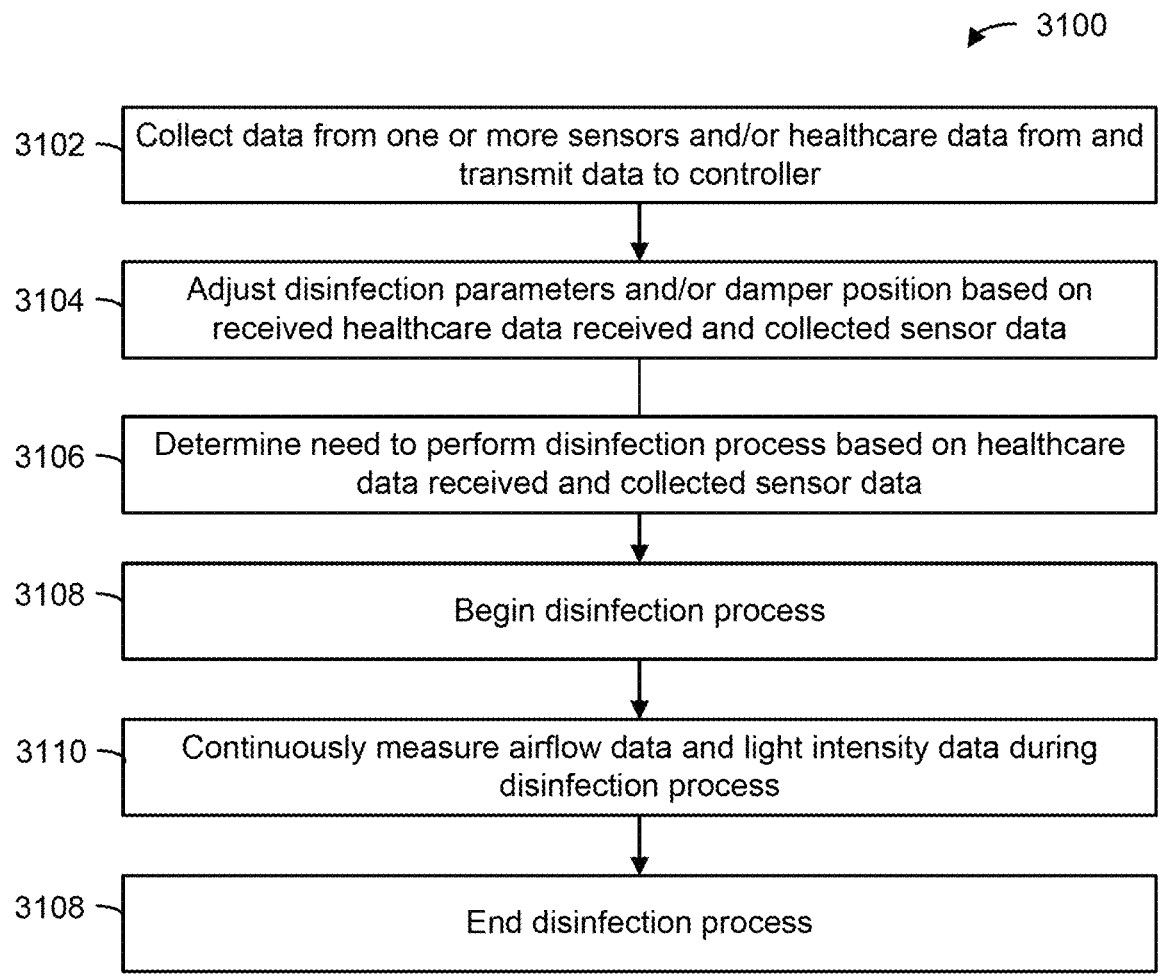
FIG. 31 is a flowchart illustrating a process of disinfecting an HVAC component, system, or device which can be performed by the HVAC disinfectant subsystem of FIG. 28, according to some embodiments.

Referring now to FIG. 31, a flowchart illustrating a process 3100 of disinfecting various HVAC components is shown, according to some embodiments. Process 3100 can facilitate a disinfection subsystem controller (e.g., disinfection system controller 2500) to transmit activation signals to a UVC source (e.g., UVC source 2806) configured to emit a germicidal dosage of UVC based on the activation signal. The process 3100 can also facilitate the adjustment of a plenum damper to control airflow past a UVC source to substantially disinfect air as the air passes through the plenum.

Process 3100 is shown to include collecting data from one or more sensors (step 3102), according to some embodiments. In some embodiments, the data collected from one or more sensors (e.g., airflow sensor 2802, photodetector 2804) includes airflow data, light intensity data, and/or air quality of air passing through a particular HVAC system, component, or device. The collected sensor data can be used to determine the need to perform a disinfection process. In some embodiments, the sensor data is continuously collected. In other embodiments, the sensor data is collected at predetermined intervals (e.g., every minute, every 5 minutes, etc.). In various embodiments, the sensor data is collected when a change in sensor data is detected. For example, a photodetector 2804 detects that the UVC emitted from UVC source 2806 has dimmed records the light intensity based on the change in light intensity. In some embodiments, the data is collected upon an indication of a disinfection model update. For example, based upon a user determining that a disinfection model (as can be generated by schedule generator 2520) requires an update, current sensor data (e.g., air quality, airflow, light intensity, humidity, etc.) is collected.

Step 3102 is also shown to include collecting healthcare data from a health authority (e.g., health authority information source 2032), according to some embodiments. In some embodiments, the healthcare data collected from a health authority includes disinfection parameters (e.g., disinfection cycle duration, period of time between cycles, wavelength emission, current pathogen alerts, light intensity of UVC, etc.). In some embodiments, the healthcare data is collected upon an indication of a disinfection model update. In some embodiments, the healthcare data is continuously collected. In other embodiments, the healthcare data is collected at predetermined intervals. The collected healthcare data may indicate the need to perform a disinfection process. For example, the collected healthcare data may indicate an outbreak of a particular illness and includes updated disinfection parameters associated with the particular illness and a request to perform a disinfection technique according to the updated disinfection parameters.

Process 3100 is shown to include adjusting disinfection parameters and/or damper position based on received healthcare data and collected sensor data (step 3104), according to some embodiments. In some embodiments, adjusting disinfection parameters includes changing one or more of disinfection cycle duration, disinfection period, intensity of germicidal light, wavelength emitted by the disinfection source. In some embodiments, adjusting disinfection parameters includes using the collected data to update a disinfection model. In some embodiments, adjusting the damper position involves adjusting the damper position based on collected light intensity data. In such embodiments, if light intensity data is collected indicating that the UVC source is dimming, the damper may be moved to a more closed position in order to reduce airflow past the UVC source.

Process 3100 is shown to include determining the need to perform a disinfection technique based on healthcare data and/or collected sensors data (step 3106), according to some embodiments. In some embodiments, healthcare data received from a health authority (e.g., HAIS 2526) indicates a request to perform a disinfection process. As such, based on the received request, a disinfection technique is performed. In some embodiments, collected sensor data indicates a need to perform a disinfection process. For example, collected air quality data that is below a predetermined threshold value may indicate that a disinfection technique is to be performed. Another example of sensor data indicating a need to perform a disinfection technique includes humidity of a space above a predetermined threshold value. In some embodiments, a disinfection model indicates the need to perform a disinfection process. In some embodiments, an HVAC operation schedule (e.g., a sequence of operation) defining periods of time at which various HVAC components operate indicates the need to perform a disinfection process. For example, an operating period of an air handling unit may indicate the need to perform a disinfection technique while the air handling unit is operating.

Process 3100 is shown to involve beginning a disinfection technique (step 3010), according to some embodiments. In some embodiments, beginning a disinfection technique involves activating one or more disinfection sources (e.g., a UVC source, a visible light disinfector, etc.).

Process 3100 is shown to involve continuously measure airflow data and light intensity data during a disinfection technique (step 3110), according to some embodiments. In some embodiments, measuring light intensity data involves determining if the UVC is dimming. In such embodiments, a damper actuator in a plenum adjusts the damper to reduce the airflow past the UVC source. In some embodiments, measuring airflow data involves determining if the airflow through a plenum has changed. In such embodiments, a damper actuator adjusts a damper according to the change in airflow and/or light intensity data. For example, if the collected airflow data indicates that the airflow has reduced, then the damper actuator may adjust the damper to a more closed position.

Process 3100 is shown to involve ending the disinfection technique and allow access to a particular zone. In further embodiments, ending a disinfection technique includes transmitting various data to designated receivers (e.g., disinfection system controller 2500, HAIS 2526, etc.). In further embodiments, ending a disinfection technique includes transmitting various data to designated receivers (e.g., disinfection system controller 2500, HAIS 2526, etc.).

ACS Disinfectant Subsystem

Figure 32:
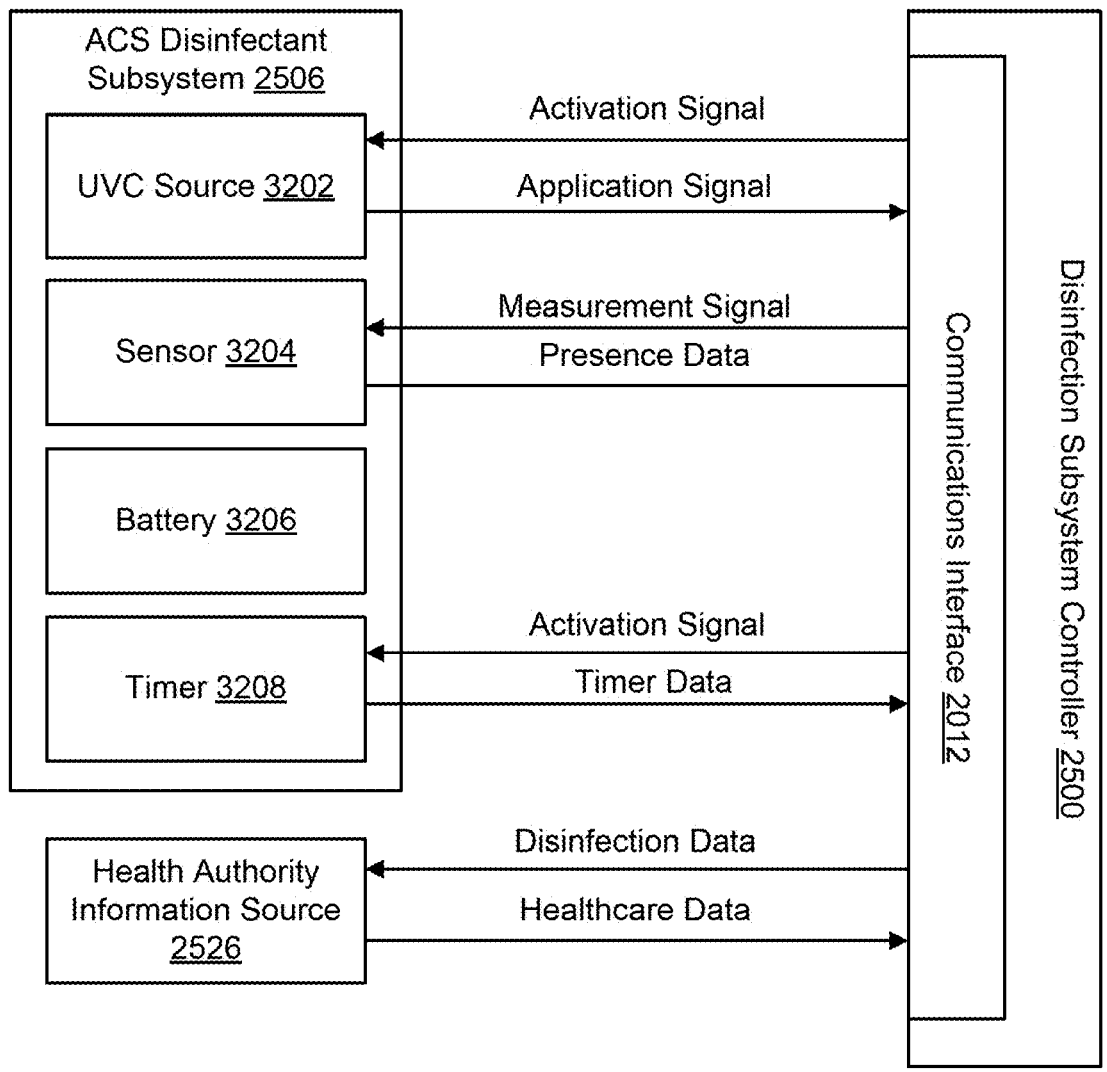
FIG. 32 is a block diagram illustrating an access control system (ACS) disinfectant subsystem which can be controlled by the disinfection subsystem controller of FIG. 25C, according to some embodiments.

Referring now to FIG. 32, a block diagram illustrating the ACS disinfectant subsystem 2506 in greater detail is shown, according to some embodiments. As will be described in greater detail with reference to FIG. 33, the ACS disinfectant subsystem 2506 is structured for installation or attachment to an external device and configured to apply germicidal dosages of light waves to the external device, according to an exemplary embodiment. In some embodiments, the external device includes a device which occupants interact with (e.g., by touch) such as a doorknob, a light switch, an elevator control panel, and the like. The ACS disinfectant subsystem 2506 is configured to adapt disinfection periods (e.g., the duration of time for applying a disinfection process), time between disinfection periods, and emitted wavelengths based on at least one of sensor data, healthcare data, and/or a disinfection model generated by schedule generator 2520. The ACS disinfectant subsystem 2506 is shown to include a UVC source 3202, a sensor 3204, a battery 3206, and a timer 3208, according to an exemplary embodiment.

As previously described, the ACS disinfectant subsystem 2506 is configured to perform a technique of disinfection to an external device (e.g., an access control system, a doorknob, a handle, a light switch, etc.). In some embodiments, the ACS disinfectant subsystem 2506 is configured for installation or attachment on an external device (e.g., an ACS, an elevator panel, etc.) and to apply, via UVC source 3202, germicidal dosages of ultraviolet radiation to the external device (not shown) in order to substantially disinfect at least a portion of the surface of the external device. In some embodiments, the ACS disinfectant subsystem 2506 is attached to or installed on an external device such that the UVC source 3202 irradiates a portion of the external device with which users interact (e.g., touch). For example, an ACS may include a screen featuring a user interface and a keyboard with which users type in order to control the system/device that the ACS is associated with. As such, the ACS disinfectant subsystem 2506 may be installed onto or provided by the ACS such that the UVC source 3202 irradiates only the keyboard.

The ACS disinfectant subsystem 2506 may include any number of, or combination of attachment structures, methods, or apparatuses configured to facilitate the installation of the ACS disinfectant subsystem 2506 on an external device. As will be described in greater detail below, in some embodiments, the ACS disinfectant subsystem 2506 is battery-operated allowing for easy implementation of the ACS disinfectant subsystem 2506 with an external device. In other embodiments, the ACS disinfectant subsystem 2506 receives power from an external power source via a wired connection.

The various components included in ACS disinfectant subsystem 2506 are shown to communicate disinfection system controller 2500. In some embodiments, the controller 2500 receives healthcare data from HAIS 2526 in order to adjust disinfection parameters of the disinfection techniques performed by ACS disinfectant subsystem 2506. In some embodiments, the healthcare data consists of applicable UVC wavelengths to emit, number of radiation cycles, duration of radiation cycle, and/or current high-threat pathogens. In some embodiments, the healthcare data is used to adjust the disinfection parameters of the UVC (e.g., wavelength, dosage duration, time between cycles, etc.) emitted from UVC source 3202. In some embodiments, controller 2500 transmits activation signals to UVC source 3202 in order to administer a dosage of UVC. In some embodiments, ACS disinfectant subsystem 2506 transmits dosage data (e.g., duration of dosage, time of dosage, wavelength applied, etc.) to disinfection system controller 2500. For example, the dosage data transmitted from the ACS disinfectant subsystem 2506 may consist of duration of dosage, wavelength of UVC, and number of cycles performed.

The ACS disinfectant 2506 is also shown to include UVC source 3202 configured to emit ultraviolet radiation at least within the germicidal range of ultraviolet wavelengths, according to some embodiments. In some embodiments, the UVC source 3202 is configured to emit variable wavelengths within the ultraviolet spectrum (approximately 10 nm-400 nm). For example, a first dosage of UVC emitted by UVC source 3202 may be at a wavelength of 150 nm while a second dosage of UVC emitted by UVC source 3202 may be at a wavelength of 200 nm. In some embodiments, the dosage duration emitted by the UVC source 3202 is configurable based on healthcare data received by HAIS 2526.

In some embodiments, the UVC source 3202 is an array of LEDs configured to emit UVC radiation. In some such embodiments, the shape of UVC source 3202 may be configurable to facilitate the spread of UVC about a surface. For example, the UVC source 3202 may be a flexible LED strip that is bendable to form a semicircle shape for placement about a doorknob. In some embodiments, the ACS disinfectant subsystem 2506 includes more than one UVC source 3202. For example, the UVC source 3202 may include multiple strips of LED arrays. In some embodiments, the UVC source 3202 is a gas-discharge lamp configured to emit UV radiation. In some embodiments, the UVC source 3202 is capable of emitting light within the germicidal spectrum of visible light (approximately 400 nm-450 nm).

Still referring to FIG. 32, the ACS disinfectant subsystem 2506 is also shown to include a sensor 3204 configured to detect the presence of a user within a predetermined region associated with the UVC source 3202, according to some embodiments. As will be described, in some embodiments, the sensor 3204 is in communication with disinfection system controller 2500 and transfers presence data to the controller. In some embodiments, the sensor 3204 communicates with the UVC source 3202 to prevent UVC source 3202 from emitting a dose of UVC when the sensor 3204 detects a user is within a predetermined proximity of the UVC source 3202. In some embodiments, the sensor 3204 is a passive infrared sensor. In some embodiments, ACS disinfectant subsystem 2506 includes more than one sensor 3204. In some embodiments, the sensor 3204 is not provided as a component of ACS disinfectant subsystem 2506. For example, the sensor 3204 may be provided as an external component configured to communicate with the ACS disinfectant subsystem 2506 via disinfection system controller 2500.

In some embodiments, the ACS disinfectant subsystem 2506 includes a battery 3206 configured to supply power to the components included in ACS disinfectant subsystem 2506. In some embodiments, battery 3206 generates electrical power via a chemical reaction (e.g., lithium-ion, alkaline, lead-acid, etc.) and transmit the electrical power to the various components in disinfection device 2500. In some embodiments, battery 3206 generates power via a solar cell and transmits the electrical power to the various components in ACS disinfectant subsystem 2506. In some embodiments, the ACS disinfectant subsystem 2506 does not include battery 3206. In some such embodiments, the ACS disinfectant subsystem 2506 provides a wired connection configured to physically and/or electrically couple to an external power source. In some such embodiments, the ACS disinfectant subsystem 2506 includes electrical conduits configured to couple to and transfer power from a power supply of a building. In other embodiments, the ACS disinfectant subsystem 2506 includes electrical conduits configured to physically and/or electrically couple to the external device on which the ACS disinfectant subsystem 2506 is installed and transfer power provided by the external device to the ACS disinfectant subsystem 2506.

ACS disinfectant subsystem 2506 is also shown to include a timer 3208, according to some embodiments. In some embodiments, timer 3208 is configured to count down from a predetermined period of time (e.g., 15 seconds, 30 seconds, 1 minute, etc.). In some embodiments, the period of time from which the timer 3208 counts down is configurable based on user preference or healthcare data and/or disinfection parameters received from HAIS 2526. The timer 3208 receives an activation signal from the disinfection system controller 2500 configured to activate the timer 3208 and begin a countdown, according to some embodiments. In some embodiments, the timer 3208 is configured to begin a countdown from the predetermined period of time upon an occupancy sensor (e.g., sensors 3204) transmitting a signal that a user has removed any part of his/her body from a predetermined region or space associated with an ACS. The timer 3208 is also shown to provide timer data to disinfection system controller 2500, according to some embodiments. The timer data may include information such as countdown period, activation time, etc.

Figure 33:
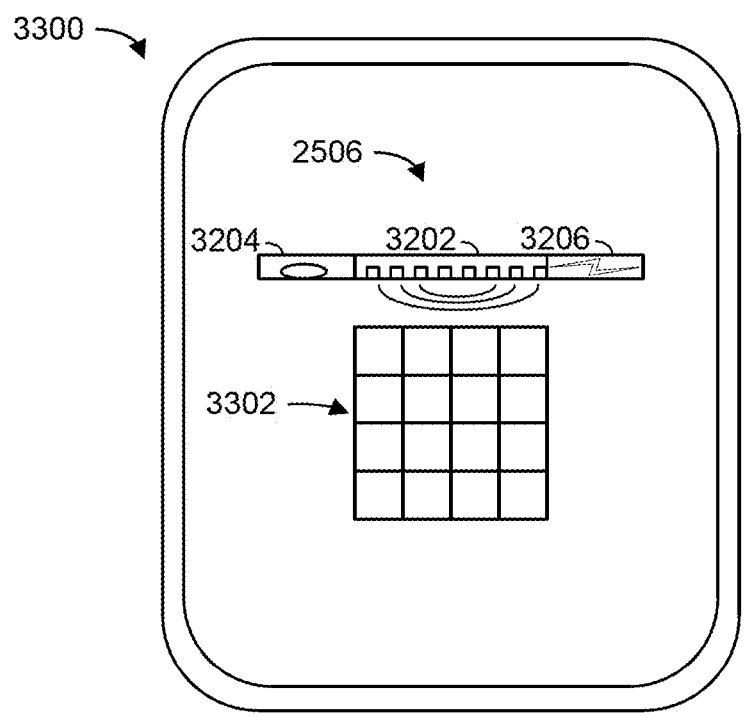
FIG. 33 is a schematic drawing illustrating an ACS equipped with the ACS disinfectant subsystem of FIG. 32, according to some embodiments.

Referring now to FIG. 33, a schematic drawing of physical components included in ACS disinfectant subsystem 2506 as installed onto an ACS 3300 is shown, according to some embodiments. As previously described, the ACS disinfectant subsystem 2506 is configured to perform a disinfection technique to a surface. More specifically, the ACS disinfectant subsystem 2506 is configured to emit germicidal UVC to at least a portion of a surface that is provided by ACS 3300 with which users interact. According to some embodiments, the components of ACS disinfectant subsystem 2506 are configured for installation on or attachment to ACS 3300. In other embodiments, the components of ACS disinfection subsystem 2506 are provided as components integrated on and/or within the ACS 3300 such that the ACS 3300 is manufactured with such components.

The ACS 3300 is shown as a panel with a keypad 3302 with which users may interact (e.g., touch) in order to operate a device associated with the ACS 3300. For example, the ACS 3300 may be a telephone panel providing a keypad 3302 with which users may use to dial a phone number. As such, the keypad 3302 is considered a disinfection surface of the ACS 3300. In some embodiments, the disinfection surface of the ACS 3300 may be the entirety of a surface defined by the ACS 3300. The keypad 3302 is shown to be irradiated by UVC source 3202, according to some embodiments.

As previously described, in some embodiments, the UVC source 3202 is configured to emit variable wavelengths within the ultraviolet spectrum (approximately 10 nm-400 nm). For example, a first dosage of UVC emitted by UVC source 3202 may be at a wavelength of 150 nm while a second dosage of UVC emitted by UVC source 504 may be at a wavelength of 200 nm. In some embodiments, the dosage duration emitted by the UVC source 3202 is configurable based on healthcare data received by HAIS 2526.

As shown, the UVC source 3202 is an array of LEDs configured to emit UVC radiation. In some embodiments, the shape of UVC source 3202 is to facilitate the spread of UVC radiation about a surface. For example, the UVC source 3202 may be a flexible LED strip that may be bendable to form a semicircle shape for placement about a doorknob. In some embodiments, the ACS disinfector 2506 includes more than one UVC source 3202. For example, the UVC source 3202 may include multiple strips of LED arrays. In some embodiments, the UVC source 3202 is a gas-discharge lamp configured to emit UV radiation.

Still referring to FIG. 33, the ACS disinfectant subsystem 506 is also shown to include sensor 3204 configured to detect the presence of a user within a predetermined region associated with the UVC source 3202, according to some embodiments. In some embodiments, the sensor 3204 communicates with the UVC source 3202 via the disinfection subsystem controller 444 to prevent UVC source 3202 from emitting a dose of UVC when the sensor 3204 detects a user is within a predetermined proximity. In some embodiments, the sensor 3204 is a passive infrared sensor. In some embodiments, the ACS disinfectant subsystem 2506 includes more than one sensor 3204. In some embodiments, the sensor 3204 is not provided as a component of ACS disinfectant subsystem 2506. For example, the sensor 506 may be provided as an external component (e.g., provided by ACS 3300, provided by BMS 400, etc.) configured to communicate with the UVC source 3202.

Figure 34:
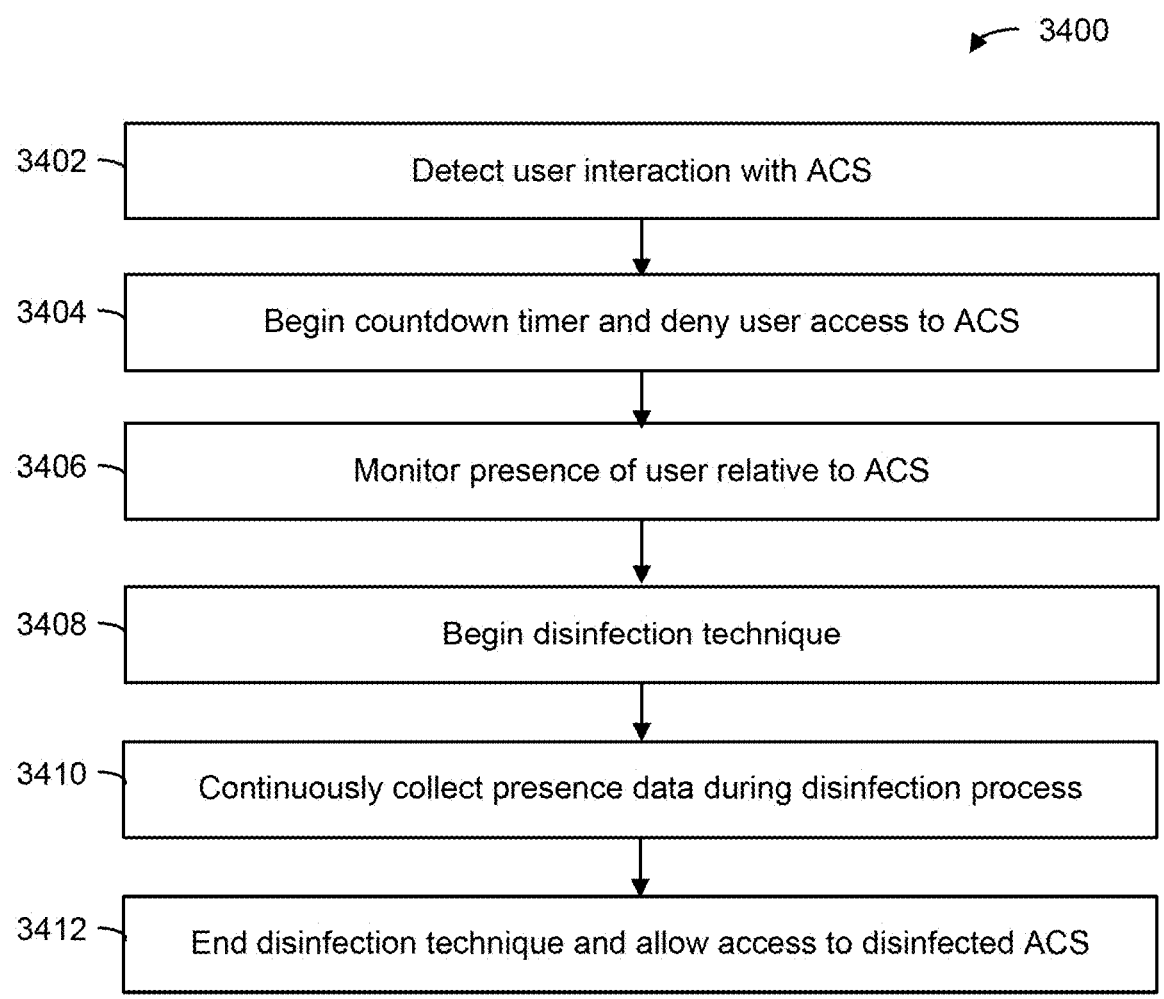
FIG. 34 is a flowchart illustrating a process of disinfecting an ACS which can be performed by the ACS disinfectant subsystem of FIG. 32, according to some embodiments.

Referring now to FIG. 34, a process 3400 for disinfecting an ACS is shown, according to some embodiments. Process 3400 can facilitate a disinfection subsystem controller (e.g., disinfection system controller 2500) to transmit activation signals to a UVC source (e.g., UVC source 3202) configured to perform a disinfection technique based on the received activation signal. In some embodiments, general disinfection techniques such as expelling disinfectant aerosols and manual cleaning of various surfaces in a zone results in time-consuming tasks and inadequate disinfection of the surfaces. As such, process 3400 can allow for the disinfection techniques to be adjusted based on various sensor data and healthcare information.

Process 3400 is shown to include detecting user interaction with an ACS (step 3402), according to some embodiments. In some embodiments, detecting user interaction involves sensor keypad detecting the presence of a user has entered a predetermined region associated with an ACS (e.g., ACS 3300). For example, sensor 3204 may detect an arm of a user reaching to interact with the touchpoint 3302 provided by ACS 3300. In some embodiments, user interaction with an ACS is not detected by sensor 3304. In such embodiments, detecting user interaction with an ACS involves detecting a user has touched, interacted with, or otherwise engaged with a user interface provided by an ACS. For example, user interaction may be detected by a user inputting data via a keyboard. In another example, user interaction may be detected by a user swiping a touchscreen to initiate a control command.

Process 3400 is shown to include beginning a countdown timer and denying user access to an ACS (step 3404), according to some embodiments. In some embodiments, beginning a countdown timer involves activating a countdown performed by timer 3208. In some embodiments, beginning a countdown timer involves commencing a countdown from a predetermined time period (e.g., 15 seconds, 30 seconds, 45 seconds, etc.). The predetermined time period may be configurable based on user preference, healthcare data received from a health authority (e.g., HAIS 2526), etc. In some embodiments, the countdown timer begins upon detection of user interaction with an ACS (e.g., step 3402). In some embodiments, the countdown timer begins upon completion of user interaction with an ACS. For example, the countdown timer may begin upon determination that a user's hand has vacated a predetermined region associated with an ACS.

In some embodiments, denying user access to an ACS involves moving a barrier (e.g., a cover, a shield, etc.) to a location between a user and disinfection surface of the ACS such that users are substantially prevented from interacting and/or being irradiated by a UVC source. In such embodiments, the ACS provides a barrier that is movably coupled to the ACS. In some embodiments, denying user access to an ACS involves disabling a user interface. Disabling a user interface may discourage users from touching, approaching, or otherwise interacting with the disinfection surface of the ACS. It should be understood that the previous examples of denying user access to an ACS are not intended to be limiting. Any other technique, method, and/or device may be used to substantially prevent users from interacting with a disinfection surface. For example, an audible warning or visual queue may be presented to users to notify the users of an impending disinfection process.

Process 3400 is shown to include monitoring presence of one or more users relative to an ACS (step 3406), according to some embodiments. In some embodiments, monitoring presence of one or more users involves sensor 3204 collecting presence data within a predetermined region associated with an ACS. In some embodiments in which a user has been detected to enter and/or be present, the countdown timer is canceled (e.g., turned off, terminated, etc.) and reset. In such embodiments, the countdown timer begins upon detection that a user has vacated the predetermined region associated with the ACS.

Process 3400 is shown to include beginning a disinfection technique (step 3408), according to some embodiments. In some embodiments, beginning a disinfection technique involves activating UVC source 3202 to emit a germicidal dosage of UVC. In such embodiments, beginning a disinfection technique involves adjusting the disinfection parameters (e.g., duration, number of cycles, light intensity, etc.) based on the collected sensor data and/or collected healthcare data.

Process 3400 is shown to include continuously collecting presence data during a disinfection technique (step 3410), according to some embodiments. In some embodiments, collecting presence data involves sensor 3204 collecting presence data within a predetermined region of an ACS (e.g., ACS 3300). In some embodiments in which the presence data indicates a user is present within the predetermined region, a deactivation signal is transmitted to the UVC source 3202. For example, a sensor detects a user who is reaching towards a keypad on an ACS while a disinfection technique is being performed. Accordingly, upon detection of the user, a deactivation signal is transmitted to the UVC source which deactivates (e.g., turns off) the UVC source.

Process 3400 is shown to involve ending the disinfection technique and allowing access to the disinfected ACS (step 3412), according to some embodiments. In some embodiments, users are allowed access to the disinfected ACS upon completion of a countdown that begins following the end of the disinfection cycle. Such a countdown may help ensure that the UVC source has been substantially turned off or otherwise adjusted to a safe operation mode. In some embodiments, ending a disinfection technique includes transmitting various data to designated receivers (e.g., disinfection system controller 2500, HAIS 2526, etc.). Such data may include wavelength of UVC emitted, duration of disinfection technique, and number of disinfection technique cycles performed over a period of time.

Building Management System

Figure 35:
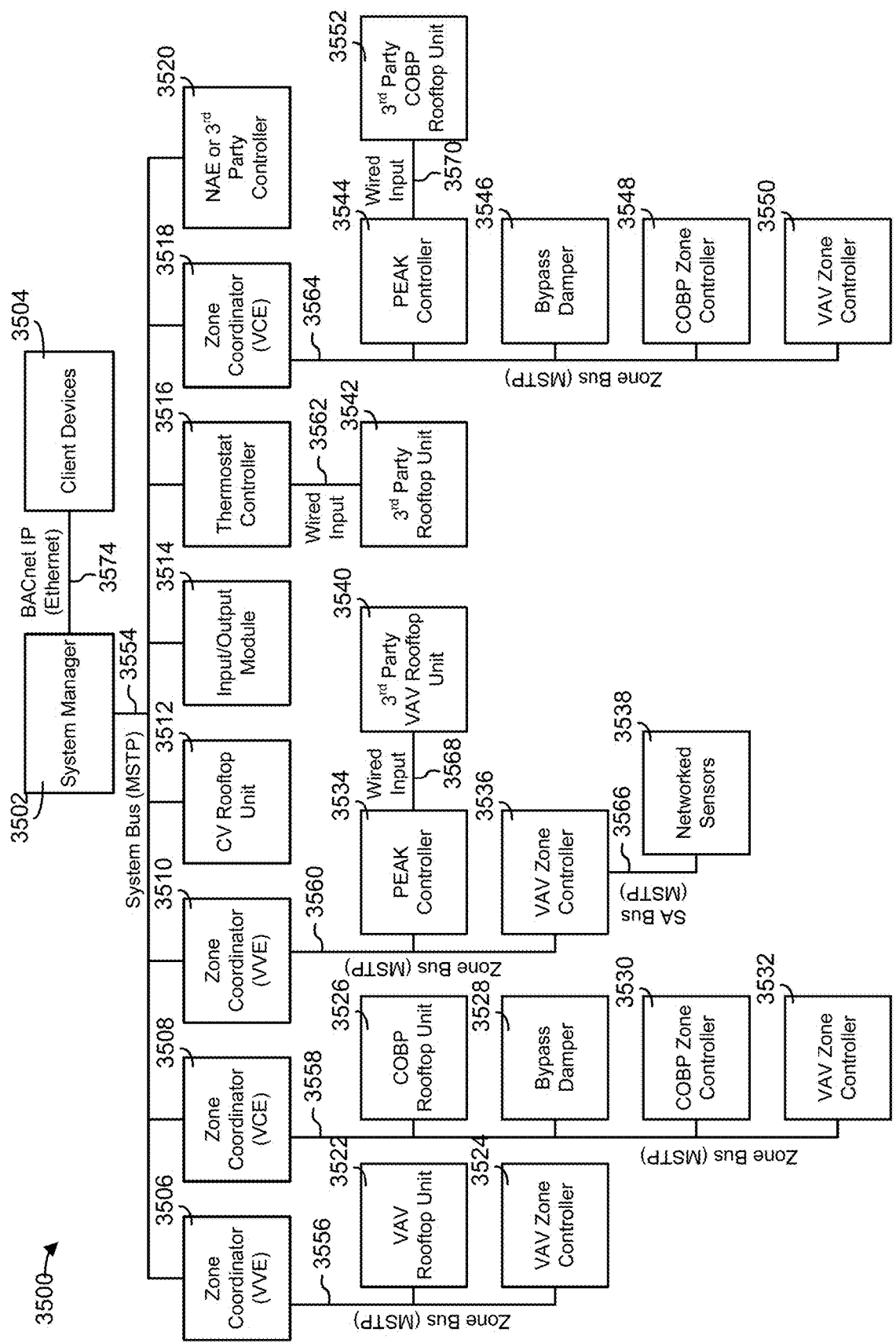
FIG. 35 is a block diagram of another BMS which can be used to monitor and control the building of FIG. 1, according to some embodiments.

Referring now to FIG. 35, a block diagram of another building management system (BMS) 3500 is shown, according to some embodiments. BMS 3500 can be used to monitor and control the devices of HVAC system 100, waterside system 200, airside system 300, building subsystems 428, as well as other types of BMS devices (e.g., lighting equipment, security equipment, etc.) and/or HVAC equipment.

BMS 3500 provides a system architecture that facilitates automatic equipment discovery and equipment model distribution. Equipment discovery can occur on multiple levels of BMS 3500 across multiple different communications busses (e.g., a system bus 3554, zone buses 3556-3560 and 3564, sensor/actuator bus 3566, etc.) and across multiple different communications protocols. In some embodiments, equipment discovery is accomplished using active node tables, which provide status information for devices connected to each communications bus. For example, each communications bus can be monitored for new devices by monitoring the corresponding active node table for new nodes. When a new device is detected, BMS 3500 can begin interacting with the new device (e.g., sending control signals, using data from the device) without user interaction.

Some devices in BMS 3500 present themselves to the network using equipment models. An equipment model defines equipment object attributes, view definitions, schedules, trends, and the associated BACnet value objects (e.g., analog value, binary value, multistate value, etc.) that are used for integration with other systems. Some devices in BMS 3500 store their own equipment models. Other devices in BMS 3500 have equipment models stored externally (e.g., within other devices). For example, a zone coordinator 3508 can store the equipment model for a bypass damper 3528. In some embodiments, zone coordinator 3508 automatically creates the equipment model for bypass damper 3528 or other devices on zone bus 3558. Other zone coordinators can also create equipment models for devices connected to their zone busses. The equipment model for a device can be created automatically based on the types of data points exposed by the device on the zone bus, device type, and/or other device attributes. Several examples of automatic equipment discovery and equipment model distribution are discussed in greater detail below.

Still referring to FIG. 35, BMS 3500 is shown to include a system manager 3502; several zone coordinators 3506, 3508, 3510 and 3518; and several zone controllers 3524, 3530, 3532, 3536, 3548, and 3550. System manager 3502 can monitor data points in BMS 3500 and report monitored variables to various monitoring and/or control applications. System manager 3502 can communicate with client devices 3504 (e.g., user devices, desktop computers, laptop computers, mobile devices, etc.) via a data communications link 3574 (e.g., BACnet IP, Ethernet, wired or wireless communications, etc.). System manager 3502 can provide a user interface to client devices 3504 via data communications link 3574. The user interface may allow users to monitor and/or control BMS 3500 via client devices 3504.

In some embodiments, system manager 3502 is connected with zone coordinators 3506-3510 and 3518 via a system bus 3554. System manager 3502 can be configured to communicate with zone coordinators 3506-3510 and 3518 via system bus 3554 using a master-slave token passing (MSTP) protocol or any other communications protocol. System bus 3554 can also connect system manager 3502 with other devices such as a constant volume (CV) rooftop unit (RTU) 3512, an input/output module (TOM) 3514, a thermostat controller 3516 (e.g., a TEC5000 series thermostat controller), and a network automation engine (NAE) or third-party controller 3520. RTU 3512 can be configured to communicate directly with system manager 3502 and can be connected directly to system bus 3554. Other RTUs can communicate with system manager 3502 via an intermediate device. For example, a wired input 3562 can connect a third-party RTU 3542 to thermostat controller 3516, which connects to system bus 3554.

System manager 3502 can provide a user interface for any device containing an equipment model. Devices such as zone coordinators 3506-3510 and 3518 and thermostat controller 3516 can provide their equipment models to system manager 3502 via system bus 3554. In some embodiments, system manager 3502 automatically creates equipment models for connected devices that do not contain an equipment model (e.g., IOM 3514, third party controller 3520, etc.). For example, system manager 3502 can create an equipment model for any device that responds to a device tree request. The equipment models created by system manager 3502 can be stored within system manager 3502. System manager 3502 can then provide a user interface for devices that do not contain their own equipment models using the equipment models created by system manager 3502. In some embodiments, system manager 3502 stores a view definition for each type of equipment connected via system bus 3554 and uses the stored view definition to generate a user interface for the equipment.

Each zone coordinator 3506-3510 and 3518 can be connected with one or more of zone controllers 3524, 3530-3532, 3536, and 3548-3550 via zone buses 3556, 3558, 3560, and 3564. Zone coordinators 3506-3510 and 3518 can communicate with zone controllers 3524, 3530-3532, 3536, and 3548-3550 via zone busses 3556-3560 and 3564 using a MSTP protocol or any other communications protocol. Zone busses 3556-3560 and 3564 can also connect zone coordinators 3506-3510 and 3518 with other types of devices such as variable air volume (VAV) RTUs 3522 and 3540, changeover bypass (COBP) RTUs 3526 and 3552, bypass dampers 3528 and 3546, and PEAK controllers 3534 and 3544.

Zone coordinators 3506-3510 and 3518 can be configured to monitor and command various zoning systems. In some embodiments, each zone coordinator 3506-3510 and 3518 monitors and commands a separate zoning system and is connected to the zoning system via a separate zone bus. For example, zone coordinator 3506 can be connected to VAV RTU 3522 and zone controller 3524 via zone bus 3556. Zone coordinator 3508 can be connected to COBP RTU 3526, bypass damper 3528, COBP zone controller 3530, and VAV zone controller 3532 via zone bus 3558. Zone coordinator 3510 can be connected to PEAK controller 3534 and VAV zone controller 3536 via zone bus 3560. Zone coordinator 3518 can be connected to PEAK controller 3544, bypass damper 3546, COBP zone controller 3548, and VAV zone controller 3550 via zone bus 3564.

A single model of zone coordinator 3506-3510 and 3518 can be configured to handle multiple different types of zoning systems (e.g., a VAV zoning system, a COBP zoning system, etc.). Each zoning system can include a RTU, one or more zone controllers, and/or a bypass damper. For example, zone coordinators 3506 and 3510 are shown as Verasys VAV engines (VVEs) connected to VAV RTUs 3522 and 3540, respectively. Zone coordinator 3506 is connected directly to VAV RTU 3522 via zone bus 3556, whereas zone coordinator 3510 is connected to a third-party VAV RTU 3540 via a wired input 3568 provided to PEAK controller 3534. Zone coordinators 3508 and 3518 are shown as Verasys COBP engines (VCEs) connected to COBP RTUs 3526 and 3552, respectively. Zone coordinator 3508 is connected directly to COBP RTU 3526 via zone bus 3558, whereas zone coordinator 3518 is connected to a third-party COBP RTU 3552 via a wired input 3570 provided to PEAK controller 3544.

Zone controllers 3524, 3530-3532, 3536, and 3548-3550 can communicate with individual BMS devices (e.g., sensors, actuators, etc.) via sensor/actuator (SA) busses. For example, VAV zone controller 3536 is shown connected to networked sensors 3538 via SA bus 3566. Zone controller 3536 can communicate with networked sensors 3538 using a MSTP protocol or any other communications protocol. Although only one SA bus 3566 is shown in FIG. 35, it should be understood that each zone controller 3524, 3530-3532, 3536, and 3548-3550 can be connected to a different SA bus. Each SA bus can connect a zone controller with various sensors (e.g., temperature sensors, humidity sensors, pressure sensors, light sensors, occupancy sensors, etc.), actuators (e.g., damper actuators, valve actuators, etc.) and/or other types of controllable equipment (e.g., chillers, heaters, fans, pumps, etc.).

Each zone controller 3524, 3530-3532, 3536, and 3548-3550 can be configured to monitor and control a different building zone. Zone controllers 3524, 3530-3532, 3536, and 3548-3550 can use the inputs and outputs provided via their SA busses to monitor and control various building zones. For example, a zone controller 3536 can use a temperature input received from networked sensors 3538 via SA bus 3566 (e.g., a measured temperature of a building zone) as feedback in a temperature control algorithm. Zone controllers 3524, 3530-3532, 3536, and 3548-3550 can use various types of control algorithms (e.g., state-based algorithms, extremum seeking control (ESC) algorithms, proportional-integral (PI) control algorithms, proportional-integral-derivative (PID) control algorithms, model predictive control (MPC) algorithms, feedback control algorithms, etc.) to control a variable state or condition (e.g., temperature, humidity, airflow, lighting, etc.) in or around building 10.

Micro-Climate Measurement, Actuation, and Control

Figure 36A:
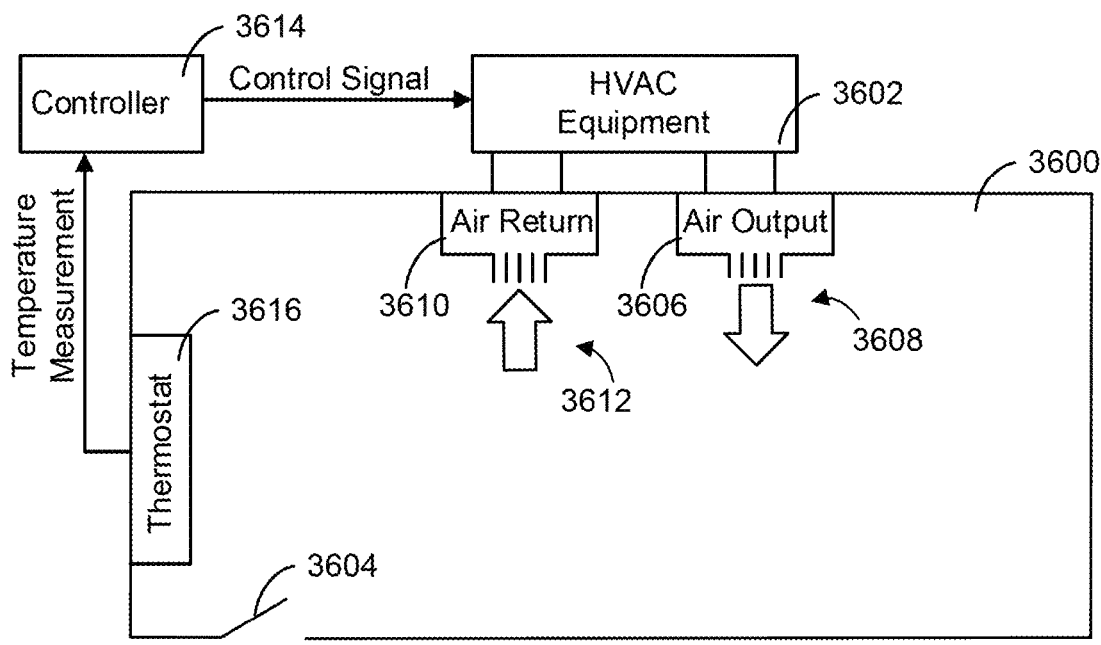
FIGS. 36A-36B are two schematic diagrams showing the current state of the art of temperature measurement, according to some embodiments.
Figure 36B:
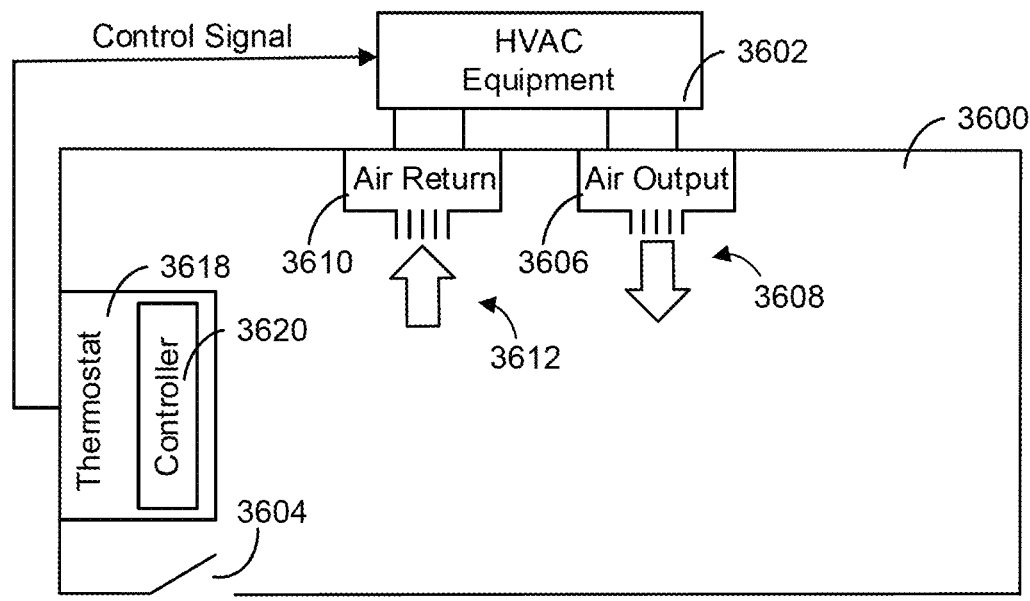

Referring now to FIGS. 36A-B, two schematic diagrams showing the current state of the art of temperature measurement can be seen, according to exemplary embodiments. With regard to FIG. 36A, a room and its corresponding measurement, control, and actuation components are shown, according to an exemplary embodiment. FIG. 36A shows a room 3600 that is shown to include a door 3604, according to one embodiment. Depending on the embodiment, the shape, size, and contents of room 3600 may vary, as well as the position and configuration of door 3604. Room 3600 may also be connected to one or more other rooms, hallways, or other areas, with the configuration as well as the size and shape of any adjacent and/or connected areas varying according to the specific embodiment. Room 3600 is also shown to include a thermostat 3616, positioned on a wall of room 3600, according to an exemplary embodiment. The specific placement of thermostat 3616 may vary depending on embodiment in terms of which of the walls of room 3600 it is placed on. Thermostat 3616 may be configured to collect a temperature measurement for room 3600, which may be taken by one or more of a variety of means, depending on the embodiment. Thermostat 3616 may also be connected to a controller 3614, according to an exemplary embodiment. According to the embodiment of FIG. 36A, controller 3614 is a separate entity from thermostat 3616 and is not integrated as a component of thermostat 3616.

Controller 3614 of FIG. 36A, which is connected to and receives a temperature measurement from thermostat 3616 is also coupled to HVAC equipment 3602, according to the exemplary embodiment of FIG. 36A. HVAC equipment 3602 may vary depending on the embodiment, and may also vary in terms of location depending on the configuration, shape, and size of room 3600, the placement of door 3604, as well as other factors specific to certain embodiments. In some embodiments, HVAC equipment 3602 is a component of an HVAC system such as HVAC system 100 of FIG. 1 or may be a component of an HVAC subsystem such as HVAC subsystem 440 of FIG. 4. HVAC equipment 3602 may include various HVAC components including those shown and described previously. For example, HVAC equipment 3602 which may be controlled by controller 3614 may include air handling units (AHUs) such as AHU 106 and/or AHU 302 of FIG. 1 and FIG. 3, respectively. Variable Air Volume units (VAVs) can also be included in HVAC equipment 3602 of FIG. 6. In some embodiments, HVAC equipment 3602 can include air ducts for both air supply and air return such as air supply ducts 112 and air return ducts 114 of FIG. 1 and/or return air 304 of return air duct 308 and supply air 310 and supply air duct 312. Additionally, HVAC equipment 3602 can include components of HVAC systems which can include chillers and boilers such as chiller 102 and boiler 104 of FIG. 1, as well as various dampers such as exhaust damper 316, mixing damper 318, and outside air damper 320 of FIG. 3 and/or bypass dampers 3528 and 3546 of FIG. 35. Other HVAC equipment and/or components of HVAC systems can also be included in HVAC equipment 3602, such as fan 338, valves 346 and 352, and actuator 354 of FIG. 3 which can be configured to adjust direction of airflow as well as size of an orifice through which air passes. It should also be noted that other equipment not mentioned previously that can be configured to operate in conjunction with an HVAC system and any components thereof may also be included in HVAC equipment 3602. Generally, HVAC systems and components thereof that can be configured to affect air temperature, quality, humidity, and airflow (including velocity) may be included in HVAC equipment 3602 as all of the previously mentioned parameters can be adjusted in order to affect occupant comfort for an area.

HVAC equipment 3602 may be configured to receive a control signal from controller 3614, according to the exemplary embodiment of FIG. 36A. HVAC equipment 3602 is also shown to be connected with an air output 3606, according to an exemplary embodiment. Air output 3606 is shown to produce an output airflow 3608, according to the exemplary embodiment of FIG. 36A. As also seen in the embodiment of FIG. 36A, HVAC equipment 3602 is also shown to be connected to an air return 3610, which is configured to receive a return airflow 3612. Depending on the embodiment, as well as factors specific to room 3600 such as size, shape, and other variables, air output 3606 and air return 3610 may be positioned in various locations of the room. Air output 3606 and air return 3610 may also be connected to HVAC equipment 3602 through a variety of means, and HVAC equipment may not always be in the same proximity as shown in the exemplary embodiment of FIG. 36A. It should also be noted that the configuration of thermostat 3616, controller 3614, HVAC equipment 3602, air output 3606, air return 3610 and door 3604 may be configured differently depending on embodiment, and may not be positioned in the same proximity to one another as indicated in the exemplary embodiment of FIG. 36A.

Referring now to FIG. 36B, another room and corresponding measurement, control, and actuation components are shown, according to an exemplary embodiment. FIG. 36B shares some common components with FIG. 36A, including room 3600, HVAC equipment 3602, door 3604, air output 3606, output airflow 3608, air return 3610, and return airflow 3612. As with the embodiment shown in FIG. 36A, the common components may vary in terms of their placement about room 3600 depending on the specific embodiment. Additionally, room 3600 itself may also vary depending on the embodiment and may include various shapes, sizes, points of entry and exit, adjacent areas and hallways, as well as other possible configurations. In the embodiment shown in FIG. 36B, a thermostat 3618 is shown configured on a wall of room 3600. Depending on the embodiment, thermostat 3618 may be located elsewhere in room 3600. Thermostat 3618 of FIG. 36B is shown to include a controller 3620 which may be adjacent to or embedded in thermostat 3618, depending on the embodiment. It should also be noted that controller 3620 may be positioned within thermostat 3618, or may be positioned adjacent to thermostat 3618 depending on the embodiment. Controller 3620 is shown to be in communication with HVAC equipment 3602, and may communicate a control signal to HVAC equipment, depending on the embodiment.

Referring again to FIG. 36B, HVAC equipment 3602 is shown to be connected to air output 3606 and air return 3610, according to an exemplary embodiment. HVAC equipment 3602 is shown to be connected to air output 3606 and air return 3610, according to the exemplary embodiment of FIG. 36B. Additionally, air output 3606 is shown to eject an output airflow 3608, and air return 3610 is shown to receive a return airflow 3612 according to some embodiments. Depending on the embodiment, air output 3606 and corresponding output airflow 3608, as well as air return 3610 and corresponding return airflow 3612 may be positioned differently in relation to room 3600, depending on other components and variables of room 3600. HVAC equipment 3602 may be configured differently than that seen in the exemplary embodiment of FIG. 36B, and also may be positioned and spaced in a manner different from that of the exemplary embodiment. In reference to both FIGS. 36A and 36B, it should be noted that the components of room 3600 may vary or be a combination of those seen in FIG. 36A and FIG. 36B, depending on the embodiment.

Referring now to FIG. 36A and FIG. 36B, it should be noted that the embodiments of both FIG. 36A and FIG. 36B include a thermostat positioned on a wall of room 3600. In terms of the positioning of the thermostats seen in FIG. 36A and FIG. 36B, both thermostat 3616 of FIG. 36A and thermostat 3618 of FIG. 36B are located on walls of room 3600. That is to say that while output airflow 3608 and return airflow 3612 are directed to the middle of room 3600, any temperature measurements taken by thermostat 3616 or thermostat 3618 may not accurately reflect the temperature in the central portion of room 3600 where occupants may be positioned. As such, the comfort of occupants potentially occupying a central portion of room 3600 may not be able to adequately manipulate various parameters for room 3600 given that the parameters of an area occupied by occupants may differ substantially from those measured adjacent to the wall by thermostat 3616 or thermostat 3618.

Figure 37:
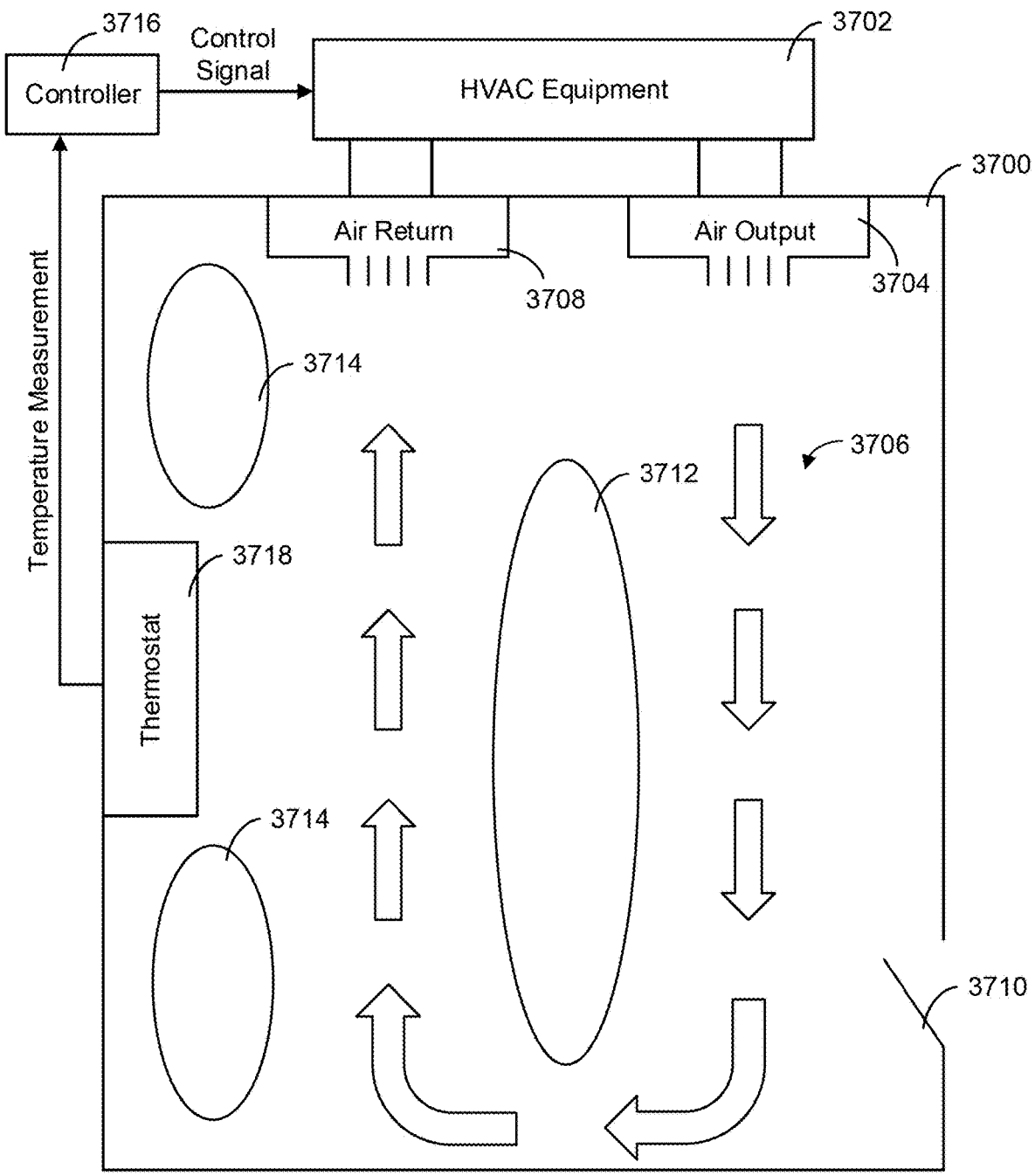
FIG. 37 is a schematic diagram showing deficiencies of the current state of the art in terms of temperature measurement and airflow actuation, according to some embodiments.

Referring now to FIG. 37, a schematic diagram showing deficiencies of the current state of the art in terms of temperature measurement and airflow actuation is shown, according to an exemplary embodiment. With reference to FIG. 37, a room 3700 is shown, according to an exemplary embodiment. Room 3700 is shown to include door 3710, with variables such as location, size, shape, as well as other variables applicable to both room 3700 and door 3710. It should be noted that the placement of all components of room 3700 seen in FIG. 37 may vary in placement and position, both relative to room 3700 and relative to other components. Room 3700 is shown to include an HVAC equipment 3702, according to the exemplary embodiment of FIG. 37. As seen in the embodiment of FIG. 37, HVAC equipment 3702 is shown to be connected to an air output 3704 and an air return 3708. The configuration of HVAC equipment 3702 and corresponding connection to air output 3704 and air return 3708 may vary depending on embodiment in terms of position, spacing, specific connection, and other possible factors. Air output 3704 and air return 3708 are shown to have an airflow 3706, as seen in the exemplary embodiment of FIG. 37. Airflow 3706 is shown to be ejected from air output 3704 and be received by air return 3708, according to an exemplary embodiment. Airflow 3706 is also shown to have a rectangular path according to the exemplary embodiment of FIG. 37, but this may vary depending on a number of factors. For example, if air output 3704 and air return 3708 were to be positioned differently relative to HVAC equipment 3702, room 3700, or each other, airflow 3706 may assume a path shaped differently than that of airflow 3706 seen in the exemplary embodiment of FIG. 37.

Referring again to FIG. 37, room 3700 is shown to include a thermostat 3718, according to an exemplary embodiment. Depending on the embodiment, thermostat 3718 may be similar to either thermostat 3616 of FIG. 36A and/or thermostat 3618 of FIG. 36B. In the embodiment shown in FIG. 37, thermostat 3718 is shown to be connected to a controller 3716, and is shown to send a temperature measurement to be received by controller 3716. Controller 3716 of FIG. 37 may be similar to controller 3614 of FIG. 36A and/or controller 3620 of FIG. 37B, depending on the embodiment. In the embodiment of FIG. 37, controller 3716 is shown to also be connected to HVAC equipment 3702, and is shown to send a control signal to HVAC equipment 3702. The connection between thermostat 3718 and controller 3716 may vary depending on the embodiment, just as the connection between controller 3716 and HVAC equipment 3702 may also vary. Additionally, the configuration and positioning of HVAC equipment 3702, controller 3716, and thermostat 3718 may vary relative to room 3700 and relative to each other, depending on the embodiment.

Referring still to FIG. 37, room 3700 is shown to include a central dead spot 3712, according to an exemplary embodiment. Central dead spot 3712 of FIG. 37 may assume a different shape or location depending on a number of factors specific to an embodiment such as the size, position, and configuration of air output 3704 and air return 3708, as well as variables associated with room 3700 including size and shape, among others. For example, central dead spot 3712 may differ according to embodiment based on the contents of room 3700 of FIG. 37, such as the contents of room 3700, which may include occupants and/or furniture in some embodiments. Central dead spot 3712 is specific to the configuration of air output 3704 and air return 3708 of FIG. 37, but may also be true of other possible configurations of air output 3704 and air return 3708. Central dead spot is located near the middle of room 3700, which also includes a pair of lateral dead spots 3714, according to the exemplary embodiment of FIG. 37. Lateral dead spots 3714 are positioned between airflow 3706 and a wall of room 3700, according to an exemplary embodiment. Similar to central dead spot 3712, lateral dead spots 3714 may vary in size, shape, position and quantity depending on a number of factors relating to room 3700 and its associated components. For example, the configuration of HVAC equipment 3702 and its corresponding connections to air output 3704 and air return 3708 may vary depending on factors relating to room 3700 such as size and shape, and may be adjusted in different embodiments.

The embodiment of FIG. 37 serves to demonstrate the current state of the art in HVAC systems and their management of rooms and/or areas in terms of the equipment designed to produce and regulate airflow, as well as control temperature and ultimately occupant comfort. In the embodiment shown in FIG. 37, air output 3704 and air return 3708 are static in that airflow 3706 cannot be adjusted or aimed in any manner. That is to say that airflow 3706 may be the only possible airflow that air output 3704 and air return 3708 are capable of providing to room 3700. In the embodiment seen in FIG. 37, occupants of a room may be positioned in the center of the room, and may overlap with central dead spot 3712. Given the proximity of central dead spot 3712 to thermostat 3718, the temperature where occupants may be located may differ drastically from the temperature measured at thermostat 3718, which may be located on a wall of room 3700. Additionally, the temperature of lateral dead spots 3714 may also differ greatly from a majority of the room, and may also fall in an area where occupants may be positioned. In the instance that occupants are positioned within central dead spot 3712 or lateral dead spots 3714, the temperature and comfort of occupants may not be consistent with the measurement taken by thermostat 3718 or airflow 3706, depending on the embodiment.

Figure 38A:
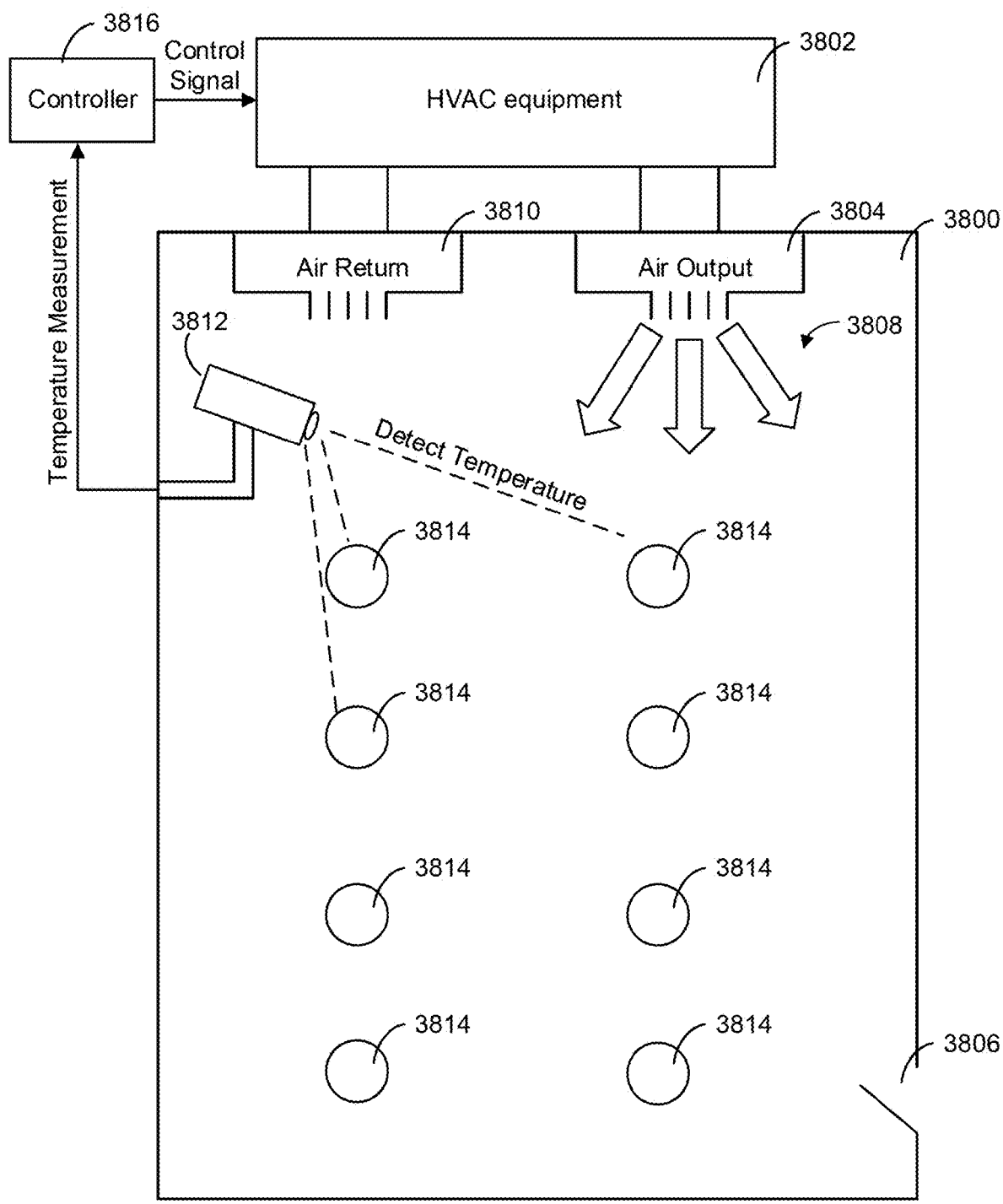
FIGS. 38A-38B are two schematic diagrams showing the measurement and actuation of variables in order to maximize occupant comfort, according to some embodiments.
Figure 38B:
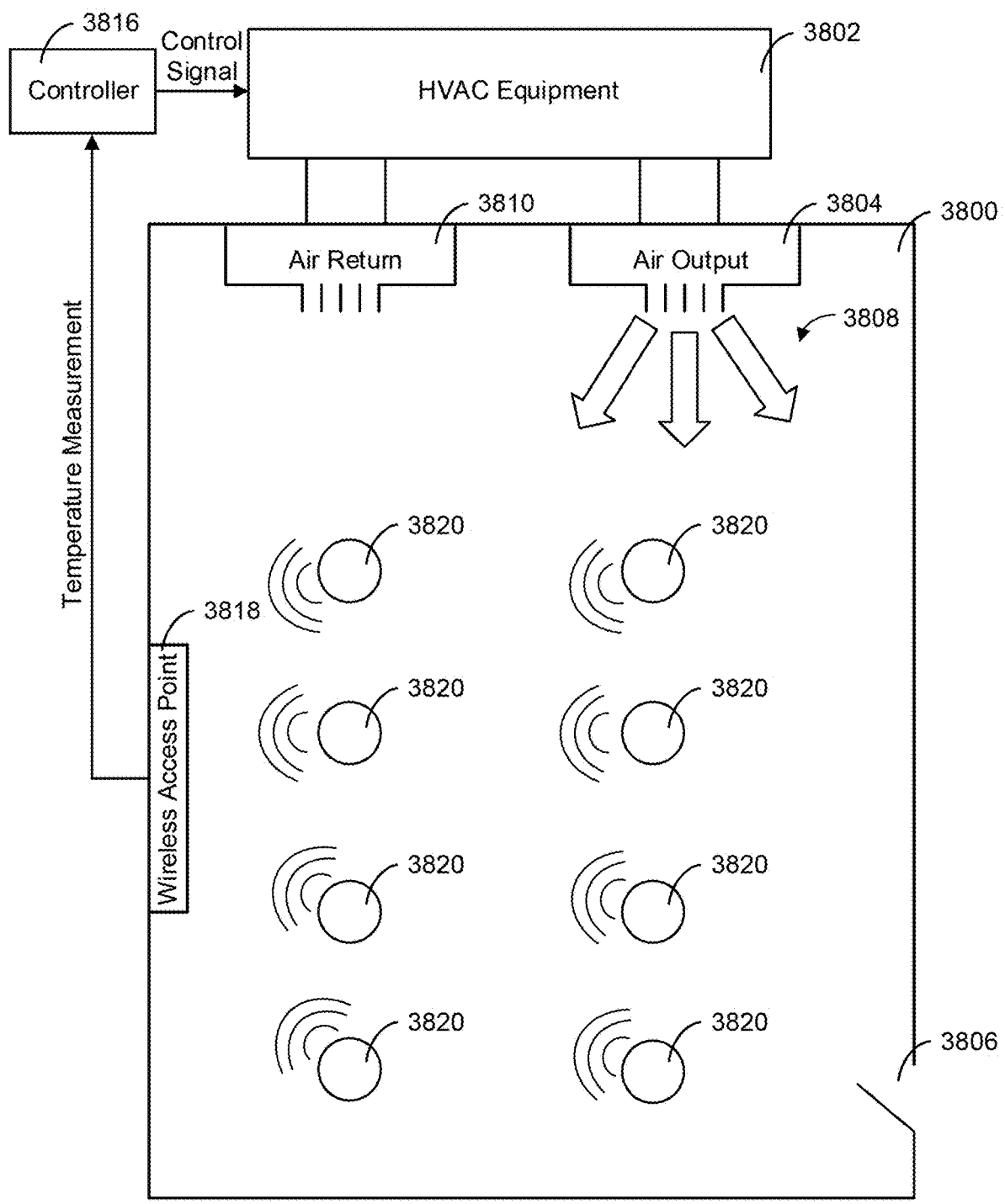

Referring now to FIG. 38A-B, two schematic diagrams showing the measurement and actuation of variables in order to maximize occupant comfort are shown, according to some embodiments. With reference to FIG. 38A, a system for maximizing occupant using HVAC equipment connected to a camera is shown, according to an exemplary embodiment. FIG. 38A is shown to include a room 3800 as well as a door 3806. It should be noted that the size and shape of the room as well as the size, shape and location of the door may vary according to embodiment. Room 3800 is also shown to include a camera 3812, which is shown to be mounted on a wall of room 3800 as seen in the exemplary embodiment of FIG. 38A. Depending on embodiment, camera 3812 may be an IR camera. FIG. 38A also indicates that, according to an exemplary embodiment, camera 3812 is mounted on a wall of room 3800 in order to cover all or the majority of room 3800. Depending on the embodiment, as well as the shape and size of room 3800, camera 3812 may be positioned differently. Camera 3812 may be connected to a controller 3816, according to the exemplary embodiment of FIG. 38A. This connection may allow for camera 3812 to communicate a temperature measurement to controller 3816. Controller 3816 is also connected to an HVAC equipment 3802, and communicates a control signal to HVAC equipment 3802. It should be noted that the means of connection between camera 3812 and controller 3816, as well as the connection means between controller 3816 and HVAC equipment 3802 may vary depending on embodiment, and also may differ from one another. HVAC equipment 3802 is seen in FIG. 38A to be connected to an air output 3804 and an air return 3810. Depending on the embodiment, air output 3804 and air return 3810 may be positioned differently in relation to each other, HVAC equipment 3802, and room 3800.

Referring still to FIG. 38A, room 3800 is also shown to include a collection of occupants 3814 positioned in a central portion of room 3800. As indicated in FIG. 38A, camera 3812 may locate occupants 3814 and register the position of occupants within room 3800. In the instance that camera 3812 is an IR camera which is preferable, temperature of various areas of room 3800 can be measured from the remote position where camera 3812 is located within room 3800. That is to say that camera 3812 may measure the temperature of various locations within room 3800 from a stationary position within room 3800, and may also identify the location of occupants 3814 within room 3800. By measuring temperature in a central portion of room 3800 from a non-invasive location on the perimeter of room 3800 such as that occupied by camera 3812 in the exemplary embodiment of FIG. 38A, camera 3812 may communicate with controller 3816, which may in turn communicate with HVAC equipment 3802 in order to affect change within room 3800. However, contrary to the embodiments of FIG. 36A, FIG. 36B, and FIG. 37, in which temperature is measured adjacent to the thermostat located on a wall of a room, the components of FIG. 38A are configured to measure temperature at multiple points in the room from a remotely located camera, seen as camera 3812.

Referring still to FIG. 38A, air output 3804 is configured to eject air in a variety of directions depending on the control signal sent from controller 3816 to HVAC equipment 3802, according to the exemplary embodiment. According to the embodiment seen in FIG. 38A, camera 3812 is configured to measure temperature and identify locations of occupants 3814 within room 3800, and can in turn communicate temperature measurements that correspond to locations of occupants 3814 to controller 3816. Controller 3816 may then send a control signal to HVAC equipment 3802, which may in turn actuate air output 3804 in order to affect temperature in the portion of the room that contains occupants 3814, according to the exemplary embodiment of FIG. 38A. Air output 3804 may be configured to direct an airflow 3808 to one or more portions of room 3800, according to an exemplary embodiment. Depending on the location of occupants 3814, air output 3804 may direct air toward or away from occupants 3814, depending on occupant comfort preferences as well as pre-determined parameters for the overall components and room of FIG. 38A.

Referring now to FIG. 38B, a system for maximizing occupant using HVAC equipment connected to a wireless access point is shown, according to an exemplary embodiment. Similar to FIG. 38A, room 3800 includes door 3806, according to an exemplary embodiment. Also included in FIG. 38B that is common to FIG. 38A is controller 3816, an HVAC equipment 3802, air output 3804, air return 3810, and airflow 3808. FIG. 38B is also shown to include a wireless access point 3818, positioned on a wall of room 3800, according to an exemplary embodiment. Wireless access point 3818 is shown to be located on the wall of room 3800, according to the exemplary embodiment of FIG. 38B. Wireless access point 3818 is configured to receive a signal from mobile sensors 3820, which are positioned in a central portion of room 3800, according to an exemplary embodiment. Mobile sensors 3820 may be assigned to specific occupants, employees, departments or other groups, and may also be configured to perform multiple functions including but not limited to providing location data, measuring temperature, among other possible functions. Mobile sensors 3820 may be located in various places, including but not limited to on personal identification badges, personal computers, chairs, as well as other possible locations depending on the embodiment. Wireless access point 3818 is shown to be connected to controller 3816, with controller 3816 also connected to HVAC equipment 3802, according to the exemplary embodiment of FIG. 38B. Additionally, wireless access point 3818 may communicate one or more temperature measurements to controller 3816, which may then communicate a control signal to HVAC equipment 3802. It should be noted that wireless access point 3818, controller 3816, and HVAC equipment 3802 may be connected by a variety of different means, with the connection between wireless access point 3818 and controller 3816 potentially being the same, similar to, or different than the connection between controller 3816 and HVAC equipment 3802. It also must be noted that the placement of wireless access point 3818, controller 3816, and HVAC equipment 3802 may vary from that seen in the embodiment of FIG. 38B, both in terms of placement around room 3800 and relative to each other.

Again referring to FIG. 38B, wireless access point 3818 is configured to communicate with mobile sensors 3820. There may be one or multiple wireless mobile sensors in room 3800 at one time, with all present mobile sensors 3820 communicating with wireless access point 3818. Mobile sensors pay be specific to personnel, for example each mobile sensor may be coupled to an identification card or badge, a personal computer, or other personal object. As such, a mobile sensor 3820 may be representative of a specific individual or group, and as such may carry certain permissions and/or parameters. For example, mobile sensors 3820 may be substantially the same, with each mobile sensor 3820 having a unique sensor ID. The mobile sensors 3820 may be configured to transmit various measurements collected along with the unique sensor ID to the wireless access point 3818. The unique ID of each of the mobile sensors 3820 can be associated with a specific individual (e.g., John Doe) or with a specific user class (e.g. management, technicians, visitors) within system implemented by controller 3816. Different individuals and/or different classes can be assigned various relative weights indicating importance of a specific individual or user class. Accordingly, controller 3816 can be configured to determine the optimal actions to be taken with regard to occupant comfort for the room 3800 according to measured comfort levels at the location of the mobile sensors 3820 of the more highly weighted individuals or user classes. Ultimately, mobile sensors 3820 may be configured to carry a priority level which may then be communicated with wireless access point 3818 and ultimately impact the control signal sent form controller 3816 to HVAC equipment 3802, as well as the subsequent activity of HVAC equipment 3802 upon receiving said control signal.

Referring still to FIG. 38B, HVAC equipment 3802 is shown to be connected to air output 3804 and air return 3810, according to an exemplary embodiment. Air output 3804 is shown to produce airflow 3808, which may be adjustable by means of air output 3804, according to the embodiment of FIG. 38B. Additionally, it should be noted that the positioning of HVAC equipment 3802, air output 3804, and air return 3810 may vary depending on embodiment, both in relation to room 3800 and each other. Air output 3804 may be capable of producing a variety different variations of airflow 3808, according to the exemplary embodiment of FIG. 38B. For example, depending on the control signal sent form controller 3816 to HVAC equipment 3802, air output 3804 may project airflow 3808 in a specific direction or multiple directions throughout room 3800. Air output 3804 may behave in order to satisfy other parameters for room 3800 and/or for HVAC equipment 3802, such as operating efficiency levels, noise levels from fan speed, room temperature, and occupant comfort levels, among others.

Figure 39A:
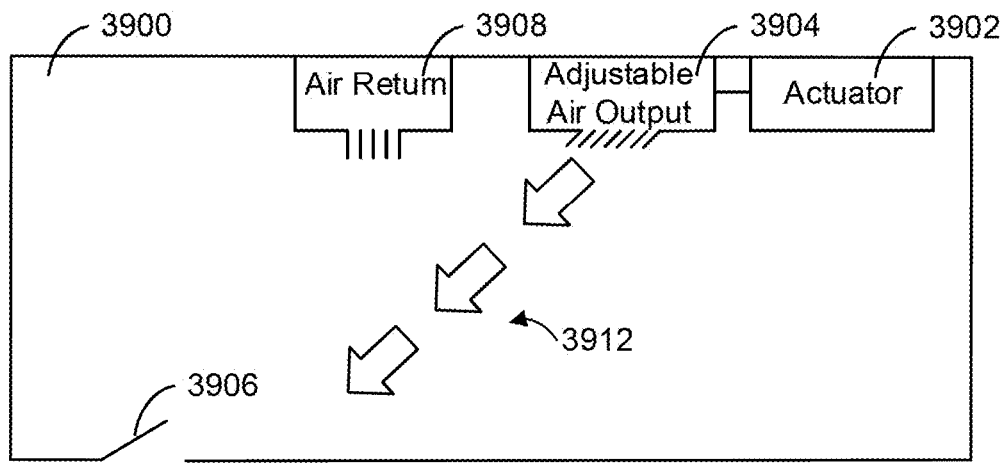
FIGS. 39A-39C are three schematic diagrams showing the actuation of airflow with a space in order to maximize occupant comfort, according to some embodiments.
Figure 39B:
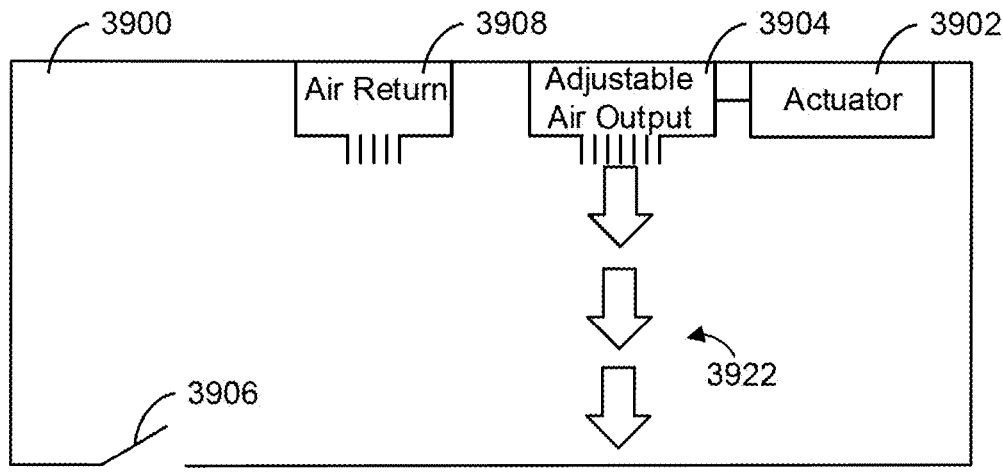
Figure 39C:
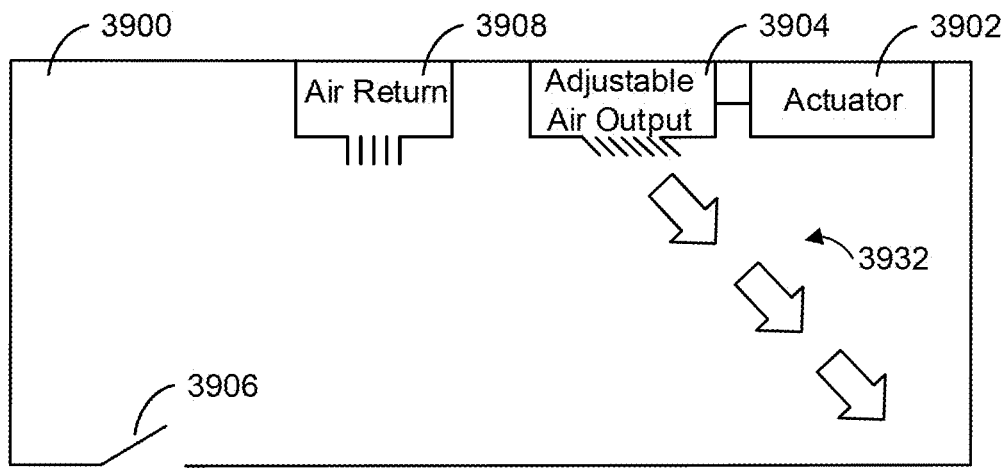

Referring now to FIG. 39A-C, three schematic diagrams showing the actuation of airflow with a space in order to maximize occupant comfort are shown, according to some embodiments. With reference to FIG. 39A, an adjustable air output for a room is shown, according to an exemplary embodiment. FIG. 39A includes a room 3900, which includes a door 3906, according to an exemplary embodiment. Depending of the specific embodiment, room 3900 as well as door 3906 may vary in size, shape, and location, as well as other factors. Room 3900 is also shown to include an actuator 3902, which is connected to an adjustable air output 3904, as seen in the exemplary embodiment of FIG. 39A. Additionally, room 3900 may include an air return 3908. It should be noted that the location of actuator 3902, adjustable air output 3904, and air return 3908 may vary in size and position, both in relation to room 3900 and in relation to each other. Adjustable air output 3904 is shown to produce a first airflow 3912, according to the exemplary embodiment of FIG. 39A. First airflow 3912 is shown to be produced from adjustable air output at an oblique angle, and in the instance of FIG. 39A, adjustable air output 3904 is configured to eject first airflow 3912 toward door 3906. For example, if room 3900 included occupants positioned between adjustable air output 3904 and door 3906, it may be preferable for adjustable air output 3904 to produce first airflow 3912 so as to directly affect the portion of room 3900 containing any occupants, and thus adjust the comfort level of the occupants as quickly as possible.

Referring now to FIG. 39B, adjustable air output is shown to produce an airflow at an orthogonal angle, according to an exemplary embodiment. Depending of the specific embodiment, room 3900 as well as door 3906 may vary in size, shape, and location, as well as other factors. Room 3900 is also shown to include an actuator 3902, which is connected to an adjustable air output 3904, as seen in the exemplary embodiment of FIG. 39A. Additionally, room 3900 may include an air return 3908. It should be noted that the location of actuator 3902, adjustable air output 3904, and air return 3908 may vary in size and position, both in relation to room 3900 and in relation to each other. FIG. 39B is shown to include room 3900, with adjustable air output 3904 producing a second airflow 3922 at an angle orthogonal to the wall of room 3900 on which adjustable air output is positioned, according to the exemplary embodiment of FIG. 39B. In the exemplary embodiment of FIG. 39B, adjustable air output 3904 has been adjusted from the position seen in the exemplary embodiment of FIG. 39A shown to produce first airflow 3912, to the position seen in the exemplary embodiment of FIG. 39B, in which adjustable air output 3904 is shown to produce second airflow 3922. In some instances, second airflow 3922 may be preferable to first airflow 3912, depending on the embodiment as well as other factors. For example, if the priority for occupant comfort of room 3900 was the central portion of the room, second airflow 3922 may be preferable to first airflow 3912, and can be achieved by the adjustment of adjustable air output 3904 as seen between FIG. 39A and FIG. 39B.

Referring now to FIG. 39C, an adjustable air output is shown to produce an airflow at an oblique angle, according to an exemplary embodiment. Depending of the specific embodiment, room 3900 as well as door 3906 may vary in size, shape, and location, as well as other factors. Room 3900 is also shown to include an actuator 3902, which is connected to an adjustable air output 3904, as seen in the exemplary embodiment of FIG. 39A. Additionally, room 3900 may include an air return 3908. It should be noted that the location of actuator 3902, adjustable air output 3904, and air return 3908 may vary in size and position, both in relation to room 3900 and in relation to each other. FIG. 39B is shown to also include adjustable air output 3904, which is shown to produce a third airflow 3932, according to an exemplary embodiment. Adjustable air output 3904 may produce third airflow at an oblique angle relative to the wall of room 3900 on which adjustable air output 3904 is positioned, according to the exemplary embodiment of FIG. 39C. In some instances, it may be desirable for adjustable air output 3904 to be directed as seen in FIG. 39C, in which third airflow 3932 is directed away from a central portion of room 3900. For example, if room 3900 were to include a window, or a portion of the room that was presented challenges in terms of reaching and/or maintaining occupant comfort, it may be desirable for adjustable air output 3904 to direct third airflow 3932 toward that direction, as seen in the exemplary embodiment of FIG. 39C.

Referring to FIGS. 39A-C, it should be noted that adjustable air output 3904 and air return 3908, as well as actuator 3902 may be part of a system similar to that seen in FIG. 38A-B which included controller 3816, HVAC equipment 3802, camera 3812 and/or wireless access point 3818.

Actuator 3902 of FIG. 39A-C may also be connected to some or all of the previously mentioned components, depending on embodiment.

Figure 40A:
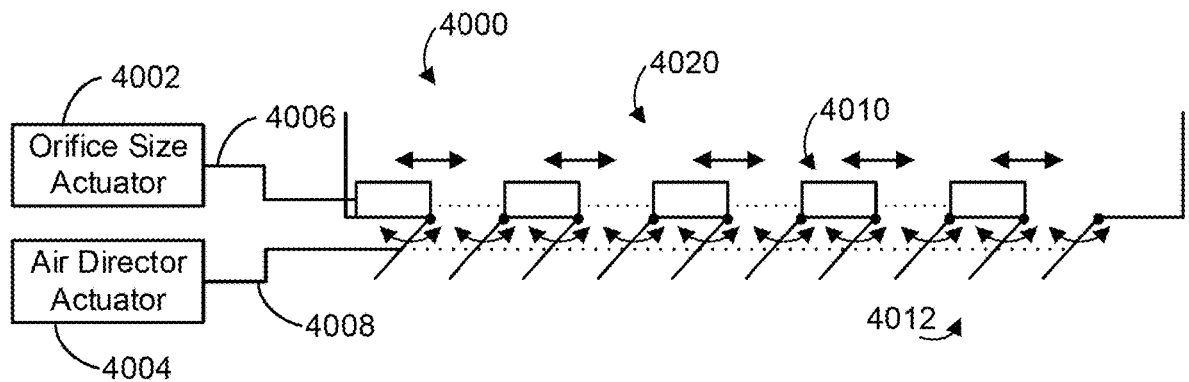
FIGS. 40A-40C are three schematic diagrams showing an actuation mechanism to control airflow and air ejection angle, according to some embodiments.
Figure 40B:
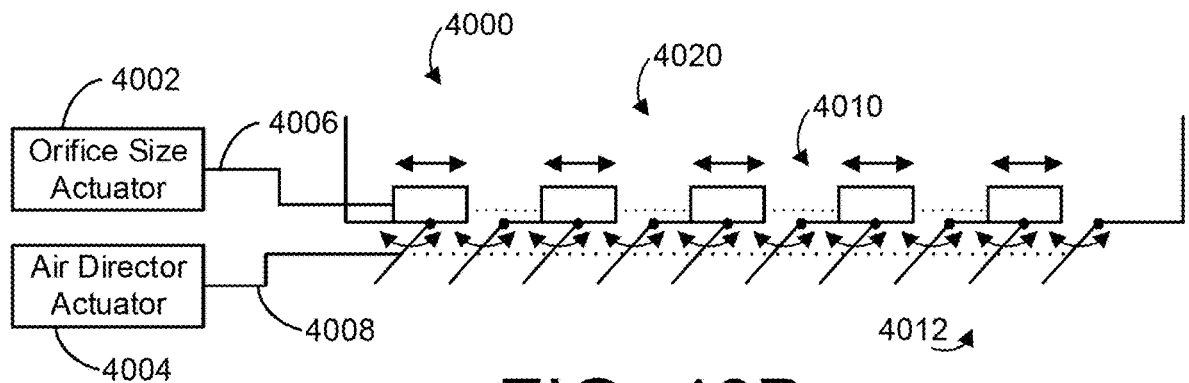
Figure 40C:
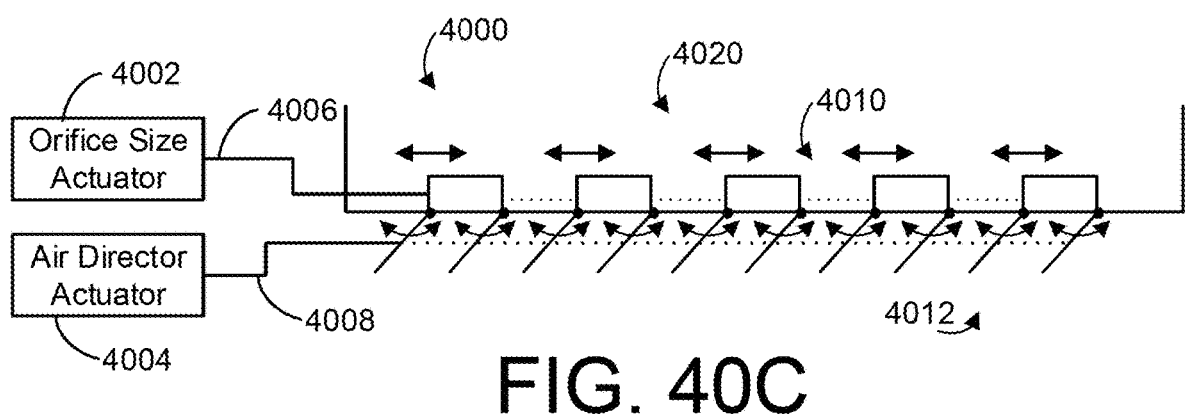

Referring now to FIGS. 40A-C, an adjustable portion of an airway is shown, according to an exemplary embodiment. FIGS. 40A-C are shown to include an airway 4000, which includes orifices 4020, according to one embodiment. Orifices 4020 may be coupled to an orifice size actuator 4002, depending on embodiment. Orifice size actuator 4002 is shown to include an orifice shaft 4006, which is shown to be coupled to one or more orifice adjusters 4010, as seen in an exemplary embodiment. Airway 4000 is also shown to be connected to an air director actuator 4004, which is coupled to a director shaft 4008, according to an exemplary embodiment. Director shaft 4008 may be coupled to one or more director adjusters 4012 by the same means, similar means, or different means than orifice shaft 4006 may be connected to orifice adjusters 4010. Orifice adjusters 4010 are configured to translate within airway 4000 with the translation being driven by orifice size actuator 4002 and enabled by orifice shaft 4006, according to an exemplary embodiment. Similarly, director adjusters 4012 are configured to move adjacent to airway 4000, with movement of director adjusters driven by air director actuator 4004, which is coupled to director shaft 4008, according to one embodiment. Director adjusters 4012 are configured to direct air moving through airway 4000 in order to affect an area, similar to room 3900 of FIGS. 39A-C, for example. For example, director adjusters 4012 may be moved independently, or in conjunction with and corresponding to translation of orifice adjusters 4010, according to some embodiments. Thus, orifice adjusters 4010 and director adjusters 4012 may allow for air passing through airway 4000 to be actuated both in terms of volumetric flow rate and ejection angle, according to the exemplary embodiment of FIGS. 40A-C.

Referring still to FIGS. 40A-C, orifice adjusters 4010 are seen to be translatable within airway 4000, according to an exemplary embodiment. When managing airflow, two main factors may be actuated in order to affect occupant comfort for an area, with those two factors being volumetric flow rate, and direction angle of air ejected from the airway. Orifice adjusters allow for the volumetric flow rate to be managed in conjunction with orifice size actuator 4002 and orifice shaft 4006, according to one embodiment. Orifice adjusters 4010 may be configured within airway 4000 so that they may allow, impede, or prevent air from passing through airway 4000, thus managing volumetric flow rate of air within airway 4000. For example. FIG. 40A shows orifice adjusters 4010 in a fully open position which may allow maximum volumetric flow rate within airway 4000. FIG. 40B shows orifice adjusters 4010 partially closed position, in which orifice adjusters 4010 partially impede the flow of air within airway 4000 thereby allowing for adjustment of volumetric flow rate of air. FIG. 40C shows orifice adjusters 4010 in a fully closed position, in which airway 4000 may be blocked from ejecting air from airway 4000. Orifice adjusters 4010 can, in some embodiments, ultimately allow for volumetric flow rate within airway 4000 to be actuated. Similarly, director adjusters 4012 may allow for another means of airflow management, ejection angle of air within airway 4000 according to an exemplary embodiment. Director adjusters 4012 may be configured to rotate about pivot points within a defined range of motion, allowing air within airway 4000 to be ejected at one or more angles. Movement of director adjusters 4012, including but not limited to pivoting of director adjusters 4012, may correspond to activity of air director actuator 4004 and director shaft 4008, which may ultimately allow for air to be ejected from airway 4000 at a plurality of angles.

Referring again to FIGS. 40A-C, it should be noted that the components of FIGS. 40A-C may be connected and/or coupled to other components, including but not limited to the components of FIGS. 38A-B and FIGS. 39A-C. For example, in order for orifice size actuator 4002 and air director actuator 4004 to properly actuate their respective parameters, a signal may drive these components to actuate. Depending on embodiment, such a signal may be sent from a controller, and may be received through a variety of different means. Additionally, in order for actuation of orifices 4020 and actuation of director adjusters 4012 to occur, a measurement may be taken with said measurement of a given parameter then affected by the components of FIGS. 40A-C.

Figure 41:
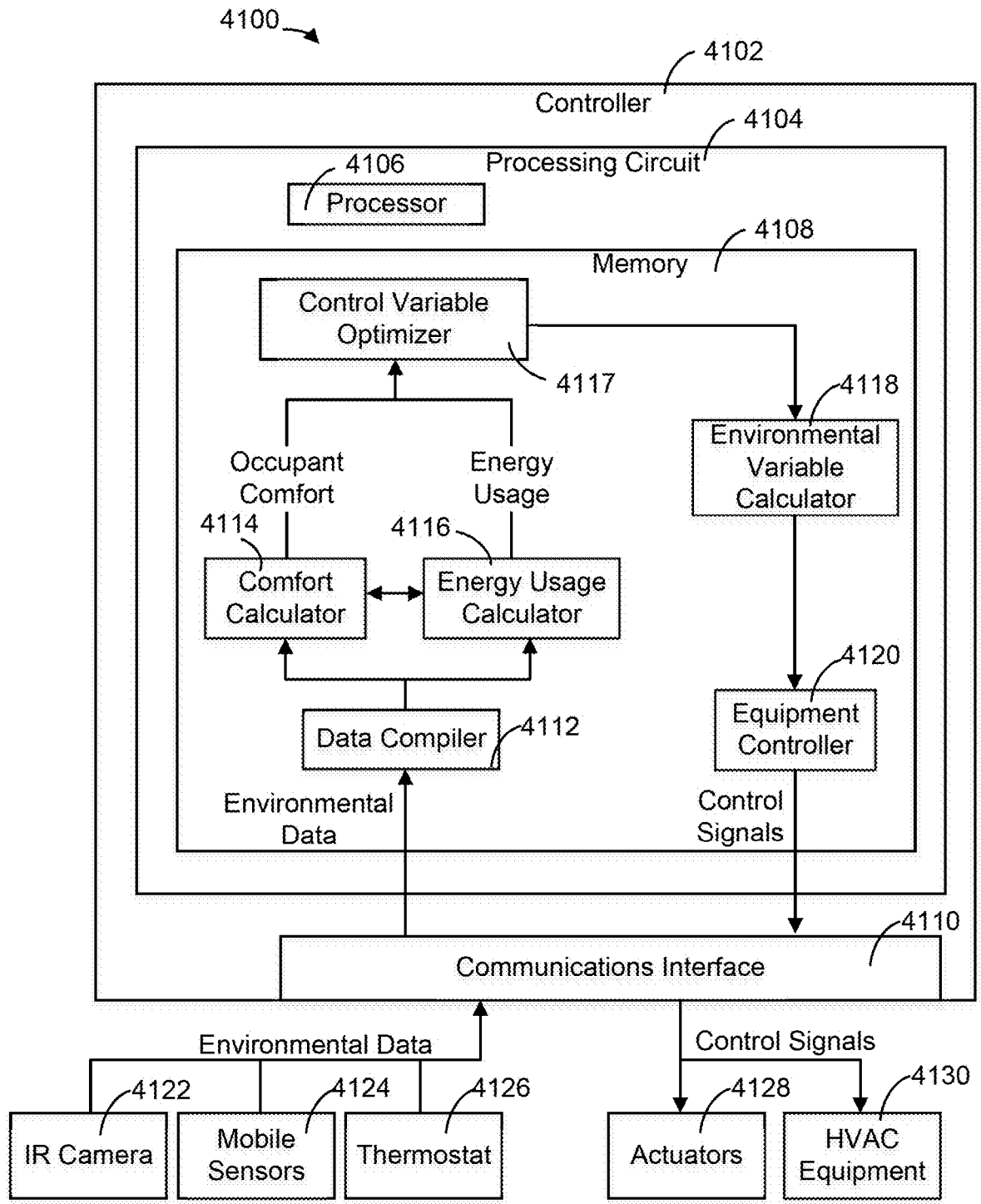
FIG. 41 is a block diagram of a system for maximizing occupant comfort which can be used to monitor and control the building of FIG. 1, according to some embodiments.

Referring now to FIG. 41, a system 4100 for maximizing occupant comfort is shown, according to an exemplary embodiment. System 4100 of FIG. 41 can be used in conjunction with building 10 of FIG. 1, and can further be used to affect and maximize occupant comfort within building 10. In some embodiments, system 4100 may be implemented for a single room, multiple rooms, or for a building such as building 10 in its entirety. Additionally, system 4100 may be configured to function differently and/or implement different components or techniques for different areas. For example, some rooms, areas, or buildings may include different measurement means for collecting environmental data, such as temperature sensors, IR cameras, airflow monitors, and other measurement components. System 4100 is shown to include a controller 4102, a processing circuit 4104, a processor 4106, and a memory 4108, as shown in the exemplary embodiment of FIG. 41. Additionally, controller 4102 is shown to include a communications interface 4110, according to some embodiments. Communications interface 4110 can be configured to facilitate communication between components of system 4100 existing separate from controller 4102 and components of controller 4102, such as components of memory 4108. It should be noted that, in some embodiments, system 4100 may include additional or alternative components relative to those shown in the exemplary embodiment of FIG. 41.

System 4100 is shown to include an IR camera 4122, mobile sensors 4124, and a thermostat 4126, as seen in the exemplary embodiment of FIG. 41. In some embodiments of system 4100, IR camera 4122, mobile sensors 4124, and thermostat 4126 may be configured within a single room, area, or building or may also be configured about an area or building. That is to say that, for example, a building such as building 10 being controlled by system 4100 may include multiple areas such as a first area including IR camera 4122 and mobile sensors 4124, as well as a second area with mobile sensors 4124 and thermostat 4126. IR camera 4122, mobile sensors 4124, and thermostat 4126 can all be configured variously about one or more areas in order to collect environmental data for the one or more areas. In some embodiments, IR camera 4122, mobile sensors 4124, and a thermostat 4126 can collect environmental data. Generally, environmental data can include data collected that can be analyzed and used to estimate occupant comfort within a given area. For example, environmental data collected IR camera 4122, mobile sensors 4124, and thermostat 4126 can include temperature data, humidity data, air flow velocity data, skin temperature measurements, as well as other data that can be used to estimate occupant comfort.

IR camera 4122 can be configured to provide spatial estimates for an area, which may include both dimensions of an area as well as population, according to some embodiments. In some embodiments, IR camera 4122 can be configured with a field of view including an entire room or area, and can further be configured to collect thermal images of said room or area, or of any occupants thereof. Thermal images captured by IR camera 4122 may include data indicating spatial location of occupants of a room or area, temperature measurements of various objects within a room, and skin temperatures of said occupants. Temperature measurements collected for various objects within a room may be processed so as to create a "heat map" indicating temperature at each location within said room. Skin temperature data collected from IR images may be analyzed relative to temperature of surrounding air (based on air temperature data collected by IR camera 4122, mobile sensors 4124, and/or thermostat 4126) as an indicator of occupant comfort. Advantageously, images captured by IR camera 4122 indicating skin temperature of occupants can be a more accurate measure of occupant comfort, as skin temperature accounts for both external air temperature as well as internal heat generation influenced by metabolic activity with an occupant's body. Additionally, IR camera 4122 may be configured to provide real-time measurement of spatial location and temperature of air streams within a given room or area prior to said air streams mixing with air already in the given room or area. In such an embodiment, the images captures by IR camera 4122 may indicate hot or cold air supply and proximity to occupants.

Skin temperature data collected by IR camera 4122 can be analyzed in order for controller 4102 to affect occupant comfort for an area. It should also be noted that skin temperature data collected may be done iteratively, which is to say that skin temperature data may be collected over time at set intervals so as to indicate change over time (e.g., rates). For example, temperature data measured from the surface of an individual's skin can be used to estimate body temperature, as well as other parameters known to impact occupant comfort such as the rate of metabolic heat generation within the body. In some embodiments, an individual may be most comfortable (e.g., occupant comfort is maximized) when the rate of heat transfer out of the body is equal to the rate of metabolic heat generation within the body. Accordingly, an equilibrium or near-equilibrium between the rate of heat transfer out of the body and the rate of metabolic heat generation within the body results in a relatively stable internal temperature, thereby maximizing occupant comfort.

The rate of heat transfer out of the body can include consideration of data and measurements other than skin temperature. For example, rate of heat transfer out of the body can be a function of several factors including but not limited to skin temperature, air temperature, airflow velocity across the skin, and humidity, all of which can impact heat transfer as defined by thermodynamic laws of convection. For example, increasing airflow velocity across the skin can help dissipate heat at the surface of the skin, thus creating a sensation that can make a person feel cooler. This concept is also applicable to evaporative cooling. In the instance that an occupant has perspired, increasing airflow velocity and/or targeting airflow to the occupant can aid in providing a cooling sensation and facilitate heat transfer out of the body at an increased rate. Ultimately, various environmental data collected can be analyzed in order to determine one or more variables that may be affected in order to maximize occupant comfort.

Mobile sensors 4124 may be similar to mobile sensors 3820 as shown in the exemplary embodiment of FIG. 38B. In some embodiments, mobile sensors 3820 may be configured on employee badges, computers, tablets, phones, or in static locations about a room or area. For example, mobile sensors 4124 may be configured on employee badges and indicate both occupancy of an area (collectively, in conjunction with other mobile sensors 4124) and may further be configured to collect temperature measurements in various locations within any room or area. In some embodiments, temperature measurements collected by mobile sensors 4124 for a given room or area may be analyzed collectively, with averages (including weighted averages, for example) computed in order to determine temperature in various locations and subsequent occupant comfort. Thermostat 4126 may be configured within an area or room such that it may collect temperature measurements for a given area and/or allow one or more users to observe temperature within said area. Additionally, thermostat 4126 may be configured to collect data in conjunction with mobile sensors 4124 and/or IR camera 4122 for a given room or general area.

System 4100 is also shown to include a data compiler 4112 in communication with communications interface 4110, as shown in the exemplary embodiment of FIG. 41. Further to FIG. 41, IR camera 4122, mobile sensors 4124, and thermostat 4126 may be configured to communicate collected environmental data to communications interface 4110, which may then be communicated to data compiler 4112. In some embodiments, communications interface 4110 may be configured to translate, reformat, or otherwise process received environmental data prior to communicating said environmental data to data compiler 4112. Environmental data such as that compiled by data compiler 4112 can include multiple streams of environmental data, with each stream of environmental data specific to a particular microclimate location within a building space. In some embodiments, environmental data may include identifying characteristics or tags associated with a location attribute defining the particular micro-climate location to which said environmental data pertains. Accordingly, upon receipt of various streams of environmental data controller 4102 may analyze the environmental for each of the micro-climate locations in order to determine proper control action to be taken. Data compiler 4112 may be configured to sort or otherwise organize environmental data in various ways, such as by location, collection mechanism (e.g., IR camera 4122, mobile sensors 4124, thermostat 4126) and/or prioritize said environmental data. For example, if environmental data collected from a specific area is indicative of a temperature substantially above or below temperatures for other locations, the data indicative of the abnormal temperature may be flagged or otherwise prioritized. Additionally, data compiler 4112 may be configured to organize data relative to concerns with occupant comfort and energy consumption. For example, data indicative of high occupant comfort (e.g., ideal skin temperature level) may be separated from data indicative of energy usage concerns (e.g. detection of hot air blown into a room that is already warm).

Data compiler 4112 is shown to be in communication with a comfort calculator 4114, as shown in the exemplary embodiment of FIG. 41. In some embodiments, data compiler 4112 may be configured to communicate compiled environmental data such as that collected by IR camera 4122, mobile sensors 4124, and thermostat 4126 to comfort calculator 4114. Comfort calculator 4114 may be configured such that environmental data received from data compiler 4112 is analyzed to determine current occupant comfort and predict future occupant comfort. Additionally, comfort calculator 4114 may compare collected environmental data indicative of occupant comfort to accepted values (e.g. set points) for occupant comfort. If collected environmental data indicative of occupant comfort levels falls outside of acceptable ranges for system 4100, comfort calculator may perform various calculations and/or other operations in order to determine occupant comfort data that, upon implementation, may restore occupant comfort levels to acceptable values.

The controller 4102 and components thereof such as comfort calculator 4114 may implement various equations in order to determine operations that will be taken in order to affect occupant comfort. Generally, occupant comfort can be quantified using various calculations and estimations based on control variables and the relationship between the control variables and body activity that correspond to the comfort of an individual. For example, one function that may be implemented by comfort calculator 4114 based on the environmental data may have the following form:

$$Q = mC\Delta t$$

where Q is the amount of heat released from processes within the body over a change in time $\Delta t$, for which the mass m is assumed to be a typical body mass of 70 kg and the specific heat capacity of the human body C is known to be approximately 58 kcal/° C. It should be noted that this equation may be applied for multiple processes within the body, computed iteratively, and may also be summed with results from this equation being applied to other bodily processes. The heat generated within the body is offset by heat loss of the body which, as mentioned previously, can be attributed to various sources including, for example, convection. Heat loss of the body due to convection may be attributed to a slight breeze, such as may be provided the systems as shown and described previously. In order to estimate heat loss of the body due to convection, comfort calculator 4114 may implement an equation having the following form:

$$\Delta Q = KA(Ts - Ta)$$

where $\Delta Q$ is the change in heat of the body over a given time (in this instance, heat lost), K is a convection factor dependent upon a wind speed for the area (which may be generated by one or more HVAC systems, for example), A is uncovered body area of a user (which may be estimated or assumed based on common attire, or according to user/operator preferences), Ts is the temperature of the skin and Ta is the temperature of the outer environment (e.g., a room or building space).

System 4100 and components thereof such as comfort calculator 4114 may also implement other equations in various calculations performed. For example, comfort calculator 4114 may implement a general equation accounting for heat generated by the body, such as that by body processes, as well as heat lost from the body, such as that lost through convective processes. One such equation incorporating the previous factors that may be implemented by comfort calculator 4114 may have the following form:

$$\Delta Q = Q\text{gen} - Q\text{out}$$

where Qgen includes all heat generated within the body by various body processes which may include metabolic activity as well as possible light physical activity of an individual, and Qout includes all heat lost by the body which may include convective cooling, for example. Ultimately, $\Delta Q$ is found to be the net heat generated or lost by the body as a result of body activity and environmental factors. Accordingly, comfort calculator 4114 can be configured to estimate $\Delta Q$ and subsequently adjust system 4100 so as to affect the comfort of one or more individuals within an area based on an estimated or calculates $\Delta Q$ for one or more of said individuals.

System 4100 is also shown to include an energy usage calculator 4116, according to an exemplary embodiment. Energy usage calculator 4116 is shown to be in communication with data compiler 4112, and similar to comfort calculator 4114, may receive environmental data initially collected by IR camera 4122, mobile sensors 4124, and thermostat 4126. Environmental data received by energy usage calculator 4116 may be processed and otherwise analyzed. System 4100 can have various control variables that controller 4102 may be configured to affect such as fan speed, air temperature, orifice size, damper blade position, and other possible control variables. Controller 4102 is also shown to include a control variable optimizer 4117, which can be configured to perform optimization operations based on the control variables according to various user and/or operator preferences. For example, control variable optimizer 4117 may run optimization operations in order to determine and implement the most energy (and accordingly, cost) efficient means of achieving a level of occupant comfort by affecting one or more of the control variables. Further to the previous example, this may involve increasing fan speed in order to achieve a cooling effect and thus increase occupant comfort over time, which may be more energy efficient that implementing a chiller to affect air temperature within an area. Conversely, control variable optimizer 4117 may also be configured to perform optimization operations in order to determine the fastest means to achieving a level of occupant comfort. Contrary to the previous example, in order to achieve the desired level of occupant comfort as quickly as possible control variable optimizer 4117 may prioritize occupant comfort over energy use (and cost), and implement a chiller to affect air temperature for a space rather than implementing a fan. It should be noted that control variable optimizer 4117 may perform optimization operations that identify one or more control variables to be affected by one or more HVAC systems of components thereof to achieve a desired level of occupant comfort. Generally, control variable optimizer 4117 can be configured to analyze energy usage and cost in determining control variables (and corresponding equipment/components) to be affected in order to improve occupant comfort. This analysis may involve determining cost of energy usage in order to achieve desired conditions for a given room or area over a given time period.

In some embodiments, comfort calculator 4114 and energy usage calculator may be configured to implement various equations and/or functions in order to determine occupant comfort as well as energy usage and corresponding cost. Additionally, data from both comfort calculator 4114 and energy usage calculator 4116 can be communicated to control variable optimizer 4117, which can then accordingly incorporate both comfort and energy cost/usage considerations in various optimization processes as described previously. Some comfort calculations performed by both comfort calculator 4114 and energy usage calculator 4116 may be for a specified optimization period having one or more steps, or for multiple optimization periods. Control variable optimizer 4117 can then be configured to perform various optimization functions according to energy usage and occupant comfort data. With regard to occupant comfort, for example, skin temperatures of occupants and airflow patterns indicated in IR images captured by IR camera 4122 may be incorporated into an equation as well as temperature, occupant location, and identity data collected by mobile sensors 4124. Conversely, with regard to energy usage, airflow velocities and pressures required by equipment as well as corresponding cost considerations may be incorporated. Both comfort calculator 4114 and energy usage calculator 4116 can be configured to weight comfort and/or energy usage and corresponding cost in various calculations performed. For example one function that may be implemented by control variable optimizer 4117 based on data received from comfort calculator 4114 and/or in energy usage calculator 4116 may have the following form:

$$J(x) = \sum_{k=1}^{h} (\text{Quantified Comfort})_k - \sum_{k=1}^{h} (\text{Quantified energy usage})_k$$

where the index k denotes a time step in the optimization period and h is the total number of time steps in the optimization period. Quantified comfort may, for example, be quantified in terms of time or energy required to change and/or sustain a certain comfort level. Quantified energy usage may correspond to energy required to operate fans, heating/cooling equipment, and other possible components and may also be presented in terms of cost. As shown and described previously, occupant comfort may be estimated and/or calculated based on heat generated and heat lost by the bodies of one or more users within the space. For example, heat generated may be due to various metabolic processes within the body, while heat lost may be due to convective cooling as a function of air movement within a space. It should be noted that, in some embodiments, quantified comfort or quantified energy usage may be weighted according to preferences of a user and/or operator so as to prioritize the optimization of either comfort or energy usage and corresponding cost. For example, a weight parameter may be applied to (i.e., multiplied by) the quantified comfort term, the quantified energy use term, or both, in order to assign greater or lesser importance to occupant comfort or energy use.

Occupant comfort data and energy usage data are shown to be communicated from comfort calculator 4114 and energy usage calculator 4116, respectively, to control variable optimizer 4117 as shown in the exemplary embodiment of FIG. 41. Occupant comfort data and energy usage data can be weighted according to a variety of factors. In some embodiments, both occupant comfort data and energy usage data can be functions of one or more control variables that may be affected in order to improve occupant comfort within and area. Control variable optimizer 4117 is configured to receive the occupant comfort data and the energy usage data and, based on one or more user preferences and/or weights applied to either occupant comfort or energy usage, determine the optimal values of the control variables in order to improve occupant comfort for a given area. Additionally, control variable optimizer 4117 may be configured to segment a given area into one or more microclimates based on occupant comfort data and energy usage data received. For one or more microclimates within a given area, occupant comfort can be calculated for each microclimate and summed together in order to determine an aggregate occupant comfort value for a given area. Depending on the contents of various microclimates, one or more microclimates may be weighted based on occupation of the microclimate, for example, or importance of a specific individual in a given location. That is to say that occupant comfort may be prioritized (e.g., weighted) for specific areas (including microclimates within a given area), high-profile individuals, times of day/week/year, and energy usage data may be similarly weighted depending on circumstance and user/operator preferences. In some embodiments, occupant comfort data can include desired occupant comfort levels, for example desired average occupant skin temperatures as measured by IR camera 4122. Energy usage data communicated to environmental variable calculator 4118 may include desired energy usage levels, for example with regard to costs of operation calculated by energy usage calculator 4116. Based on received occupant comfort data and energy usage data, environmental variable calculator 4118 can be configured to calculate variables to be affected in order to satisfy said occupant comfort data and energy usage data. For example, environmental variable calculator 4118 can be configured to determine various control variable that can be affected in order to achieve the desired comfort and energy usage data. In some embodiments, environmental variable calculator 4118 may perform operations to determine combinations of one or more of fan speed, heating/cooling activity, air pressure, air direction via deflector angle, and orifice size as well as other possible control variables in order to satisfy comfort and energy usage data.

In determining which control variable(s) are to be affected, both comfort and energy usage and corresponding cost are to be considered. For example, in the event that high-profile individual has a measured skin temperature outside of an accepted range, control variable optimizer 4117 may be configured to disregard energy usage and corresponding cost in order to restore occupant comfort as fast as possible by affecting one or more of the aforementioned control variables. This may be implemented by applying a larger weight to the occupant comfort relative to the energy usage (and cost) for a particular microclimate in which the high-profile individual is located. Ultimately, this would result in the specific microclimate in which the high profile individual is located being prioritized over other microclimates within the given area.

System 4100 is shown to include an equipment controller 4120 which is configured to receive control signals generated and communicated by environmental variable calculator 4118. Equipment controller 4120 may be in communication with various equipment that operates as a part of or in conjunction with system 4100, and may further be configured to generate control signals capable of affecting various equipment to achieve desired outcomes. For example, with reference to the exemplary embodiment of FIG. 41, equipment controller is shown to receive data from environmental variable calculator 4118. In some embodiments, data received from environmental variable calculator 4118 may include determinations made by environmental variable calculator for various control variables to be affected in order to satisfy specific parameters for occupant comfort and energy consumption/cost. Based on said determinations, equipment controller 4120 can be configured to generate corresponding control signals in order to affect behavior of various equipment thus affecting the various control variables through operations of different equipment. Equipment controller 4120 is shown to communicate said control signals to affect control equipment to communications interface 4110, where control signals may be translated and/or otherwise processed prior to transmittal to destination control equipment.

Communications interface 4110 is shown to communicate control signals received from equipment controller 4120 to actuators 4128 and HVAC equipment 4130, as shown in the exemplary embodiment of FIG. 41. In some embodiments, actuators 4128 and HVAC equipment 4130 may be the same as and/or similar to actuator 3902 of FIGS. 39A-C (and/or actuators 4002 and 4004 of FIGS. 40A-C) and HVAC equipment 3802 as shown in FIGS. 38A-B, respectfully. Control signals received by actuators 4128 and HVAC equipment 4130 may be configured to affect both actuators 4128 and HVAC equipment in a variety of ways in order to satisfy comfort and/or energy usage/cost parameters. For example, with regard to actuators 4128, control signals may be transmitted thereto in order to affect orifice size (and subsequently air pressure and/or air velocity), air ejection angle, ejector oscillation, and other possible variables controlled through actuation of actuators 4128. With regard to HVAC equipment 4130, control signals may be configured to increase or decrease cooling or heating, adjust fan speed and also adjust other features of HVAC equipment 4130 that can affect control variables as described previously.

Figure 42:
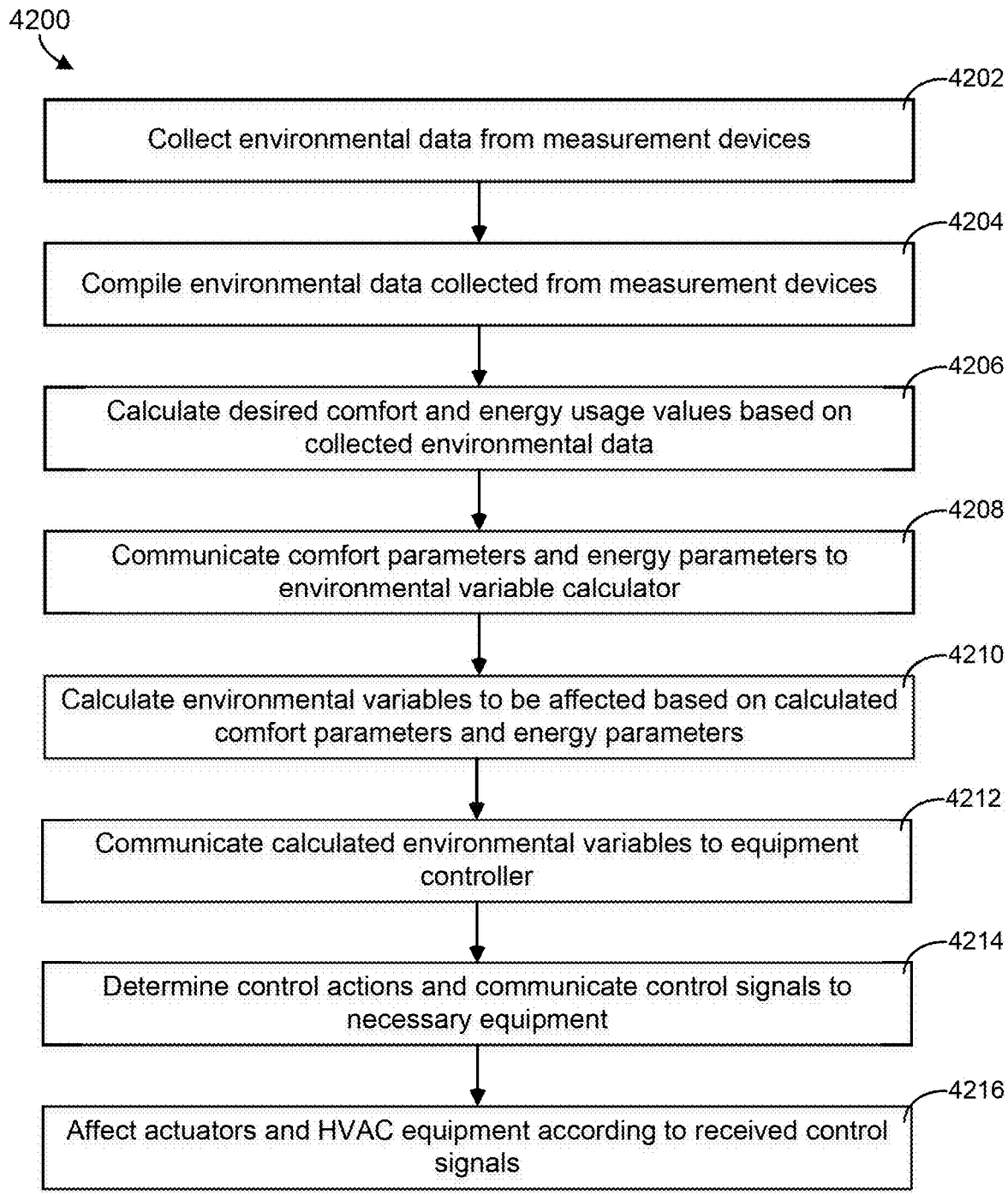
FIG. 42 is a flow diagram of a process for maximizing occupant comfort for an area that can be performed by the system of FIG. 41, according to some embodiments.

Referring now to FIG. 42, a process 4200 for measuring and actuating occupant comfort is shown, according to an exemplary embodiment. Process 4200 can be performed by system 4100 as shown in FIG. 41, for example, which may be used to control a room, area, or the entirety of building 10 as shown in FIG. 1. Process 4200 may be performed as shown in FIG. 42, or may also be performed alternatively. For example, in some embodiments, process 4200 may be performed with some steps shown in the exemplary embodiment of FIG. 42 skipped, repeated, or completed in parallel (e.g., concurrently). It should also be noted that the steps of process 4200 as well as process 4200 as a whole may be completed by some or all of the components of system 4100 as shown in FIG. 41, or may be completed by other systems and/or components which may include but is not limited to other components shown and described previously such as, for example, those of FIGS. 39A-C and FIGS. 40A-C.

Process 4200 is shown to include collecting environmental data from measurement devices (step 4202), according to an exemplary embodiment. Step 4202 may be performed by the various measurement devices shown in FIG. 41 such as IR camera 4122, mobile sensors 4124, and thermostat 4126, as well as other possible measurement devices including those shown and described previously. Step 4202 can include any collection of environmental data which may include skin temperature measurements, occupancy or spot temperature data, and/or general temperature data as collected by IR camera 4122, mobile sensors 4124, and thermostat 4126, respectively. Data collected in step 4202 may be collected in a variety of formats and may be subsequently stored and transmitted using various methods. Collected data may be communicated by wired or wireless means, and may also be stored and/or communicated using cloud technologies as well as other possible technologies.

Process 4200 is shown to include compiling environmental data collected from measurement devices (step 4204), according to an exemplary embodiment. Step 4204 can, in some embodiments, be executed by data compiler 4112 of system 4100 as shown in FIG. 41. In some embodiments, environmental data compiled by data compiler 4112 may be compiled in various formats. For example, data compiler 4112 may be configured to compiler environmental locally, such as on a local hard drive, or may also be configured to compile environmental data using cloud storage methods such that the compiled data may be accessible from remote locations. Additionally, data compiled by data compiler 4112 may also be formatted and or organized. Data compiler 4112 may be configured to organize data according to source, data type, or other parameters that may be implemented by a user and/or operator. Organization of environmental data by data compiler 4112 may also be done in order to facilitate analysis of said data by other components involved in process 4200, for example those of system 4100 as shown in the exemplary embodiment of FIG. 41.

Process 4200 is shown to include calculating desired comfort and energy usage values based on collected environmental data (step 4206), according to an exemplary embodiment. Step 4206 can, in some embodiments, be performed by one or both of comfort calculator 4114 and/or energy usage calculator 4116 as shown in FIG. 41. With respect to step 4206, comfort values and/or parameters may be calculated by comfort calculator 4114 based on environmental data received from and compiled by data compiler 4112. Energy usage values and/or parameters may be determined by energy usage calculator 4116 based on environmental data received from and compiled by data compiler 4112. It should also be noted that comfort values and energy usage values may be determined in parallel, with comfort values depending on energy usage values and/or energy usage values dependent on comfort values, according to some embodiments.

Process 4200 is shown to include communicating occupant comfort data and energy usage data to a control variable optimizer (step 4208), according to an exemplary embodiment. In some embodiments, occupant comfort data may be weighted relative to energy usage data. For example, if environmental data initially collected in step 4202 indicates that high-profile personnel may be within a given area, comfort may be prioritized over cost, which is to say that a system such as system 4100 of FIG. 41 may be configured to achieve desired comfort levels as quickly as possible regardless of energy usage and/or cost. Conversely, in the instance that energy usage/cost may be weighted, systems such as system 4100 of FIG. 41 may be configured to achieve desired comfort levels through the most energy and/or cost effective avenue. Weighted and prioritized features which may be implemented in step 4208 can be configured according to user and/or operator preferences.

Process 4200 is shown to include determining optimal control variables to be affected based on occupant comfort and energy usage data (step 4210), according to an exemplary embodiment. Step 4210 may be executed by control variable optimizer 4117 as shown in the exemplary embodiment of FIG. 41, according to some embodiments. Control variables calculated in step 4210 may consider received comfort and energy usage data of step 4208, which is to say that control variables may be calculated according to weighted or prioritized functions such as occupant comfort or energy usage. Control variables may include various control variables such as air velocity, air ejection angle, fan speed, cooling/heating activity, orifice size, as well as other possible control variables. Step 4210 may also vary according to system, for example in the instance of system 4100 of FIG. 41 control variables may be calculated relative to environmental data collected by IR camera 4122, mobile sensors 4124, and thermostat 4126. That is to say that, in some embodiments, control variables may only be calculated relative to environmental data collected so as to affect conditions indicated by the collected environmental data.

Process 4200 is shown to include communicating optimized control variables to an environmental variable calculator (step 4212), according to an exemplary embodiment. Step 4212 may include communicating optimization data of step 4210 to an environmental variable calculator through wired and/or wireless means. In some embodiments, calculated optimization data communicated to the environmental variable calculator, which may be the same as and/or similar to environmental variable calculator 4118 of system 4100 as shown in FIG. 41, may be done via a cloud connection. Additionally, optimization data communicated to the environmental variable calculator may be relative to other components of a system, such as system 4100 of FIG. 41. That is to say that optimization data of step 4212 can be specific to available equipment, for example providing data relating to actuation of an ejector of an air vent only in the event that the equipment controller is configured to operate said equipment.

Process 4200 is shown to include communicating environmental preferences to an equipment controller (step 4214), according to an exemplary embodiment. Environmental preferences of step 4214 may be generated according to optimization data of step 4212, according to some embodiments. For example, environmental preferences may include increased air speed for an area based on received optimization data indicating that air speed is a control variable to be affected in order to ultimately affect occupant comfort for an area. Environmental preferences of step 4214 may include specifics relating to the adjusted air speed such as direction, duration, as well as other possible variations of one or more control variables to be affected.

Process 4200 is shown to include determining control actions and communicating control signals to necessary equipment (step 4216), according to an exemplary embodiment. Step 4216 may be executed in part or in whole by equipment controller 4120 as shown in the exemplary embodiment of FIG. 41. Step 4216 includes, in some embodiments, translating received environmental preferences into control signals to be sent to various control equipment in order to initiate various operations (e.g., affecting one or more control variables) to affect occupant comfort within an area. Additionally, once control actions are determined such actions may be formatted specific to data formats that correspond to various control equipment to be implemented in order to affect various environmental variables. Step 4216 can include an equipment controller communicating control signals to actuators and HVAC equipment such as actuators 4128 and HVAC equipment 4130 also shown in FIG. 41. In some embodiments, control signals may be communicated to actuators and HVAC equipment via a communications interface, such as communications interface 4110 of FIG. 41. Step 4216 may also include the communications interface formatting and transmitting control signals into a format compatible with various control equipment.

Process 4200 is shown to include affecting actuators and HVAC equipment according to received control signals (step 4218), according to an exemplary embodiment. Step 4218 can include affecting actuators and/or HVAC equipment in various ways in order to maximize occupant comfort in a given space while also considering energy usage and cost, depending on user preferences. Examples of the implementation and affecting of control variables in step 4218 may include actuators having ejection angle adjusted or oscillated, or orifice size being adjusted in order to adjust air pressure and/or volumetric airflow rate. Additionally, HVAC equipment may be actuated in order to adjust fan speed, initiate or alter heating or cooling activity, and/or otherwise adjust air temperature or air speed as air is processed by various HVAC equipment. Accordingly, a given room, area, or building may have air directed at various angles, speeds, flow rates, and temperatures in order to affect occupant comfort such that it returns to or is maintained within an acceptable range as indicated by environmental data such as that collected in step 4202 of process 4200.

Building Control System with Integrated Temperature and Infection Level Management Referring generally to FIGS. 43A-69B, systems and methods for managing temperature and infection levels in a building are shown, according to some embodiments. FIGS. 43A-69B can describe how aspects of FIGS. 5-42 can be combined for a system that can perform functionality of both an HVAC system and a disinfection system. It should be appreciated that various components of the systems described throughout FIGS. 43A-69B can be used independently and/or in conjunction with one another to provide additional functionality to a BMS. It should also be appreciated that while certain components discussed below with reference to FIGS. 43A-69B (e.g., a comfort controller, a model generator, etc.) can be included in a larger component that can perform the respective functionality of each component described below. For example, various sensors described below with reference to FIGS. 43A-69B can be included in a sensor package that includes multiple sensors. Likewise, components with the same names discussed below with reference to FIGS. 43A-69B may indicate components with similar and/or the same functionality. In this way, descriptions of some components can be applied across FIGS. 43A-69B. For example, an air handling unit (AHU) described in one FIGURE may include some and/or all the functionality of an AHU described in a separate FIGURE. In some embodiments, however, some and/or all FIGURES are considered independent from one another.

As described throughout FIGS. 43A-69B, various components are shown to exchange information between one another. The components can communicate via a variety of wired and/or wireless communication channels. For example, the components may communicate sensor measurements over WiFi, an Ethernet connection, a cellular communication, etc. As such, it should be appreciated that each component can include any communication devices that are necessary to exchange information. Likewise, a space as described below can refer to any area of a building in which environmental conditions (e.g., temperature, contamination level, humidity, etc.) can be managed. For example, a space can be a zone of the building, a room, a hallway, the building itself, etc.

Figure 43A:
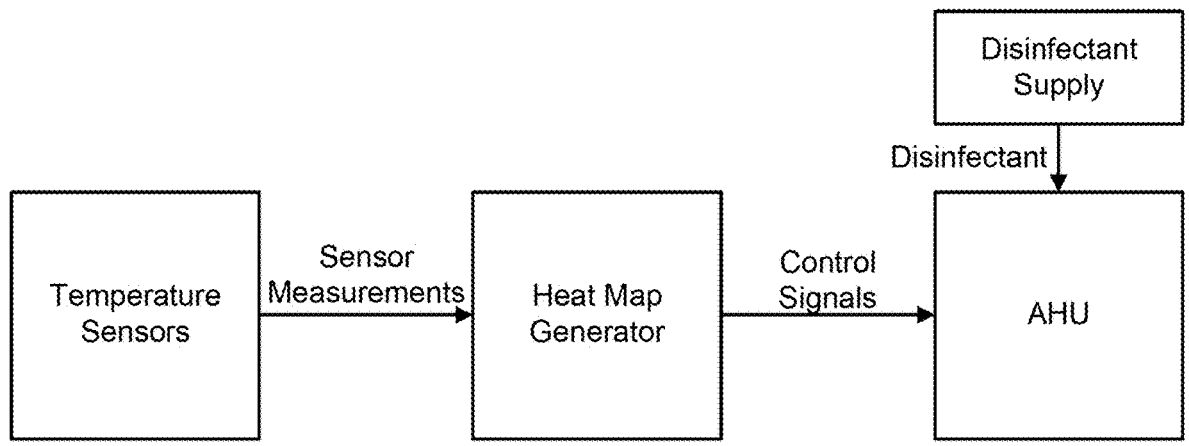
FIG. 43A is a block diagram of a system for determining where disinfection is needed in a space based on a heat map, according to some embodiments.

Referring now to FIG. 43A, a system for determining where disinfection is needed in a space based on a heat map is shown, according to some embodiments. In FIG. 43A, temperature sensors are shown to provide sensor measurements to a heat map generator. The temperature sensors can be placed at various locations in the space and can include a variety of sensors. For example, a temperature sensor may be installed in a thermostat on a wall of the space, another temperature sensor may be placed on a table in the space, a temperature sensor can be installed in a mobile device carried by a user in the space, etc. The temperature measurements can indicate a specific temperature at a particular point in the space. Based on each temperature measurement, the heat map generator can generate a heat map that can be used to determine how temperature varies across the space. In general, the heat map can be more accurately determined as more temperature sensors are placed throughout the space. In particular, the heat map generator can indicate hot and cold spots in the space.

Based on the heat map, the heat map generator can identify a location with a high temperature in comparison to other points in the space. In some embodiments, high temperature locations are associated with areas in the space that are more likely to include higher concentrations of bacteria and other contaminants. For example, if a person sits in a chair and then steps up, residual heat from the person may linger near the chair for an amount of time. As people can be carriers of germs, the location where the person sat can be identified for disinfection. As such, the heat map generator can generate control signals to operate an air handling unit (AHU) to disinfect the location. Based on the control signals, the AHU perform a disinfection method to disinfect the location. The AHU is shown to receive a disinfectant from a disinfectant supply. The disinfectant can be any various disinfectant that can be distributed by the AHU such as, for example, an aerosol spray. In some embodiments, the disinfectant supply is not included if the AHU uses an alternative disinfection method such as shining UV light at the location. In any case, the AHU can operate based on the control signals to target the location specifically for disinfection. In some embodiments, a different device other than the AHU is operated to disinfect the location. However, the AHU is shown for ease of explanation.

Figure 43B:
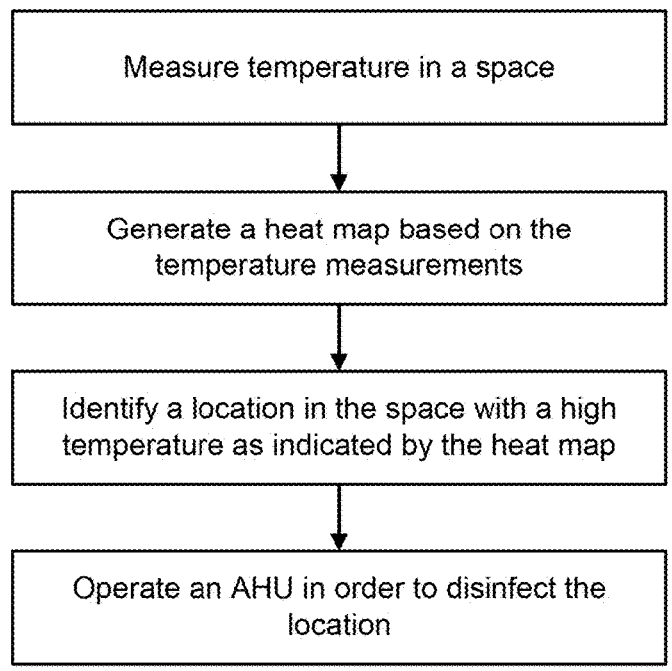
FIG. 43B is a flow diagram of a process for operating an air handling unit (AHU) in order to disinfect a location, according to some embodiments.

Referring now to FIG. 43B a process for operating an AHU in order to disinfect a location is shown, according to some embodiments. In some embodiments, the process described in FIG. 43B is performed by components described above with reference to FIG. 43A. The process is shown to include measuring temperature in a space. The temperature can be measured by various temperature sensors placed around the space such as the temperature sensors described with reference to FIG. 43A.

The process is also shown to include generating a heat map based on the temperature measurements. The heat map can indicate a temperature distribution around the space.

The process is also shown to include identifying a location in the space with a high temperature as indicated by the heat map. For example, if the heat map indicates cold locations by a blue color and hot locations by a red color, the location can be identified by a red location. In some embodiments, multiple locations are identified in this step of the process.

The process is also shown to include operating an AHU in order to disinfect the location. Based on the location identified, control signals can be generated and provided to the AHU to operate to disinfect the location. The disinfection can include, for example, shining UV light at the location, releasing a spray directed at the location, etc.

Figure 44A:
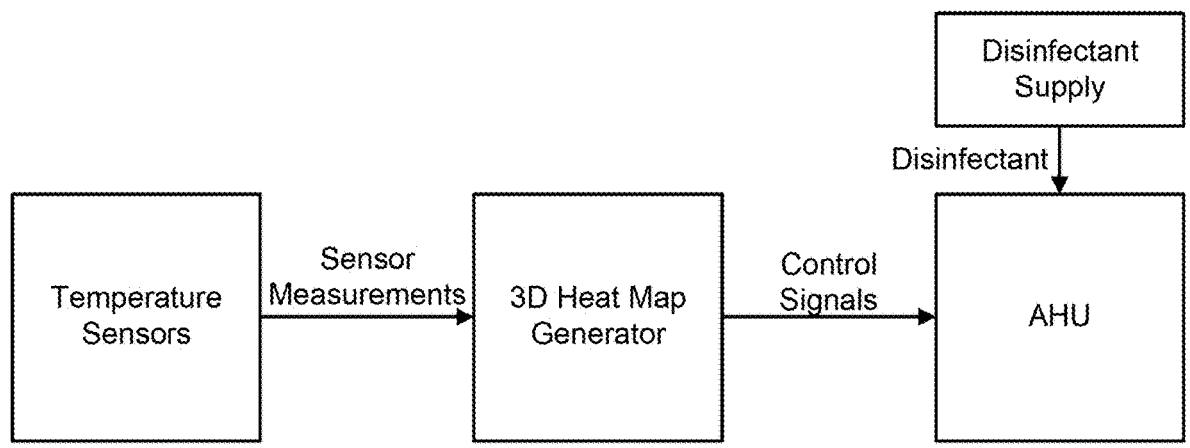
FIG. 44A is a block diagram of a system for determining where disinfection is needed in a space based on a three-dimensional heat map, according to some embodiments.

Referring now to FIG. 44A, a system for determining where disinfection is needed in a space based on a three-dimensional heat map is shown, according to some embodiments. In some embodiments, FIG. 44A is similar to and/or the same as FIG. 43A. As shown in FIG. 44A, temperature sensors can provide sensor measurements to a 3D heat map generator. The sensor measurements, can include both temperature measurements and a three-dimensional position (e.g., x, y, and z coordinates) of where each measurement is taken. In this way, the 3D heat map generator can generate a three-dimensional heat map that can identify hot and cold spots. Based on the three-dimensional heat map, control signals can be generated to disinfect hot areas on the space. In some embodiments, a disinfection method is determined dependent on what vertical location a hot spot is determined to be at. For example, it may be more effective to shine disinfecting UV light at the ground of the space whereas it may be more effective to release a disinfectant spray towards the ceiling if the AHU is mounted on the ceiling. As such, the three-dimensional heat map can be used by the 3D heat map generator to determine particular control decisions based on where in the space a hot spot is determined to be based on the heat map.

Figure 44B:
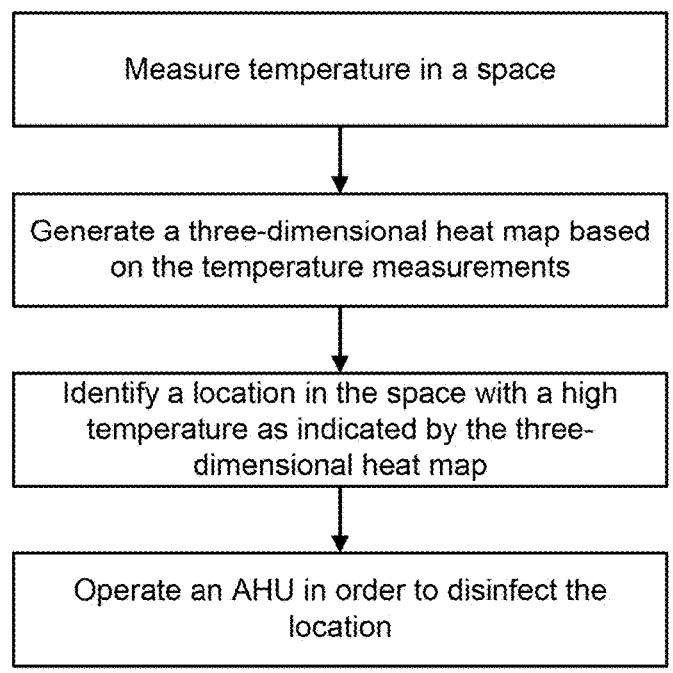
FIG. 44B is a flow diagram of a process for disinfecting a location determined based on a three-dimensional heat map, according to some embodiments.

Referring now to FIG. 44B, a process for disinfecting a location determined based on a three-dimensional heat map is shown, according to some embodiments. In some embodiments, the process described in FIG. 44B is similar to and/or the same as the process described with reference to FIG. 43B. In some embodiments, steps of the process described in FIG. 44B can be performed by components of the system described with reference to FIG. 44A.

The process is shown to include measuring a temperature in a space. The temperature can be measured by various temperature sensors (e.g., in a thermostat, in a wearable device, in a drone, etc.) around the space. Each temperature measurement taken can be associated with a three-dimensional point in the space. As such, it can be advantageous to have temperature sensors both at various horizontal positions around the space and at various vertical positions around the space.

The process is also shown to include generating a three-dimensional heat map based on the temperature measurements. Each temperature measurement taken by the temperature sensors can be used to identify a temperature at some three-dimensional point in the space. Based on each temperature measurement, the three-dimensional heat map can be generated to illustrate how temperatures vary around the space.

The process is also shown to include identifying a location in the space with a high temperature as indicated by the three-dimensional heat map. High temperature locations can indicate locations that are more likely to require disinfection. For example, a high temperature location may be due to a person being nearby, a window being open in summer letting in outdoor bacteria, a location where germs are more likely to reproduce, etc. In some embodiments, the location is identified based on the location exceeding a threshold temperature (e.g., 76° F., 82° F., etc.). The threshold temperature can be some predetermined value that is expected to indicate a location requiring disinfection. In some embodiments, multiple locations are identified such that each of the multiple locations exceeds the threshold temperature.

The process is also shown to include operating an AHU in order to disinfect the location. By operating the AHU, the location (or locations) can be disinfected to reduce an infection level of the space. In some embodiments, a different disinfection device other than an AHU is operated.

Figure 45A:
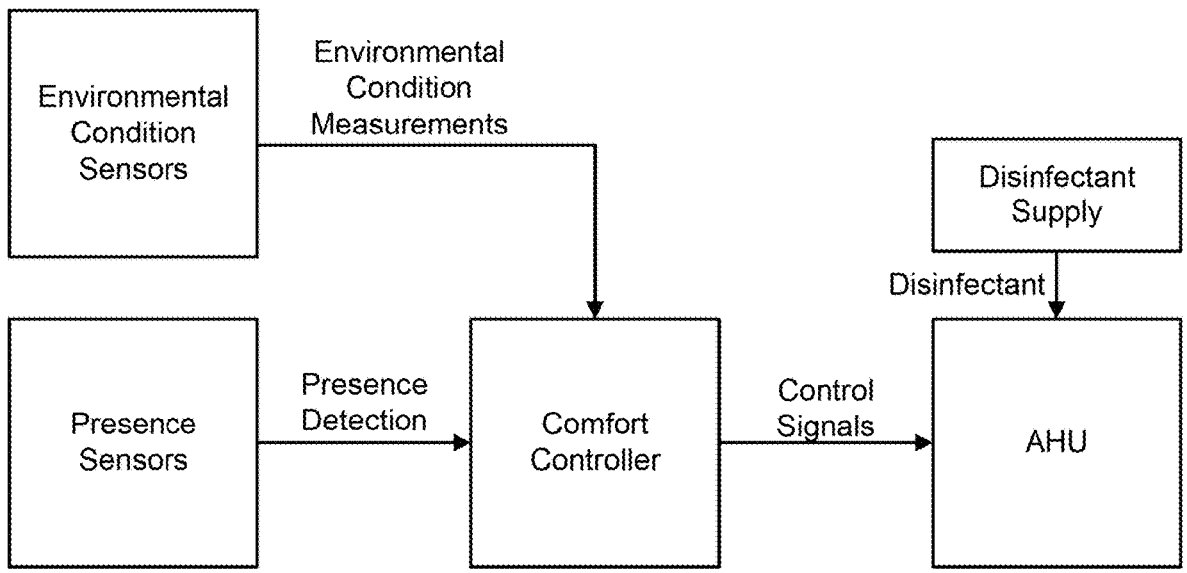
FIG. 45A is a block diagram of a system that provides airflow to locations based on a presence detection of occupants, according to some embodiments.

Referring now to FIG. 45A, a system that provides airflow to locations based on a presence detection of occupants is shown, according to some embodiments. The system is shown to include presence sensors that can detect a presence of occupants within a space. The presence sensors can include, for example, motion detectors, visible light and/or infrared cameras, audio sensors, etc. The presence sensors can monitor the space until an occupant is detected to be in the space. Based on the detection, the presence sensors can provide a presence detection to comfort controller. In some embodiments, the presence detection indicates a number of occupants estimated to be in the space. In some embodiments, the presence detection includes a location where the occupant(s) is detected to be.

The comfort controller is also shown to receive environmental condition measurements from environmental condition sensors. The environmental condition measurements can include various measurements of environmental conditions such as, for example, temperature measurements, humidity measurements, air quality measurements, lighting measurements, etc. Based on the presence detection and the environmental condition measurements, the comfort controller can determine if additional airflow is needed to be provided in the space. The comfort controller can identify if certain environmental conditions are not comfortable for occupants and estimate how environmental conditions may change due to the occupants. For example, the comfort controller can anticipate an infection level of the space to increase due to the occupants and as such may determine the airflow should include additional disinfectant spray. Alternatively, if the temperature in the space is too high to be comfortable, the comfort controller can determine additional cooling should be provided. Advantageously, the airflow can be determined such that the airflow provides additional heating/cooling, humidity/dehumidification, disinfection, and/or other environmental condition changes to the space. Based on what and where environmental conditions are determined to require adjustment, the comfort controller can generate control signals and operate an AHU based on said control signals. In this way, the comfort controller can direct airflow that provides heating/cooling, humidification/dehumidification, disinfection, etc. to specific locations in the space based on where occupants are detected to be. In some embodiments, if disinfection is needed, the AHU may shine UV light or perform another disinfection method rather than adjusting airflow.

Figure 45B:
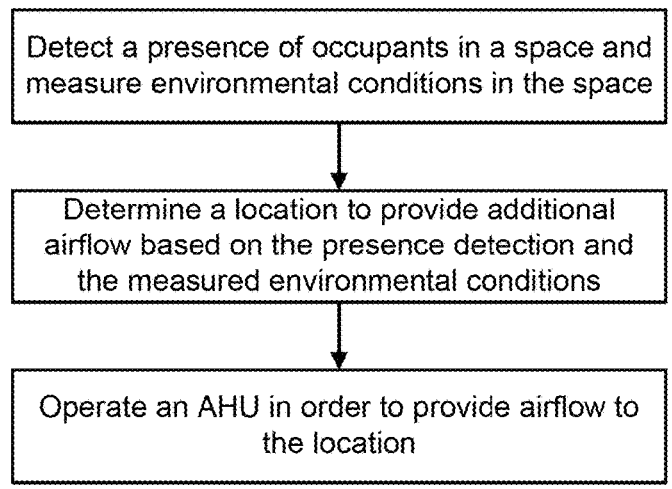
FIG. 45B is a flow diagram of a process for providing airflow to locations based on a presence detection of occupants, according to some embodiments.

Referring now to FIG. 45B, a process for providing airflow to locations based on a presence detection of occupants is shown, according to some embodiments. In some embodiments, steps of the process are performed by components of the system described with reference to FIG. 45A. The process is shown to include detecting a presence of occupants in a space and measuring environmental conditions in the space.

The process is also shown to include determining a location to provide additional airflow based on the presence detection and the measured environmental conditions. The presence detection may indicate that additional germs and heat may affect the space due to the occupants. Likewise, the measured environmental conditions can be used to determine if conditions are currently comfortable for the occupants. As such, locations that may require disinfection and/or adjustment of other environmental conditions can be determined.

The process is also shown to include operating an AHU in order to provide airflow to the location. In some embodiments, if disinfection is determined to be needed, the AHU (or other device) can perform a separate disinfection method other than providing airflow to the location.

Figure 46A:
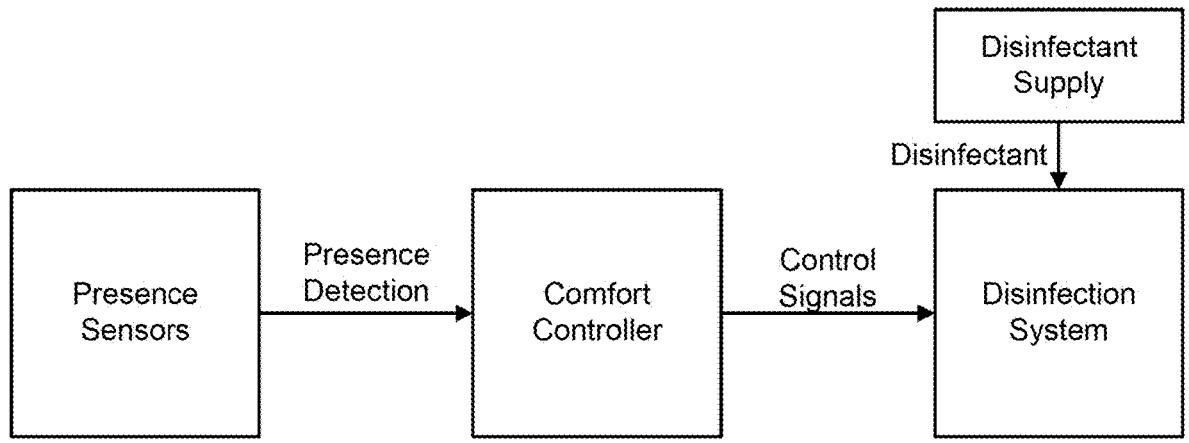
FIG. 46A is a block diagram of a system that can alternate between occupant friendly and non-occupant friendly disinfection methods based on a presence detection, according to some embodiments.

Referring now to FIG. 46A, a system that can alternate between occupant friendly and non-occupant friendly disinfection methods based on a presence detection is shown, according to some embodiments. The system is shown to include a comfort controller that can operate a disinfection system to disinfect a space. The disinfection system can include various devices that can be operated to disinfect the space. For example, the disinfection system can include disinfectant UV lights, AHUs that can spray disinfect in the space, a gas release system that releases disinfecting chemicals, etc. Prior to receiving a presence detection from presence sensors in the space, the comfort controller can operate the disinfection system to perform a non-occupant friendly disinfection method. For example, spraying poisonous gas that kills bacteria may be effective for disinfecting the space but may cause serious medical complications and/or death for occupants. If a presence detection is received, the comfort controller can transition to an occupant friendly disinfection method that is safe for occupants. For example, the comfort controller may operate the disinfection system to shine UV light at locations as to not harm occupants. In this way, disinfection can be maximized without harming occupants.

In some embodiments, the space is locked during a non-occupant friendly disinfection process of the space. In this case, the presence detection may be a request to access the space (e.g., by an occupant scanning a badge to access the space, pressing a doorbell, etc.). Based on the presence detection, the comfort controller can disable the non-occupant friendly disinfection process and subsequently unlock the space for access by occupants. In some embodiments, the comfort controller switches between disinfecting air currently in the space which may be non-occupant friendly, to disinfecting air in an air duct which may be occupant friendly based on the presence detection.

Figure 46B:
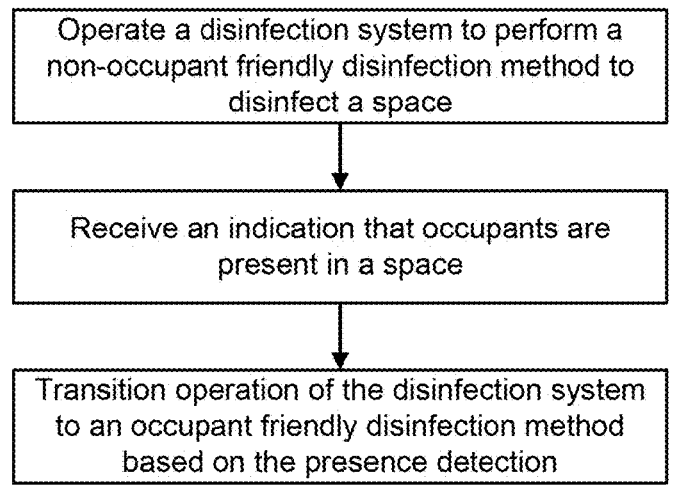
FIG. 46B is a flow diagram of a process for transitioning operation of a disinfection system between non-occupant friendly and occupant friendly disinfection methods based on a presence detection of occupants, according to some embodiments.

Referring now to FIG. 46B, a process for transitioning operation of a disinfection system between non-occupant friendly and occupant friendly disinfection methods based on a presence detection of occupants is shown, according to some embodiments. In some embodiments, steps of the process are performed by components of the system described with reference to FIG. 46A. The process is shown to include operating a disinfection system to perform a non-occupant friendly disinfection method to disinfect the space. The non-occupant friendly disinfection method may include any disinfection method that occupants may find uncomfortable, dangerous, etc. However, non-occupant friendly disinfection methods may be provide additional disinfection and can thereby be advantageous to perform if occupants are not present.

The process is also shown to include receiving an indication that occupants are present in the space. The process is also shown to include transitioning operation of the disinfection system to an occupant friendly disinfection method based on the presence detection. Based on the presence detection, it can be determined that performing the non-occupant friendly disinfection method is no longer viable and therefore should be disabled. By transitioning to between disinfection methods, disinfection of the space can be maximized without jeopardizing comfort and/or safety occupants.

Figure 47A:
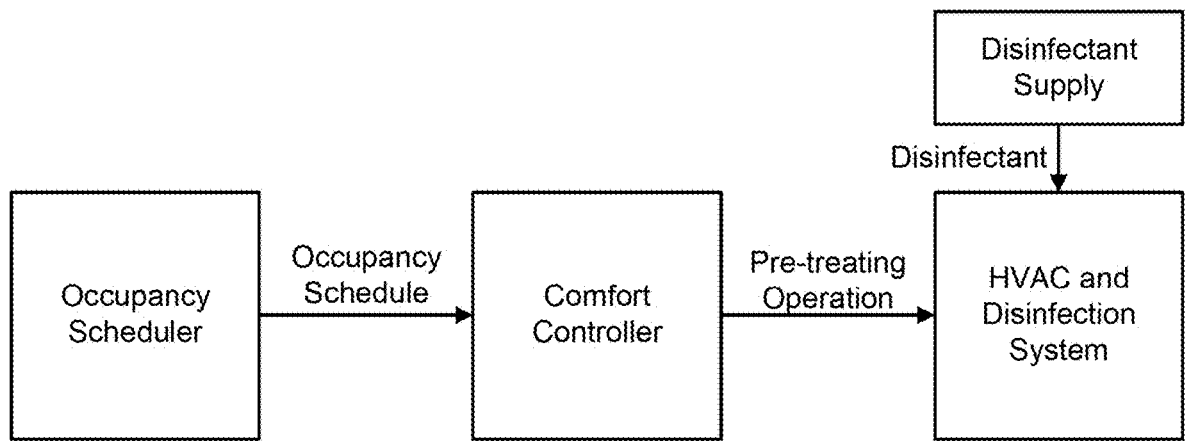
FIG. 47A is a block diagram of a system for pre-treating a space based on expected occupancy in the space, according to some embodiments.

Referring now to FIG. 47A, a system for pre-treating a space based on expected occupancy in the space is shown, according to some embodiments. Pre-treating the space can include various operations that ensure the space is comfortable for occupants before the occupants are in the space. For example, pre-treating can include pre-heating/pre-cooling the space and/or pre-disinfecting the space before occupants arrive.

The system is shown to include an occupancy scheduler. The occupancy scheduler can include various systems that can be used to schedule a space to be occupied. For example, the occupancy schedule may be an online calendar that occupants can access to reserve the space (e.g., for a meeting). The occupancy scheduler is shown to provide an occupancy schedule to a comfort controller. The occupancy schedule can indicate various times when the space is expected to be occupied and/or vacant.

Based on the occupancy schedule, the comfort controller can generate a pre-treating operation to be performed by an HVAC and disinfection system to pre-treat the space. The HVAC and disinfection system can include various building devices that can disinfect the space and/or affect environmental conditions of the space. For example, the HVAC and disinfection system may include a disinfectant distribution system, a heater, a humidifier, UV lights, a chiller, an AHU/economizer, etc. Based on the occupancy schedule, the comfort controller can determine how to operate devices of the HVAC and disinfection system to ensure some and/or all environmental conditions are comfortable prior to occupants arriving at the space. In some embodiments, the comfort controller also monitors the space with presence detectors to determine if any unexpected occupants enter the space (i.e., occupants are present at times not indicated by the occupancy schedule). If unexpected occupants are present, the comfort controller can operate the HVAC and disinfection system to provide immediate changes in disinfection levels and/or other environmental conditions. In some embodiments, the occupancy schedule indicates a number of expected occupants which can be utilized by the comfort controller to refine the pre-treating operation such that the space is ready for changes due to the number of occupants (e.g., due to a heat disturbance or germs of the occupants).

In some embodiments, comfort controller determines a rate at which to change various conditions in the space to be included in the pre-treating operation. Rapidly changing environmental conditions can be less cost efficient and/or may result in quicker degradation of equipment. As such, it can be beneficial to determine how to gradually change conditions prior to the time period when occupants are expected to be present. In some embodiments, the rate is determined by performing an optimization of an objective function that includes costs of operating devices of the HVAC and disinfection system over an optimization period. The optimization can be constrained by certain constraints that indicate certain conditions in the space (e.g., a particular temperature, a certain infection level, etc.) should be at a particular value prior to the time period when occupants are expected to be present beginning. In this way, the comfort controller can optimize (e.g., reduce) costs while maintaining occupant comfort in the space when occupants are present.

Figure 47B:
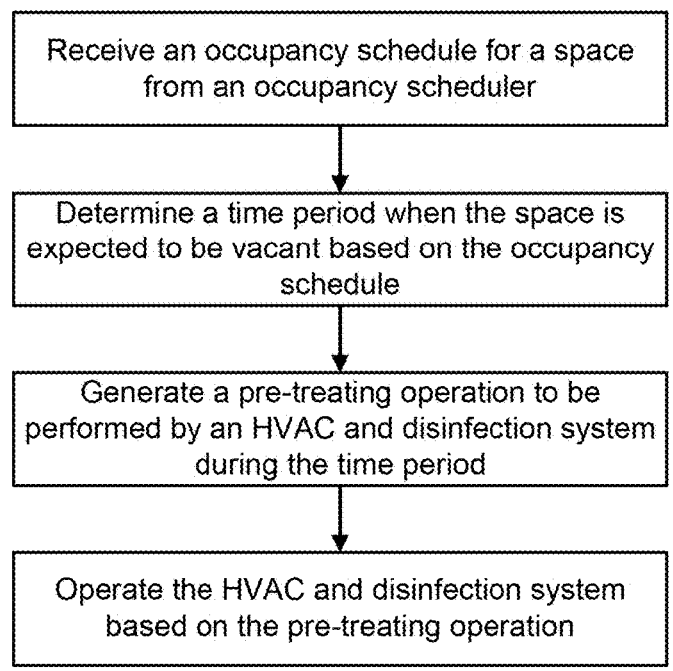
FIG. 47B is a flow diagram of a process for operating an HVAC and disinfection system to pre-treat a space, according to some embodiments.

Referring now to FIG. 47B, a process for operating an HVAC and disinfection system to pre-treat a space is shown, according to some embodiments. In some embodiments, steps of the process are performed by components of the system described with reference to FIG. 47A. The process is shown to include receiving an occupancy schedule for a space from an occupancy scheduler. The occupancy schedule can indicate various information such as when the space is expected to be occupied, how many people are expected to occupy the space, etc.

The process is shown to include determining a time period when the space is expected to be vacant based on the occupancy schedule. For example, the occupancy schedule may indicate that the space is to be occupied from 9:00 a.m. to 3:00 p.m. on a next Monday.

The process is also shown to include generating a pre-treating operation to be performed by an HVAC and disinfection system during the time period. Based on the time period determined, the pre-treating operation can be generated such that the space is comfortable for occupants prior to their arrival. As such, the pre-treating operation can include directions to affect a disinfection level and/or other environmental conditions such as temperature and humidity prior to the occupants arriving.

The process is shown to include operating the HVAC and disinfection system based on the pre-treating operation. In some embodiments, the pre-treating operation indicates specific devices of the HVAC and disinfection system to operate to affect conditions in the space. Alternatively, the pre-treating operation can indicate setpoints for the HVAC and disinfection system to achieve prior to occupants arriving (e.g., 72° F., 50% humidity, etc.).

Figure 48A:
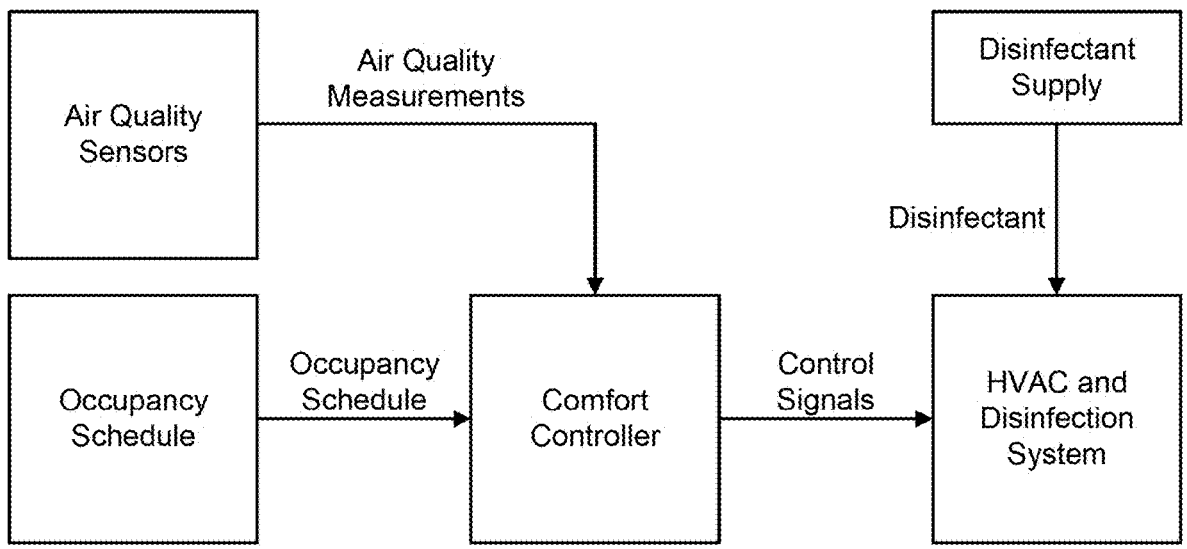
FIG. 48A is a block diagram of a system for optimizing disinfection cycles based on air quality measurements and an occupancy schedule, according to some embodiments.

Referring now to FIG. 48A, a system for optimizing disinfection cycles based on air quality measurements and an occupancy schedule is shown, according to some embodiments. The system is shown to include a comfort controller that receives air quality measurements from air quality sensors and an occupancy scheduler from an occupancy scheduler. The air quality sensors can be placed throughout a space to measure an air quality in the space. The air quality can be determined based on various measurements of contaminants in the air such as, for example, carbon dioxide, particulate matter 2.5 (PM2.5), PM10, and/or other contaminants. Based on the determined air quality and the occupancy schedule, the comfort controller can determine how to optimize full and partial disinfection cycles and what a disinfection method to use over time. In some embodiments, a full disinfection cycle can refer to a complete disinfection process that performs at maximum or near-maximum output whereas a partial disinfection cycle can refer to a limited disinfection process that may not span a same time length, operate at a same performance, etc. as a full cycle. To optimize the disinfection cycles and method of disinfection, the comfort controller can determine when occupants are expected to be present in the space and perform disinfection cycles that are optimal for reducing a disinfection level and maintaining occupant comfort. In some embodiments, results of the optimization is integrated with a pre-treating operation similar to and/or the same as the pre-treating operation described with reference to FIGS. 47A-B.

Figure 48B:
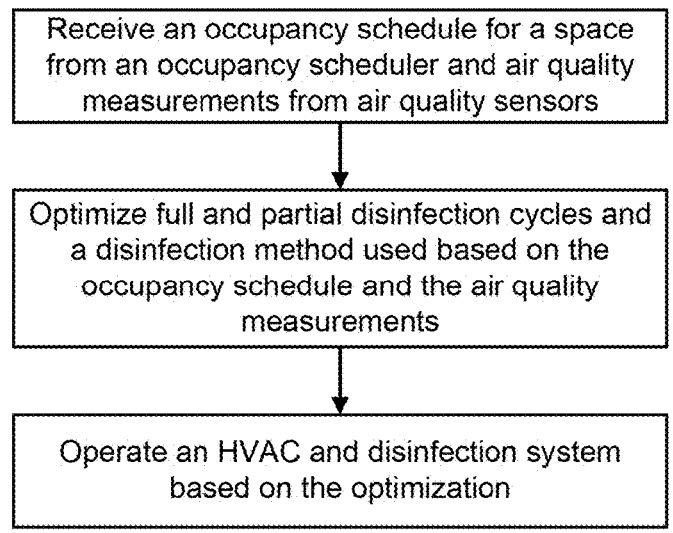
FIG. 48B is a flow diagram of a process for operating an HVAC and disinfection system based on optimized disinfection cycles and disinfection methods, according to some embodiments.

Referring now to FIG. 48B, a process for operating an HVAC and disinfection system based on optimized disinfection cycles and disinfection methods is shown, according to some embodiments. In some embodiments, steps of the process are performed by components of the system as described with reference to FIG. 48A. The process is shown to include receiving an occupancy schedule for a space from an occupancy scheduler and air quality measurements from air quality sensors.

The process is also shown to include optimizing full and partial disinfection cycles and a disinfection method used based on the occupancy schedule and the air quality measurements. Depending on a current air quality and a next time occupants are expected to be in the space, an amount of disinfection that can be achieved in the meantime can be estimated. Based on said estimation, disinfection cycles and what disinfection method(s) is used can be optimized to provide maximum disinfection at a lowest cost.

The process is also shown to include operating an HVAC and disinfection system based on the optimization. By operating the HVAC and disinfection system based on the optimization, the space can be disinfected prior to the occupants arriving at the space as much as possible by ensuring the disinfection cycles and method of disinfection achieves a greatest disinfection in the time prior to the occupants arriving.

Figure 49A:
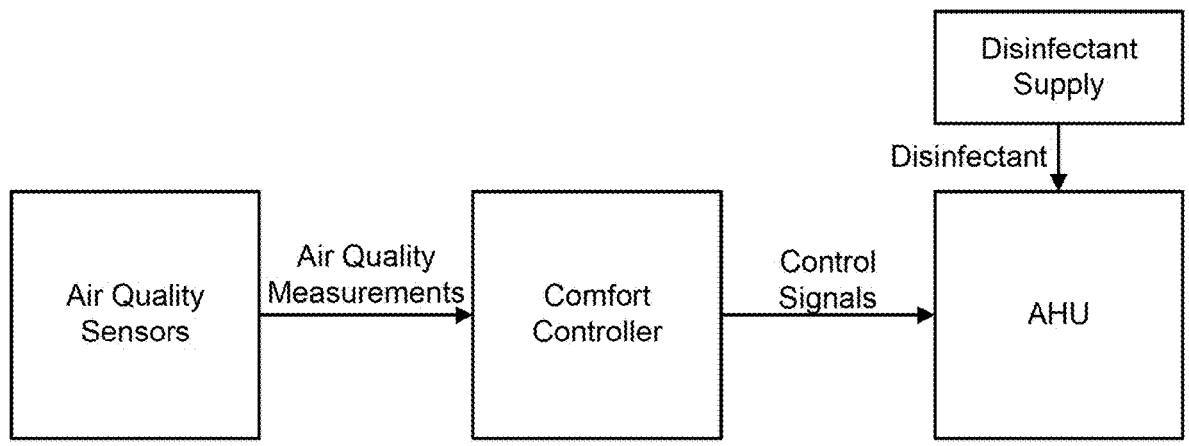
FIG. 49A is a block diagram of a system for operating an AHU to recirculate air and/or introduce new outdoor air to a space based on current air quality, according to some embodiments.

Referring now to FIG. 49A, a system for operating an AHU to recirculate air and/or introduce new outdoor air to a space based on current air quality is shown, according to some embodiments. The system is shown to include a comfort controller that receives air quality measurements from air quality sensors. The air quality sensors can be located in various locations such as, for example, within the space, inside an air duct, attached to the outside of a building, and/or at other locations. Particularly, the air quality sensors can determine an air quality of both indoor air within the space and outdoor air. In some embodiments, outdoor air quality is provided by an external service such as a weather service.

Based on the air quality of the indoor and outdoor air, the comfort controller can determine whether recirculating indoor air in the space and/or introducing outdoor air can achieve desired changes in conditions within the space. For example, if the comfort controller determines the space should be cooled, introducing outdoor air via an AHU may provide sufficient cooling and reduce an overall cost as cooling indoor air may require operation of additional building devices (e.g., an air conditioner). However, outdoor air may include additional contaminants that can increase an infection level in the space. As such, the comfort controller can utilize the air quality measurements to estimate an amount the infection level may increase due to introducing outdoor air. If the amount is high, it may be more cost effective to cool and recirculate air as opposed to disinfecting outdoor air. However, if the outdoor air is relatively clean, the outdoor air can be introduced to cool the space. In some embodiments, the comfort controller determines an amount of outdoor air to introduce while still recirculating the indoor air. In this case, the comfort controller may determine a ratio between indoor air and outdoor air to maintain in the space (e.g., 50% indoor and 50% outdoor, 70% indoor and 30% outdoor, etc.). It should be appreciated that, while the AHU is shown to be operated, any building device/system that can recirculate indoor air and introduce outdoor air can perform said operation.

Figure 49B:
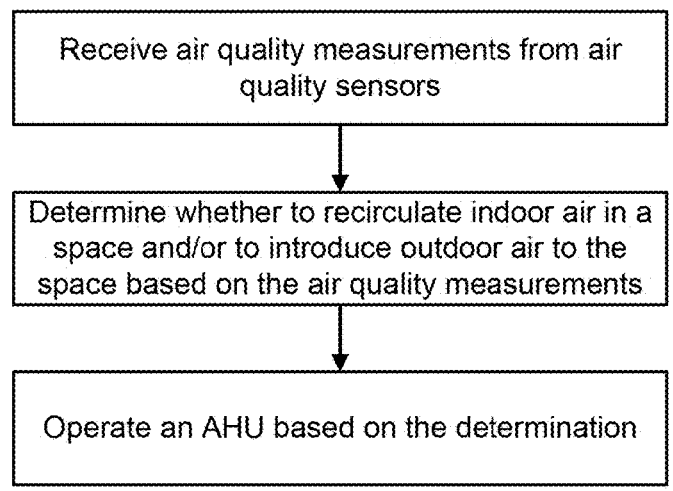
FIG. 49B is a flow diagram of a process for operating an AHU to recirculate indoor air and/or introduce outdoor air based on indoor and outdoor air quality, according to some embodiments.

Referring now to FIG. 49B, a process for operating an AHU to recirculate indoor air and/or introduce outdoor air based on indoor and outdoor air quality is shown, according to some embodiments. In some embodiments, steps of the process are performed by components of the system described with reference to FIG. 49A. The process is shown to include receiving air quality measurements from air quality sensors. The air quality measurements can include measurements regarding both indoor air being circulated in a space and outdoor air from an outdoor environment.

The process is also shown to include determining whether to recirculate indoor air in a space and/or to introduce outdoor air to the space based on the air quality measurements. If the air quality measurements indicate the outdoor air is highly contaminated, it may be more cost effective and/or more comfortable for occupants to recirculate indoor air to affect environmental conditions (e.g., temperature, humidity, etc.) of the space. However, if the outdoor air is clean, introducing the outdoor air may satisfy desired changes in environmental conditions without significant reduction air quality of the space.

The process is also shown to include operating an AHU based on the determination. The determination can indicate an amount of air to recirculate in the space as well as an amount of outdoor air to introduce. As such, the AHU can operate to fulfil said indications in order to affect environmental conditions of the space at a reduced cost without compromising occupant comfort. Operating the AHU can include filtering air that will be circulated in a building space. For example, in the case of infectious disease control and prevention, if it is determined that a space served by the AHU is associated with a high health risk, increased air filtering can be activated within the AHU. Further, the AHU can be controlled to increase the amount of outdoor air (clean air) provided to the building space with the high health risk.

Figure 50A:
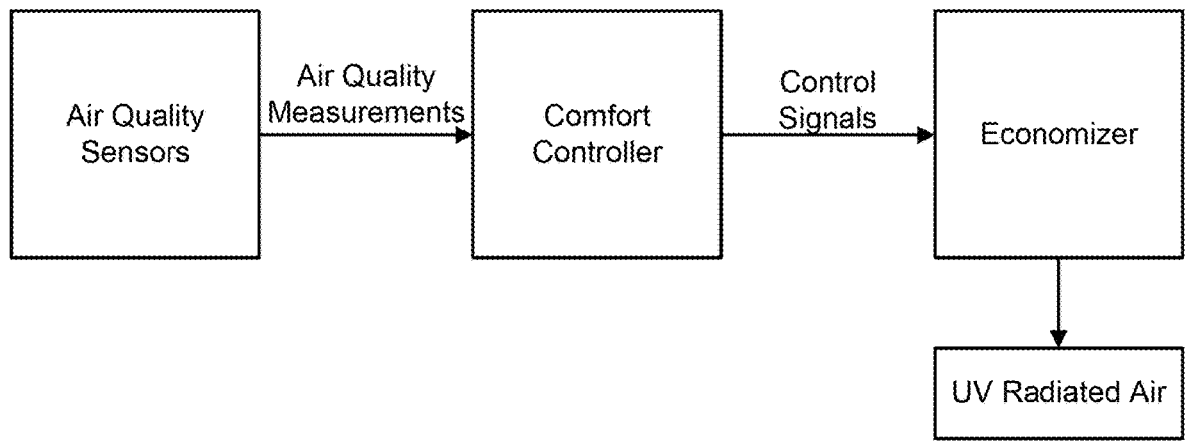
FIG. 50A is a block diagram of a system for operating an economizer that uses UV radiation to disinfect air, according to some embodiments.

Referring now to FIG. 50A, a system for operating an economizer that uses UV radiation to disinfect air is shown, according to some embodiments. The system is shown to include a comfort controller that receives air quality measurements from air quality sensors. Based on the measurements, the comfort controller can determine a current contamination level of the air (also referred to as an infection level of the air). Based on the current contamination level, the comfort controller can generate control signals to provide to an economizer equipped with an ultraviolet light to disinfect the air. Based on the control signals, the economizer can project UV light at the air to reduce the contamination level before the air enters a space.

Figure 50B:
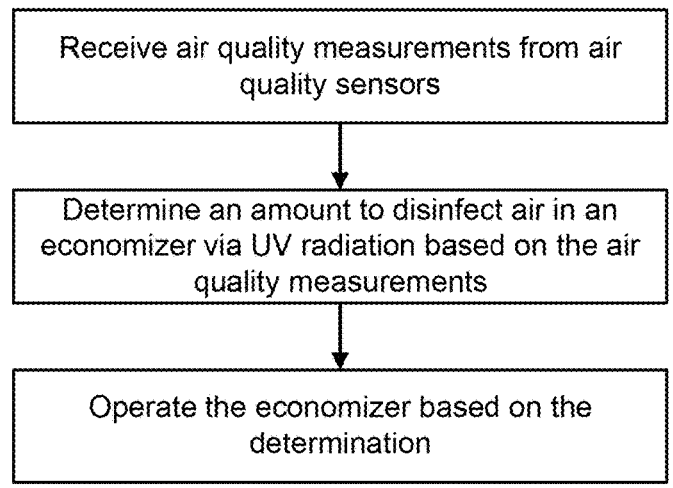
FIG. 50B is a flow diagram of a process for operating an economizer to disinfect air via a UV light, according to some embodiments.

Referring now to FIG. 50B, a process for operating an economizer to disinfect air via a UV light is shown, according to some embodiments. In some embodiments, steps of the process are performed by components of the system described with reference to FIG. 50A. The process is shown to include receiving air quality measurements from air quality sensors. As an economizer can utilize air from various sources (e.g., in a space, in another location of a building, outside, etc.), it can be beneficial to gather air quality measurements from locations where the air is being gathered/used.

The process is shown to include determining an amount to disinfect air in an economizer via UV radiation based on the air quality measurements. If the air quality measurements indicate the air passing through the economizer is heavily contaminated, operating the UV light at a high intensity may be necessary to sufficiently reduce the contamination level prior to the air entering the space. However, if the contamination level is relatively low and not harmful/uncomfortable for occupants, the UV light can be operated at a lower intensity and/or not at all, thereby reducing costs.

The process is shown to include operating the economizer based on the determination. In some embodiments, the economizer is operated based on control signals generated based on the determination. By operating the economizer, the air entering the space can have a low contamination level that is not harmful/uncomfortable for occupants.

Figure 51A:
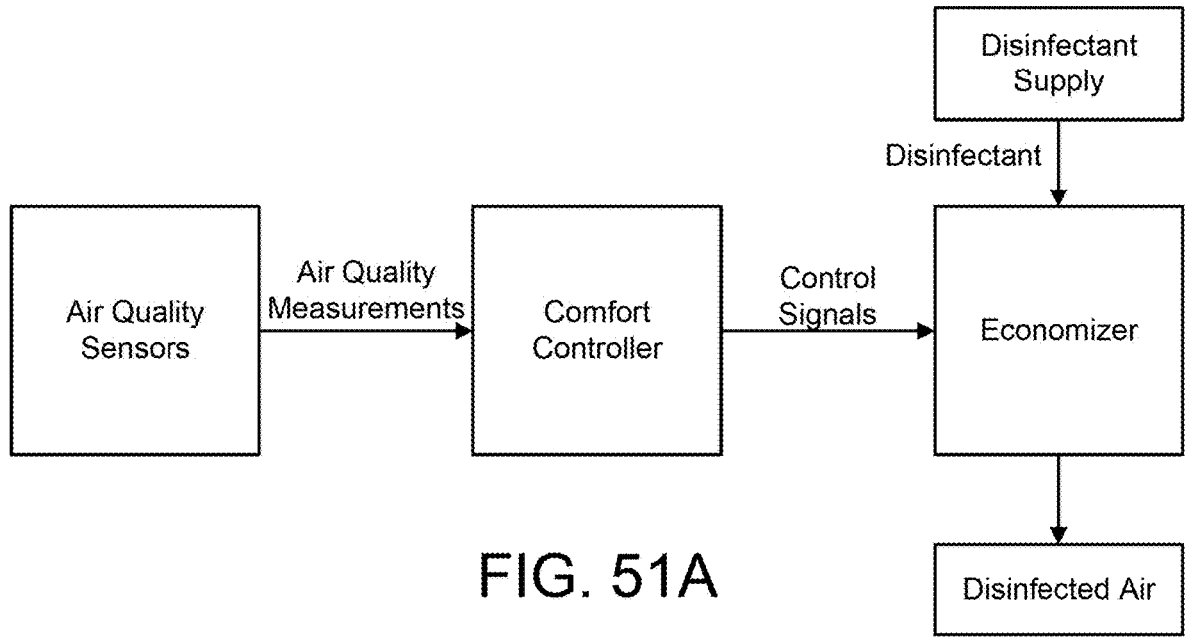
FIG. 51A is a block diagram of a system for operating an economizer that uses a disinfectant to disinfect air, according to some embodiments.

Referring now to FIG. 51A, a system for operating an economizer that uses a disinfectant to disinfect air is shown, according to some embodiments. In some embodiments, the system shown in FIG. 51A is similar to the system as described with reference to FIG. 50A. The economizer of FIG. 51A can apply the disinfectant to the air prior to the air entering the space. Based on a determined air quality in the economizer, an amount of disinfectant required can be determined. The more contaminated the air, the higher an amount of disinfectant can be applied to the air. In some embodiments, the comfort controller sets an upper threshold on an amount of disinfectant that can be applied. The upper threshold can be determined such that an amount of disinfectant applied is not harmful and/or uncomfortable to occupants. In some embodiments, applying disinfectant to the air is beneficial as the, once the air is pumped into the space by the economizer, the disinfectant may come into contact with air already in the space and/or objects in the space (e.g., tables, walls, lamps, people, etc.) to provide additional disinfection.

Figure 51B:
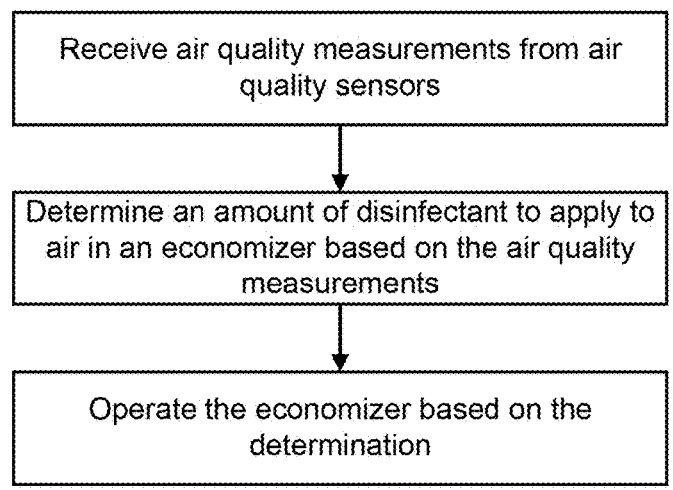
FIG. 51B is a flow diagram of a process for operating an economizer to disinfect air via a disinfectant, according to some embodiments.

Referring now to FIG. 51B, a process for operating an economizer to disinfect air via a disinfectant is shown, according to some embodiments. In some embodiments, steps of the process are performed by components of the system described with reference to FIG. 51A. In some embodiments, the process is similar to the process described with reference to FIG. 50A. The process is shown to include receiving air quality measurements from air quality sensors. The process is also shown to include determining an amount of disinfectant to apply to air in an economizer based on the air quality measurements. In general, more disinfectant can be applied as the contamination level of the air increases. The disinfectant can be any sort of material that reduces the contamination level such as, for example, an aerosol spray, another chemical gas, etc.

The process is also shown to include operating the economizer based on the determination. By operating the economizer, the disinfectant can be applied to the air as to ensure a contamination level of the air is safe and comfortable for occupants. In some implementations, if the building is unoccupied, the building or spaces in the building can be flooded with ozone in order to disinfect the space. Humidifiers can also be used to provide circulate disinfectant within a building space.

Figure 52A:
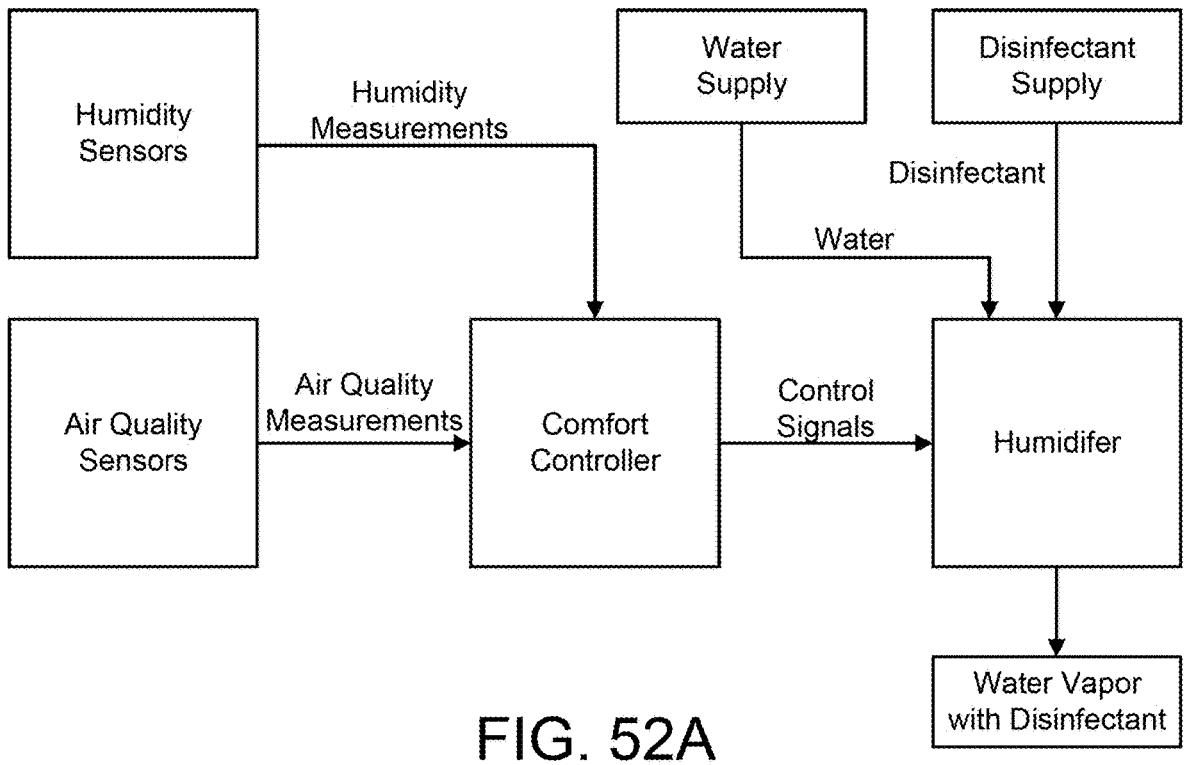
FIG. 52A is a block diagram of a system for operating a humidifier to release water vapor with mixed in disinfectant, according to some embodiments.

Referring now to FIG. 52A, a system for operating a humidifier to release water vapor with mixed in disinfectant is shown, according to some embodiments. The system is shown to include a comfort controller that receives humidity measurements from humidity sensors and air quality measurements from air quality sensors. Based on the measurements, the comfort controller can determine a current humidity and air quality in a space. If a humidity level in the space is too low, a humidifier can be operated to provide additional moisture into the air. Advantageously, the moisture provided by the humidifier can be combined with a disinfectant to provide disinfecting properties to the space along with humidification. As such, the comfort controller can determine an amount of disinfectant to mix with water for the humidifier to release. As a result, water vapor with disinfectant can be released by the humidifier by combining water from a water supply with disinfectant from a disinfectant supply, thereby increasing humidity and disinfecting air/objects that the vapor comes into contact with. In some embodiments, the disinfectant mixed with the water should be safe for human consumption to prevent health complications for occupants due to inhaling the vapor.

Figure 52B:
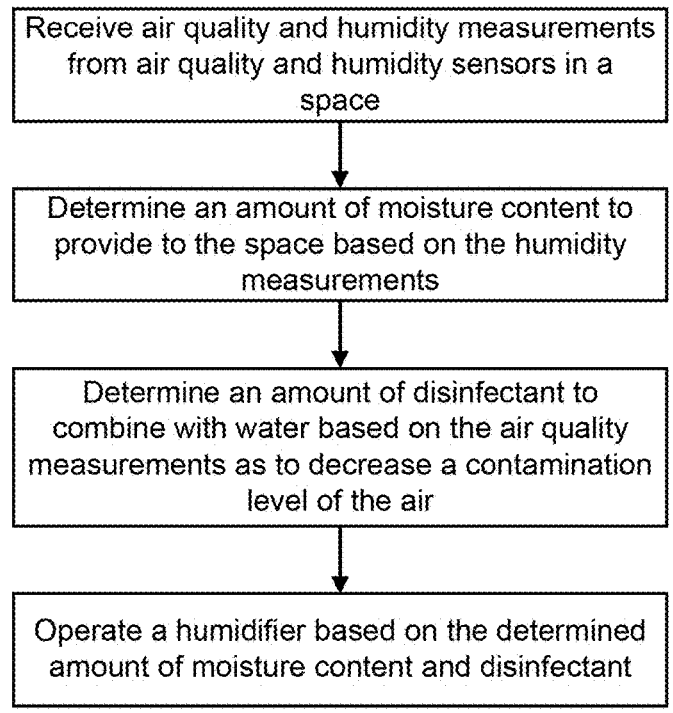
FIG. 52B is a flow diagram of a process for operating a humidifier to apply a disinfectant to water, according to some embodiments.

Referring now to FIG. 52B, a process for operating a humidifier to apply a disinfectant to water is shown, according to some embodiments. In some embodiments, steps of the process are performed by components of the system described with reference to FIG. 52A. The process is shown to include receiving air quality and humidity measurements from air quality and humidity sensors in a space.

The process is also shown to include determining an amount of moisture content to provide to the space based on the humidity measurements. If a current humidity level is too high in the space, the humidifier can be run in a dehumidification mode as to remove moisture content from the air. However, if the current humidity level is too low, additional moisture content should be applied. To determine an amount of moisture than should be introduced/removed from the space, the current humidity level can be compared to a comfortable humidity range (e.g., 30% to 50% relative humidity) that is comfortable for occupants.

The process is also shown to include determining an amount of disinfectant to combine with water based on the air quality measurements as to decrease a contamination level of the air. In general, the higher the contamination level is in the air, the more disinfectant should be applied. In some embodiments, a maximum disinfectant amount is set such that an amount of disinfectant applied to the water is less than the maximum disinfectant amount.

The process is also shown to include operating a humidifier based on the determined amount of moisture content and disinfectant. By mixing the disinfectant with the water used to produce the moisture content, the humidifier can perform disinfection functionality in conjunction with humidification/dehumidification. In some embodiments, if it is determined that the humidity level of the space should be reduced, the humidifier can run in a dehumidification mode and therefore may not mix disinfectant with the water as no additional moisture content should be applied to the air.

Figure 53A:
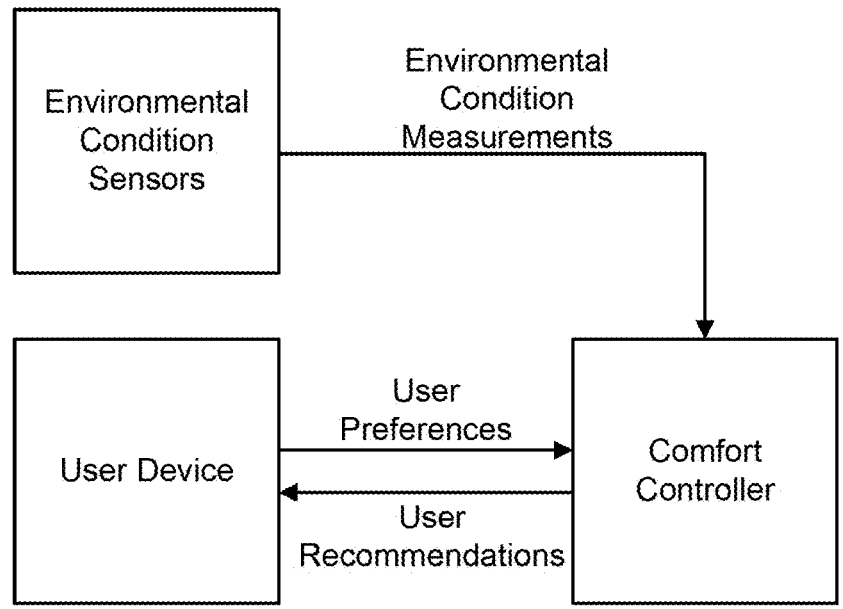
FIG. 53A is a block diagram of a system for providing user recommendations to a user, according to some embodiments.

Referring now to FIG. 53A, a system for providing user recommendations to a user is shown, according to some embodiments. The system is shown to include a comfort controller that receives environmental condition measurements from environmental condition sensors and user preferences from a user device. The user preferences can include various preferences of the user regarding environmental conditions. For example, the user preferences can include a preferred temperature/temperature range, a preferred humidity level/humidity range, a maximum contamination level, etc. In some embodiments, the user preferences include other information such as allergy information of the user. Allergy information can be used to estimate a preferred contamination level of air as users with more allergies may require lower contamination levels in the air to be comfortable as compared to users with little to no allergies. The user device can be any various device that allows a user to provide the user preferences to the comfort controller. For example, the user device may be a mobile phone, a laptop, a desktop computer, a thermostat accessible by the user, a wearable device, etc.

Based on the user preferences, the comfort controller can generate user recommendations to provide to the user. The user recommendations can include indications on actions the user can take to ensure comfort and/or safety in the space. For example, the recommendations can include indications on where to sit in the space, if a different space should be used, when to use to the space, etc. As a particular example, if the user has a large number of allergies, the comfort controller may provide a user recommendation indicating that the user should sit far from a window that can let in contaminants and should instead sit near an AHU that provides disinfected air into the space. In some embodiments, the comfort controller determines user recommendations such that recommendations provided to different users do not conflict with one another. For example, the comfort controller may ensure that no two users are recommended to stand at a same location in the space as such an action is not physically possible.

Figure 53B:
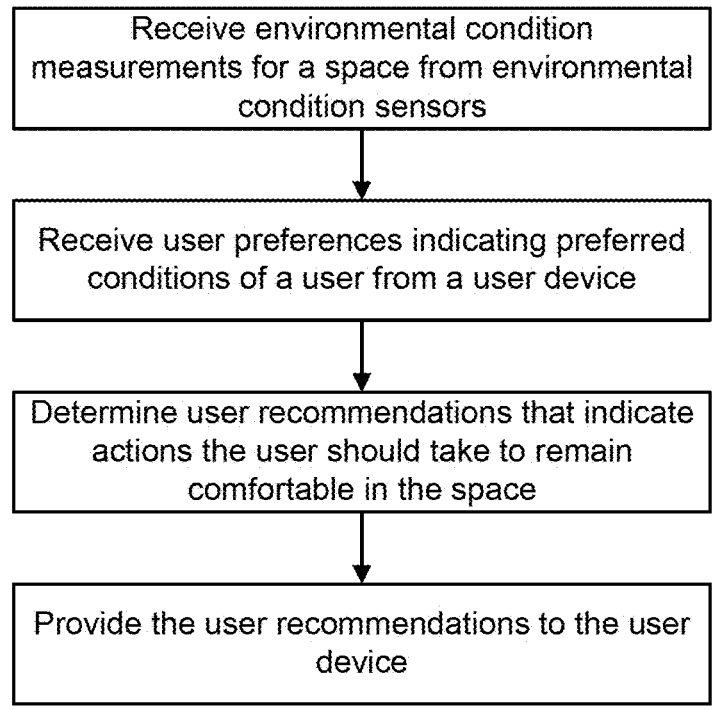
FIG. 53B is a flow diagram of a process for generating and providing user recommendations to a user, according to some embodiments.

Referring now to FIG. 53B, a process for generating and providing user recommendations to a user is shown, according to some embodiments. In some embodiments, steps of the process are performed by components of the system described with reference to FIG. 53A. The process is shown to include receiving environmental condition measurements for a space from environmental condition sensors. The environmental condition measurements can indicate values of various environmental conditions in a space such as temperature, humidity, air quality, etc.

The process is also shown to include receiving user preferences indicating preferred conditions of a user from a user device. In some embodiments, certain user preferences are extrapolated based on other preferences. For example, a user that indicates they prefer extremely clean air quality may be associated with cooling temperatures that do not foster germ growth. In some embodiments, if no preferences are provided by the user, default preferences can be set that are generally comfortable for a majority of users.

The process is also shown to include determining user recommendations that indicate actions the user should take to remain comfortable in the space. Based on the environmental conditions and the user preferences, the recommendations can be generated such that the user is recommended to be in a location that maximizes their comfort by ensuring environmental conditions at the location are as close to preferred conditions as possible. In some embodiments, the preferences indicate a weight associated with each condition. For example, a temperature preference may have a weight of 0.6 whereas an air quality preference may have a weight of 0.4. Based on the weights, the recommendations can be molded such that more heavily weighted preferences are satisfied prior to less heavily weight preferences.

The process is also shown to include providing the user recommendations to the user device. Based on the preferences, the user can determine actions to take in order to maximize a comfort level in the space (or in another space if the space is too uncomfortable).

Figure 54A:
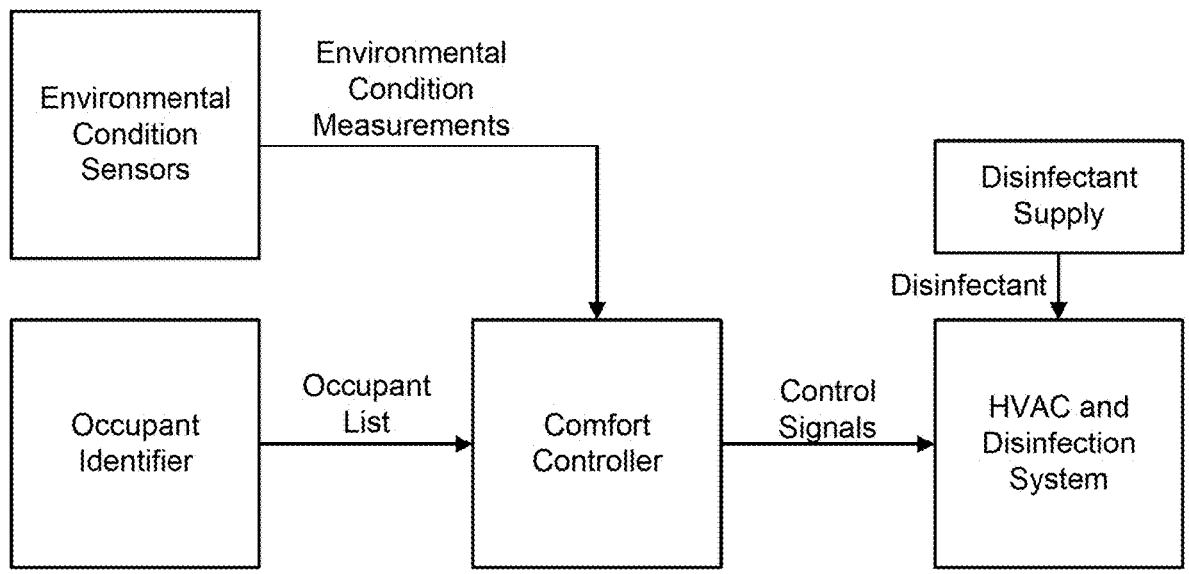
FIG. 54A is a block diagram of a system for operating an HVAC and disinfection system such that comfort of high priority occupants is maintained, according to some embodiments.

Referring now to FIG. 54A, a system for operating an HVAC and disinfection system such that comfort of high priority occupants is maintained is shown, according to some embodiments. A high priority occupant can be any person deemed by the system to be of importance in maintaining their comfort over other occupants. For example, a high priority occupant may be a chief executive officer (CEO) of a company, a guest from another company, the president, etc. The system is shown to include a comfort controller that receives an occupant list from an occupant identifier and environmental conditions measurements from environmental condition sensors. The occupant identifier can be any various device that can determine what occupants are currently present in a space. For example, the occupant identifier may be a visible camera, an RFID scanner that scans an RFID chip on occupants, etc. The occupant list can include a listing of all occupants currently in a space and a priority level of each occupant. Each occupant can be assigned a priority level. For example, priority levels can range from 1-5 with 1 indicating high importance and 5 indicating low importance. In general, priority levels can be indicated by numbers, phrases, terms, letters, symbols, etc. that can be interpreted to determine a priority level of an occupant.

Based on the occupant list, the comfort controller can determine an occupant with a highest priority to base control decisions on. Particularly, predetermined preferences of the highest priority occupant can be used to base the control decisions on. If multiple occupants have a same highest priority level, the comfort controller may determine control decisions that maximize comfort of a largest number of the high priority occupants. Based on the control decisions generated, the comfort controller can operate an HVAC and disinfection system to maintain the comfort of the high priority occupant(s) by changing environmental conditions in the space to preferred values of the high priority occupants.

Figure 54B:
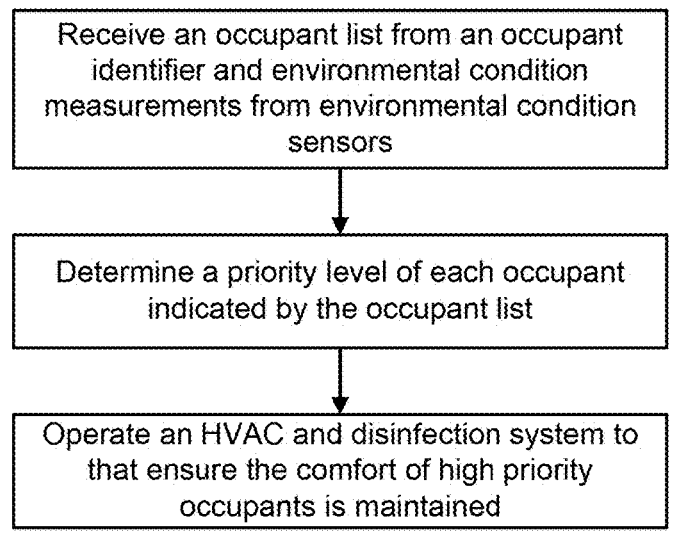
FIG. 54B is a flow diagram of a process for operating an HVAC and disinfection system such that comfort of high priority occupants is maintained, according to some embodiments.

Referring now to FIG. 54B, a process for operating an HVAC and disinfection system such that comfort of high priority occupants is maintained is shown, according to some embodiments. In some embodiments, steps of the process are performed by components of the system described with reference to FIG. 54A. The process is shown to include receiving an occupant list from an occupant identifier and environmental condition measurements from environmental condition sensors. The occupant list can indicate what occupants are currently present in a space and a priority level of each occupant.

The process is also shown to include determining a priority level of each occupant indicated by the occupant list. The occupants can be grouped into priority groups such that occupants with a similar priority levels are grouped together for purposes of determining how to operate building equipment.

The process is also shown to include operating an HVAC and disinfection system to ensure the comfort of high priority occupants is maintained. The HVAC and disinfection system can be operated based on current environmental conditions to move said conditions to values comfortable to the high priority occupants. In this way, high priority occupants can be comfortable in the space even if their preferences are not standard for a majority of people.

Figure 55A:
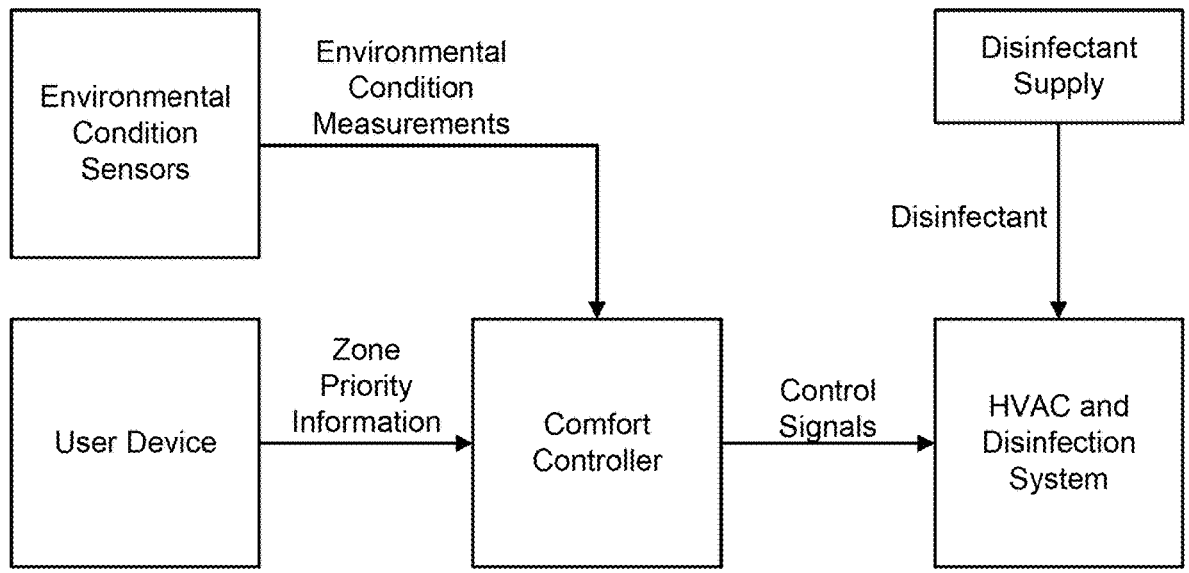
FIG. 55A is a block diagram of a system for operating an HVAC and disinfection system to ensure that conditions of high priority zones is maintained, according to some embodiments.

Referring now to FIG. 55A, a system for operating an HVAC and disinfection system to ensure that conditions of high priority zones is maintained is shown, according to some embodiments. In some embodiments, the system is similar to the system of FIG. 54A. The system is shown to include a comfort controller that receives environmental condition measurements from environmental condition sensors and zone priority information from a user device. Zone priority information can indicate what zones should have their environmental conditions maintained over others. For example, it may be critical to maintain certain environmental conditions in a zone dedicated to research and development (R&D). Particularly, the R&D zone may be required to have a constant temperature and humidity maintained along with minimal air contamination. As such, the R&D zone can be given a high priority value such that conditions of the R&D zone are prioritized to be maintained. The zone priority information can be set by a user (e.g., a building manager) and/or inferred based on settings related to each zone. It should be appreciated that a zone can refer to any space in a building.

Similar to the system of FIG. 54A, the comfort controller can operate an HVAV and disinfection system to maintain conditions in high priority zones first and then lower priority zones. By maintaining conditions in high priority zones first, the system can ensure that devices do not waste resources and operational time on lower priority zones at the cost of compromising conditions in high priority zones.

Figure 55B:
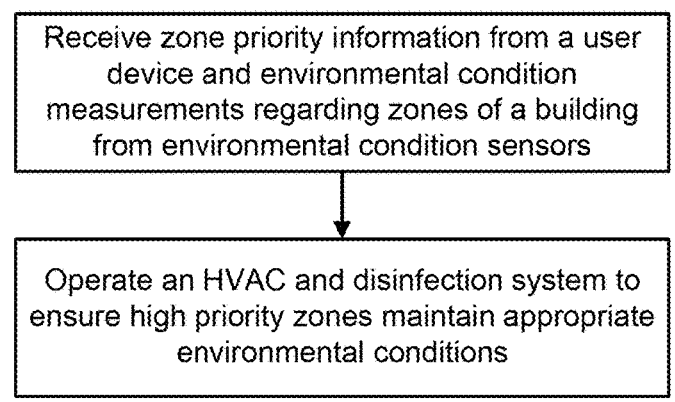
FIG. 55B is a flow diagram of a process for operating an HVAC and disinfection system to ensure that conditions of high priority zones is maintained, according to some embodiments.

Referring now to FIG. 55B, a process for operating an HVAC and disinfection system to ensure that conditions of high priority zones is maintained is shown, according to some embodiments. In some embodiments, steps of the process are performed by components of the system described with reference to FIG. 55A. The process is shown to include receiving zone priority information from a user device and environmental condition measurements regarding zones of a building from environmental condition sensors.

The process is also shown to include operating an HVAC and disinfection system to ensure high priority zones maintain appropriate environmental conditions. The HVAC and disinfection system can be operated such that high priority zones have their respective conditions closely monitored and maintained. If conditions in a high priority zone begin to stray from preferred values, the HVAC and disinfection system can reduce/abandon maintaining conditions in lower priority zones as to return conditions in the high priority zone back to preferred conditions. In this way, resources and operation of the HVAC and disinfection system is targeted towards the high priority zones.

Figure 56A:
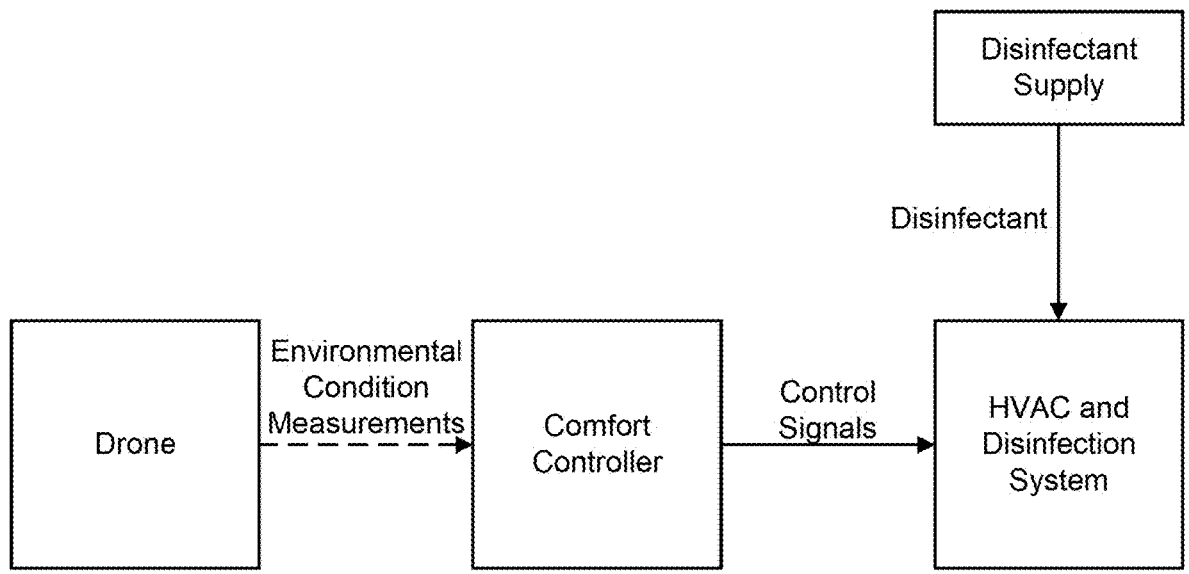
FIG. 56A is a block diagram of a system for operating an HVAC and disinfection system based on environmental conditions measured by a drone, according to some embodiments.

Referring now to FIG. 56A, a system for operating an HVAC and disinfection system based on environmental conditions measured by a drone is shown, according to some embodiments. The drone can include various sensors that can measure environmental conditions of a space. For example, the drone can include air quality sensors, temperature sensors, humidity sensors, etc. Advantageously, the drone can move (e.g., fly, crawl, etc.) around the space to gather measurements of environmental conditions around the space to provide to a comfort controller. In this sense, the drone can act as a mobile sensor package that can provide more accurate measurements of the space for determining control actions. The communication between the drone and the comfort controller is shown as a dashed line in FIG. 56A to indicate that the communication is a wireless communication. However, a wired connection can also be utilized by wiring the drone to a communication channel. Based on the measurements, the comfort controller can determine how to operate an HVAC and disinfection system to move environmental conditions to be comfortable for occupants. In some embodiments, the drone measurements are used by the comfort controller to generate a heat map that can be further used to operate the HVAC and disinfection system. In some embodiments, the measurements taken by the drone are supplemented with measurements taken by other sensors in the space. In some embodiments, the drone is a component of the HVAC and disinfection system.

Figure 56B:
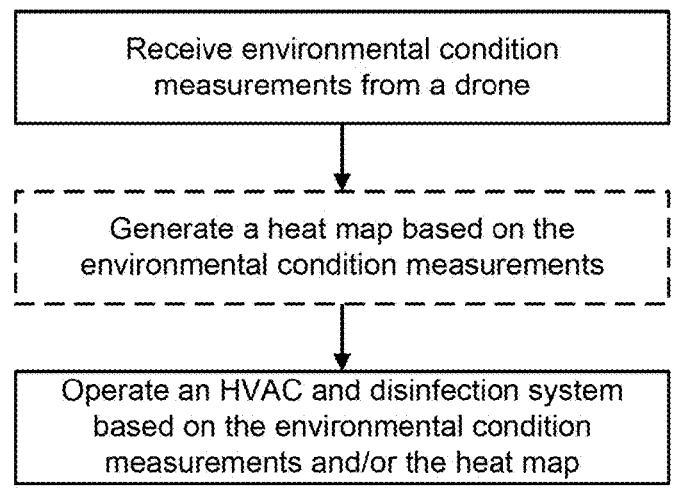
FIG. 56B is a flow diagram of a process for operating an HVAC and disinfection system based on environmental conditions measured by a drone, according to some embodiments.

Referring now to FIG. 56B, a process for operating an HVAC and disinfection system based on environmental conditions measured by a drone is shown, according to some embodiments. In some embodiments, steps of the process are performed by components of the system described with reference to FIG. 56A. The process is shown to include receiving environmental condition measurements from a drone. The drone can be outfitted with various sensors to capture an array of different environmental conditions.

The process is also shown to include an optional step of generating a heat map based on the environmental conditions. Generating the heat map can provide a more detailed understanding of how temperature varies around the space. However, generating the heat map is shown as an optional step as the measurements can be directly used to determine how to operate the HVAC and disinfection system.

The process is also shown to include operating an HVAC and disinfection system based on the environmental condition measurements and/or the heat map. Based on the environmental condition measurements and/or the heat map, control decisions can be generated to operate the HVAC and disinfection system to affect a contamination level, temperature, and/or other conditions at locations in the space where conditions are not comfortable. For example, the heat map may indicate a particular location is extremely hot. Based on said indication, the HVAC and disinfection system can be operated to provide cooling and disinfection to the location.

Figure 57A:
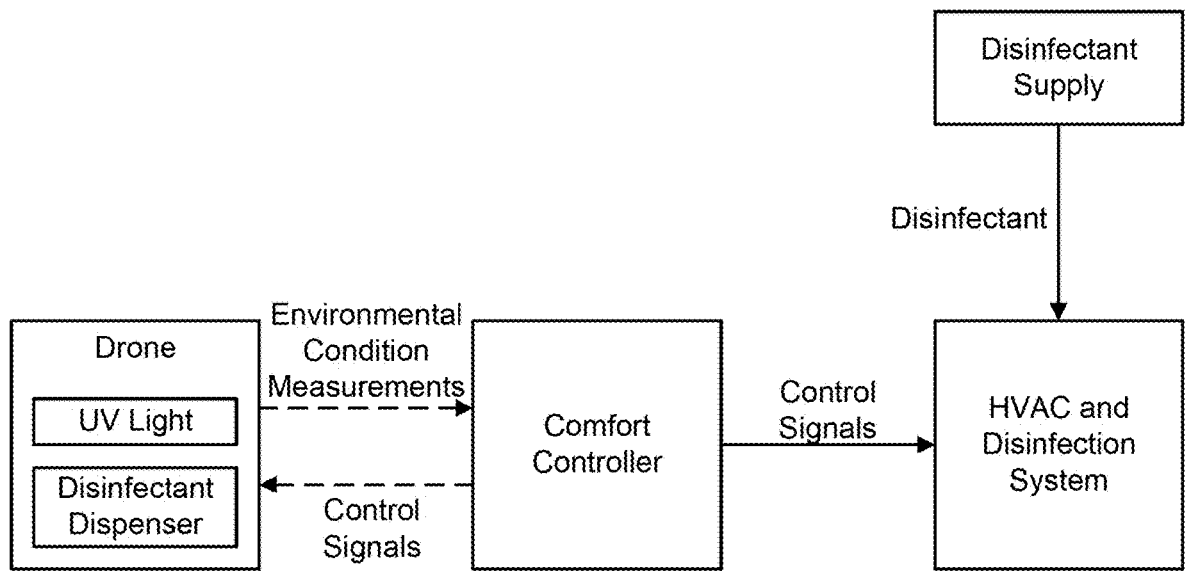
FIG. 57A is a block diagram of a system for operating a drone and an HVAC and disinfection system based on environmental conditions measured by the drone, according to some embodiments.

Referring now to FIG. 57A, a system for operating a drone and an HVAC and disinfection system based on environmental conditions measured by the drone is shown, according to some embodiments. In some embodiments, the system is similar to and/or the same as the system described with reference to FIG. 56A. As shown in FIG. 57A, the drone includes a UV light and a disinfectant dispenser. In this way, the drone can be equipped to disinfect locations in a space separate from the HVAC and disinfection system. It should be appreciated that while the drone is shown to include the UV light and the disinfectant dispenser, the drone can be equipped with different disinfectant mechanisms that can be used to disinfect the space.

Based on measurements provided by the drone, the comfort controller can determine control signals to provide to both the HVAC and disinfection system. In particular, the comfort controller can determine disinfection control signals to provide back to the drone. Due to maneuverability of the drone, the drone may be able to disinfect certain locations in the space that the HVAC and disinfection system cannot. For example, the drone may be able to disinfect a location under a table. In this way, the comfort controller can operate the drone to supplement actions performed by the HVAC and disinfection system. In some embodiments, the comfort controller generates a heat map that can be used to control the drone. In particular, the drone can be moved to hot spots in the space as indicated by the heat map to disinfectant the hot spots.

Figure 57B:
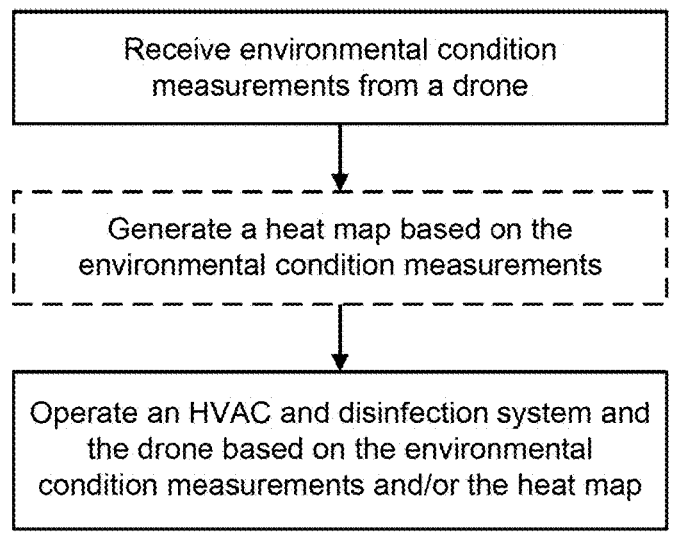
FIG. 57B is a flow diagram of a process for operating a drone and an HVAC and disinfection system based on environmental conditions measured by the drone, according to some embodiments.

Referring now to FIG. 57B, a process for operating a drone and an HVAC and disinfection system based on environmental conditions measured by the drone is shown, according to some embodiments. In some embodiments, steps of the process are performed by components of the system described with reference to FIG. 57A. The process is shown to include receiving environmental condition measurements from a drone.

The process is also shown to include an optional step of generating a heat map based on the environmental condition measurements. Generating the heat map is optional as the heat map can supplement the information indicated by the measurements, but control actions can be determined without the heat map.

The process is also shown to include operating an HVAC and disinfection system and the drone based on the environmental condition measurements and/or the heat map. In particular, the drone can be operated to disinfect locations that are not easily disinfected by the HVAC and disinfection system.

Figure 58A:
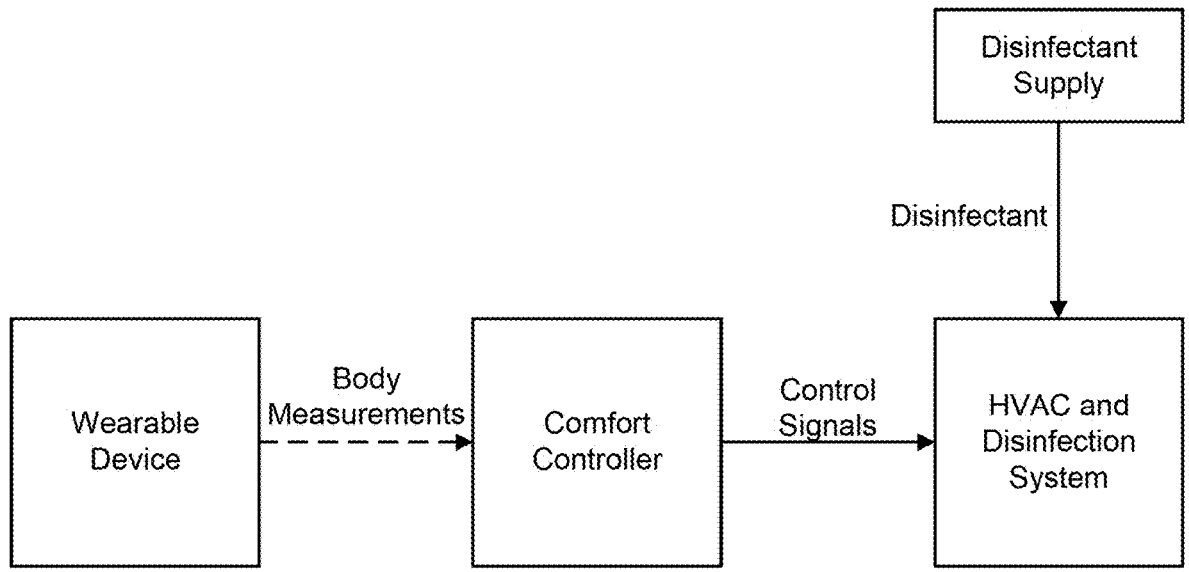
FIG. 58A is a block diagram of a system for operating an HVAC and disinfection system based on measurements taken of a user by a wearable device, according to some embodiments.

Referring now to FIG. 58A, a system for operating an HVAC and disinfection system based on measurements taken of a user by a wearable device is shown, according to some embodiments. The system is shown to include a comfort controller that receives body measurements from a wearable device. The wearable device can include various devices worn by a user such as, for example, a smart watch, a pulse monitor, a headset, etc. The body measurements can include information regarding the user such as, for example, a body temperature, a pulse, perspiration, etc. As shown in FIG. 58A, the wearable device can wirelessly provide the body measurements to the comfort controller. However, the wearable device can provide the body measurements to the comfort controller via wired connection (e.g., by being plugged into a USB port).

Based on the body measurements, the comfort controller can determine a health status of the user. The health status can indicate whether the user has a fever, is perfectly healthy, is too hot in the space, etc. Based on the health status, the comfort controller can determine control actions for the HVAC and disinfection system perform. For example, if the health status indicates the user has a fever, the comfort controller may determine the user is likely to spread additional germs and other contaminants that can negatively affect a contamination level of the space. As such, the comfort controller can operate the HVAC and disinfection system to provide additional disinfection around a user to minimize an effect of the illness. In some embodiments, the body measurements are used to estimate a comfort level of the users. For example, if the body measurements indicate a high perspiration rate of the user, the comfort controller can indicate that additional cooling should be provided to the space to reduce an overall temperature of the space.

Figure 58B:
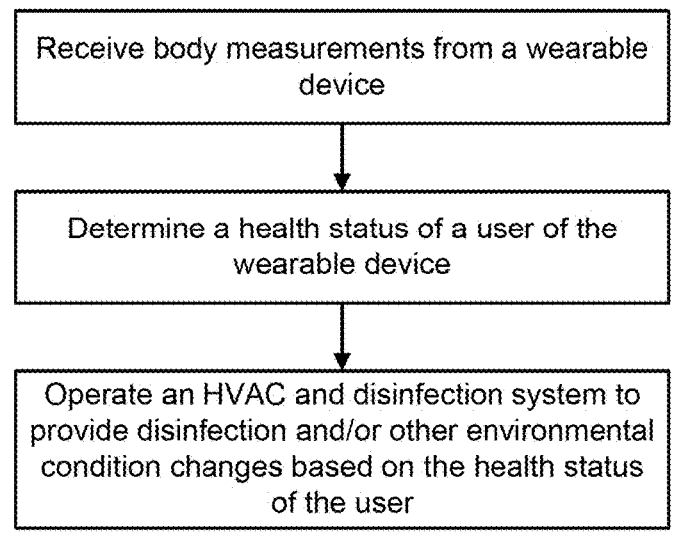
FIG. 58B is a flow diagram of a process for operating an HVAC and disinfection system based on measurements taken of a user by a wearable device, according to some embodiments.

Referring now to FIG. 58B, a process for operating an HVAC and disinfection system based on measurements taken of a user by a wearable device is shown, according to some embodiments. In some embodiments, steps of the process are performed by components of the system described with reference to FIG. 58A. The process is shown to include receiving body measurements from a wearable device. The wearable device can include sensors for measuring body conditions of a user wearing the wearable device.

The process is also shown to include determining a health status of a user of the wearable device. The health status can include information regarding whether the user is ill, is likely to be uncomfortable, etc. In some embodiments, the health status includes information regarding effects of the user in the space (e.g., germ spread, heat disturbance, etc.).

The process is shown to include operating an HVAC and disinfection system to provide disinfection and/or other environmental condition changes based on the health status of the user. Primarily, the health status can indicate an amount of additional disinfection necessary to minimize an impact of the user in the space. If the user is sick, the user is more likely to spread the disease and thereby contaminate air and objects in the space. Therefore, operating the HVAC and disinfection system to provide additional disinfection can eliminate some of the germs and other bacteria spread by the sick individual.

Figure 59A:
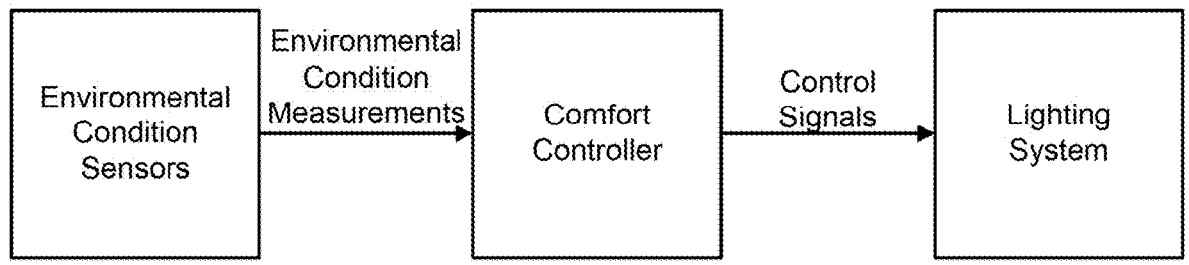
FIG. 59A is a block diagram of a system for operating a lighting system based on environmental conditions in a space, according to some embodiments.

Referring now to FIG. 59A, a system for operating a lighting system based on environmental conditions in a space is shown, according to some embodiments. In some embodiments, the lighting system includes lights that can disinfect the space and/or provide heat the space. For example, the lighting system can include UV lights for disinfection and visible lights that provide lighting and heat to the space. The system is shown to include a comfort controller that receives environmental condition measurements from environmental condition sensors. Based on environmental conditions in the space, the comfort controller can determine how to operate the lighting system in order to provide disinfection and/or heating to the space. As lights release heat during operation, operating lights can provide an inexpensive alternative to operating HVAC equipment to heat the space. Therefore, managing the lighting system to optimize an amount of heat released and provided disinfection can reduce costs for a building system.

Based on the measurements, the comfort controller can determine if the lighting system should be operated at a higher intensity to provide additional heat/disinfection/lighting, or if the lighting system should be dimmed to reduce an amount of heat/disinfection/lighting being provided to the space. In some embodiments, the comfort controller can determine specific lights of the lighting system to operate to achieve particular conditions. For example, the comfort controller may operate, via control signals, a UV light in a corner of the space to provide disinfection to the corner and not operate other lights in the space.

Figure 59B:
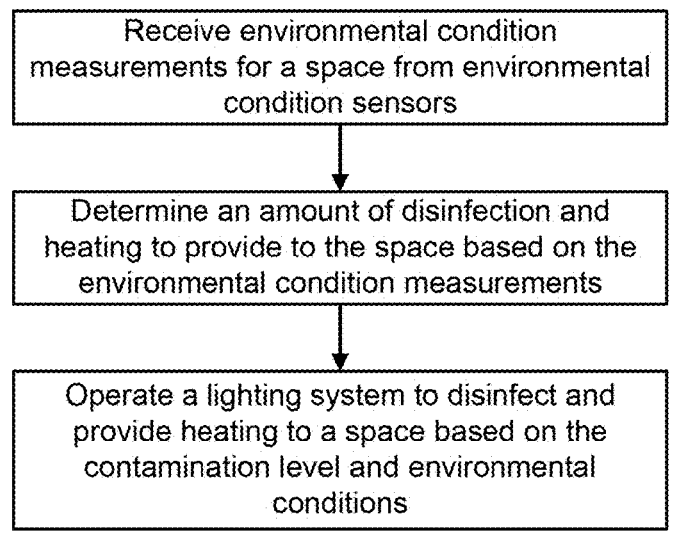
FIG. 59B is a flow diagram of a process for operating a lighting system based on environmental conditions in a space, according to some embodiments.

Referring now to FIG. 59B, a process for operating a lighting system based on environmental conditions in a space is shown, according to some embodiments. In some embodiments, steps of the process are performed by components of the system described with reference to FIG. 59A. The process is shown to include receiving environmental condition measurements for a space from environmental condition sensors.

The process is also shown to include determining an amount of disinfection and heating to provide to the space based on the environmental condition measurements. The amount of both disinfection and heating can be determined based on current conditions indicated by the measurements. For example, if air quality measurements of the environmental condition measurements indicate that air quality in the space is poor, a larger amount of disinfection can be determined to be necessary as compared to if the air quality was adequate.

The process is also shown to include operating a lighting system to disinfect and provide heating to a space based on the contamination level and environmental conditions. Dependent on what lights are installed in the lighting system, certain lights can be operated to disinfect and/or heat the space. Alternatively, to cool the space, certain lights can be disabled. In this way, operating lights of a lighting system can supplement operation of an HVAC and disinfection system by providing additional disinfecting and heating to the space.

Figure 60A:
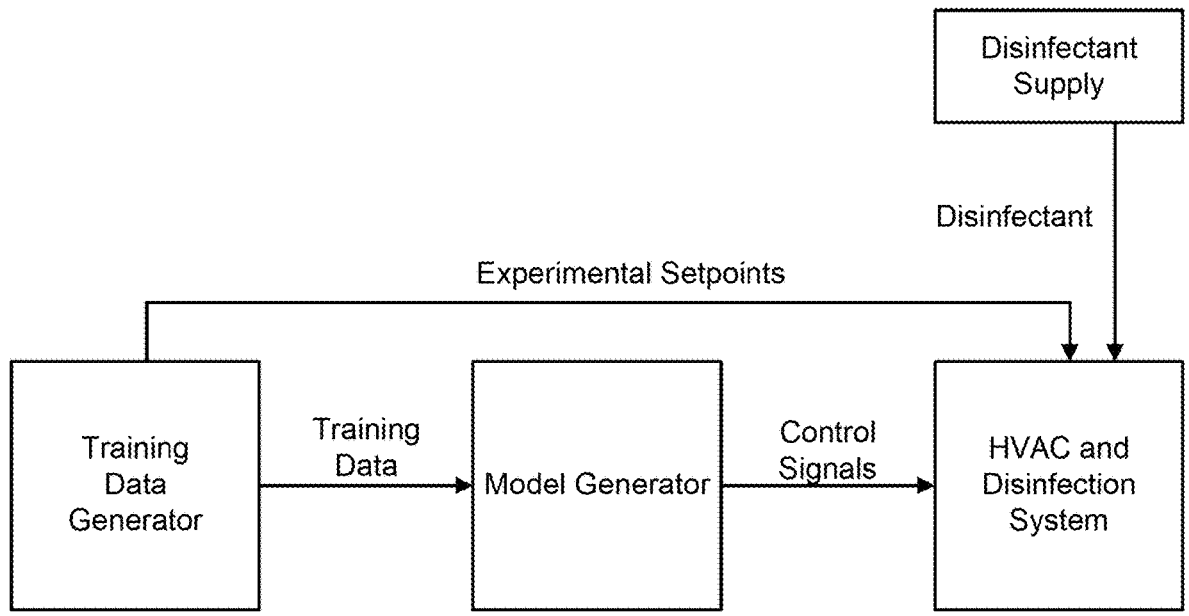
FIG. 60A is a block diagram of a system for generating a model for operating an HVAC and disinfection system based on experimental tests, according to some embodiments.

Referring now to FIG. 60A, a system for generating a model for operating an HVAC and disinfection system based on experimental tests is shown, according to some embodiments. The system is shown to include a training data generator and a model generator. The model generator can be configured to generate a model that can be used to determine how to operate the HVAC and disinfection system to maintain conditions in a space (e.g., that are comfortable to occupants). However, to generate a model that is accurately reflects the space and equipment, representative training data should be gathered. To gather representative training data, the training data generator can perform various tests to gather the training data. The tests can include providing experimental setpoints to the HVAC and disinfection system to determine how the space responds to various setpoints. For example, one experimental setpoint can instruct a heater of the HVAC and disinfection system to operate to achieve a temperature of 76° F. in the space. As another example, another experimental setpoint can instruct an AHU to spray a particular volume of disinfectant into the space to disinfect air and objects in the space. Based on the experiments, results of the experiments can be gathered in the form of occupant feedback, measurements of environmental conditions, etc. If enough setpoints are tested, the results can be provided as training data to the model generator.

Based on the training data, the model generator can perform a model generation process to generate a model that is representative of the space. Using the model, the model generator can operate the HVAC and disinfection system to affect various conditions in the space. If the training data is representative of the space, decisions determined based on the model should maintain occupant comfort, desired conditions in the space, etc.

Figure 60B:
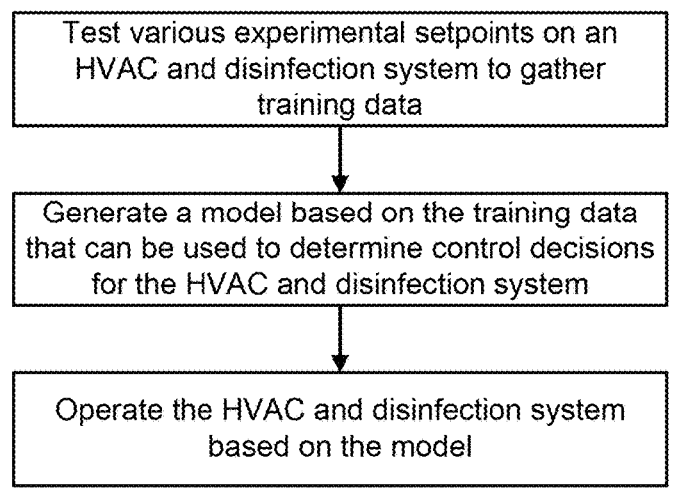
FIG. 60B is a flow diagram of a process for generating a model for operating an HVAC and disinfection system based on experimental tests, according to some embodiments.

Referring now to FIG. 60B, a process for generating a model for operating an HVAC and disinfection system based on experimental tests is shown, according to some embodiments. In some embodiments, steps of the process are performed by components of the system described with reference to FIG. 60A. The process is shown to include testing various experimental setpoints on an HVAC and disinfection system to gather training data. The training data gathered can reflect how a space and/or occupants react to various environmental conditions.

The process is also shown to include generating a model based on the training data that can be used to determine control decisions for the HVAC and disinfection system. If the training data is representative of various dynamics (e.g., thermal dynamics, contamination dynamics, etc.) in the space, the model can be used to estimate how certain control decisions may affect the space. In this way, the model can be used to determine how occupants may react to changes in conditions, how conditions in the space may change due to various setpoints, etc.

The process is also shown to include operating the HVAC and disinfection system based on the model. By operating the HVAC and disinfection system based on the model, conditions in the space can be made comfortable for occupants, safe for equipment, etc.

Figure 61A:
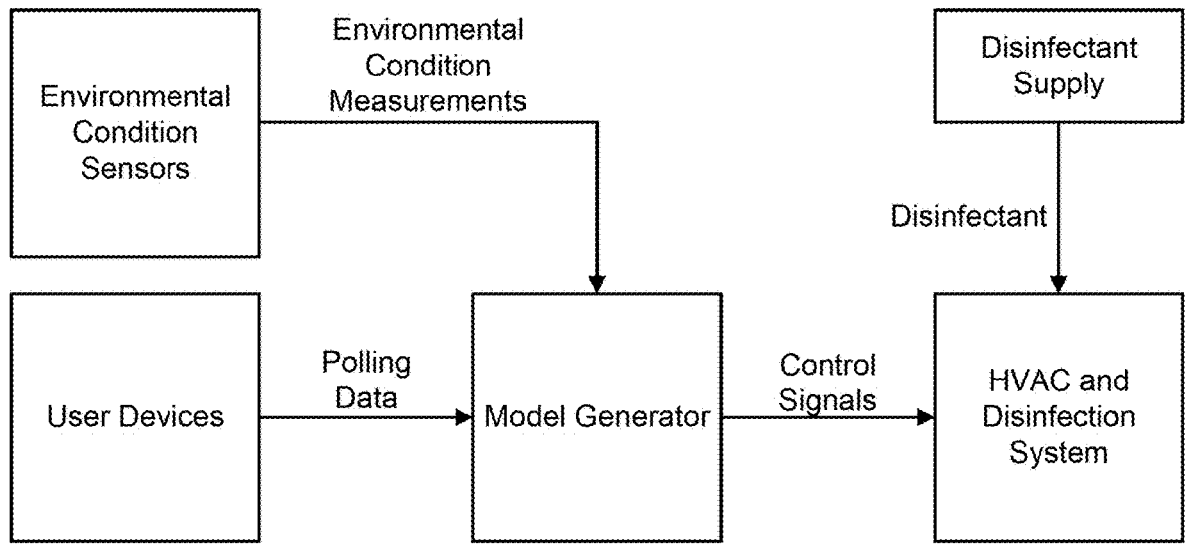
FIG. 61A is a block diagram of a system for generating a model the can be used to determine occupant preferences in a space, according to some embodiments.

Referring now to FIG. 61A, a system for generating a model the can be used to determine occupant preferences in a space is shown, according to some embodiments. In some embodiments, the system shown in FIG. 61A is similar to and/or the same as the system as described with reference to FIG. 60A. The system is shown to include a model generator that receives environmental condition measurements from environmental condition sensors and polling data from user devices. The polling data can indicate occupant preferences over time to various conditions in the space. For example, the polling data can indicate occupant preferences regarding various contamination levels in the space, various temperatures, various relative humidity values, etc. The occupant preferences can be gathered from occupants interacting with the user devices (e.g., phones, computers, etc.). A user device can display a prompt requesting an occupant to rate their current comfort levels. For example, the prompt may be a yes or no question where yes indicates the occupant is comfortable and no indicates the occupant is not comfortable. As another example, the prompt may request the occupant to rate their current comfort on a 1 to 10 scale with 1 indicating highly uncomfortable and 10 indicating highly comfortable. The polling data can be gathered over a learning period (e.g., a week, a month, etc.) to gather occupant preferences. For example, occupants may be polled three times a day over the learning period, once a day over the learning period, etc.

Based on the polling data, the model generator can generate a model that reflects occupant comfort preferences. As more polling data is gathered, the model generator can more accurately generate the model to reflect occupant preferences. Based on the model, the model generator can generate control signals to provide to the HVAC and disinfection system that maintain occupant comfort. In some embodiments, current environmental conditions are used as input to the model and control decisions are outputted by the model.

Figure 61B:
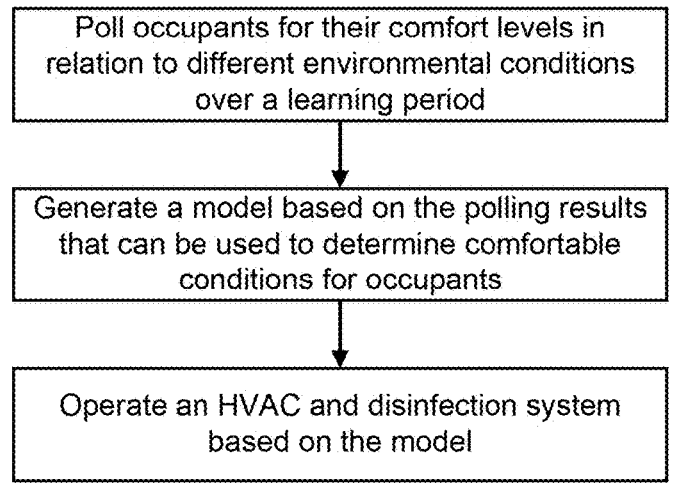
FIG. 61B is a flow diagram of a process for generating a model the can be used to determine occupant preferences in a space, according to some embodiments.

Referring now to FIG. 61B, a process for generating a model the can be used to determine occupant preferences in a space is shown, according to some embodiments. In some embodiments, steps of the process are performed by components of the system described with reference to FIG. 61A. The process is shown to include polling occupants for their comfort levels in relation to different environmental conditions over a learning period. The learning period can be a predetermined amount of time in which a sufficient amount of data for generating a model can be gathered. In particular, the learning period should be long enough that a variety of different environmental conditions are captured and polled during for occupant preferences.

The process is also shown to include generating a model based on the polling results that can be used to determine comfortable conditions for occupants. In some embodiments, polling data is analyzed prior to generating the model to determine if any outlier or inaccurate data is included in the polling data. For example, if an occupant indicates they are comfortable at 100% relative humidity in the space, said indication may be discarded from the polling data as the indication is likely to be inaccurate. In some embodiments, the generated model takes in environmental condition measurements as input and outputs control decisions.

The process is also shown to include operating an HVAC and disinfection system based on the model. In particular, control decisions for the HVAC and disinfection system can be determined by inputting current environmental conditions to the model and using outputs of the model to generate the control decisions. In this way, operation of the HVAC and disinfection system can be accurately tuned to ensure occupant comfort is maintained in the space.

It should be appreciated that the model generated based on the polling data can be generated in a similar manner to capture other preferences. For example, a building manager can instead provide polling feedback regarding various environmental conditions over the learning period such that the model is generated to capture optimal conditions to ensure safety of building equipment.

Figure 62A:
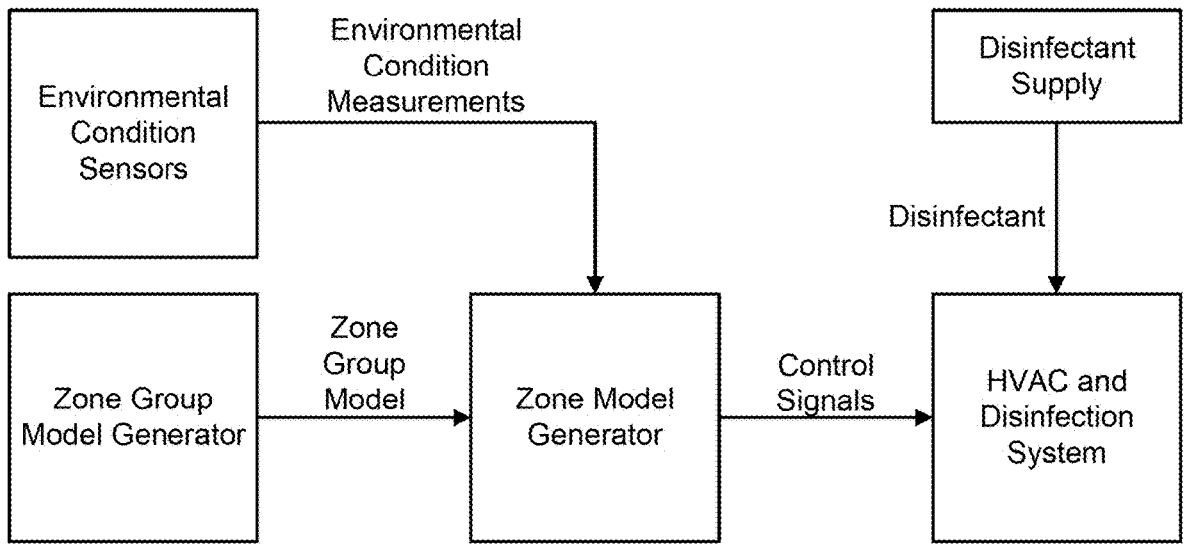
FIG. 62A is a block diagram of a system for generating a zone model for maintaining conditions in a space based on a zone group model, according to some embodiments.

Referring now to FIG. 62A, a system for generating a zone model for maintaining conditions in a space based on a zone group model is shown, according to some embodiments. The system is shown to include a zone model generator that receives environmental condition measurements from environmental condition sensors and a zone group model from a zone group model generator. The zone group model generator can be configured to generate a model indicating how environmental conditions in a zone group should be adjusted to maintain occupant comfort, safety of building equipment, etc. A zone group can include a number of related zones. For example, a zone group may include all zones in a building that are used by executives in a company. Said zone group may be related to a zone group model that ensures a temperature of all the zones in the zone group is around 72° F. and an air quality is kept below some threshold value to ensure executives at the company are consistently comfortable in the zones of the zone group.

Based on the zone group model, the zone model generator can generate a zone model that acts as a refinement of the zone group model to more accurately represent preferences for the zone. For example, the zone group model above can indicate preferences of the executives in general, whereas a zone model based on the zone group model can be specific to preferences of executives in the specific zone. In this way, computational complexity of model generation can be reduced as zone models can be generated based on zone group models that provide baseline information for the zone models. Based on the zone model, the zone model generator can generate control signals to provide to the HVAC and disinfection system. Similar to the model described with reference to FIG. 61A, the zone model can use environmental conditions as input and output control decisions.

Figure 62B:
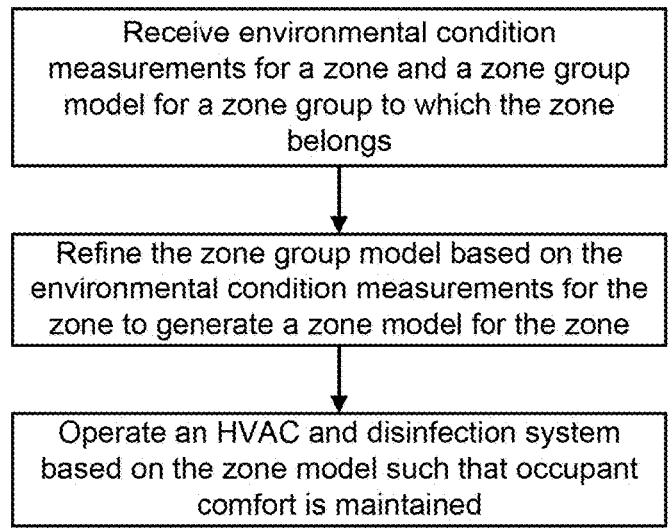
FIG. 62B is a flow diagram of a process for generating a zone model for maintaining conditions in a space based on a zone group model, according to some embodiments.

Referring now to FIG. 62B, a process for generating a zone model for maintaining conditions in a space based on a zone group model is shown, according to some embodiments. In some embodiments, steps of the process are performed by components of the system described with reference to FIG. 62A. The process is shown to include receiving environmental condition measurements for a zone and a zone group model for a zone group to which the zone belongs. The zone group can include any number of zones that are related to the zone.

The process is shown to include refining the zone group model based on the environmental condition measurements for the zone to generate a zone model for the zone. To generate the zone model the zone group model can be used as a baseline. For example, the zone group model may indicate that a temperature recommendation for zones in the zone group is a range between 70° F. to 75° F. The zone model can be generated as a refinement of the range based on preferences of occupants in the zone. In this way, the zone model accurately reflects preferences of occupants in the zone, but has a general preference range already established, thereby reducing processing requirements for model generation.

The process is shown operating an HVAC and disinfection system based on the zone model such that occupant comfort is maintained. The HVAC and disinfection system can be operated by providing current environmental conditions to the zone model as input and using output of the zone model to determine control signals to provide to the HVAC and disinfection system.

Figure 63A:
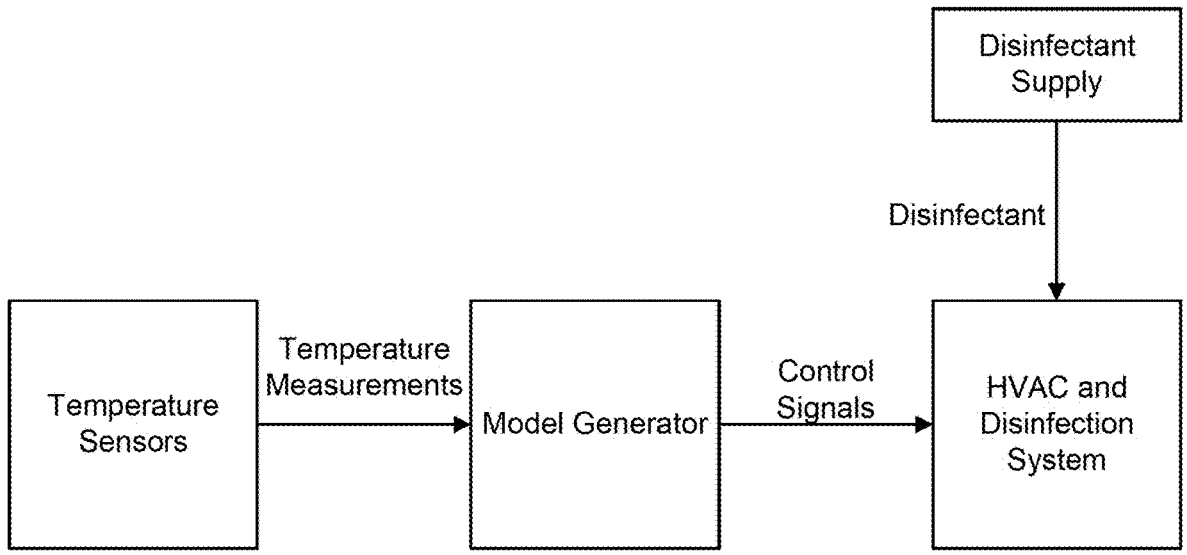
FIG. 63A is a block diagram of a system for generating a model that captures dynamics of a space based on a heat map, according to some embodiments.

Referring now to FIG. 63A, a system for generating a model that captures dynamics of a space based on a heat map is shown, according to some embodiments. The system is shown to include a model generator that receives temperature measurements from temperature sensors. Based on the temperature measurements, the model generator can generate a heat map that indicates heat across the space. Over time, the model generator can generate multiple heat maps and use each heat map to generate a model that reflects thermal dynamics of the space. Based on the model, locations in the space that may need additional heating/cooling and/or disinfection can be determined. The model can use environmental conditions as input and output control decisions that manage temperature and contamination levels in the space. As mentioned above, hot spots in the space may foster additional germ growth, therefore the model can be generated to capture spaces that may require additional disinfection to minimize contamination in the space. Based on the model, the model generator can determine control signals to provide to an HVAC and disinfection system that maintain occupant comfort and/or other desired conditions in the space.

Figure 63B:
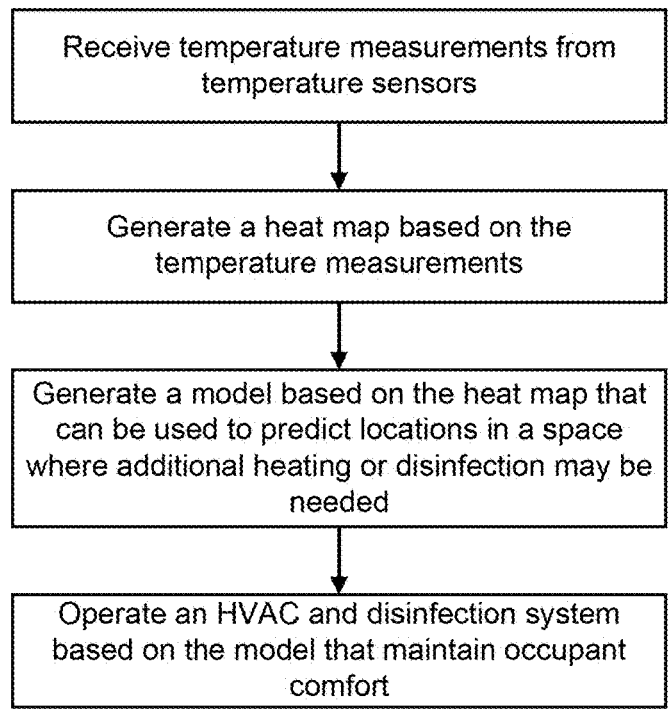
FIG. 63B is a flow diagram of a process for generating a model that captures dynamics of a space based on a heat map, according to some embodiments.

Referring now to FIG. 63B, a process for generating a model that captures dynamics of a space based on a heat map is shown, according to some embodiments. In some embodiments, steps of the process are performed by components of the system described with reference to FIG. 63A. The process is shown to include receiving temperature measurements from temperature sensors. The temperature measurements can indicate both temperatures and locations in the space where each measurement is taken.

The process is shown to include generating a heat map based on the temperature measurements. The heat map can capture how temperature varies at different locations in the space. In some embodiments, multiple heat maps are generated based on temperature measurements gathered over time.

The process is shown to include generating a model based on the heat map that can be used to predict locations in a space where additional heating or disinfection may be needed. In particular, the model can be generated to identify locations in the space that are prone to be hotter than other locations, thereby having a higher chance of fostering germ and other contaminant growth.

The process is shown to include operating an HVAC and disinfection system based on the model that maintain occupant comfort. The HVAC and disinfection system can be operated by providing current environmental conditions to the model as input and using output of the model to determine control signals to provide to the HVAC and disinfection system. In this way, occupant comfort and/or other preferences can be maintained in the space.

Figure 64A:
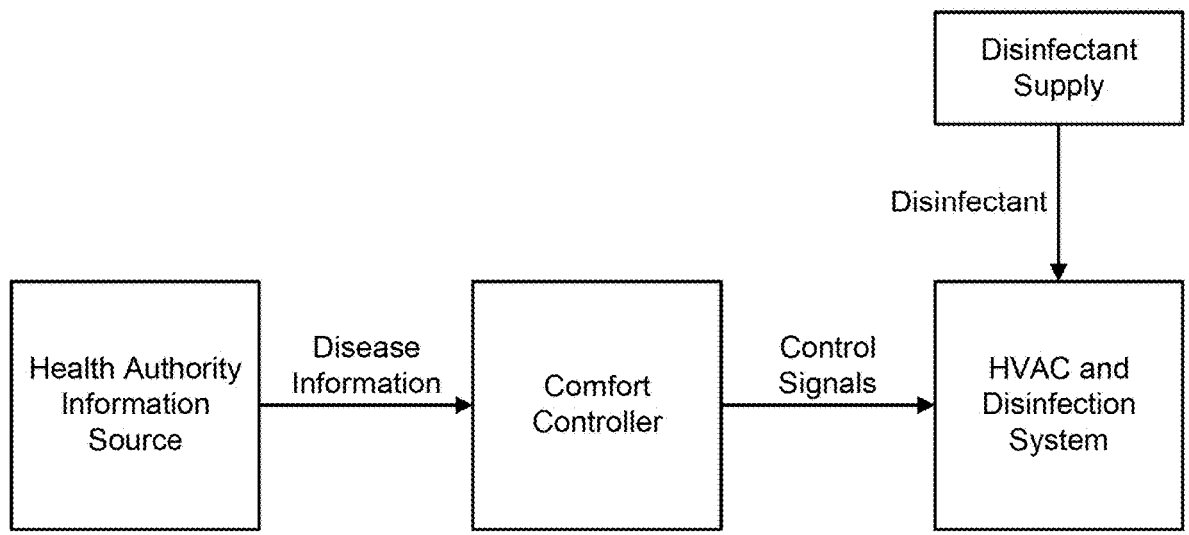
FIG. 64A is a block diagram of a system for operating an HVAC and disinfection system based on information provided by a health authority information source (HAIS), according to some embodiments.

Referring now to FIG. 64A, a system for operating an HVAC and disinfection system based on information provided by a health authority information source (HAIS) is shown, according to some embodiments. The HAIS can be any various source of health information such as, for example, a hospital, a medical website, the World Health Organization, etc. The HAIS is shown to provide disease information to the comfort controller. The disease information can indicate what viruses and other contaminants that can be spread that are currently active in a region. In some embodiments, the disease information indicates information regarding environmental conditions that help/hinder a growth rate or transmission of the diseases and other prevention techniques for slowing the diseases progression and spread. For example, the disease information may indicate a strain of the flu is in circulation in a region and can also indicate how to reduce a chance of transmission of the strain between people.

Based on the disease information, the comfort controller can generate control decisions to provide to the HVAC and disinfection system in order to maintain conditions in the space at safe levels that slow growth and/or transmission of diseases. In some embodiments, slowing disease spread takes precedence over occupant comfort due to an imminent threat of the disease on the occupants. The control decisions provided to the HVAC and disinfection system can include various instructions such as a temperature and relative humidity level to keep the space at, certain disinfectants to spray that are known to kill/hinder diseases, etc. In this way, occupants can be protected against the spread of infectious disease in the space. Without the information provided by the HAIS, the HVAC and disinfection system may otherwise be operated in a way that fosters the growth and/or transmission of diseases.

Figure 64B:
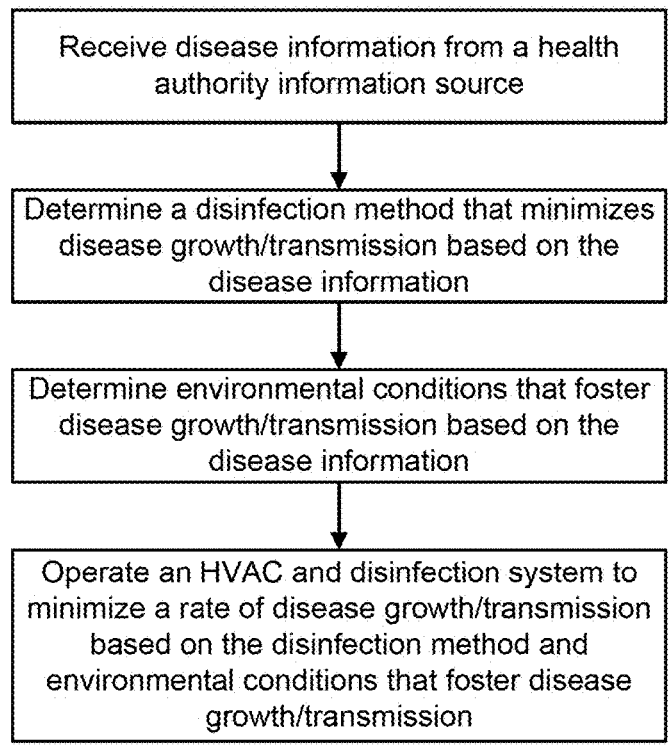
FIG. 64B is a flow diagram of a process for operating an HVAC and disinfection system based on information provided by an HAIS, according to some embodiments.

Referring now to FIG. 64B, a process for operating an HVAC and disinfection system based on information provided by an HAIS is shown, according to some embodiments. In some embodiments, steps of the process are performed by components of the system described with reference to FIG. 64A. The process is shown to include receiving disease information from a health authority information source. The disease information can include various information applicable regarding diseases and how to slow/eliminate their growth and transmission.

The process is shown to include determining a disinfection method that minimizes disease growth/transmission based on the disease information. For example, the disinfection method may include spraying a particular chemical in a space that kills a disease. In some embodiments, multiple disinfection methods are used to minimize disease growth/transmission.

The process is shown to include determining environmental conditions that foster disease growth/transmission based on the disease information. For example, temperatures above 78° F. and relative humidity values above 70% may foster growth of certain diseases.

The process is shown to include operating an HVAC and disinfection system to minimize a rate of disease growth/transmission based on the disinfection method and environmental conditions that foster disease growth/transmission. In particular, the HVAC and disinfection system can be operated to achieve environmental conditions in the space that slow the growth/transmission of diseases and applies disinfection methods that are also likely to slow the growth/transmission of the diseases. By operating the HVAC and disinfection system in this way, occupant safety can be maintained by limiting a chance of infection.

Figure 65A:
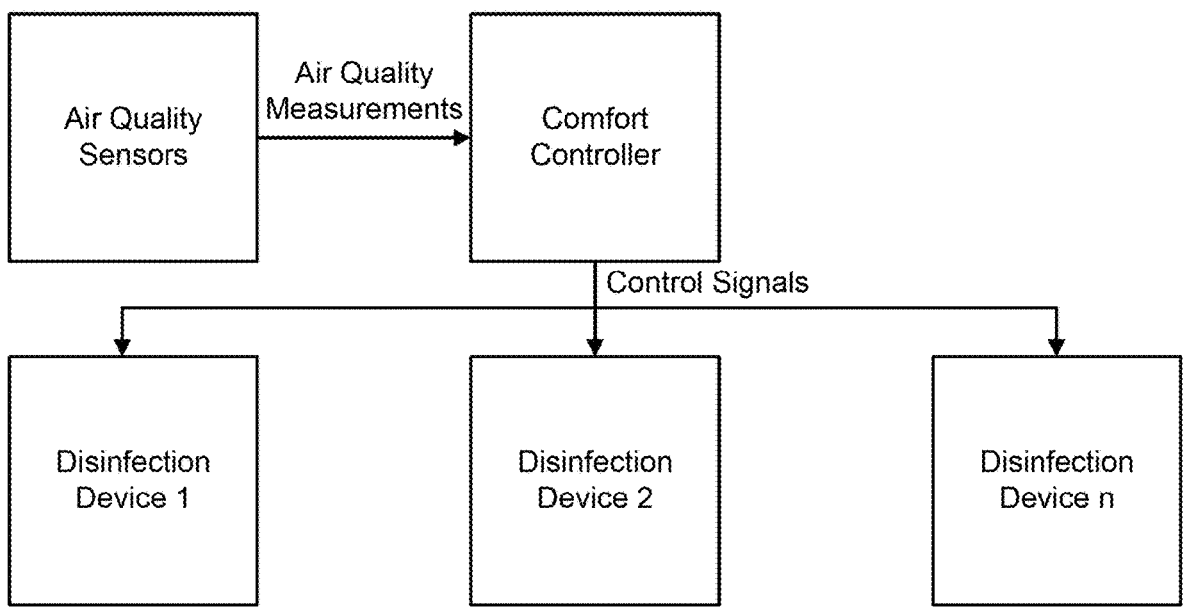
FIG. 65A is a block diagram of a system for operating multiple disinfection devices, according to some embodiments.

Referring now to FIG. 65A, a system for operating multiple disinfection devices is shown, according to some embodiments. The system is shown to include a comfort controller that receives air quality measurements from air quality sensors. Based on the air quality measurements, the comfort controller can generate control signals to provide to multiple disinfection devices. Each disinfection device can be configured to affect a contamination level of air at a different point in a building. For example, a first disinfection device may be configured to disinfect air immediately as it is drawn from the outside whereas a second disinfection device may be configured to disinfect air as it travels through an air duct. The disinfection devices may disinfect the air in similar or different ways (e.g., via UV light, a disinfectant spray, etc.). Advantageously, performing multiple disinfecting stages can ensure the air is cleanly enough for occupants and can act as a failsafe in case one disinfection stage fails.

Based on the air quality measurements, the comfort controller can determine which disinfection devices to operate and at what capacity. For example, in air is only slightly contaminated, the comfort controller may determine that a first disinfection device should not be operated, but a second and third disinfection device should be operated at half capacity to disinfect air. In this way, the comfort controller can reduce costs while still maintaining an adequate air quality for occupants.

Figure 65B:
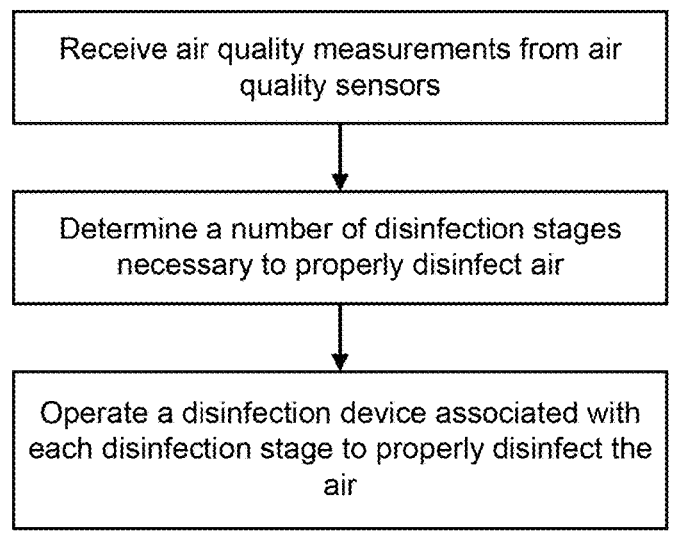
FIG. 65B is a flow diagram of a process for operating multiple disinfection devices, according to some embodiments.

Referring now to FIG. 65B, a process for operating multiple disinfection devices is shown, according to some embodiments. In some embodiments, steps of the process are performed by components of the system described with reference to FIG. 65A. The process is shown to include receiving air quality measurements from air quality sensors. The air quality measurements can indicate both indoor and outdoor air quality, depending on locations of the air quality sensors.

The process is also shown to include determining a number of disinfection stages necessary to properly disinfect air. The number of disinfection stages can be determined based on how contaminated the air quality measurements indicate the air is. As a contamination level of the air increases, more disinfection stages may be required to properly disinfect the air.

The process is also shown to include operating a disinfection device associated with each disinfection stage to properly disinfect the air. Each disinfection device can also be operated at a particular operational level. For example, a first disinfection device of a first disinfection stage may run at 20% of full operational power whereas a second disinfection device of a second disinfection stage may run at 80% of full operational power in order to properly disinfect the air.

Figure 66A:
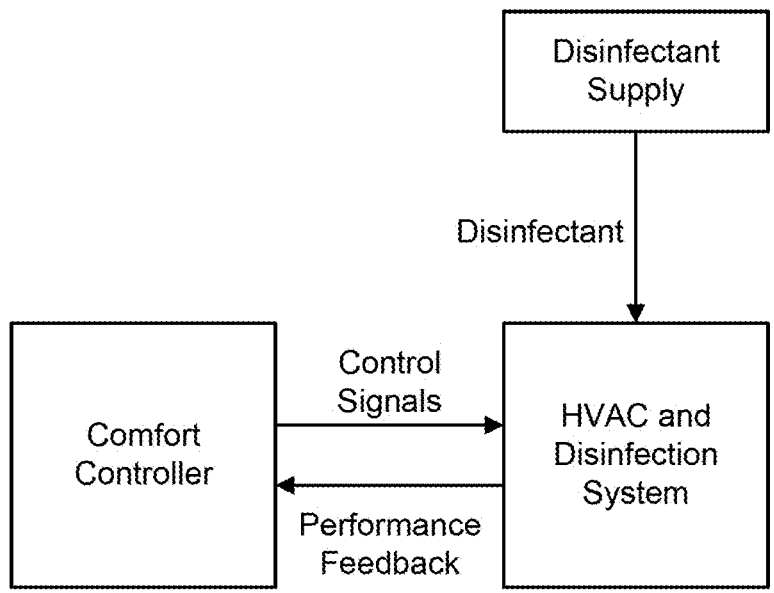
FIG. 66A is a block diagram of a system for operating an HVAC and disinfection system based on a feedback loop, according to some embodiments.

Referring now to FIG. 66A, a system for operating an HVAC and disinfection system based on a feedback loop is shown, according to some embodiments. The system is shown to include a comfort controller that receives performance feedback from the HVAC and disinfection system. The performance feedback can indicate operating conditions of the HVAC and disinfection system over time. Particularly, the performance feedback can indicate an operational level of HVAC equipment in the HVAC and disinfection system over time. The operational level of the HVAC equipment can be used to estimate an amount of people that may be in the space. If the HVAC equipment is operating at a high operational level for most of a day, a lot of people can be estimated to be in the space as each person can result in a heat disturbance affecting a temperature of the space, thereby necessitating additional operation of the HVAC equipment. Based on the estimation of people, a contamination level due to the people can be estimated. Based on the contamination level estimated, the comfort controller can generate control signals to operate disinfection equipment of the HVAC and disinfection system to reduce the contamination level of the space. Advantageously, said feedback loop can allow the comfort controller to estimate a contamination level of the space without air quality sensors scattered throughout the space. Alternatively, the feedback loop can supplement measurements made by the air quality sensors to get a more accurate determination of a current contamination level in the space.

Figure 66B:
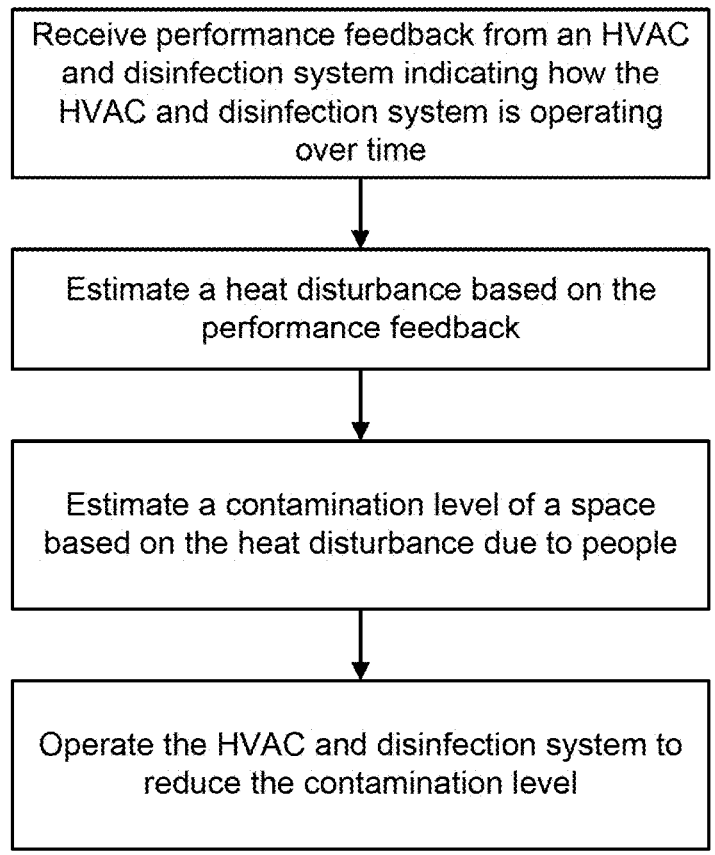
FIG. 66B is a flow diagram of a process for operating an HVAC and disinfection system based on a feedback loop, according to some embodiments.

Referring now to FIG. 66B, a process for operating an HVAC and disinfection system based on a feedback loop is shown, according to some embodiments. In some embodiments, steps of the process are performed by components of the system described with reference to FIG. 66A. The process is shown to include receiving performance feedback from an HVAC and disinfection system indicating how the HVAC and disinfection system is operating over time. The feedback loop can provide valuable information regarding contamination in a space especially if HVAC equipment of the HVAC and disinfection system is operating to maintain a certain temperature.

The process is shown to include estimating a heat disturbance based on the performance feedback. The performance feedback can indicate at what operational level certain devices are operating at over the course of a time period (e.g., a day). Equipment operating at a high load for most of the time period may indicate a lot of people are present as a high heat disturbance can be affecting the space. Said indication can be further refined if other sources of heat disturbance (e.g., solar radiation, heat generated by electronic equipment, etc.) can be estimated.

The process is shown to include estimating a contamination level of a space based on the heat disturbance due to people. In general, the contamination level can rise as more people are estimated to be in the space.

The process is shown to include operating the HVAC and disinfection system to reduce the contamination level. Based on the estimated contamination level, disinfectant devices of the HVAC and disinfection system can be operated. For example, if the contamination level is estimated to be low, shining a disinfectant UV light at certain locations in the space may be sufficient to reduce the contamination level. As another example, if the contamination level is estimated to be high, the space may be vacated and filled with disinfectant gas to reduce the contamination level. As such, a disinfection method used can be scaled in severity dependent on the contamination level.

Figure 67A:
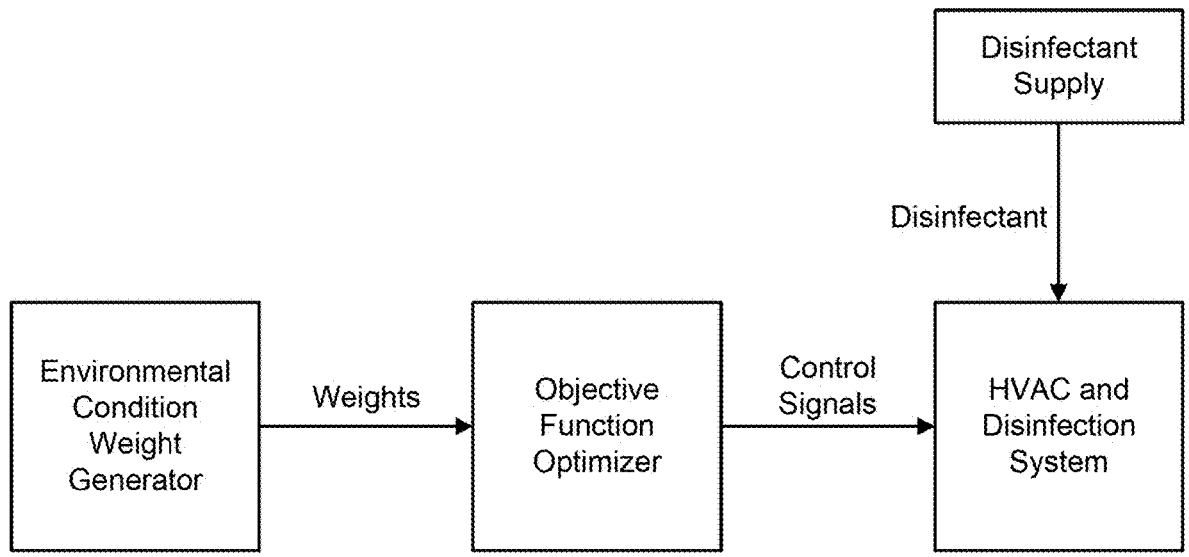
FIG. 67A is a block diagram of a system for operating an HVAC and disinfection system based on an optimization of an objective function, according to some embodiments.

Referring now to FIG. 67A, a system for operating an HVAC and disinfection system based on an optimization of an objective function is shown, according to some embodiments. The system is shown to include an environmental condition weight generator that provides weights to an objective function optimizer. The weights generated by the environmental condition weight generator can indicate a relative importance of each environmental condition considered during an optimization process. For example, an air quality weight may be set to 0.6 whereas a temperature weight may be set to 0.4, indicating it is more important for a solution to the objective function to ensure that air quality is maintained in a space. In some embodiments, a default weight of each environmental condition is equal to one divide by a total number of environmental conditions considered. In this way, the default weight of each environmental condition is equal, thereby indicating to determine a solution to the objective function that evenly accounts for each environmental condition.

Based on the weights, the objective function optimizer can optimize an objective function to determine a solution to generate control signals based on. The objective function can define how to operate equipment of the HVAC and disinfection system in such a way as to optimize (e.g., reduce) costs without compromising occupant comfort. The objective function can be optimized using any of a variety of optimization techniques, including various optimization techniques known in the art. In some embodiments, the solution to the objective function includes decision variables how and when to operate devices of the HVAC and disinfection system as to maintain occupant comfort at an optimized (e.g., reduced) cost. Based on the solution to the objective function, the objective function optimizer can generate control signals to provide to the HVAC and disinfection system and/or specific device of the HVAC and disinfection system to affect environmental conditions in the space.

Figure 67B:
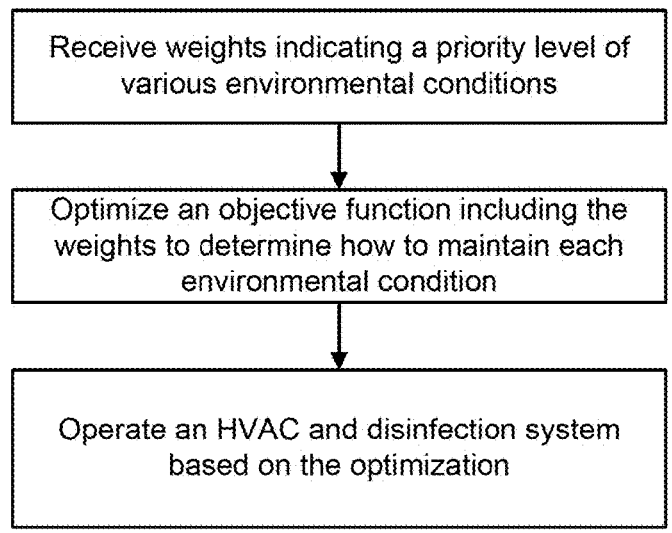
FIG. 67B is a flow diagram of a process for operating an HVAC and disinfection system based on an optimization of an objective function, according to some embodiments.

Referring now to FIG. 67B, a process for operating an HVAC and disinfection system based on an optimization of an objective function is shown, according to some embodiments. In some embodiments, steps of the process are performed by components of the system described with reference to FIG. 67A. The process is shown to include receiving weights indicating a priority level of various environmental conditions. In some embodiments, the weights are automatically generated based on learned preferences (e.g., of occupants, of building managers, based on feedback of building equipment, etc.). In some embodiments, the weights are directly provided by a user and/or based on an average of weights provided by multiple users.

The process is shown to include optimizing an objective function including the weights to determine how to maintain each environmental condition. By optimizing the objective function, decision variables can be determined that operate building devices to affect various environmental conditions (e.g., temperature, air quality, etc.) to ensure occupant comfort and to optimize (e.g., reduce) costs. In other words, optimizing the objective function can generate a solution to maintain each environmental condition.

The process is shown to include operating an HVAC and disinfection system based on the determination regarding how to maintain each environmental condition. As described above, the solution to the optimization can indicate what devices of the HVAC and disinfection system to operate to maintain each environmental condition.

Figure 68A:
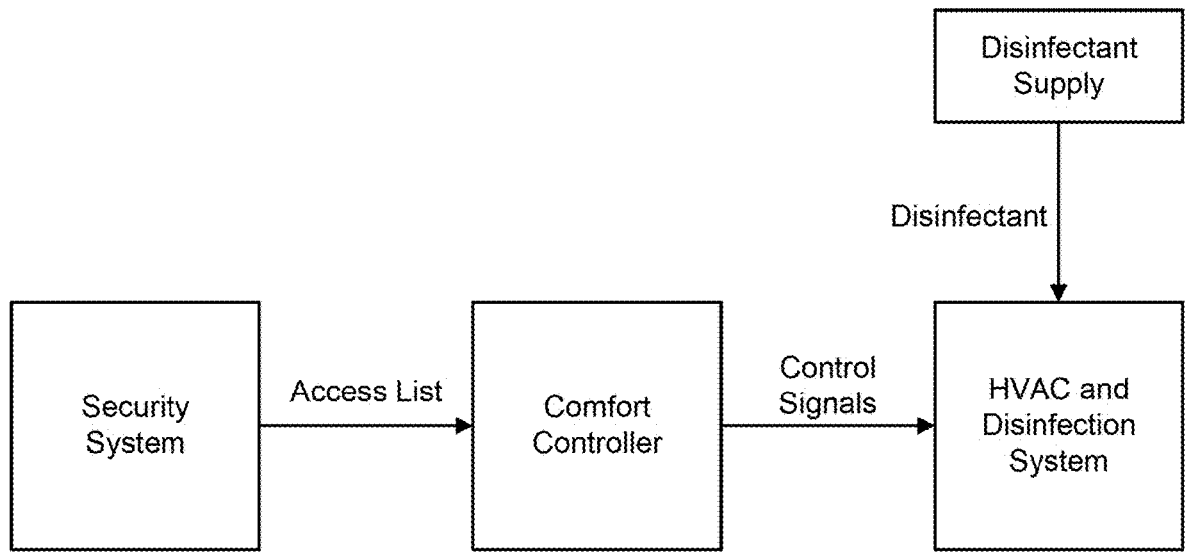
FIG. 68A is a block diagram of a system for operating an HVAC and disinfection system based on an access list to a space, according to some embodiments.

Referring now to FIG. 68A, a system for operating an HVAC and disinfection system based on an access list to a space is shown, according to some embodiments. The access list can indicate an amount of people that have access to a particular space. Some spaces in a building may be secured such that only certain individuals may have access to the space. However, some spaces may be general access spaces and as such the general public can use said spaces. As shown by the system, a security system is shown to provide the access list to a comfort controller. Based on the access list, the comfort controller can determine what spaces are restricted and/or public and generate a space priority list based on said determination. The space priority list can be constructed to identify certain spaces that should have environmental conditions more closely managed and maintained. For example, a general access space may be expected to have a larger number of people than a secured space and therefore can have a higher priority to receive additional disinfection, temperature management, etc. Alternatively, as another example, the secured space may receive a higher priority if a determination is made that important documents, equipment, etc. is stored and thus should have environmental conditions closely maintained to optimal levels. Based on the space priority list, the comfort controller can generate control signals to provide to the HVAC and disinfection system such that environmental conditions in high priority spaces are maintained.

Figure 68B:
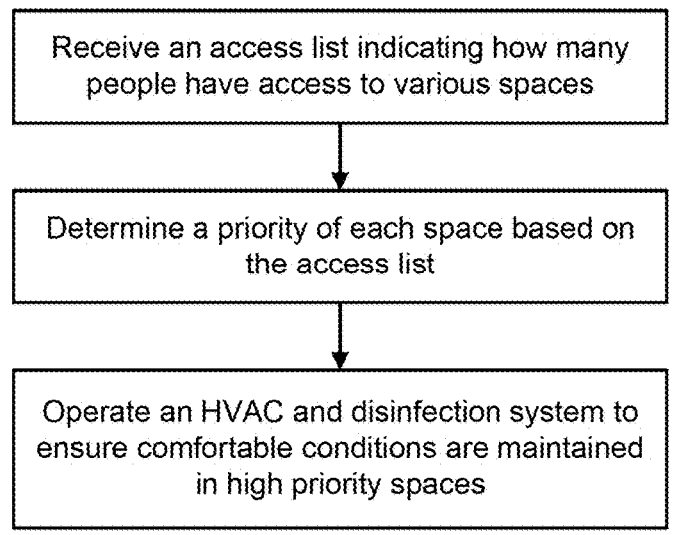
FIG. 68B is a flow diagram of a process for operating an HVAC and disinfection system based on an access list to a space, according to some embodiments.

Referring now to FIG. 68B, a process for operating an HVAC and disinfection system based on an access list to a space is shown, according to some embodiments. In some embodiments, steps of the process are performed by components of the system described with reference to FIG. 68A. The process is shown to include receiving an access list indicating how many people have access to various spaces. The access list may include a number of people that can access each space, a list of each individual that can access each space, etc.

The process is shown to include determining a priority of each space based on the access list. The number of people with access to each space can generally indicate a security level of each space. For example, a space where only five people have access may be more secure than a space where 50 people have access. As such, the priority list can be established to define which spaces should have environmental conditions prioritized.

The process is shown to include operating an HVAC and disinfection system to ensure comfortable conditions are maintained in high priority spaces. If the environmental conditions are maintained adequately in the high priority spaces, the lower priority spaces can then receive treatment. However, if conditions in the high priority spaces begin to diverge from desired levels, control signals can operate the HVAC and disinfection system to prioritize moving the conditions in the high priority spaces back to acceptable levels.

Figure 69A:
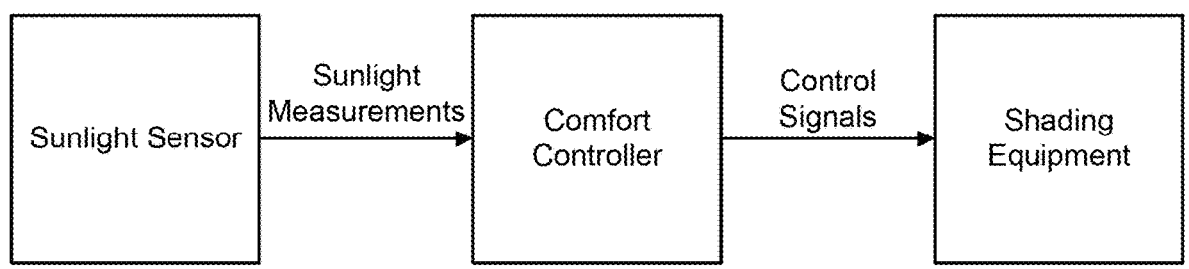
FIG. 69A is a block diagram of, a system for operating shading equipment to affect an amount of sunlight entering a space for heating and disinfection purposes, according to some embodiments.

Referring now to FIG. 69A, a system for operating shading equipment to affect an amount of sunlight entering a space for heating and disinfection purposes is shown, according to some embodiments. As sunlight can provide heat and disinfect objects it comes into contact with, managing an amount of sunlight can help a building system with integrated temperature and disinfection control. The system is shown to include a sunlight sensor that provides sunlight measurements to a comfort controller. The sunlight sensor can be an indoor or an outdoor sensor that can determine an amount of sunlight projected by the sun. Alternatively, the sunlight sensor may be a weather service that can provide a current estimation of solar intensity.

Based on the sunlight measurements, the comfort controller can determine how much sunlight to let into a space based on current environmental conditions in the space. For example, if an air quality of the space is determined to be poor, it may be beneficial to let additional sunlight in to allow the sunlight to provide natural disinfection in the space. As another example, if the space is too hot, the amount of sunlight being let into the space can be reduced. To adjust the amount of sunlight being let into the space, the comfort controller can generate and provide control signals to shading equipment. The control signals can operate the shading equipment to be more open or closed as to allow more or less sunlight in respectively. In this way, the sunlight can provide natural heating/cooling along with disinfection at relatively low cost in comparison to operating an HVAC and disinfection system. In particular, operation of shading equipment can be combined with an HVAC and disinfection system to provide more options to a controller determining how to manage temperature and contamination in a space.

Figure 69B:
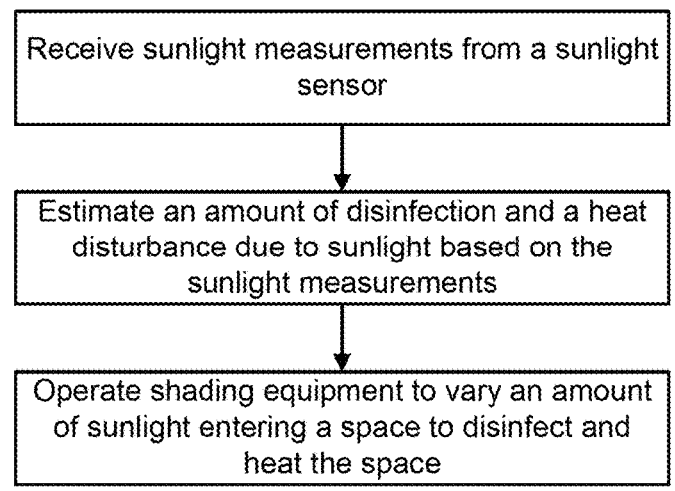
FIG. 69B is a flow diagram of a process for operating shading equipment to affect an amount of sunlight entering a space for heating and disinfection purposes, according to some embodiments.

Referring now to FIG. 69B, a process for operating shading equipment to affect an amount of sunlight entering a space for heating and disinfection purposes is shown, according to some embodiments. In some embodiments, steps of the process are performed by components of the system described with reference to FIG. 68A. The process is shown to include receiving sunlight measurements form a sunlight sensor. The sunlight measurements can indicate an amount of sunlight that is affecting a space and/or outside.

The process is shown to include estimating an amount of disinfection and a heat disturbance due to sunlight based on the sunlight measurements. As the intensity of the sunlight increases, disinfection capabilities and the heat disturbance due to the sunlight can increase. As such, the amount of disinfection and the heat disturbance can be estimated based on the sunlight intensity.

The process is shown to include operating shading equipment to vary an amount of sunlight entering a space to disinfect and heat the space. Based on the amount of disinfection and the heat disturbance that the sunlight can provide, the shading equipment can be operated based on current environmental conditions in the space to vary the amount of sunlight provided. If the environmental conditions indicate, for example, that the space is highly contaminated, the shading equipment can be opened to let additional sunlight in for natural disinfection purposes.

Configuration of Exemplary Embodiments

The construction and arrangement of the systems and methods as shown in the various exemplary embodiments are illustrative only. Although only a few embodiments have been described in detail in this disclosure, many modifications are possible (e.g., variations in sizes, dimensions, structures, shapes and proportions of the various elements, values of parameters, mounting arrangements, use of materials, colors, orientations, etc.). For example, the position of elements may be reversed or otherwise varied and the nature or number of discrete elements or positions may be altered or varied. Accordingly, all such modifications are intended to be included within the scope of the present disclosure. The order or sequence of any process or method steps may be varied or re-sequenced according to alternative embodiments. Other substitutions, modifications, changes, and omissions may be made in the design, operating conditions and arrangement of the exemplary embodiments without departing from the scope of the present disclosure.

The present disclosure contemplates methods, systems and program products on any machine-readable media for accomplishing various operations. The embodiments of the present disclosure may be implemented using existing computer processors, or by a special purpose computer processor for an appropriate system, incorporated for this or another purpose, or by a hardwired system. Embodiments within the scope of the present disclosure include program products comprising machine-readable media for carrying or having machine-executable instructions or data structures stored thereon. Such machine-readable media can be any available media that can be accessed by a general purpose or special purpose computer or other machine with a processor. By way of example, such machine-readable media can comprise RAM, ROM, EPROM, EEPROM, CD-ROM or other optical disk storage, magnetic disk storage or other magnetic storage devices, or any other medium which can be used to carry or store desired program code in the form of machine-executable instructions or data structures and which can be accessed by a general purpose or special purpose computer or other machine with a processor. When information is transferred or provided over a network or another communications connection (either hardwired, wireless, or a combination of hardwired or wireless) to a machine, the machine properly views the connection as a machine-readable medium. Thus, any such connection is properly termed a machine-readable medium. Combinations of the above are also included within the scope of machine-readable media. Machine-executable instructions include, for example, instructions and data which cause a general purpose computer, special purpose computer, or special purpose processing machines to perform a certain function or group of functions.

Although the figures show a specific order of method steps, the order of the steps may differ from what is depicted. Also two or more steps may be performed concurrently or with partial concurrence. Such variation will depend on the software and hardware systems chosen and on designer choice. All such variations are within the scope of the disclosure. Likewise, software implementations could be accomplished with standard programming techniques with rule based logic and other logic to accomplish the various connection steps, processing steps, comparison steps and decision steps.

What is claimed is:

1. A method in a building management system (BMS) performed by one or more processors, the method comprising:
   receiving health risk data from a health agency, the health risk data indicating new cases of an infectious disease in a geographic area of a building and comprising an identification of the infectious disease in the geographic area of the building;
   determining a building-specific health risk level comprising a probability of infection for at least one space in the building based on both (i) the health risk data for the geographic area of the building, a quanta generation rate for the infectious disease, and (ii) building-specific information comprising occupancy data for the building and a control strategy for the at least one space in the building comprising an outdoor air ventilation rate; and
   controlling equipment to perform at least one of an air handling action or a disinfection action in the building based on the building-specific health risk level.

2. The method of claim 1, wherein performing the air handling action comprises increasing an outdoor air ventilation rate in the space in the building.

3. The method of claim 1, wherein performing the disinfection action comprises using disinfectant light to sanitize air circulated through the space in the building.

4. The method of claim 1, wherein performing the disinfection action comprises performing air filtration at an air handling unit of the BMS.

5. The method of claim 1, further comprising receiving a user input, wherein the user input comprises weightings indicating importance of health risk reduction relative to energy consumption.

6. The method of claim 1, wherein the health agency is a national or international organization.

7. A building management system (BMS), the system comprising:
   one or more processors; and
   one or more computer-readable storage media having instructions stored thereon that, upon execution by the one or more processors, cause the one or more processors to implement operations comprising:
receiving health risk data from a health agency, the health risk data indicating new cases of an infectious disease in a geographic area of the building and comprising an identification of the infectious disease in the geographic area of the building;
determining a health risk level comprising a probability of infection for at least one space in the building based on both the health risk data, a quanta generation rate for the infectious disease, occupancy data for the building, and a control strategy for the at least one space in the building comprising an outdoor air ventilation rate; and
controlling equipment to perform at least one of an air handling action or a disinfection action in the building based on the health risk level.

8. The system of claim 7, wherein the operations further comprise receiving a user input, wherein the user input comprises weightings indicating importance of health risk reduction relative to energy consumption.

9. The system of claim 7, wherein performing the air handling action comprises increasing an outdoor air ventilation rate in the space in the building.

10. The system of claim 7, wherein performing the disinfection action comprises at least one of using disinfectant light to sanitize air circulated through the space in the building, performing air filtration at an air handling unit of the BMS, providing ozone in the space in the building, or using a humidifier to add disinfectant to air in the space in the building.

11. The system of claim 7, wherein the health agency is a national or international organization.

12. The system of claim 7, wherein determining the health risk level comprises determining whether any individuals in the building have been infected with the infectious disease.

13. A method in a building management system (BMS) performed by one or more processors, the method comprising:
receiving health risk data from a health agency, the health risk data indicating new cases of an infectious disease in a geographic area of a building and comprising an identification of the infectious disease in the geographic area of the building;
receiving occupant data for one or more individuals in the building;
determining a health risk level comprising a probability of infection for at least one space in the building based on the health risk data, a quanta generation rate for the infectious disease, the occupant data comprising occupancy data for the building, and a control strategy for the at least one space in the building comprising an outdoor air ventilation rate; and
controlling equipment to perform at least one of an air handling action or a disinfection action in the building based on the health risk level.

14. The method of claim 13, wherein receiving the occupant data comprises receiving biometric data from one or more wearable devices associated with the one or more individuals in the building and receiving health record data regarding the infectious disease for the one or more individuals in the building.

15. The method of claim 13, wherein performing the air handling action comprises increasing an outdoor air ventilation rate in the space in the building, and wherein performing the disinfection action comprises at least one of using disinfectant light to sanitize air circulated through the space in the building or performing air filtration at an air handling unit of the BMS.

16. The method of claim 13, wherein the health agency is a national or international organization.

17. The method of claim 13, further comprising receiving a user input, wherein the user input comprises a first weight indicating an importance to reduce health risks, and a second weight indicating an importance to reduce energy cost.

* * * * *